(12) United States Patent
Benfey et al.

(10) Patent No.: US 7,026,530 B2
(45) Date of Patent: Apr. 11, 2006

(54) WOODEN LEG GENE, PROMOTER AND USES THEREOF

(75) Inventors: Philip N. Benfey, Dobbs Ferry, NY (US); Yrjo Helariutta, Helsinki (FI); Ari Pekka Mahonen, Helsinki (FI); Albertus Wilhelm Martinus Bonke, Vantaa (FI); Leila Kauppinen, Helsinki (FI); Marjukka Riikonen, Helsinki (FI)

(73) Assignee: New York University, New York, NY (US)

( * ) Notice: Subject to any disclaimer, the term of this patent is extended or adjusted under 35 U.S.C. 154(b) by 157 days.

(21) Appl. No.: 10/135,322

(22) Filed: Apr. 30, 2002

(65) Prior Publication Data

US 2002/0173017 A1    Nov. 21, 2002

Related U.S. Application Data

(63) Continuation of application No. PCT/US01/45053, filed on Nov. 29, 2001.

(60) Provisional application No. 60/253,739, filed on Nov. 29, 2000.

(51) Int. Cl.
   *C12N 15/29* (2006.01)
   *C12N 15/82* (2006.01)
   *C12N 5/04* (2006.01)
   *A01H 5/00* (2006.01)

(52) U.S. Cl. .................. 800/298; 800/287; 800/290; 800/278; 536/23.1; 536/23.6; 435/69.1; 435/252.3; 435/320.1; 435/468; 435/410

(58) Field of Classification Search ............... 800/298, 800/290, 287, 278; 536/23.1, 23.6; 435/468, 435/320.1, 252.3, 69.1, 410, 183
See application file for complete search history.

(56) References Cited

U.S. PATENT DOCUMENTS

5,097,025 A    3/1992   Benfey et al.
5,110,732 A    5/1992   Benfey et al.

FOREIGN PATENT DOCUMENTS

WO    WO 97/41152    11/1997

OTHER PUBLICATIONS

Bowie et al, Science 247:1306-1310, 1990.*
McConnell et al, Nature 411 (6838):709-713, 2001.*
Fourgoux-Nicol et al (1999, Plant Molecular Biology 40 : 857-872).*
Larkin et al (1994, The Plant Cell 6:1065-1076).*
Covitz et al (1998 Plant Physiol. 117:1325-1332).*
Bryant (1989, Trends in Biotechnology 7(2):20-21).*
Martienssen (1998, PNAS 95:2021-2026).*
Aeschbacher et al., "The Genetic and Molecular Basis of Root Development," *Annual Rev. of Plant Physiol. and Plant Mol. Biol.* 45:25-45 (1994).
Aeschbacher et al., "Genes That Regulate Plant Development," *Plant Science* 83:115-126 (1992).
The Arabidopsis Genome Initiative, "Analysis of the Genome Sequence of the Flowering Plant *Arabidopsis thaliana,*" *Nature* 408:796-815 (2000).
Benfey et al., "Root Development in *Arabidopsis:* Four Mutants with Dramatically Altered Root Morphogenesis," *Development* 119:57-70 (1993).
Benfey et al., "Regulated Genes in Transgenic Plants," *Science* 244:174-181 (1989).
Benfey et al., "Getting to the Root of Plant Development: The Genetics of *Arabidopsis* Root Formation," *Trends in Genetics* 10:84-88 (1994).
Benfey et al., "Root Development," *Current Biology* 10(22): R813-815 (2000).
Benfey, "Is the Shoot a Root with a View?" *Current Opinion in Plant Biology* 2:39-43 (1999).
Benfey et al., "Insights into Root Development from *Arabidopsis* Root Mutants," *Plant, Cell, and Environment* 17:675-680 (1994).
Caño-Delgado et al., "The *eli1* Mutation Reveals a Link Between Cell Expansion and Secondary Cell Wall Formation in *Arabidopsis thaliana,*" *Development* 127(15):3395-3405 (2000).
Carland et al., "Genetic Regulation of Vascular Tissue Patterning in *Arabidopsis,*" *Plant Cell* 11(11):2123-2137 (1999).

(Continued)

*Primary Examiner*—David T. Fox
*Assistant Examiner*—Stuart F. Baum
(74) *Attorney, Agent, or Firm*—Nixon Peabody LLP

(57) ABSTRACT

The structure and function of a regulatory gene, WOODEN LEG (WOL), is described. The WOL gene is expressed specifically in the vasculature during early stages of embryogenesis with expression continuing throughout development. WOL encodes a novel two component signal transducer and is required for asymmetric cell divisions during vascular tissue morphogenesis. Also described are WOL nucleic acids, WOL gene products, (including, but not limited to, transcriptional products such as mRNAs, antisense, and ribozyme molecules, and translational products such WOL proteins, polypeptides, peptides and fusion proteins related thereto), antibodies to WOL gene products, WOL promoters and regulatory regions and the use of the foregoing to improve agronomically valuable plants.

9 Claims, 23 Drawing Sheets

OTHER PUBLICATIONS

Figure 1:
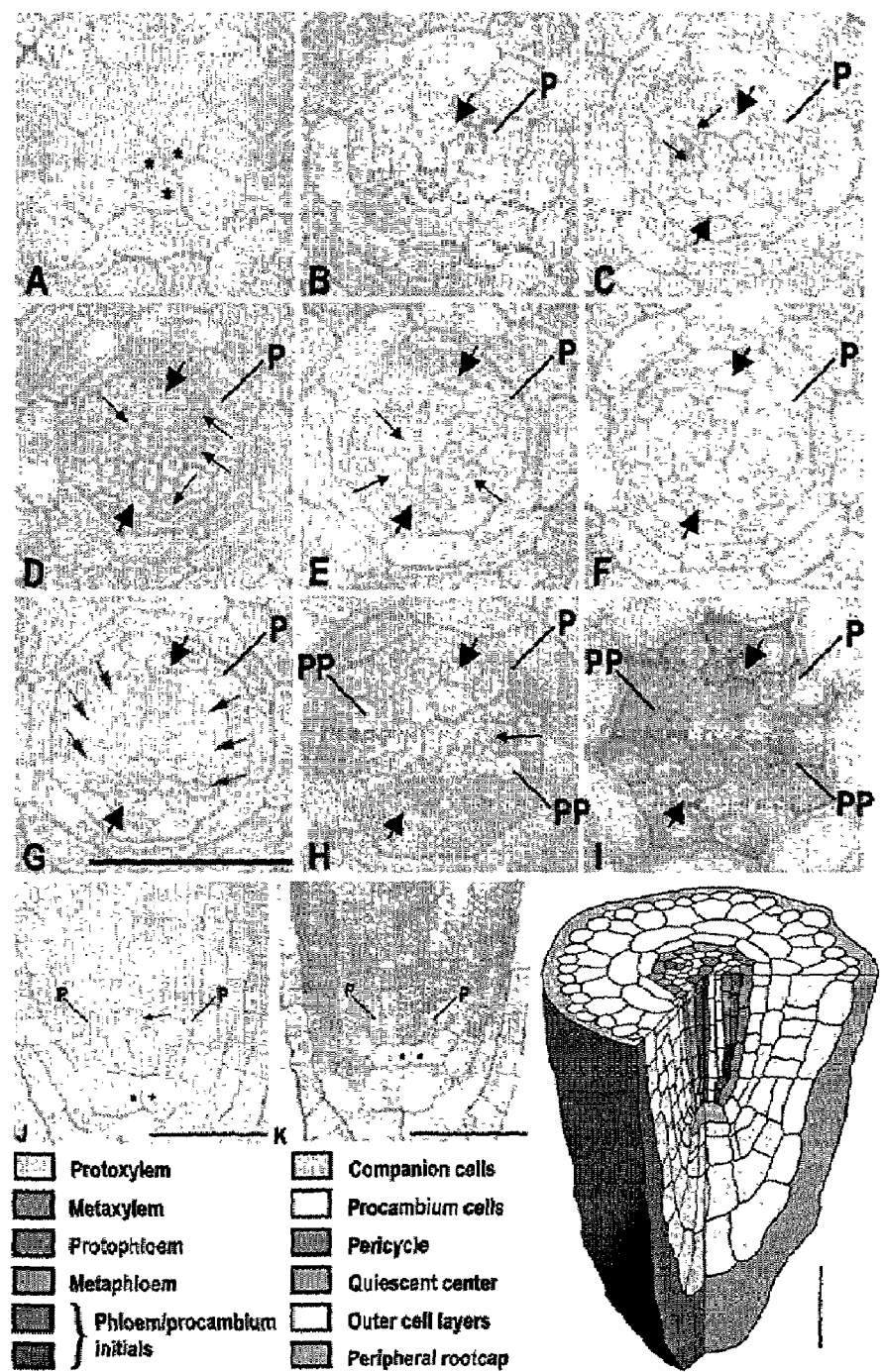

Carland et al., "*LOPI:* A Gene Involved in Auxin Transport and Vascular Patterning in *Arabidopsis,*" *Development* 122 (6): 1811-1819 (1996).

Di Laurenzio et al., "The *SCARECROW* Gene Regulates an Asymmetric Cell Division that is Essential for Generating the Radial Organization of the Arabidopsis Root," *CELL* 86:423-433 (1996).

Dolan et al., "Cellular Organisation of the *Arabidopsis thaliana* Root," *Development* 119(1):71-84 (1993).

Freshour et al., "Development and Tissue-Specific Structural Alterations of the Cell-Wall Polysaccharides of *Arabidopsis thialiana* Roots," *Plant Physiol.* 110:1413-1429 (1996).

Graham et al., "Expression Patterns of Vascular-Specific Promoters *RolC* and *Sh* in Transgenic Potatoes and Their Use in Engineering PLRV-Resistant Plants," *Plant Molecular Biology* 33(4):729-735 (1997).

Hardtke et al., "The *Arabidopsis* Gene *MONOPTEROS* Encodes a Transcription Factor Mediating Embryo Axis Formation and Vascular Development, " *EMBO J.* 17(5): 1405-1411 (1998).

Hauser et al., "Genetic Regulation of Root Expansion in *Arabidopsis thaliana,*" in *Plant Molecular Biology: Molecular Genetic Analysis of Plant Development and Metabolism,* Coruzzi et al., eds., Springer-Verlag: Berlin, pp. 31-40 (1994).

Hauser et al., "Conditional Root Expansion Mutants of *Arabidopsis,*" *Development* 121:1237-1252 (1995).

Helariutta et al., "The *SHORT-ROOT* Gene Controls Radial Patterning of the *Arabidopsis* Root through Radial Signaling," *Cell* 101:555-567 (2000).

Hobbie et al., "The *axr6* Mutants of *Arabidopsis thaliana* Define a Gene Involved in Auxin Response and Early Development," *Development* 127(1):23-32 (2000).

Horvitz et al., "Mechanisms of Asymmetric Cell Division: Two Bs or Not Two Bs, That is the Question," *Cell* 68(2): 237-255 (1992).

Inoue et al., "Identification of CRE1 as a Cytokinin Receptor from *Arabidopsis,*" *Nature* 409:1060-1063 (2001).

Inoue et al., NCBI Database for Nucleotide Sequences, National Center for Biotechnology Information, National Library of Medicine, NIH (Bethesda, MD, USA), Accession No. AB049934 (2001).

Inoue et al., NCBI Database for Nucleotide Sequences, National Center for Biotechnology Information, National Library of Medicine, NIH (Bethesda, MD, USA), Accession No. AB049935 (2001).

Kakimoto, "Genes Involved in Cytokinin Signal Transduction," *J. of Plant Research* 111:261-265 (1998).

Kieber, "The Ethylene Signal Transduction Pathway in *Arabidopsis,*" *J. Experimental Botany* 48(307):211-218 (1997).

Koizumi et al., "A Series of Novel Mutants of *Arabidopsis thialiana* that are Defective in the Formation of Continuous Vascular Network: Calling the Auxin Signal Flow Canalization Hypothesis into Question," *Development* 127(15):3197-3204 (2000).

Lin et al., "Sequence and Analysis of Chromosome 2 of the Plant *Arabidopsis thaliana,*" *Nature* 402:761-768 (1999).

Lin et al., NCBI Database for Nucleotide Sequences, National Center for Biotechnology Information, National Library of Medicine, NIH (Bethesda, MD, USA), Accession No. AAD21777 (versions 1 and 2) (2000 & 2002).

Lim et al., "Molecular Analysis of the *SCARECROW* Gene in Maize Reveals a Common Basis for Radial Patterning in Diverse Meristems," *Plant Cell* 12:1307-1318 (2000).

Mähönen et al., "A Novel Two-Component Hybrid Molecule Regulates Vascular Morphogenesis of the *Arabidopsis* Root," *Genes & Dev.* 14(23):2938-2943 (2000).

Mahonen et al., NCBI Database for Nucleotide Sequences, National Center for Biotechnology Information, National Library of Medicine, NIH (Bethesda, MD, USA), Accession No. ATH278530 (2000).

Malamy et al., "Down and Out in *Arabidopsis:* The Formatin of Lateral Roots," *Trends in Plant Science* 2(10): 390-396 (1997).

Malamy et al., "Organization and Cell Differentiation in Lateral Roots of *Arabidopsis thaliana,*" *Development* 124: 33-44 (1997).

Malamy et al., "Analysis of *SCARECROW* Expression Using a Rapid System for Assessing Transgene Expression in *Arabidopsis* Roots," *Plant Journal* 12(4):957-963 (1997).

Mollier et al., "Tagging of a Cryptic Promoter That Confers Root-Specific *gus* Expression in *Arabidopsis thaliana,*" *Plant Cell Reports* 19:1076-1083 (2000).

Oyama et al., "The *Arabidopsis HY5* Gene Encodes a bZIP Protein that Regulates Stimulus-Induced Development of Root and Hypocotyl," *Genes & Dev.* 11(22):2983-2995 (1997).

Pysh et al., "Root Cell Extension: Genetic and Molecular Approaches," in *Radical Biology: Advances and Perspectives on the Function of Plant Roots,* Flores et al., eds., American Soc. of Plant Physiologists: Maryland, pp. 34-47 (1997).

Rounsley et al., NCBI Database for Nucleotide Sequences, National Center for Biotechnology Information, National Library of Medicine, NIH (Bethesda, MD, USA), Accession No. B22489 (1997).

Sabatini et al., "An Auxin-Dependent Distal Organizer of Pattern and Polarity in the *Arabidopsis* Root," *Cell* 99:463-472 (1999).

Scheres et al., "Asymmetric Cell Division in Plants," *Annu. Rev. Plant Physiol. Plant Mol. Biol.* 50:505-537 (1999).

Scheres et al., "Mutations Affecting the Radial Organisation of the *Arabidopsis* Root Display Specific Defects Throughout the Embryonic Axis," *Development* 121:53-62 (1995).

Scheres et al., "Embryonic Origin of the *Arabidopsis* Primary Root and Root Meristem Initials," *Development* 120:2475-2487 (1994).

Schiefelbein et al., "The Development of Plant Roots: New Approaches to Underground Problems," *Plant Cell* 3:1147-1154 (1991).

Schiefelbein et al., "Root Development in *Arabidopsis,*" in *Arabidopsis,* Meyerowitz et al., eds., Cold Spring Harbor Laboratory Press: Cold Spring Harbor, pp. 335-354 (1994).

Schiefelbein et al., "Meeting Report: International Symposium on the Molecular Genetics of Root Development," *Plant Molecular Biology Reporter* 11(1):60-64 (1993).

Schrick et al., "FACKEL is a Sterol C-14 Reductase Required for Organized Cell Division and Expansion in *Arabidopsis* Embryogenesis," *Genes & Dev.* 14(12):1471-1484 (2000).

Steinmann et al., "Coordinated Polar Localization of Auxin Efflux Carrier PIN1 by GNOM ARF GEF," *Science* 286 (5438): 316-318 (1999).

Suzuki et al., "The *Arabidopsis* Sensor His-Kinase, AHK4, Can Respond to Cytokinins," *Plant Cell Physiol.* 42(2):107-113 (2001).

Tieman et al., "Differntial Expression of Two Novel Members of the Tomato Ethylene-Receptor Family," *Plant Physiology* 120:165-172 (1999).

Urao et al., "A Transmembrane Hybrid-Type Histidine Kinase in *Arabidopsis* Functions as an Osmosensor," *The Plant Cell* 11:1743-1754 (1999).

Wysocka-Diller et al., "Root Radial Organization," *Plant Physiology* (Supp.)111:12 (1996) (abstract).

Wysocka-Diller et al., "Root Development: Signaling Down and Around," *BioEssays* 19(11):959-965 (1997).

Wysocka-Diller et al., "Molecular Analysis of SCARECROW Function Reveals a Radial Patterning Mechanism Common to Root and Shoot," *Development* 127:595-603 (2000).

* cited by examiner

AGTTGGAGCAAAGTTGCTTCTTTTGAGAACCATGCGTTTCTTTCTCTCTTTTGTTCTTGAATTCGC
AAAAACATGTCCTTTTTCGTCTACAGGTTTCTAGGGTTTGTTTCTGTACTATAAACTATGTTTATG
CTCAGATATGAACTGGGCACTCAACAATCATCAAGAAGAAGAAGAAGAGCCACGAAGAATTG
AAATTTCTGATTCCGAGTCACTAGAAAACTTGAAAAGCAGCGATTTTTATCAACTGGGTGGTGG
TGGTGCTCTGAATTCGTCAGAAAAGCCGAGAAAGATCGATTTTTGGCGTTCGGGGTTGATGGGT
TTTGCGAAGATGCAGCAGCAGCAACAGCTTCAGCATTCAGTGGCGGTGAAGATGAACAATAAT
AATAATAACGATCTAATGGGTAATAAAAAAGGGTCAACTTTCATACAAGAACATCGAGCATTG
TTACCAAAAGCTTTGATTCTGTGGATCATCATTGTTGGGTTTATAAGCAGTGGGATTTATCAGTG
GATGGATGATGCTAATAAGATTAGAAGGGAAGAGGTTTTGGTCAGCATGTGTGATCAAAGAGC
TAGAATGTTGCAGGATCAATTTAGTGTTAGTGTTAATCATGTTCATGCTTTGGCTATTCTCGTCT
CCACTTTTCATTACCACAAGAACCCTTCTGCAATTGATCAGGAGACATTTGCGGAGTACACGGC
AAGAACAGCATTTGAGAGACCGTTGCTAAGTGGAGTGGCTTATGCTGAAAAGTTGTGAATTTT
GAGAGGGAGATGTTTGAGCGGCAGCACAATTGGGTTATAAAGACAATGGATAGAGGAGAGCCT
TCACCGGTTAGGGATGAGTATGCTCCTGTTATATTCTCTCAAGATAGTGTCTCTTACCTTGAGTC
ACTCGATATGATGTCAGGCGAGGAGGATCGTGAGAATATTTTGCGAGCTAGAGAAACCGGAAA
AGCTGTCTTGACTAGCCCTTTTAGGTTGTTGGAAACTCACCATCTCGGAGTTGTGTTGACATTCC
CTGTCTACAAGTCTTCTCTTCCTGAAAATCCGACTGTCGAAGAGCGTATTGCAGCCACTGCAGG
GTACCTTGGTGGTGCGTTTGATGTGGAGTCTCTAGTCGAGAATTTACTTGGTCAGCTTGCTGGTA
ACCAAGCAATAGTTGTGCATGTGTATGATATCACCAATGCATCAGATCCACTTGTCATGTATGG
TAATCAAGATGAAGAAGCCGACAGATCTCTCTCTCATGAGAGCAAGCTCGATTTTGGAGACCCC
TTCAGGAAACATAAGATGATATGCAGGTACCACCAAAAGGCACCAATACCGTTGAATGTGCTC
ACAACTGTGCCATTGTTCTTTGCGATTGGTTTCTTGGTGGGTTATATACTGTATGGTGCAGCTAT
GCACATAGTAAAAGTCGAAGATGATTTCCATGAAATGCAAGAGCTTAAAGTTCGAGCAGAAGC
TGCTGATGTCGCTAAATCGCAGTTTCTTGCTACCGTGTCTCACGAGATCAGGACACCAATGAAT
GGCATTCTCGGAATGCTTGCTATGCTCCTAGATACAGAACTAAGCTCGACACAGAGAGATTACG
CTCAAACCGCTCAAGTATGTGGTAAAGCTTTGATTGCATTGATAAATGAGGTTCTTGATCGCGC
CAAGATTGAAGCTGGAAAGCTGGAGTTGGAATCAGTACCATTTGATATCCGTTCAATATTGGAT
GATGTCCTTTCTCTATTCTCTGAGGAGTCAAGGAACAAAAGCATTGAGCTCGCGGTTTTCGTTTC
AGACAAAGTACCAGAGATAGTCAAAGGAGATTCAGGGAGATTTAGACAGATAATCATAAACCT
TGTTGGAAATTCGGTTAAATTCACAGAGAAAGGACATATCTTTGTTAAAGTCCATCTTGCGGAA
CAATCAAAAGATGAATCTGAACCGAAAAATGCATTGAATGGTGGAGTGTCTGAAGAAATGATC
GTTGTTTCCAAACAGTCAAGTTACAACACATTGAGCGGTTACGAAGCTGCTGATGGTCGGAATA

FIGURE 5A

GCTGGGATTCATTCAAGCATTTGGTCTCTGAGGAGCAGTCATTATCGGAGTTTGATATTTCTAGC
AATGTTAGGCTTATGGTTTCAATCGAAGACACGGGTATTGGAATCCCTTTAGTTGCGCAAGGCC
GTGTGTTTATGCCGTTTATGCAAGCAGATAGCTCGACTTCAAGAAACTATGGAGGTACTGGTAT
TGGTTTGAGTATAAGCAAGTGTCTTGTTGAACTTATGCGTGGTCAGATAAATTTCATAAGCCGG
CCTCATATTGGAAGCACGTTCTGGTTCACGGCTGTTTAGAGAAATGCGATAAATGCAGTGCGA
TTAACCATATGAAGAAACCTAATGTGGAACACTTGCCTTCTACTTTTAAAGGAATGAAAGCTAT
AGTTGTTGATGCTAAGCCTGTTAGAGCTGCTGTGACTAGATACCATATGAAAAGACTCGGAATC
AATGTTGATGTCGTGACAAGTCTCAAAACCGCTGTTGTTGCAGCTGCTGCGTTTGAAAGAAACG
GTTCTCCTCTCCCAACAAAACCGCAACTTGATATGATCTTAGTAGAGAAAGATTCATGGATTTC
AACTGAAGATAATGACTCAGAGATTCGTTTATTGAATTCAAGAACCAACGGAAACGTTCATCAC
AAGTCTCCGAAACTAGCTCTATTCGCAACAAACATCACAAATTCGGAGTTCGACAGAGCTAAAT
CCGCAGGATTTGCAGATACGGTAATAATGAAACCGTTAAGAGCAAGCATGATTGGGGCGTGTC
TGCAACAAGTTCTCGAGCTGAGAAAAACAAGACAACAACATCCAGAAGGATCATCACCCGCAA
CTCTCAAGAGCTTGCTTACAGGGAAGAAGATTCTTGTGGTTGATGATAATATAGTTAACAGGAG
AGTAGCTGCAGGAGCTCTCAAGAAATTGGAGCAGAAGTGGTTTGTGCAGAGAGTGGTCAAGT
TGCTTTGGGTTTGCTTCAGATTCCACACACTTTCGATGCTTGCTTCATGGATATTCAAATGCCAC
AGATGGACGGATTTGAAGCAACTCGTCAGATAAGAATGATGGAGAAGGAAACTAAAGAGAAG
ACAAATCTCGAATGGCATTTACCGATTCTAGCGATGACTGCGGATGTGATACACGCGACCTACG
AGGAATGTCTGAAAAGTGGGATGGATGGTTACGTCTCCAAACCTTTTGAAGAAGAGAATCTCTA
TAAATCCGTTGCCAAATCATTCAAACCTAATCCTATCTCACCTTCGTCGTAATCCAATCTTCCG
GCGAGTTTTTTTTCTCTCTCCGCAGCCGGAAGAGTGGACCGATTCTGCTGATTGATATGCATTTT
GGTTTCTGTACATACAGTAGGTTCACAATCTAGAGATTTTGAAGGTTTTTTTTCTTTCACCGAA
GTAATGTAGCTTGCCATGACTAGTGTATGTTGTTAAACGACAACGTCTAAGACGACGGTTCAGT
GTTGATCTTAGCGTAAGTATTAATCCCACGGGATCGTTTGTACTGTATCAGATTTGGTTAGTCGT
TTAAACATTGTAATGTTCTAATAATAACTTTTCCAT

FIGURE 5A CONT.

CACAACTCATTACAGCTCAGATATGAACTGGGCACTCAACAATCATCAAGAAGAAGAAGAAG
AGCCACGAAGAATTGAAATTTCTGATTCCGAGTCACTAGAAAACTTGAAAAGCAGCGATTTTTA
TCAACTGGGTGGTGGTGGTGCTCTGAATTCGTCAGAAAAGCCGAGAAAGATCGATTTTTGGCGT
TCGGGGTTGATGGGTTTTGCGAAGATGCAGCAGCAGCAACAGCTTCAGCATTCAGTGGCGGTGA
AGATGAACAATAATAATAATAACGATCTAATGGGTAATAAAAAAGGGTCAACTTTCATACAAG
AACATCGAGCATTGTTACCAAAAGCTTTGATTCTGTGGATCATCATTGTTGGGTTTATAAGCAGT
GGGATTTATCAGTGGATGGATGATGCTAATAAGATTAGAAGGGAAGAGGTTTTGGTCAGCATGT
GTGATCAAAGAGCTAGAATGTTGCAGGATCAATTTAGTGTTAGTGTTAATCATGTTCATGCTTTG
GCTATTCTCGTCTCCACTTTTCATTACCACAAGAACCCTTCTGCAATTGATCAGGAGACATTTGC
GGAGTACACGGCAAGAACAGCATTTGAGAGACCGTTGCTAAGTGGAGTGGCTTATGCTGAAAA
AGTTGTGAATTTTGAGAGGGAGATGTTTGAGCGGCAGCACAATTGGGTTATAAAGACAATGGA
TAGAGGAGAGCCTTCACCGGTTAGGGATGAGTATGCTCCTGTTATATTCTCTCAAGATAGTGTC
TCTTACCTTGAGTCACTCGATATGATGTCAGGCGAGGAGGATCGTGAGAATATTTTGCGAGCTA
GAGAAACCGGAAAAGCTGTCTTGACTAGCCCTTTTAGGTTGTTGGAAACTCACCATCTCGGAGT
TGTGTTGACATTCCCTGTCTACAAGTCTTCTCTTCCTGAAAATCCGACTGTCGAAGAGCGTATTG
CAGCCACTGCAGGGTACCTTGGTGGTGCGTTTGATGTGGAGTCTCTAGTCGAGAATTTACTTGG
TCAGCTTGCTGGTAACCAAGCAATAGTTGTGCATGTGTATGATATCACCAATGCATCAGATCCA
CTTGTCATGTATGGTAATCAAGATGAAGAAGCCGACAGATCTCTCTCTCATGAGAGCAAGCTCG
ATTTTGGAGACCCCTTCAGGAAACATAAGATGATATGCAGGTACCACCAAAAGGCACCAATAC
CGTTGAATGTGCTCACAACTGTGCCATTGTTCTTTGCGATTGGTTTCTTGGTGGGTTATATACTGT
ATGGTGCAGCTATGCACATAGTAAAAGTCGAAGATGATTTCCATGAAATGCAAGAGCTTAAAG
TTCGAGCAGAAGCTGCTGATGTCGCTAAATCGCAGTTTCTTGCTACCGTGTCTCACGAGATCAG
GACACCAATGAATGGCATTCTCGGAATGCTTGCTATGCTCCTAGATACAGAACTAAGCTCGACA
CAGAGAGATTACGCTCAAACCGCTCAAGTATGTGGTAAAGCTTTGATTGCATTGATAAATGAGG
TTCTTGATCGCGCCAAGATTGAAGCTGGAAAGCTGGAGTTGGAATCAGTACCATTTGATATCCG
TTCAATATTGGATGATGTCCTTTCTCTATTCTCTGAGGAGTCAAGGAACAAAAGCATTGAGCTC
GCGGTTTTCGTTTCAGACAAAGTACCAGAGATAGTCAAAGGAGATTCAGGGAGATTTAGACAG
ATAATCATAAACCTTGTTGGAAATTCGGTTAAATTCACAGAGAAAGGACATATCTTTGTTAAAG
TCCATCTTGCGGAACAATCAAAAGATGAATCTGAACCGAAAAATGCATTGAATGGTGGAGTGT
CTGAAGAAATGATCGTTGTTTCCAAACAGTCAAGTTACAACACATTGAGCGGTTACGAAGCTGC
TGATGGTCGGAATAGCTGGGATTCATTCAAGCATTTGGTCTCTGAGGAGCAGTCATTATCGGAG
TTTGATATTTCTAGCAATGTTAGGCTTATGGTTTCAATCGAAGACACGGGTATTGGAATCCCTTT

FIGURE 5B

```
AGTTGCGCAAGGCCGTGTGTTTATGCCGTTTATGCAAGCAGATAGCTCGACTTCAAGAAACTAT
GGAGGTACTGGTATTGGTTTGAGTATAAGCAAGTGTCTTGTTGAACTTATGCGTGGTCAGATAA
ATTTCATAAGCCGGCCTCATATTGGAAGCACGTTCTGGTTCACGGCTGTTTTAGAGAAATGCGA
TAAATGCAGTGCGATTAACCATATGAAGAAACCTAATGTGGAACACTTGCCTTCTACTTTTAAA
GGAATGAAAGCTATAGTTGTTGATGCTAAGCCTGTTAGAGCTGCTGTGACTAGATACCATATGA
AAAGACTCGGAATCAATGTTGATGTCGTGACAAGTCTCAAAACCGCTGTTGTTGCAGCTGCTGC
GTTTGAAAGAAACGGTTCTCCTCTCCCAACAAAACCGCAACTTGATATGATCTTAGTAGAGAAA
GATTCATGGATTTCAACTGAAGATAATGACTCAGAGATTCGTTTATTGAATTCAAGAACCAACG
GAAACGTTCATCACAAGTCTCCGAAACTAGCTCTATTCGCAACAAACATCACAAATTCGGAGTT
CGACAGAGCTAAATCCGCAGGATTTGCAGATACGGTAATAATGAAACCGTTAAGAGCAAGCAT
GATTGGGGCGTGTCTGCAACAAGTTCTCGAGCTGAGAAAAACAAGACAACAACATCCAGAAGG
ATCATCACCCGCAACTCTCAAGAGCTTGCTTACAGGGAAGAAGATTCTTGTGGTTGATGATAAT
ATAGTTAACAGGAGAGTAGCTGCAGGAGCTCTCAAGAAATTTGGAGCAGAAGTGGTTTGTGCA
GAGAGTGGTCAAGTTGCTTTGGGTTTGCTTCAGATTCCACACACTTTCGATGCTTGCTTCATGGA
TATTCAAATGCCACAGATGGACGGATTTGAAGCAACTCGTCAGATAAGAATGATGGAGAAGGA
AACTAAAGAGAAGACAAATCTCGAATGGCATTTACCGATTCTAGCGATGACTGCGGATGTGAT
ACACGCGACCTACGAGGAATGTCTGAAAAGTGGGATGGATGGTTACGTCTCCAAACCTTTTGAA
GAAGAGAATCTCTATAAATCCGTTGCCAAATCATTCAAACCTAATCCTATCTCACCTTCGTCGT
AATCCAATCTTCCGGCGAGTTTTTTTCTCTCTCCGCAGCCGGAAGAGTGGACCGATTCTGCTG
ATTGATATGCATTTTGGTTTCTGTACATACAGTAGGTTCACAATCTAGAGATTTTGAAGGTTTTT
TTTTCTTTCACCGAAGTAATGTAGCTTGCCATGACTAGTGTATGTTGTTAAACGACAACGTCTAA
GACGACGGTTCAGTGTTGATCTTAGCGTAAGTATTAATCCCACGGGATCGTTTGTACTGTATCA
GATTTGGTTAGTCGTTTAAACATTGTAATGTTCTAATAATAACTTTTCCAT
```

ACTGCATTCATCTATGACTGAAAGCTTCTGATCAAGCCATGAAATTAAGTTATAGAAGCTACTG
TCTCTAAGCGCACGAGAGAAAGCTACACAACCCACGTCAGTTTCCATCTACACATATAAGCTCA
GATATGAACTGGGCACTCAACAATCATCAAGAAGAAGAAGAAGAGCCACGAAGAATTGAAAT
TTCTGATTCCGAGTCACTAGAAAACTTGAAAAGCAGCGATTTTTATCAACTGGGTGGTGGTGGT
GCTCTGAATTCGTCAGAAAGCCGAGAAAGATCGATTTTTGGCGTTCGGGGTTGATGGGTTTTG
CGAAGATGCAGCAGCAGCAACAGCTTCAGCATTCAGTGGCGGTGAAGATGAACAATAATAATA
ATAACGATCTAATGGGTAATAAAAAAGGGTCAACTTTCATACAAGAACATCGAGCATTGTTACC
AAAAGCTTTGATTCTGTGGATCATCATTGTTGGGTTTATAAGCAGTGGGATTTATCAGTGGATG
GATGATGCTAATAAGATTAGAAGGGAAGAGGTTTTGGTCAGCATGTGTGATCAAAGAGCTAGA
ATGTTGCAGGATCAATTTAGTGTTAGTGTTAATCATGTTCATGCTTTGGCTATTCTCGTCTCCACT
TTTCATTACCACAAGAACCCTTCTGCAATTGATCAGGAGACATTTGCGGAGTACACGGCAAGAA
CAGCATTTGAGAGACCGTTGCTAAGTGGAGTGGCTTATGCTGAAAAAGTTGTGAATTTTGAGAG
GGAGATGTTTGAGCGGCAGCACAATTGGGTTATAAAGACAATGGATAGAGGAGAGCCTTCACC
GGTTAGGGATGAGTATGCTCCTGTTATATTCTCTCAAGATAGTGTCTCTTACCTTGAGTCACTCG
ATATGATGTCAGGCGAGGAGGATCGTGAGAATATTTTGCGAGCTAGAGAAACCGGAAAAGCTG
TCTTGACTAGCCCTTTTAGGTTGTTGGAAACTCACCATCTCGGAGTTGTGTTGACATTCCCTGTC
TACAAGTCTTCTCTTCCTGAAAATCCGACTGTCGAAGAGCGTATTGCAGCCACTGCAGGGTACC
TTGGTGGTGCGTTTGATGTGGAGTCTCTAGTCGAGAATTTACTTGGTCAGCTTGCTGGTAACCAA
GCAATAGTTGTGCATGTGTATGATATCACCAATGCATCAGATCCACTTGTCATGTATGGTAATC
AAGATGAAGAAGCCGACAGATCTCTCTCTCATGAGAGCAAGCTCGATTTTGGAGACCCCTTCAG
GAAACATAAGATGATATGCAGGTACCACCAAAAGGCACCAATACCGTTGAATGTGCTCACAAC
TGTGCCATTGTTCTTTGCGATTGGTTTCTTGGTGGGTTATATACTGTATGGTGCAGCTATGCACA
TAGTAAAAGTCGAAGATGATTTCCATGAAATGCAAGAGCTTAAAGTTCGAGCAGAAGCTGCTG
ATGTCGCTAAATCGCAGTTTCTTGCTACCGTGTCTCACGAGATCAGGACACCAATGAATGGCAT
TCTCGGAATGCTTGCTATGCTCCTAGATACAGAACTAAGCTCGACACAGAGAGATTACGCTCAA
ACCGCTCAAGTATGTGGTAAAGCTTTGATTGCATTGATAAATGAGGTTCTTGATCGCGCCAAGA
TTGAAGCTGGAAAGCTGGAGTTGGAATCAGTACCATTTGATATCCGTTCAATATTGGATGATGT
CCTTTCTCTATTCTCTGAGGAGTCAAGGAACAAAAGCATTGAGCTCGCGGTTTTCGTTTCAGACA

FIGURE 5C

AAGTACCAGAGATAGTCAAAGGAGATTCAGGGAGATTTAGACAGATAATCATAAACCTTGTTG
GAAATTCGGTTAAATTCACAGAGAAAGGACATATCTTTGTTAAAGTCCATCTTGCGGAACAATC
AAAAGATGAATCTGAACCGAAAAATGCATTGAATGGTGGAGTGTCTGAAGAAATGATCGTTGT
TTCCAAACAGTCAAGTTACAACACATTGAGCGGTTACGAAGCTGCTGATGGTCGGAATAGCTGG
GATTCATTCAAGCATTTGGTCTCTGAGGAGCAGTCATTATCGGAGTTTGATATTTCTAGCAATGT
TAGGCTTATGGTTTCAATCGAAGACACGGGTATTGGAATCCCTTTAGTTGCGCAAGGCCGTGTG
TTTATGCCGTTTATGCAAGCAGATAGCTCGACTTCAAGAAACTATGGAGGTACTGGTATTGGTT
TGAGTATAAGCAAGTGTCTTGTTGAACTTATGCGTGGTCAGATAAATTTCATAAGCCGGCCTCA
TATTGGAAGCACGTTCTGGTTCACGGCTGTTTAGAGAAATGCGATAAATGCAGTGCGATTAAC
CATATGAAGAAACCTAATGTGGAACACTTGCCTTCTACTTTTAAAGGAATGAAAGCTATAGTTG
TTGATGCTAAGCCTGTTAGAGCTGCTGTGACTAGATACCATATGAAAAGACTCGGAATCAATGT
TGATGTCGTGACAAGTCTCAAAACCGCTGTTGTTGCAGCTGCTGCGTTTGAAAGAAACGGTTCT
CCTCTCCCAACAAAACCGCAACTTGATATGATCTTAGTAGAGAAAGATTCATGGATTTCAACTG
AAGATAATGACTCAGAGATTCGTTTATTGAATTCAAGAACCAACGGAAACGTTCATCACAAGTC
TCCGAAACTAGCTCTATTCGCAACAAACATCACAAATTCGGAGTTCGACAGAGCTAAATCCGCA
GGATTTGCAGATACGGTAATAATGAAACCGTTAAGAGCAAGCATGATTGGGGCGTGTCTGCAA
CAAGTTCTCGAGCTGAGAAAAACAAGACAACAACATCCAGAAGGATCATCACCCGCAACTCTC
AAGAGCTTGCTTACAGGGAAGAAGATTCTTGTGGTTGATGATAATATAGTTAACAGGAGAGTA
GCTGCAGGAGCTCTCAAGAAATTTGGAGCAGAAGTGGTTTGTGCAGAGAGTGGTCAAGTTGCTT
TGGGTTTGCTTCAGATTCCACACACTTTCGATGCTTGCTTCATGGATATTCAAATGCCACAGATG
GACGGATTTGAAGCAACTCGTCAGATAAGAATGATGGAGAAGGAAACTAAAGAGAAGACAAA
TCTCGAATGGCATTTACCGATTCTAGCGATGACTGCGGATGTGATACACGCGACCTACGAGGAA
TGTCTGAAAAGTGGGATGGATGGTTACGTCTCCAAACCTTTTGAAGAAGAGAATCTCTATAAAT
CCGTTGCCAAATCATTCAAACCTAATCCTATCTCACCTTCGTCG<u>TAA</u>TCCAATCTTCCGGCGAG
TTTTTTTTCTCTCTCCGCAGCCGGAAGAGTGGACCGATTCTGCTGATTGATATGCATTTTGGTTTC
TGTACATACAGTAGGTTCACAATCTAGAGATTTTGAAGGTTTTTTTTCTTTCACCGAAGTAATG
TAGCTTGCCATGACTAGTGTATGTTGTTAAACGACAACGTCTAAGACGACGGTTCAGTGTTGAT
CTTAGCGTAAGTATTAATCCCACGGGATCGTTTGTACTGTATCAGATTTGGTTAGTCGTTTAAAC
ATTGTAATGTTCTAATAATAACTTTTCCAT

FIGURE 5C CONT.

```
  1 MNWALNNHQE EEEEPRRIEI SDSESLENLK SSDFYQLGGG GALNSSEKPR

51 KIDFWRSGLM GFAKMQQQQQ LQHSVAVKMN NNNNNDLMGNKKGSTFIQEH

101 RALLPKALIL WIIIVGFISS GIYQWMDDAN KIRREEVLVS MCDQRARMLQ

151 DQFSVSVNHV HALAILVSTF HYHKNPSAID QETFAEYTAR TAFERPLLSG

201 VAYAEKVVNF EREMFERQHN WVIKTMDRGE PSPVRDEYAP VIFSQDSVSY

251 LESLDMMSGE EDRENILRAR ETGKAVLTSP FRLLETHHLG VVLTFPVYKS

301 SLPENPTVEE RIAATAGYLG GAFDVESLVE NLLGQLAGNQ AIVVHVYDIT

351 NASDPLVMYG NQDEEADRSL SHESKLDFGD PFRKHKMICR YHQKAPIPLN

401 VLTTVPLFFA IGFLVGYILY GAAMHIVKVE DDFHEMQELK VRAEAADVAK

451 SQFLATVSHE IRTPMNGILG MLAMLLDTEL SSTQRDYAQT AQVCGKALIA

501 LINEVLDRAK IEAGKLELES VPFDIRSILD DVLSLFSEES RNKSIELAVF

551 VSDKVPEIVK GDSGRFRQII INLVGNSVKF TEKGHIFVKV HLAEQSKDES

601 EPKNALNGGV SEEMIVVSKQ SSYNTLSGYE AADGRNSWDS FKHLVSEEQS

651 LSEFDISSNV RLMVSIEDTG IGIPLVAQGR VFMPFMQADS STSRNYGGTG

701 IGLSISKCLV ELMRGQINFI SRPHIGSTFW FTAVLEKCDK CSAINHMKKP

751 NVEHLPSTFK GMKAIVVDAK PVRAAVTRYH MKRLGINVDV VTSLKTAVVA

801 AAAFERNGSP LPTKPQLDMI LVEKDSWIST EDNDSEIRLL NSRTNGNVHH
```

FIGURE 5D

851 KSPKLALFAT NITNSEFDRA KSAGFADTVI MKPLRASMIG ACLQQVLELR

901 KTRQQHPEGS SPATLKSLLT GKKILVVDDN IVNRRVAAGA LKKFGAEVVC

951 AESGQVALGL LQIPHTFDAC FMDIQMPQMD GFEATRQIRM MEKETKEKTN

1001 LEWHLPILAM TADVIHATYE ECLKSGMDGY VSKPFEEENL YKSVAKSFKP

1051 NPISPSS

FIGURE 5D CONT.

(A)

Forward primer
5' AG ATI (TC)T(ACGT) (GA)TI GT(ACGT) GA(TC) GA(TC) AA

Reverse primer
5' TG(AGT) ATI AC(AG) TCI GC(ACGT) GTC AT(ACGT) GC (B)
cDNA
1 AGATGCTGGT GGTGGATGAC AATGCAGTTA ATAGAAGAGT AGCAGAAGGT

51 GCTCTAAAGA AGTATGGAGC AATTGTGACC TGTGTAGAGA GTGGCAAGGC

101 TGCTTTAGCG ATGCTTAAGC CACCCCACAA CTTTGATGCT TGCTTTATGG

151 ATCTCCAGAT GCCAGAAATG GATGGGTTTG AAGCAACAAG GCGAATCCGC

201 AGTTTAGAAA GTGAGGCTAA TGAGGAAGTT GCATCAAGAG AAATGTTTGG

251 GAATGTGGCT TATTGGCACA CACCAATATT AGCTATGACC GCCGAGTCAT

301 CCAGT protein
M L V V D D N A V N R R V A E G A L K K Y G A I V T C V E S G K
A A L A M L K P P H N F D A C F M D L Q M P E M D G F E A T R R
I R S L E S E A N E E V A S R E M F G N V A Y W H T P I L A M T A
E S S

FIGURE 6A AND 6B cDNA
1 AGATGCTTGT GGTGGATGAC AATAGGGTTA ACCGCAGAGT TGCTGAAGGT

51 GCACTAAAGA AGTTTGGAGC TGATGTAGAG TGTGCTGAGA GTGGCAAAGC

101 TGCACTGGCG CTGCTTCAAC TACCACATAA TTTCGATGCC TGCTTCATGG

151 ACATTCAGAT GCCAGAAATG GATGGGTTTG AGGCAACCCG TCAAATACGC

201 GTAATGGAGA GCAAGGAAAA TGAGCAAATA AATGGTGGAG CCACAGATGA

251 AGGAGCTATT AGAAAGAGAG AGTGGCATGT GCCAATATTA GCCATGACCG

301 CCGACGTCAT CGTA protein
M L V V D D N R V N R R V A E G A L K K F G A D V E C A E S G K
A A L A L L Q L P H N F D A C F M D I Q M P E M D G F E A T R Q
I R V M E S K E N E Q I N G G A T D E G A I R K R E W H V P I L A
M T A D V I V

FIGURE 6C

```
   1 ccaaactact aagatatggg aagacccttg gcttccaaca cttcccccgc
  51 gacctgctcg tggcccaatt ctggatgagg acatgaaagt agcagattta
 101 tggagagaaa ataaacgaga atgggatcct gtgattttcg aaggagttct
 151 taatccggag gatcaacaac tggctaaatc tttgtatctc tctaactatg
 201 ccgctagaga ctcttataaa tgggcgtata ctcgcaatac tcaatatacg
 251 gtgagatcgg ggtattgggt tgccactcat gtcaatctta cagaggagga
 301 aatcattaat ccccttgaag gagacgttcc attaaaacaa gaaatctgga
 351 gattgaagat cactccaaag atcaagcatt tcatttggcg ctgtttatcc
 401 ggagctttat ccacaaccac tcaactccgg aacaggaaca ttccagcaga
 451 cccgacttgt caaagatgct gcaatgccga cgagacaatt aaccacataa
 501 tttttacttg ttcttatgcg caggttgtat ggagaagtgc aaacttttct
 551 gggagtaatc gactttgctt cacggataat cttgaagaga atatacgact
 601 aatattgcag gggaagaaaa accaaaacct tcccattctt aatggcttga
 651 tgccttttg gataatgtgg cgcttatgga aatcacgtaa cgaatacctt
 701 tttcaacagc ttgatcgttt cccttggaag gtggcacaga aagcagaaca
 751 agaagcaacc gaatgggtcg aaactatggt taatgatacg gctatctcac
 801 acaacacggc acagtccaat gatcgaccgt tgagccgaag taaacaatgg
 851 agttcaccac cggagggatt tctcaaatgt aactttgaca gtggctatgt
 901 tcagggaagg gattatacaa gcacaggttg gatactccgt gactgcaatg
 951 gacgtgtact acattcaggt tgtgcgaaac tacaacaatc atactcagcc
1001 ctacaagcag aagccttggg attcttacat gccctacaaa tggtttggat
1051 acgtggatac tgttatgtgt ggtttgaagg cgacaatctg gagctaacga
1101 acctaattaa caagactgaa gatcatcatc tccttgaaac actgctttat
1151 gacattcggt tttggatgac taagttaccc ttctcatcaa ttggttatgt
1201 caatcgggag agaaacttgg cagcggacaa actcacaaag tatgcaaact
1251 caatgtcttc tttgtatgaa acctttcatg taccaccaag atggctacaa
1301 ctctatttgt actatccctt tacaaattaa taaagtcaga tgttaaaaaa
1351 aaaaaaaaaa tagagtaagt agttgttagg aaaataatat cattatattt
1401 gacagattat ttaatttcat tatcattttc ctcataacat tttaaagatg
1451 ataagattag tgtaattact aattagtgag gctgtcgcat tagttgatga
1501 tgttgtagat aaaaaaaatg atcaaacaag aaatgattac caattatcat
1551 atgtaggaca cgtataaatg ttaaaaacgg aaaattaata accattccaa
1601 ttgatcaact tgatggtggt cattaaaaat cactttagaa aatacggaat
1651 tttataaaat ataaaatata gtttggtttt attttgtctg atgaattttt
1701 tttttatgta aagtaaaagg ttaaagaga aaaatgatta acaaaggcac
1751 taagaatatt gagaagagtg ctttgagaat tgtggcaaat acagtgacaa
1801 ccactataaa atcattatct cttaattaat actggtatta gtcatcctct
1851 taaaaaaaca ttttttttta tgggtaggat tcttaaaatt atttattatc
1901 gttaaacaac aaaatctatt ttattttgtt ttgttgtttg aatttctcta
1951 ttttatggga atgttctcat ttaaattaaa actaacaggg cacgaatatg
2001 ggccttaaat tatcaagccc agtagagccc atacttcttc tactatctca
2051 aatatctgat atacatttca gaggaactat attcgtcttt ttcaaaccgg
2101 cccagctcaa taagttcttt aatatatggc tacccaaccc aaatacgaaa
```

FIGURE 7A

```
2151  tactcgtcca attatgaaat ctcacgtaaa agcccactta atggtagttt
2201  tatggttcta atattttcta agtattagat ctatgactct gttacgaaca
2251  taatgtacaa tttagcggcc caaagcaatg taagaaggta aaaagaaaa
2301  actaaagaaa ttagttaggt tatataaaaa aaagtataat cagagaaatt
2351  taatctctct tttgcataaa ttattaaaac taaattggaa aatgacattt
2401  caaagagaa atattttca aaaatggaaa ataaaaccat taaaaatta
2451  aatatgattt aaaatatttc tcgtaccaaa gtccacacga ttccatgaaa
2501  tatgtggaaa gtctagtaat cgctatttaa ggtgtcaaaa caatgtatag
2551  agagattcaa agacttgttt ccaaatcata tattagtatt aaattagtaa
2601  atggcttcat gttttaatg attgtgagtc aaaaattaat ttttaatatc
2651  tttttgacaa tgttgttagt atatatttaa tgatatatgt gaactttata
2701  atcttttaat gatttgtgac aatgttctta atcttaggta aatttatgaa
2751  atttcaagca tccgtttgtg tttgttcatg aacatggaca atctttattc
2801  ttgaaaacaa atatgctaga ttttgtgtgt catttgagtg tgaaatcttt
2851  ggatttttc acctaattac aataactta tcttggtcaa agaatcattg
2901  atcgatgttg atttatgagt gataattata gtttaacata ggatatctta
2951  tttaatgaat gtagttgatc ttatctctat aaaatattct attggacttt
3001  cgaattacga ttgattgaga tagtaattat taaatcgtga ttgtttatat
3051  aaacttttga agaaggacg attacactag tctgcttttt tgactcaaaa
3101  tagtgaacac tttgtatgaa gaatcgttaa aagttataaa catgcagtat
3151  aagaactaac gaaaatataa ccaaattaat ttatgaaata cagtggattg
3201  gttttggtgt tatttaaat aaatgaattg gttgaatggg agtgattgtc
3251  gagcatgtga caaaaaaaca taatttgaga gtaaatacaa acaccgaaaa
3301  atagaatatg ttacaaaatc ttataaaatc ttaataaata aggagaattt
3351  gtaaattgta accactaaat gatttaatga tataaagtca aacatgaatc
3401  tcacatggcc gacacacaca cattttgtta gcaccacttc ctttgtgtac
3451  cccctttcc ccctatcttt gtgtactact aaatccatat attctacttt
3501  tttacatctt tgtgaataaa ggataaaaat tagcaaactt gtcgaaaaa
3551  tagagtgtgt cctacatgaa catgaaatgg atgctttata tgaatctcac
3601  gtcggaaaac tataattgat agaaactgag tagcaatatt gccacaccaa
3651  cgtcgccatc ttcatcttca tctagtcaca tttaacatcg atcatcaaca
3701  agttgcgaaa aagagtgttt aaattaaaag aaaaagttca agaatatttg
3751  tgtagaacat ggttcaagcg aagatgaaac taaagtaaa atgagattgg
3801  ttcgactcca tatcatacaa aagaatgtcc atcctaggta gtagaaatat
3851  agatatcaaa gagaatgaag tataagaaaa agaggaaaca atggtcaatg
3901  ccaaacggat caccttttt ataagacatt tccctaaatt aaccatacat
3951  aacaaaaaaa ggatatttga tatttccatc gacccatttt gtcaattttc
4001  aaacaattt tttcaatgca ttgactaata atgtataggg attcacacat
4051  tgtattttg ttttcaatta ttttcgttag gttttaacca tttatgtttc
4101  tctaaggtct aacccaaacc catttgagtt aaattttaat atatatatat
4151  attaaaaat aaataaaag aacaaaaag aaaataaaat aaattctttt
4201  tcctttataa tataaagtac aagtcccttg cccaataaaa ttatgccaca
4251  taagatttgt ttataattta agaattatt taaattttt taaaaaaaaa
4301  acgctcattt tttttttcta catatttaaa aacaaaaaaa tattcctaga
```

FIGURE 7B

```
4351  ttttctcaca caccacacca tcattatctt tggaaatttg taaccaactc
4401  aagattttcc aaaccgtttt atcttcctct acaaaaatcc aattcacgtt
4451  aaatctatct cttgctcttg cttcctccaa aaaaaaaaaa aaatcattcc
4501  cagatccatc gatatgaaat tgtatagaaa aatggtatt  cgatccaagt
4551  ttattgtctt ctattttct  taggttaatt tcactttatt ccagattcat
4601  tgtttgtttt ttctttctcg gaagagcaca atgtgagttt cactggcctc
4651  tgttataaac atatatagaa atctgtaaca aaaatcatta ctaaaattct
4701  gtgacatgtg cagcgatcaa agaatcaata gcggaaaaag aaactacact
4751  gcattcatct atgactgaaa gcttctgatc aagccatgaa attaaggtat
4801  cccaaacacg tatcttctct atgtttatca atcttgcttt aagttctaat
4851  tctgcatatt tcaaggaac  catacaagtg ttcctaaaat ccatttgaat
4901  attcaaaaac ttctctcaaa tatcatgtag ttatagaagc tactgtctct
4951  aagcgcacga gagaaagcta cacaacccac gtcagtttcc atctacacat
5001  ataaggtaat aataatattt tcatgtatct ttaataatag ctctatgttt
5051  ttttctgtat ttttcattat aaaactcata actatgttat catttaatat
5101  ggtactaatt taatgggatt gatttactat tgcctcaaac atgtaataat
5151  ttaatgattt tttgttttta acgtttttag aaattcatga gcatttaaa
5201  tttgtggtta ggtcataaca atttgctatt acaaaaaaaa gaaacactct
5251  aaataatata aaaaatagtt taccgtataa tactagtagt aaataaataa
5301  tttgattgtt attcataaat tttgaattct aaaatctcct gaatcaactc
5351  atgcaattgt cttaagaatt acacgtggat aaatcatggg cttatgagtc
5401  aggcccattt aaccggggta ttttcgtagt taagagacta gaatggtggg
5451  tatttcaggt aaaaggtcta tggggccaga tctgcgcttt gtcgcgatgt
5501  cattatcgcc aaagatatgc gatagcgact ctcgtacaaa gtctctcact
5551  cacctatatt ttttgttttc ttatatttca acaaaaaaac gttttatttt
5601  ccttttggtg taagtaaaaa aacaaaacaa aacgtttat  ttctaaagtt
5651  cagaaaactt atttatacca aggaaaaaat agataataaa ttttgagaag
5701  ttggtgacta tatattactt cacttattca agaaatttaa acatggtaaa
5751  tgttacttta aatgttaaat gatgtataag aaatgtaatg aaattgaata
5801  aatgtagttt taaagatgtt ttaattagta agacaaacct agttagtgtc
5851  acaataatta tattttttt  tttgtcatcc aaaattatta aagctcaagt
5901  aaaccaatcc tgagggatat tatttacaaa tgtgatatga tgcggttcgg
5951  tgcggatctt ccgcgccaaa ttatacgctt ttatattagc attataaaaa
6001  attatagata aagagaagtt tgtgaattct tcattgtcgc tttgcaattt
6051  ctctaaatac acagtaaata ccgacaattc ggttagagaa aatatatcta
6101  tttcgtataa taatgttaac tttgaggaga ttttgggtaa aataataact
6151  tttgttggat ggatcatatc atgagccatt aagaaaaagt ccaaaacttt
6201  tcttcttcaa agttggactc aagttagaaa agaaaaaag  agctagagag
6251  atataaaaat gaaagaaag  ttcatggcaa aaaactgata tagacagaga
6301  cacagagaga gagaaacgta tctgaagaaa atctaaaaaa ttcgattcaa
6351  tttttttctt acttttaaaa gcaaaaaatc tcactaaaac aaaagaagaa
6401  gaaagaagaa agaaaatgga atacctacat ttgaagtgat gagaagagat
6451  ttgtgtata  ataataatgc aatgttcaat cctctcacaa ctcattacag
6501  gtaactaaaa taatttctcc atgtgcttgc ttattagtcg ttcttcctaa
```

FIGURE 7C

```
6551  tgttatgttt  ctctctgtgt  tctttctttc  tttggtcaaa  gctttaattt
6601  tttttctatt  gttggatttg  agacagtgaa  catagctatg  ttcttgttcc
6651  aataataaac  aatcacgcct  gtaaagagct  tatgattgat  tagtgtgttt
6701  tttagtatta  attaatttct  ctgacaataa  ttacttagtt  tttaattctt
6751  ctctgtaaga  aacctttgga  aactgagcaa  agttgcttct  tttgagaacc
6801  atgcgtttct  ttctctcttt  tgttcttgaa  ttcgcaaaaa  catgtccttt
6851  ttcgtctaca  ggtttctagg  gtttgtttct  gtactataaa  ctatgtttat
6901  ggtaacattc  ttaatcataa  ctacactacc  aatgctttta  tgttatatgt
6951  atgcaaaaaa  ggctctaact  tttgtttttct  ttcactattg  tttcttcttt
7001  tgttctctat  tgttgtagct  cagatATG
```

FIGURE 7D

```
        Xba1
    1   tctagatttt ctcacacacc acaccatcat tatctttgga aatttgtaac
   51   caactcaaga ttttccaaac cgttttatct tcctctacaa aaatccaatt
  101   cacgttaaat ctatctcttg ctcttgcttc tccaaaaaa  aaaaaaaat
  151   cattcccaga tccatcgata tgaaattgta tagaaaaat  ggtattcgat
  201   ccaagtttat tgtcttctat ttttcttagg ttaatttcac tttattccag
  251   attcattgtt tgttttttct ttctcggaag agcacaatgt gagtttcact
  301   ggcctctgtt ataaacatat atagaaatct gtaacaaaaa tcattactaa
  351   aattctgtga catgtgcagc gatcaaagaa tcaatagcgg aaaaagaaac
  401   tacactgcat tcatctatga ctgaaagctt ctgatcaagc catgaaatta
  451   aggtatccca aacacgtatc ttctctatgt ttatcaatct tgctttaagt
  501   tctaattctg catatttcaa aggaaccata caagtgttcc taaaatccat
  551   ttgaatattc aaaaacttct ctcaaatatc atgtagttat agaagctact
  601   gtctctaagc gcacgagaga aagctacaca acccacgtca gtttccatct
  651   acacatataa ggtaataata atattttcat gtatctttaa taatagctct
  701   atgttttttt ctgtattttt cattataaaa ctcataacta tgttatcatt
  751   taatatggta ctaatttaat gggattgatt tactattgcc tcaaacatgt
  801   aataatttaa tgatttttg  tttttaacgt tttagaaat  tcatgagcat
  851   tttaaatttg tggttaggtc ataacaattt gctattacaa aaaaaagaaa
  901   cactctaaat aatataaaaa atagtttacc gtataatact agtagtaaat
  951   aaataatttg attgttattc ataaattttg aattctaaaa tctcctgaat
 1001   caactcatgc aattgtctta agaattacac gtggataaat catgggctta
```

FIGURE 8

```
1051  tgagtcaggc ccatttaacc ggggtatttt cgtagttaag agactagaat
1101  ggtgggtatt tcaggtaaaa ggtctatggg gccagatctg cgctttgtcg
1151  cgatgtcatt atcgccaaag atatgcgata gcgactctcg tacaaagtct
1201  ctcactcacc tatattttt gttttcttat atttcaacaa aaaaacgttt
1251  tattttcctt ttggtgtaag taaaaaaaca aaacaaaacg ttttatttct
1301  aaagttcaga aacttatttt ataccaagga aaaatagat aataaatttt
1351  gagaagttgg tgactatata ttacttcact tattcaagaa atttaaacat
1401  ggtaaatgtt actttaaatg ttaaatgatg tataagaaat gtaatgaaat
1451  tgaataaatg tagttttaaa gatgttttaa ttagtaagac aaacctagtt
1501  agtgtcacaa taattatatt ttttttttg tcatccaaaa ttattaaagc
1551  tcaagtaaac caatcctgag ggatattatt tacaaatgtg atatgatgcg
1601  gttcggtgcg gatcttccgc gccaaattat acgcttttat attagcatta
1651  taaaaaatta tagataaaga gaagtttgtg aattcttcat tgtcgctttg
1701  caatttctct aaatacacag taaataccga caattcggtt agagaaaata
1751  tatctatttc gtataataat gttaactttg aggagatttt gggtaaaata
1801  ataacttttg ttggatggat catatcatga gccattaaga aaaagtccaa
1851  aacttttctt cttcaaagtt ggactcaagt tagaaaaaga aaaagagct
1901  agagagatat aaaaatgaaa agaaagttca tggcaaaaaa ctgatataga
1951  cagagacaca gagagagaga aacgtatctg aagaaaatct aaaaaattcg
2001  attcaatttt tttcttactt ttaaaagcaa aaaatctcac taaaacaaaa
2051  gaagaagaaa gaagaaagaa aatggaatac ctacatttga agtgatgaga
2101  agagattttg tgtataataa taatgcaatg ttcaatcctc tcacaactca
2151  ttacaggtaa ctaaaataat ttctccatgt gcttgcttat tagtcgttct
```

FIGURE 8 CONT.

```
2201  tcctaatgtt atgtttctct ctgtgttctt tctttctttg gtcaaagctt 2251  taattttttt tctattgttg gatttgagac agtgaacata gctatgttct 2301  tgttccaata ataaacaatc acgcctgtaa agagcttatg attgattagt 2351  gtgtttttta gtattaatta atttctctga caataattac ttagttttta 2401  attcttctct gtaagaaacc tttggaaact gagcaaagtt gcttcttttg 2451  agaaccatgc gtttctttct ctcttttgtt cttgaattcg caaaaacatg 2501  tccttttttcg tctacaggtt tctagggttt gtttctgtac tataaactat 2551  gtttatggta acattcttaa tcataactac actaccaatg cttttatgtt 2601  atatgtatgc aaaaaaggct ctaactttg ttttctttca ctattgtttc
                                                      BamHI
2651  ttcttttgtt ctctattgtt gtagctcaga taggatcc
```

FIGURE 8 CONT.

US 7,026,530 B2

WOODEN LEG GENE, PROMOTER AND USES THEREOF

This application is a continuation of Application PCT/US01/45053 filed Nov. 29, 2001 and claims priority of Application Ser. No. 60/253,739, filed Nov. 29, 2000.

1. TECHNICAL FIELD

The present invention generally relates to the WOODEN LEG (WOL) gene family and its promoter. The invention more particularly relates to ectopic expression of members of the WOODEN LEG gene family in transgenic plants to artificially modify plant structures. The invention also relates to utilization of the WOODEN LEG promoter for expression of heterologous gene products in certain tissues and organs during stages of development. In trees, members of the WOODEN LEG gene family are active in the cambial zone of the trunk. Thus, in one embodiment, transgenic expression of WOL coding sequences in trees is used to improve wood production. In another embodiment, the WOL promoter is used to drive expression of a heterologous coding sequence in trees to improve wood production.

2. BACKGROUND OF THE INVENTION

The plant vascular system is responsible for transporting water, nutrients and photosynthates between plant organs. It also undergoes developmental adaptations such as wood formation, which involve specific proliferation of the vascular tissue. Therefore, the pattern of cell divisions is an important determinant of the cellular organization of this tissue (Esau, 1977, *Anatomy of seed Plants*. John Wiley & Sons, New York, N.Y., ed. 2.). Vascular tissue is first established during embryogenesis as an undifferentiated procambial tissue in the innermost domain of the plant embryo, enclosed by the epidermal and ground tissue layers (Esau 1977 supra; Steeves & Sussex, 1989, *Patterns in Plant Development*. Cambridge University Press, Cambridge, UK). After differentiation of the phloem and xylem strands within this domain, cell proliferation originates primarily from the initial cells of the procambial tissue immediately proximal to the mitotically quiescent regions of the terminal meristems (Esau 1977, supra; Steeves and Sussex 1989, supra; Scheres et al. 1994, *Development* 120:2475–87). Later in development, a lateral meristem (the cambium) is formed, as the undifferentiated cells begin to divide in the procambial tissue between the phloem and xylem strands. There is a high degree of diversity of the cell division patterns within the vascular tissue in plants, especially with regards to the formation and activity of the cambium. Since these patterns are species-specific, it is conceivable that the control of cell proliferation within the vascular tissue is largely under genetic regulation.

Several factors have been implicated in the regulation of cell proliferation of the vascular tissue. Based on mutation analyses, signal transduction pathways related to auxin (Carland & McHale, 1996, *Development* 122:1811–9; Oyama et al., 1997, *Genes Dev.* 11:2983–95; Hardtke & Berleth, 1998, *EMBO J.* 17:1405–11; Hobbie et al., *Development* 127:23–32; Steinmann et al., 1999, *Science* 286:316–8; Koizumi et al., 2000, *Development* 127:3197–204) and brassinosteroid (Schrick et al., 2000, *Genes Dev.* 14:1471–84; Jang et al., 2000, *Genes Dev.* 14:1485–97) phytohormones are involved. Physiological and genetic experiments have also indicated a role for other phytohormones (such as gibberellins, cytokinins and ethylene; see Aloni, 1987, *Annu. Rev. Plant Physiol.* 38:179–204; Eriksson et al., 2000, *Nat Biotechnol.* 7:784–8), sucrose (Warren Wilson, 1978, *Proc. Roy. Soc. London Series B* 203:153–76) and physical pressure (Zimmerman, 1964, *The Formation of Wood in Forest Trees*. Academic Press, New York, N.Y. pp. 389–404). Furthermore, a few genetic loci have been identified that are essential for normal cell proliferation but function in a yet uncharacterized molecular context (Carland et al., 1999, *Plant Cell* 11:2123–37; Scheres et al., 1995, *Development* 121:53–62).

Root organization is established during embryogenesis. This organization is propagated during postembryonic development by the root meristem. Following germination, the development of the postembryonic root is a continuous process, a series of initials or stem cells continuously divide to perpetuate the pattern established in the embryonic root (Steeves & Sussex, 1972, *Patterns in Plant Development*, Englewood Cliffs, N.J.: Prentice-Hall, Inc.).

Due to the organization of the *Arabidopsis* root, it is possible to follow the fate of cells from the meristem to maturity and identify the progenitors of each cell type (Dolan et al., 1993, *Development* 119:71–84). The *Arabidopsis* root is a relatively simple and well characterized organ. The radial organization of the mature tissues in the *Arabidopsis* root has been likened to tree rings with the epidermis, cortex, endodermis and pericycle forming radially symmetric cell layers that surround the vascular cylinder (Dolan et al., 1993, *Development* 119:71–84). These mature tissues are derived from four sets of stem cells or initials: i) the columella root cap initial; ii) the pericycle/vascular initial; iii) the epidermal/lateral root cap initial; and iv) the cortex/endodermal initial (Dolan et al., 1993, supra). It has been shown that these initials undergo asymmetric divisions (Scheres et al., 1995, *Development* 121:53–62). The cortex/endodermal initial, for example, first divides anticlinally (in a transverse orientation). This asymmetric division produces another initial and a daughter cell. The daughter cell, in turn, expands and then divides periclinally (in the longitudinal orientation). This second asymmetric division produces the progenitors of the endodermis and the cortex cell lineages.

Citation or identification of any reference herein shall not be construed as an admission that such reference is available as prior art to the present invention.

3. SUMMARY OF THE INVENTION

There is a need in the art for improved methods of regulating the development of tissues and organs in plants, and to express heterologous gene products in certain tissues and organs during selected stages of plant development. This invention provides compositions and methods that address this need. The structure and function of a regulatory gene, WOODEN LEG (WOL), is described. The WOL gene is expressed specifically in the vasculature during early stages of embryogenesis with expression continuing throughout development. WOL expression is essential for a set of asymmetric cell divisions that establish vascular tissue during root and hypocotyl development. The invention provides isolated nucleic acids (which encompass *Arabidopsis* WOL nucleic acids and orthologs), WOL gene products (including, but not limited to, transcriptional products such as mRNAs, antisense and ribozyme molecules, and translational products such as WOL proteins, polypeptides, peptides and fusion proteins related thereto), antibodies to WOL gene products, WOL regulatory regions and the use of the foregoing to improve agronomically valuable plants, including but not limited to trees.

The invention is based, in part, on the discovery, identification and cloning of the gene responsible for the wooden leg phenotype. WOL is believed by the inventors to be the first identified gene specifically dedicated for the regulation of vascular patterning in plants. WOL regulates vascular patterning in plants. Furthermore, WOL's structure as a two component hybrid molecule is novel with at least one receiver, and preferably, two receiver domains.

One aspect of the invention encompasses the heterologous expression of WOL nucleic acids and related nucleotide sequences, and specifically the *Arabidopsis* WOL nucleic acids or orthologs thereof, in stably transformed higher plant species. Modulation of WOL expression levels can be used to advantageously modify vasculature in transgenic plants and enhance the agronomic properties of such plants.

Another aspect of the invention encompasses the use of promoters of WOL genes, and specifically the use of the *Arabidopsis* WOL promoter to control the expression of protein and RNA products in plants. Plant WOL promoters have a variety of uses, including, but not limited to, expressing heterologous nucleic acids in the vascular tissue, including the pericycle, in roots of transformed plants.

The invention provides nucleic acid molecules that are at least 45% (or 55%, 65%, 75%, 85%, 95%, 98%, or 99%) identical to the nucleotide sequence of SEQ ID NOs:1, 2, 3, 4, 25, 26, 33, 34, or 35, or a complement thereof.

The invention provides nucleic acid molecules that are at least 45% (or 55%, 65%, 75%, 85%, 95%, 98%, or 99%) identical to the nucleotide sequence of SEQ ID NOs:1, 2, 3, 4, 25, 26, 33, 34, or 35, or a complement thereof, wherein such nucleic acid molecules encode polypeptides or proteins that exhibit at least one structural and/or functional feature of a polypeptide of the invention.

The invention provides nucleic acid molecules that include a fragment of at least 300 (325, 350, 375, 400, 425, 450, 500, 550, 600, 650, 700, 800, 900, 1000, 1200, 1400, 1600, 1800, 2000, 2400, 2600, 2800, 3000, 3200, 3400, 3600, 3800, or 4000) nucleotides of the nucleotide sequence of SEQ ID NOs:1, 2, 3, 4, 25, 26, 33, 34, or 35, or a complement thereof.

The invention also provides nucleic acid molecules that include a nucleotide sequence encoding a protein having an amino acid sequence that is at least 45% (or 55%, 65%, 75%, 85%, 95%, 98%, or 99%) identical to the amino acid sequence of SEQ ID NOs:5, 6, 7, 8, 9, 10, 11, 12, 29, or 30.

The invention also provides nucleic acid molecules that include a nucleotide sequence encoding a protein having an amino acid sequence that is at least 45% (or 55%, 65%, 75%, 85%, 95%, 98%, or 99%) identical to the amino acid sequence of SEQ ID NOs:5, 6, 7, 8, 9, 10, 11, 12, 29, or 30,wherein the protein encoded by the nucleotide sequence also exhibits at least one structural and/or functional feature of a polypeptide of the invention.

In preferred embodiments, the nucleic acid molecules have the nucleotide sequence of SEQ ID NOs: 1, 2, 3, 4, 25, or 26, or a complement thereof.

Also provided by the invention are nucleic acid molecules that encode a fragment of a polypeptide having the amino acid sequence of SEQ ID NOs:5, 6, 7, 8, 9, 10, 11, 12, 29, or 30, or a fragment including at least 15 (25, 30, 50, 100, 150, 300, 400, 500, 600, 700, 800, 900, 1000, 1100, 1200, 1300, or 1400) contiguous amino acids of SEQ ID NOs:5, 6, 7, 8, 9, 10, 11, 12, 29,or 30.

The invention provides nucleic acid molecules that encode a naturally occurring allelic variant of a polypeptide comprising the amino acid sequence of SEQ ID NOs:5, 6, 7, 8, 9, 10, 11, 12, 29, or 30, wherein the nucleic acid molecule hybridizes to a nucleic acid molecule consisting of a nucleic acid sequence encoding SEQ ID NOs:1, 2, 3, 4, 25, 26, 33, 34, or 35, or a complement thereof under stringent conditions.

The invention provides nucleic acid molecules that encode a naturally occurring allelic variant of a polypeptide comprising the amino acid sequence of SEQ ID NOs:5, 6, 7, 8, 9, 10, 11, 12, 29, or 30, wherein the nucleic acid molecule hybridizes to a nucleic acid molecule consisting of a nucleic acid sequence encoding SEQ ID NOs:1, 2, 3, 4, 25, 26, 33, 34, or 35, or a complement thereof under stringent conditions, wherein such nucleic acid molecules encode polypeptides or proteins that exhibit at least one structural and/or functional feature of a polypeptide of the invention.

Also within the invention are isolated polypeptides or proteins having an amino acid sequence that is at least about 60%, preferably 65%, 75%, 85%, 95%, 98%, or 99% identical to the amino acid sequence of SEQ ID NOs:5, 6, 7, 8, 9, 10, 11, 12, 29, or 30.

Also within the invention are isolated polypeptides or proteins that are encoded by a nucleic acid molecule having a nucleotide sequence that is at least about 60%, preferably 65%, 75%, 85%, 95%, 98%, or 99% identical the nucleic acid sequence encoding SEQ ID NOs:1, 2, 3, 4, 25, 26, 33, 34, or 35, and isolated polypeptides or proteins that are encoded by a nucleic acid molecule having a nucleotide sequence that hybridizes under stringent hybridization conditions to a nucleic acid molecule having the nucleotide sequence of SEQ ID NOs:1, 2, 3, 4, 25, 26, 33, 34, or 35, or complement thereof.

Also within the invention are isolated polypeptides or proteins that are encoded by a nucleic acid molecule having a nucleotide sequence that is at least about 60%, preferably 65%, 75%, 85%, 95%, 98%, or 99% identical the nucleic acid sequence encoding SEQ ID NOs:1, 2, 3, 4, 25, 26, 33, 34, or 35, and isolated polypeptides or proteins that are encoded by a nucleic acid molecule having a nucleotide sequence that hybridizes under stringent hybridization conditions to a nucleic acid molecule having the nucleotide sequence of SEQ ID NOs:1, 2, 3, 4, 25, 26, 33, 34, or 35, or complement thereof,,wherein such nucleic acid molecules encode polypeptides or proteins that exhibit at least one structural and/or functional feature of a polypeptide of the invention.

Also within the invention are polypeptides that are naturally occurring allelic variants of a polypeptide that includes the amino acid sequence of SEQ ID NOs:5, 6, 7, 8, 9, 10, 11, 12, 29, or 30, wherein the polypeptide is encoded by a nucleic acid molecule which hybridizes to a nucleic acid molecule having the sequence of SEQ ID NOs:1, 2, 3, 4, 25, 26, 33, 34, or 35, or a complement thereof, under stringent conditions. Such allelic variant differ at 1%, 2%, 3%, 4%, or 5% of the amino acid residues.

The invention also provides nucleic acid molecules that hybridize under stringent conditions to a nucleic acid molecule having the nucleotide sequence of SEQ ID NOs:1, 2, 3, 4, 25, 26, 33, 34, or 35, or a complement thereof. In other embodiments, the nucleic acid molecules are at least 300 (325, 350, 375, 400, 425, 450, 500, 550, 600, 650, 700, 800, 900, 1000, 1200, 1400, 1600, 1800, 2000, 2200, 2400, 2600, 2800, 3000, 3200, 3400, 3600, 3800, 4000, or 4200) nucleotides in length and hybridize under stringent conditions to a nucleic acid molecule consisting of the nucleotide sequence of SEQ ID NOs:1, 2, 3, 4, 25, 26, 33, 34, or 35, or a complement thereof.

In other embodiments, the isolated nucleic acid molecules encode an extracellular, transmembrane, cytoplasmic domain, a short N-terminal domain, histidine kinase domain, receiver domain $D_A$, or a receiver domain $D_B$ of a polypeptide of the invention.

The invention is illustrated by working examples, described infra, which demonstrate the isolation and use of *Arabidopsis* WOL nucleic acids.

Structural analysis of the deduced amino acid sequence of *Arabidopsis* WOL protein indicates that WOL encodes a two component signal transducer and is required for asymmetric cell divisions during vascular tissue morphogenesis. Northern analysis and in situ hybridization analysis show expression of *Arabidopsis* WOL in vascular tissues, including the vascular cylinder and pericycle of mature roots as well as localized expression in the vascular cylinder and pericycle in embryos.

The invention encompasses methods for altering development of vascular tissues and pericycle in roots and other organs by modifying expression of a WOL protein or polypeptide. In one embodiment, root length is increased by overexpression of a WOL protein or polypeptide. In another embodiment, root length is decreased by disrupting or inactivating the endogenous WOL gene. In other embodiments, properties of wood in trees are altered. In one such embodiment, overexpression of a WOODEN LEG protein or polypeptide in a transgenic plant is used to increase layers of wood (vascular) tissues in trees. In another embodiment, ectopic expression of a WOODEN LEG protein or polypeptide in a transgenic plant is driven by a promoter other than the WOL promoter in order to increase vascular development in certain tissue layers, thus resulting in the formation of more wood. In still other embodiments, the WOL promoters of the invention are linked to a heterologous gene known to be involved in aspects of wood formation and genetically engineered into a plant. Such heterologous genes include, but are not limited to, genes known to have an effect on lignin production and/or composition such as the Caffeic Acid O-Methyltransferase (cOMT) gene of Moyle, et al., 1999. *Plant Physiol.* 119: 1147 and the SAM gene of Meng and Campbell,1995. *Plant Physiol.* 108: 1749. Genes related to cellulose production and degradation are also of great interest such as the cellulose synthase gene of Arioli et al., 1998. Science 279:717–720. In still other embodiments, a gene controlling pigmentation and aspects of vascular patterning effecting wood grain appearance is expressed under the control of a WOL promoter incorporated into the invention. Thus, the invention provides methods that utilize WOL promoters to improve the quality of wood and/or adjust the characteristics of wood to meet specific, e.g. commercial, specifications.

The invention also encompasses methods of expressing transgene products in the pericycle and the vascular tissue of the hypocotyl, as well as in other organs, by associating a nucleic acid encoding a gene product of interest with a WOODEN LEG promoter. The various embodiments of the claimed invention presented herein are by the way of illustration and are not meant to limit the invention.

3.1. Definitions/Abbreviations

As used herein, the terms listed below will have the meanings indicated.

35S=Cauliflower mosaic virus promoter for the 35S transcript.
cDNA=Complementary DNA.
CAPS=Cleaved amplified polymorphic sequences.
Cis-regulatory element=A sequence in the proximity of a promoter that confers a specific regulatory response to that promoter. A promoter may be influenced by one or more cis-regulatory elements, each responsible for a particular regulatory response. The cis-regulatory sequence can be located 5' upstream of the promoter TATA box, in the introns, and 3' downstream of the coding sequence.
Coding sequence=A sequence that encodes a complete or partial gene product (e.g., a complete protein or a fragment thereof).
DNA=Deoxyribonucleic acid
DNase=Deoxyribonuclease
EST=Expressed sequence tag
Functional portion of a promoter=With respect to a promoter, a functional portion is any portion of the promoter that is capable of causing transcription of a linked nucleotide sequence, e.g., a truncated promoter.
Functionally equivalent=In one embodiment of the invention, "functionally equivalent," as utilized herein with respect to a WOL nucleic acid (or a WOL protein), refers to a nucleic acid encoding a protein (or a protein) that has the ability to regulate the set of asymmetric cell divisions that establish vascular tissue during root and hypocotyl development, and that indirectly regulates xylem differentiation by controlling the number of cells in the vascular cylinder. In another embodiment of the invention, "functionally equivalent," as utilized herein with respect to a WOL nucleic acid (or a WOL protein), refers to a nucleic acid encoding a protein (or a protein) that is expressed in a tissue-specific and developmental stage specific manner, and includes one or more of the following: At the globular stage of embryogenesis, expression is apparent in the four innermost cells, which are the precursors of the vascular tissue (procambium). During the heart, torpedo, and nearly mature stages of embryogenesis expression is apparent in the procambium of the developing vasculature at the base of the embryonic leaves, cotyledon shoulders, prospective hypocotyl and embryonic root, including pericycle, through at least five days after germination. In the mature plant, expression is predominantly localized in the root. Within the mature root tissues, expression is limited to the developing vascular cylinder, including the pericycle/vascular initial cells, pericycle, and procambium. In shoots, lower levels of expression are detected in comparison to the root, however tissue specificity could not be determined. In siliques, expression is observed in developing vascular tissues just below the site of fruit attachment. In trees, e.g., *Betula,* expression is apparent in the vascular cambium and developing vascular tissue.
Gene product=transcripts or protein encoded by a gene. With respect to the WOL gene, polypeptides or peptide fragments of the WOL protein are referred to as WOL polypeptides or WOL peptides. Fusions of WOL protein, polypeptides, or peptide fragments to an unrelated protein, polypeptide or peptide are referred to herein as WOL fusion proteins.
GUS=1,3-β-Glucuronidase.
Initial cell=A cell in its earliest stage of differentiation.
Isolated nucleic acid molecule=A nucleic acid molecule that is separated from other nucleic acid molecules that are present in the natural source of the nucleic acid molecule. Preferably, an "isolated" nucleic acid molecule is free of nucleic acid sequences preferably protein encoding sequences) that naturally flank the nucleic acid (i.e., sequences located at the 5' and 3' ends of the nucleic acid) in the genomic DNA of the organism from which the nucleic acid is derived. In other embodiments, the "isolated" nucleic acid is free of intron sequences. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

mRNA=Messenger RNA.

Operably linked=A linkage between a promoter and gene sequence such that the transcription of said gene sequence is controlled by said promoter.

Ortholog=Genes related by common phylogenetic descent that have the same function in various organisms. In a preferred embodiment, potential orthologous genes may be identified using alignment software including the NBLAST and XBLAST programs of Altschul, et al., 1990, *J. Mol. Biol.* 215:403–410 or the CLUSTAL W multiple sequence alignment program of Thompson, et al., 1994. *Nucleic Acids Research,* 22:4673–4680, with default parameters set for the respective programs. In a more preferred embodiment, CLUSTAL alignments are further analyzed by generating a phylogenetic tree with the PAUP (Phylogenetic Analysis Using Parsimony) software of David Swofford, 2000. Sinauer Associates, Inc. Sunderland Mass. Orthologous genes, having similar sequences and a common ancestry group together on adjoining branches, further confirming there status as orthologs.

Paralog=A related gene in the same plant (e.g., *Arabidopsis* MXH1.16 and F17L21.11 are paralogs of *Arabidopsis* WOL gene).

RACE=Rapid amplification of cDNA ends. A method of PCR designed to isolate the ends (either 5' or 3') of a particular cDNA clone.

RNA=Ribonucleic acid.

RNase=Ribonuclease.

Vascular cylinder=Vascular tissue of the root, including the pericycle.

WOL=WOODEN LEG, and is used with respect to nucleic acids, encompasses WOL and its orthologs.

WOL=WOODEN LEG, and is used with respect to proteins, polypeptides or peptides.

wol=wooden leg mutant.

Figure 3:
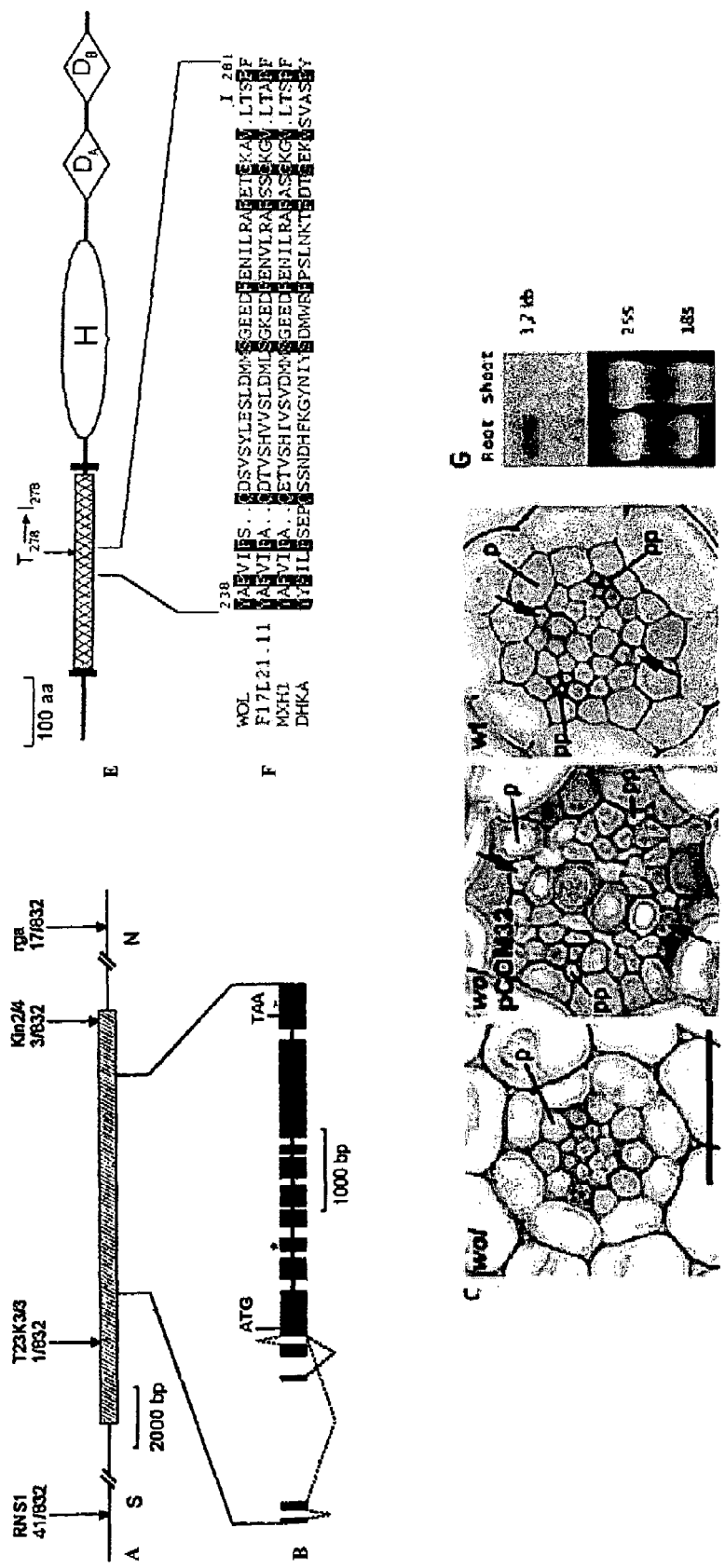
Figure 3:
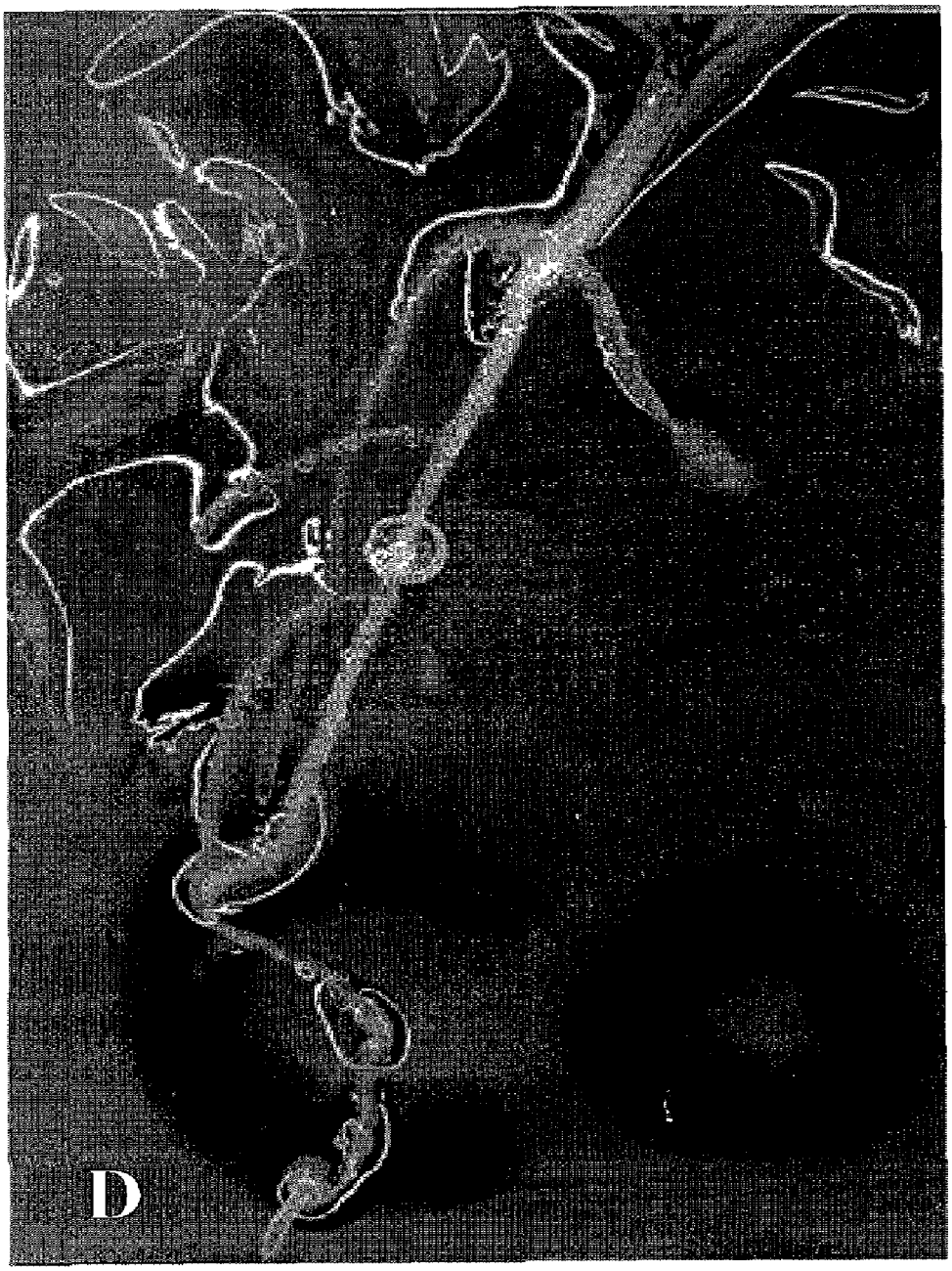

WOL protein means a protein containing sequences or a domain substantially similar to one or more domains of *Arabidopsis* WOL protein as shown in FIG. 3 (SEQ ID NOs:5, 6, 7, 8, 9, 10, 11, 12, 29, or 30). WOL proteins include WOL ortholog and paralog proteins having the structure and activities described herein.

The term "substantially similar" or "substantial similarity," when used herein with respect to two amino acid sequences, means that the two sequences have at least 75% identical residues, preferably at least 85% identical residues, more preferably at least 95% identical residues, and most preferably at least 99% identical residues. The same term, when used herein with respect to two nucleotide sequences, means that the two sequences have at least 70% identical residues, preferably at least 85% identical residues, more preferably at least 95% identical residues, and most preferably at least 99% identical residues. Determining whether two sequences are substantially similar may be carried out using any methodologies known to one skilled in the art, preferably using computer assisted analysis.

WOL polypeptides and peptides include deleted or truncated forms of the WOL protein, and fragments corresponding to the WOL domains described herein.

WOL fusion proteins encompass proteins in which the WOL protein or an WOL polypeptide or peptide is fused to a heterologous protein, polypeptide or peptide.

WOL gene, nucleotides or coding sequences means nucleotides, e.g., genomic DNA or cDNA encoding WOL protein, WOL polypeptides or peptides, or WOL fusion proteins.

WOL gene products include transcriptional products such as mRNAs, antisense and ribozyme molecules, as well as translational products of the WOL nucleotides described herein including, but not limited to, the WOL protein, polypeptides, peptides and/or WOL fusion proteins.

WOL promoter is intended to mean the regulatory region native to the WOL gene in a variety of species, which promotes the specific pattern of WOL expression described herein.

WOL expression pattern is intended to mean a tissue-specific and developmental stage specific expression pattern. By combining their observations obtained from several experimental techniques, including in situ hybridization with WOL mRNA, northern blot analysis, and anatomical analysis of the wol mutant phenotype, the present inventors have discovered that a consistent pattern of expression of WOL emerges. Furthermore, the expression patterns generated by the WOL promoter sequences, when operatively linked to a heterologous reporter gene, match the tissue-specificity of the observed WOL gene expression pattern. This expression pattern of WOL and WOL promoters is tissue-specific and developmental stage specific, and includes one or more of the following: At the globular stage of embryogenesis, expression is apparent in the four innermost cells, which are the precursors of the vascular tissue (procambium). During the heart, torpedo, and nearly mature stages of embryogenesis expression is apparent in the procambium of the developing vasculature at the base of the embryonic leaves, cotyledon shoulders, prospective hypocotyl and embryonic root, including pericycle, through at least five days after germination. In the mature plant, expression is predominantly localized in the root. Within the mature root tissues, expression is limited to the developing vascular cylinder, including the pericycle/vascular initial cells, pericycle, and procambium. In shoots, lower levels of expression are detected in comparison to the root, however tissue specificity could not be determined. In siliques, expression is observed in developing vascular tissues just below the site of fruit attachment. In trees, e.g., *Betula,* expression is apparent in the vascular cambium and developing vascular tissue.

The expression pattern of WOL occurs throughout a plant in numerous organs at varying stages of development, but is consistently tissue-specific. The pattern may be utilized to target desired tissues encompassed by the expression pattern, but that targeting is not consistently exclusive to a single organ.

4. BRIEF DESCRIPTION OF THE FIGURES

FIGS. 1(A–K). Cell lineages in the vascular bundle of primary root in *Arabidopsis*. Panels A–I are a cross section series of the wild type primary root (3 mm thick sections). (A) is at the level of the quiescent center (QC). (B) 3 mm, (C) 6 mm, (D) 9 mm, (E) 12 mm, (F) 15 mm, (G) 27 mm, (H) 69 mm, and (I) approximately 120 mm above the QC. Panels J and K are longitudinal sections of the primary root. (J) is the primary root from a wild-type *Arabidopsis*. (K) is the primary root from an *Arabidopsis* mutant for wol. Cells of the QC are labeled with asterisks. Newly formed cell walls after the cell divisions in the procambium in panels C–G are indicated with small black arrows. The specific set of newly formed cell walls associated with phloem development (panel G) is indicated by two separate sets of three arrows. Prospective protoxylem cells are indicated with thick arrows while the pericycle is indicated by "p" and sieve elements of the protophloem are indicated by "pp". Scale bar: 30 mm. Schematic: Cell lineages of the vascular bundle. The categories refer to the cell lineages only, the differentiation status of the cells is not known. The first and second maturing sieve elements are indicated as protophloem and metaphloem, respectively.

Figure 2:
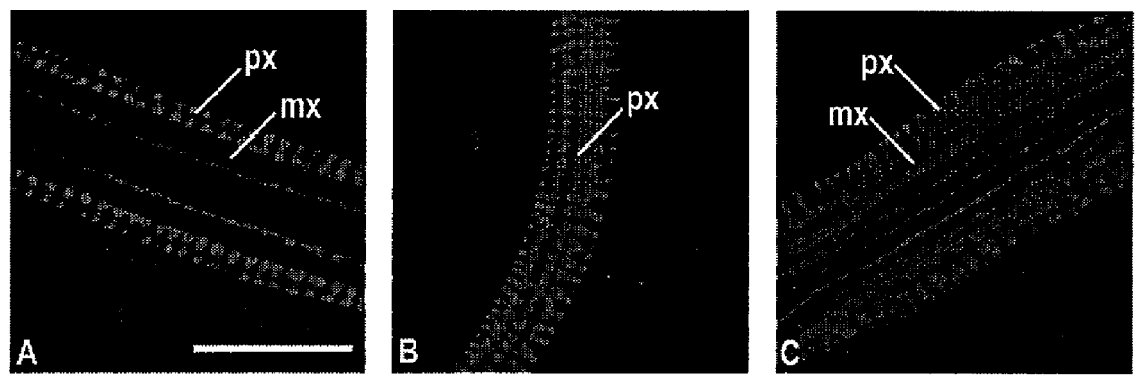

FIGS. 2(A–C). WOL is not necessary for metaxylem development. The confocal images were taken from wholemounts of seedlings stained with fuchsin. (A) is wild type *Arabidopsis* and shows that the metaxylem is gradually differentiating in an axis flanked by two files of protoxylem cells. (B) is *Arabidopsis* mutant for wol and shows that the entire vascular bundle is differentiated as protoxylem. (C) is a wol x fass double mutant *Arabidopsis* and shows that protoxylem and metaxylem organization analogous to that in wild type. Scale bar: 30 mm.

FIGS. 3(A–G). Molecular cloning of the WOL locus. (A) Fine mapping. RNS1 (SEQ ID NO:27) and rga (SEQ ID NO:28) are CAPS (cleaved amplified polymorphic sequences, see Konieczny & Ausubel, 1993, *Plant J.* 4:403–10) markers at the top of chromosome 2. T23K3/3 (SEQ ID NO:21) and Kin2/4 (SEQ ID NO:22) are the closest markers (designed in this study) for mutations in the BAC T23K3 (SEQ ID NO:13). The number of recombination events between markers and the wol locus are indicated below the markers. Hatched bar represents the 13.8 kb MscI fragment of the T23K3 BAC clone fragment (cloned in pCOM32), which complemented the wol mutation. (B) Structure of the WOL gene. Exons are indicated as solid bars. Three combinations of dotted lines show the alternative splicing variations of the WOL gene (deposited in GenBank as Accession Numbers AJ278528 (SEQ ID NO:1); AJ278529 (SEQ ID NO:2); and AJ278530 (SEQ ID NO:3). All result in the identical longest open reading frame and code for an identical polypeptide of 1057 amino acids (SEQ ID NO:5). The wol mutation is located in the exon with the asterisk where it converts a cytosine to a thymidine at nucleotide position 972, 855, or 964 (for splice variant 1 (SEQ ID NO:1), splice variant 2 (SEQ ID NO:2), or splice variant 3 (SEQ ID NO:3), respectively) so that a threonine is converted to an isoleucine at amino acid residue 278 of the WOL protein. The small hatched bar represents the 256 bp probe used in hybridization analyses. (C) Complementation of the wol mutation. Left to right: Cross sections of wol, wol transformed with the pCOM32 construct and wild-type primary roots. Arrows—protoxylem in wild type and rescued root; p—pericycle; pp—sieve elements of protophloem. Scale bar: 30 mm. (D) Wild type root architecture is conferred by complementation of the wol mutation. wol mutant plants were transformed with the pCOM32 construct and displayed lateral branches and indeterminate root growth. (E) Predicted domain structure of WOL. There is a short N-terminal region at residues 1–105 of SEQ ID NO:5 (SEQ ID NO:6). The extracellular receptor domain (hatched bar, residues 127–400 of SEQ ID NO:5 (SEQ ID NO:8) is located between the two transmembrane regions (vertical solid bars) located at residues 106–126 of SEQ ID NO:5 (SEQ ID NO:7) and residues 401–421 of SEQ ID NO:5 (SEQ ID NO:9). The C-terminal domain consists of a histidine kinase domain (H, residues 449–737 of SEQ ID NO:5 (SEQ ID NO:10) and two receiver domains ($D_A$ and $D_B$). Receiver domain $D_A$ is located at residues 762–893 of SEQ ID NO:5 (SEQ ID NO:11) and is followed by receiver domain $D_B$ at residues 922–1044 of SEQ ID NO:5 (SEQ ID NO:12). (F) Amino acid sequence alignment. A region in the WOL putative receptor domain which surrounds the wol mutation site was aligned with corresponding regions in two paralogs [F17L21.11 (SEQ ID NO:18) and MXH1.16 (SEQ ID NO:19)] and one ortholog [*Dictyostelium discoideum* DhkA (SEQ ID NO:17)]. Identical amino acids are indicated by black boxes. The altered amino acid residue in wol (isoleucine at position 278) is shown above the alignment. (G) Northern blot of total RLNA from wild-type roots and shoots. Ethidium bromide stained ribosomal RNA is shown as a loading control.

Figure 4:
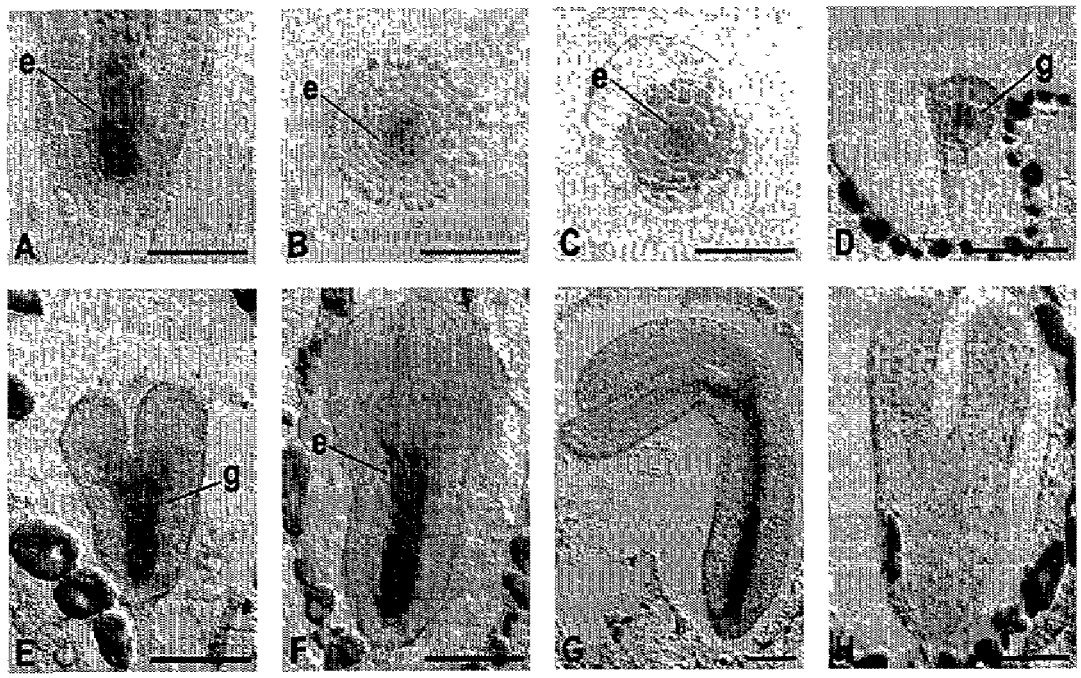

FIGS. 4(A–H). Localization of WOL mRNA during embryonic and primary root development by in situ hybridization. (A–G) Antisense probe. (A) Longitudinal and (B) cross sections of the wild-type primary root. (C) Cross section of wol primary root; (D) globular stage; (E) late heart stage; (F) torpedo stage; (G) bent-cotyledon stage of the wild-type embryo. (H) Torpedo stage embryo hybridized with a sense WOL probe. The endodermal (e) and the innermost ground tissue (g) layer next to the WOL expression domain are indicated. Scale bar: 50 mm.

FIGS. 5(A–D). *Arabidopsis* WOODEN LEG cDNA and protein sequence of the three splice variants. (A) The sequence of WOL splice variant 1 (SEQ ID NO:1). The cDNA sequence (SEQ ID NO:1, GenBank Accession No. AJ278528) of *Arabidopsis* WOODEN LEG is depicted. The open reading frame of SEQ ID NO:1 extends from nucleotide 140 to 3310 of SEQ ID NO:1 (SEQ ID NO:4). (B) The sequence of WOL splice variant 2 (SEQ ID NO:2). The cDNA sequence (SEQ ID NO:2, GenBank Accession No. AJ278529 of *Arabidopsis* WOODEN LEG is depicted. The open reading frame of SEQ ID NO:2 extends from nucleotide 23 to 3193 of SEQ ID NO:2 (SEQ ID NO:4). (C) The sequence of WOL splice variant 3 (SEQ ID NO:3). The cDNA sequence (SEQ ID NO:3, GenBank Accession No. AJ278530) of *Arabidopsis* WOODEN LEG is depicted. The open reading frame of SEQ ID NO:2 extends from nucleotide 132 to 3302 of SEQ ID NO:3 (SEQ ID NO:4). (D) The predicted amino acid sequence of *Arabidopsis* WOODEN LEG (SEQ ID NO:5) is depicted. The 1057 residue protein is identical for all three splice variants.

FIGS. 6(A–C). The cDNA sequence and the predicted amino acid sequence of two *Betula pendula* WOODEN LEG orthologs are depicted. (A) Degenerate primers (SEQ ID NOs:31 and 32) used to isolate WOL genes from *Betula pendula*. "I" indicates inosine; brackets indicate that any of the enclosed nucleotides can be found at that position. (B) WOL gene 1 cDNA (SEQ ID NO: 25) and protein sequence (SEQ ID NO: 29) are depicted. (C) WOL gene 2 cDNA (SEQ ID NO: 26) and protein sequence (SEQ ID NO: 30) are depicted.

FIGS. 7(A–D). WOL promoter sequence. The WOL promoter sequence is located in the region 5' to the transcription start site. The DNA sequence that includes this promoter is depicted (SEQ ID NO:33). The ATG denoted in bold represents the transcription start site of WOL.

FIG. 8. DNA sequence (SEQ ID NO: 36) of the 2.7 kb WOL promoter incorporated into the heterologous expression constructs WOLpro::GUS and WOLpro:GFP. See Section 6.8 for details.

Figure 9:

FIGS. 9(A–H). Expression patterns in *Arabidopsis* driven by the WOL promoter of SEQ ID NO: 36 linked to a reporter transgene. (A) GUS staining of the stipe and silique base of a wol mutant plant transformed with the WOLpromoter::GUS construct; (B) GUS staining of a Columbia ecotype seedling transformed with the WOLpromoter::GUS construct six days after germination; (C, D) GUS staining of the apical meristem of a Columbia ecotype seedling transformed with the WOL promoter::GUS construct six days after germination; (E, F) GUS staining of the apical meristem of a wol mutant seedling transformed with the WOLpromoter::GUS construct six days after germination; (G) GUS staining of the root tip of a Columbia ecotype seedling transformed with the WOLpromoter::GUS construct five days after germination; (H) GFP expression in the root tip of a Columbia ecotype seedling transformed with the WOLpromoter::GFP construct five days after germination. See Section 6.8 for details.

5. DETAILED DESCRIPTION OF THE INVENTION

The invention provides WOODEN LEG (WOL) nucleic acids (including, but not limited to, WOL promoters and nucleic acid sequences, WOL gene products, including, but not limited to, transcriptional products such as mRNAs, antisense and ribozyme molecules, and translational products such as the WOL protein, polypeptides, peptides and fusion proteins related thereto; antibodies to WOL gene products; WOL regulatory regions; and the use of the foregoing to improve agronomically valuable plants.

The WOL nucleic acids and promoters of the present invention have a number of important agricultural uses. The WOL promoters of the invention may be used, for example, in expression constructs to express desired heterologous gene products in the embryo, root, vascular cylinder, and pericycle of transgenic plants transformed with such constructs. In a specific embodiment, a WOL promoter may be used to express the gene product of a disease resistance gene, such as a lysozyme, cecropin, maganin, or thionin, for anti-bacterial protection. In another embodiment, a WOL promoter may be used to express a pathogenesis-related (PR) protein such as a glucanase or a chitinase for anti-fungal protection. WOL promoters also may be used to express a variety of pest resistance genes in the aforementioned plant structures and tissues. Examples of useful gene products for controlling nematodes or insects include *Bacillus thuringiensis* endotoxins, protease inhibitors, collagenases, chitinase, glucanases, lectins, and glycosidases.

Gene constructs that express or ectopically express WOL, and the WOL-suppression constructs of the invention in vascular tissues may be used to alter the structure of organs in transgenic plants. Since one function of WOL is to regulate cell divisions in the root, overexpression of WOL can be used to increase division of certain cells in roots and thereby form thicker and stronger roots. Thicker and stronger roots are beneficial in preventing plant lodging. Conversely, suppression of WOL expression can be used to decrease cell division in roots and thereby form thinner roots. Thinner roots are more efficient in uptake of soil nutrients. The invention also encompasses methods of directing expression in, but not exclusive to, root structures by associating a gene of interest with a WOL promoter.

In one embodiment, transgenic expression of WOL coding sequences in trees is used to improve wood production. In another embodiment, the WOL promoter is used to drive expression of a heterologous coding sequence in trees to improve wood production.

Further, a WOL nucleic acid may be used as a molecular marker for a qualitative trait, e.g., longer roots or enhanced wood production, in molecular breeding of crop plants.

For purposes of clarity, and not by way of limitation, the invention is described in the subsections below in terms of (a) WOL nucleic acids; (b) WOL gene products; (c) antibodies to WOL gene products; (d) WOL promoters and promoter elements; (e) transgenic plants that ectopically express WOL; (f) transgenic plants in which endogenous WOL expression is suppressed; and (g) transgenic plants in which expression of a transgene of interest is controlled by a WOL promoter.

5.1. WOL Nucleic Acids

The WOODEN LEG (WOL) nucleic acids of the invention include: (a) a nucleic acid comprising the nucleotide sequence shown in SEQ ID NOs:1, 2, or 3, or a segment of such nucleotide sequence; (b) a nucleic acid that encodes a protein comprising the amino acid sequence depicted in SEQ ID NO:5, or a segment of such amino acid sequence, or any segment of such genes and/or nucleotide sequences; (c) any nucleic acid comprising a nucleotide sequence that hybridizes to the complement of any one of the nucleic acids and/or nucleotide sequences described in (a) or (b) above, or any segment of such nucleic acids and/or nucleotide sequences, under highly stringent conditions, e.g., hybridization to filter-bound DNA in 0.5 M NaHPO$_4$, 7% SDS, 1 mM EDTA at 65° C., and washing in 0.1×SSC/0.1% SDS at 68° C. (Ausubel. et al., eds., 1989, *Current Protocols in Molecular Biology*, Vol. I, Green Publishing Associates, Inc., and John Wiley & Sons, Inc., New York, at p. 2.10.3) and that encodes a gene product functionally equivalent to a WOL gene product; (d) any nucleic acid comprising a nucleotide sequence that hybridizes to the complement of any one of the nucleic acids and/or nucleotide sequences described in (a) or (b) above, or any segment of such nucleic acids and/or nucleotide sequences, under less stringent conditions, such as moderately stringent conditions, e.g., washing in 0.2×SSC/0.1% SDS at 42° C. (Ausubel et al., 1989, supra), and that encodes a functionally equivalent WOL gene product; (e) any nucleic acid comprising a nucleotide sequence that hybridizes to the complement of any one of the nucleic acids and/or nucleotide sequences described in (a) or (b) above, or any segment of such nucleic acids and/or nucleotide sequences, under the following low stringency conditions: pre-hybridization in hybridization solution containing 43% formamide, 5×SSC, 1% SDS, 10% dextran sulfate, 0.1% sarkosyl, 2% block (Genius kit, Boehringer-Mannheim), followed by hybridization overnight at 30° to 33° C., followed by washing in 2×SSC/0.1% SDS two times for 15 minutes at room temperature and then two times at 50° C., and that encodes a functionally equivalent WOL gene product; and/or (f) any nucleic acid comprising a nucleotide sequence that encodes a polypeptide or protein containing a WOL domain as shown in SEQ ID NOs:6, 7, 8, 9, 10, 11, or 12 or a segment of such polypeptide or protein.

FIG. 3 indicates exon and intron boundaries of the WOL gene. Nucleic acid molecules comprising WOL exon and intron sequences are encompassed by the present invention. In one embodiment, ten exons are included (SEQ ID NO:1; GenBank Accession No. AJ278528). WOL exon 1 encompasses nucleotides 1 to 132 of the sequence shown in SEQ ID NO:1; exon 2 encompasses nucleotides 133 to 682 of the sequence shown in SEQ ID NO:1; exon 3 encompasses nucleotides 683 to 919 of the sequence shown in SEQ ID NO:1; exon 4 encompasses nucleotides 920 to 1089 of the sequence shown in SEQ ID NO:1; exon 5 encompasses nucleotides 1090 to 1308 of the sequence shown in SEQ ID NO:1; exon 6 encompasses nucleotides 1309 to 1547 of the sequence shown in SEQ ID NO:1; exon 7 encompasses nucleotides 1548 to 1777 of the sequence shown in SEQ ID NO:1; exon 8 encompasses nucleotides 1778 to 1876 of the sequence shown in SEQ ID NO:1; exon 9 encompasses nucleotides 1877 to 3081 of the sequence shown in SEQ ID NO: 1; and exon 10 encompasses nucleotides 3082 to 3620 of the sequence shown in SEQ ID NO:1.

In another embodiment ten exons are included (SEQ ID NO:2, GenBank Accession No. AJ278529). This is the splice variant that is most predominantly found in vivo. WOL exon 1 encompasses nucleotides 1 to 15 of the sequence shown in SEQ ID NO:2; exon 2 encompasses nucleotides 16 to 565 of the sequence shown in SEQ ID NO:2; exon 3 encompasses nucleotides 566 to 802 of the sequence shown in SEQ ID NO:2; exon 4 encompasses nucleotides 803 to 972 of the sequence shown in SEQ ID NO:2; exon 5 encompasses nucleotides 973 to 1191 of the sequence shown in SEQ ID NO:2; exon 6 encompasses nucleotides 1192 to 1430 of the sequence shown in SEQ ID NO:2; exon 7 encompasses nucleotides 1431 to 1660 of the sequence shown in SEQ ID NO:2; exon 8 encompasses nucleotides 1661 to 1759 of the sequence shown in SEQ ID NO:2; exon 9 encompasses nucleotides 1760 to 2964 of the sequence shown in SEQ ID NO:2; and exon 10 encompasses nucleotides 2965 to 3503 of the sequence shown in SEQ ID NO:2.

In yet another embodiment, eleven exons are included (SEQ ID NO:3, GenBank Accession No. AJ278530). WOL exon 1 encompasses nucleotides 1 to 47 of the sequence shown in SEQ ID NO:3; exon 2 encompasses nucleotides 48 to 124 of the sequence shown in SEQ ID NO:3; exon 3 encompasses nucleotides 125 to 674 of the sequence shown in SEQ ID NO:3; exon 4 encompasses nucleotides 675 to 911 of the sequence shown in SEQ ID NO:3; exon 5 encompasses nucleotides 912 to 1081 of the sequence shown in SEQ ID NO:3; exon 6 encompasses nucleotides 1082 to 1300 of the sequence shown in SEQ ID NO:3; exon 7 encompasses nucleotides 1301 to 1539 of the sequence shown in SEQ ID NO:3; exon 8 encompasses nucleotides 1540 to 1769 of the sequence shown in SEQ ID NO:3; exon 9 encompasses nucleotides 1770 to 1868 of the sequence shown in SEQ ID NO:3; exon 10 encompasses nucleotides 1869 to 3073 of the sequence shown in SEQ ID NO:3; and exon 11 encompasses nucleotides 3074 to 3612 of the sequence shown in SEQ ID NO:3.

The invention also includes nucleic acid molecules, preferably DNA molecules, that hybridize to, and are therefore the complements of the nucleotide sequences (a) through (f), in the first paragraph of this section. Such hybridization conditions may be highly stringent, less highly stringent, or low stringency as described above. In instances wherein the nucleic acid molecules are oligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as WOL antisense molecules, useful, for example, in WOL gene regulation and/or as antisense primers in amplification reactions of WOL gene and/or nucleic acid sequences. Further, such sequences may be used as part of ribozyme and/or triple helix sequences, also useful for WOL gene regulation. Still further, such molecules may be used as components in probing methods whereby the presence of a WOODEN LEG allele may be detected.

The invention also includes nucleic acid molecules, preferably DNA molecules, that are amplified using the polymerase chain reaction and that encode a gene product functionally equivalent to a WOL gene product.

The invention also encompasses (a) DNA vectors that contain any of the foregoing nucleic acids and/or coding sequences and/or their complements (i.e., antisense or ribozyme molecules); (b) DNA expression vectors that contain any of the foregoing nucleic acids and/or coding sequences operatively associated with a regulatory element that directs the expression of the nucleic acids and/or coding sequences; and (c) genetically engineered host cells that contain any of the foregoing nucleic acids and/or coding sequences operatively associated with a regulatory element that directs the expression of the gene and/or coding sequences in the host cell. As used herein, regulatory elements include, but are not limited to, inducible and non-inducible promoters, enhancers, operators and other elements known to those skilled in the art that drive and regulate expression of a nucleic acid.

The invention also encompasses nucleotide sequences that encode mutant WOL gene products, peptide fragments of the WOL gene product, truncated WOL gene products, and WOL fusion proteins. These gene products include, but are not limited to, nucleotide sequences encoding mutant WOL gene products; polypeptides or peptides corresponding to one or more of the domains as shown in FIG. 3, or portions of these domains; truncated WOL gene products in which one or more of the domains is deleted, e.g., a truncated, nonfunctional WOL lacking some of the domains of the WOL. The deleted WOL domains can be lacking completely or in part.

Nucleotides encoding fusion proteins may include, but are not limited to, nucleotides encoding full length WOL, truncated WOL, or peptide fragments of WOL fused to an unrelated protein or peptide, such as for example, an enzyme, fluorescent protein, or luminescent protein that can be used as a marker.

A fusion construct or gene fusion construct is a genetic construct comprising a promoter operably linked to a heterologous nucleic acid, wherein said promoter controls the transcription of the heterologous nucleic acid. With respect to fusion constructs, a heterologous nucleic acid is a nucleic acid that is linked to a promoter to which the nucleic acid is not naturally linked. The heterologous nucleic acid may or may not be from the organism contributing said promoter. The heterologous gene may encode messenger RNA (mRNA), antisense RNA or ribozymes.

In particular, the invention includes, for example, fragments of WOL genes encoding one or more of the following domains as shown in FIG. 3: amino acid residues 1–105 (SEQ ID NO:6), amino acid residues 106–126 (SEQ ID NO:7), amino acid residues 127–400 (SEQ ID NO:8), amino acid residues 401–421 (SEQ ID NO:9), amino acid residues 449–737 (SEQ ID NO:10), amino acid residues 762–893 (SEQ ID NO:11), and amino acid residues 922–1044 (SEQ ID NO:12).

In addition to the nucleic acid and/or coding sequences described above, homologous WOL nucleic acids, and other nucleic acids related by DNA sequence, may be identified and may be readily isolated, without undue experimentation, by molecular biological techniques well known in the art. More specifically, such homologs include, for example, paralogs (i.e., members of the WOL gene family occurring in the same plant such as F17L21.11, SEQ ID NO:18; and MXH1.16, SEQ ID NO:19) as well as orthologs (i.e., members of the WOL gene family which occur in a different plant species such as *Dictyostelium discoideum*, SEQ ID NO:17) of the *Arabidopsis* WOL gene.

A specific embodiment of a WOL nucleic acid and coding sequence of the invention is *Arabidopsis* WOL (see FIGS. 5, 6, and 7; SEQ ID NOs:1, 2, 3, 4, 25, 26, 33, 34, or 35).

Methods for isolating WOL nucleic acids and coding sequences are described in detail in Section 5.1.1, below.

The proteins encoded by WOL nucleic acids share substantial amino acid sequence similarities and nucleotide sequence similarities in their genes. As explained above in Section 3.1, the term "substantially similar" or "substantial similarity," when used herein with respect to two amino acid sequences, means that the two sequences have at least 75% identical residues, preferably at least 85% identical residues, more preferably at least 95% identical residues, and most preferably at least 99% identical residues. The same term, when used herein with respect to two nucleotide sequences, means that the two sequences have at least 70% identical residues, preferably at least 85% identical residues, more preferably at least 95% identical residues, and most preferably at least 99% identical residues. Determining whether two sequences are substantially similar may be carried out using any methodologies known to one skilled in the art, preferably using computer assisted analysis.

The determination of percent identity between two sequences can be accomplished using a mathematical algorithm. A preferred, non-limiting example of a mathematical algorithm utilized for the comparison of two sequences is the algorithm of Karlin & Altschul, 1990, *Proc. Natl. Acad. Sci. USA* 87:2264–2268, modified as in Karlin & Altschul, 1993, *Proc. Natl. Acad. Sci. USA* 90:5873–5877. Such an algorithm is incorporated into the NBLAST and XBLAST programs of Altschul, et al., 1990, *J. Mol. Biol.* 215: 403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, *Nucleic Acids Res.* 25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, 1988, *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically exact matches are counted.

Moreover, WOL genes show highly localized expression in embryos and, particularly, in vascular tissue in roots. Such expression patterns may be ascertained by Northern hybridizations and in situ hybridizations using antisense probes as described in Section 6.6 below.

Examples of WOL paralogs include, but are not limited to, genes F17L21.11 (SEQ ID NO:18); and MXH1.16 (SEQ ID NO:19), which have a similar deduced protein domain structure and which may be identified in the *Arabidopsis* database. This indicates that WOL belongs to a small protein family (FIG. 3F). The deduced sequence of the WOL protein was 57% identical to F17L21.11 (GenBank Accession Number AC004557 (SEQ ID NO:18)) and 54% identical to MXH1.16 (GenBank Accession Number AB011485 (SEQ ID NO:19)). To compare deduced amino acid sequences, SeqWeb Software (a web-based interface to the GCG Wisconsin Package: Gap program) was utilized with the default algorithm and parameter settings of the program: blosum62, gap weight 8, length weight 2. Furthermore, a WOL ortholog sequence has been reported in the genome of *Hordeum vulgare* (GenBank Accession Number AJ234550, SEQ ID NO:20). Among the characterized two component receptor molecules, these WOL homolog and paralog proteins are unique in having, at least one, and preferably two, putative D domains. The closest homologue of WOL-like genes is the DhkA receptor (GenBank Accession Number U42597, SEQ ID NO:17; see Wang et al., 1996, *EMBO J.* 15:3890–8 and Wang et al., 1999, *Mol Cell Biol.* 7:4750–6) of the slime mold *Dictyostelium discoideum* (FIG. 3F).

The functionality of naturally occurring or constructed variants of WOL genes may be tested using methods well known in the art, such as operably linking a reporter gene to a WOL gene variant, and which are taught in the present application at Section 5.8. Versions of the WOL genes to be tested can be fused to any number of heterologous reporter genes, including but not limited to, GUS, GFP, CAT, luciferase, β-galactosidase and C1 and R gene controlling anthocyanin production. Transgenic plants containing the WOL::reporter gene constructs can be generated using the methods described in section 5.9 for each WOL gene variant. To screen for loss-of-function variants induced by mutations, including but not limited to, deletions, point mutations, rearrangements, translocation, etc. The constructs may be transformed into the homozygous recessive wol mutant background, such as the mutant described in Section 6 below. If a wildtype WOL phenotype is restored in one of the transgenic plant lines (i.e., metaxylem and vascular bundles present, thicker roots and hypocotyl than in the mutant), then the WOL variant contained in the construct is functional.

WOL orthologs are also active in the cambial zone of a trunk of a birch tree (*Betula pendula*). Using degenerate oligonucleotides (forward primer is SEQ ID NO:31; reverse primer is SEQ ID NO:32) based on the sequence conservation within the WOL genes of *Arabidopsis,* two different WOL orthologs from a cDNA library representing the wood forming tissue of birch tree (*Betula pendula*) are described herein in Section 6.7 infra (SEQ ID Nos: 25 and 26, respectively). Because of their expression during wood development in trees, it is postulated that WOL and WOL orthologs and paralogs have more general roles regulation of vascular development during both the primary and secondary phases of plant development.

5.1.1. Isolation Of WOL Nucleic Acids

The following methods can be used to obtain WOL nucleic acids and coding sequences from a wide variety of plants, including, but not limited to, *Arabidopsis thaliana*,

*Zea mays, Nicotiana tabacum, Daucus carota, Oryza, Glycine max, Lemna gibba, Picea abies,* as well as species of the genera *Betula, Populus, Pinus,* and *Eucalyptus,* etc.

Nucleotide sequences comprising a WOL nucleic acid or a portion thereof may be obtained by PCR amplification of plant genomic DNA or cDNA. Useful cDNA sources include "free" cDNA preparations (i.e., the products of cDNA synthesis) and cloned cDNA in cDNA libraries. Root or cambial cDNA preparations or libraries are particularly preferred.

The amplification may use, as the 5'-primer (i.e., forward primer), a degenerate oligonucleotide that corresponds to a segment of a known WOL amino acid sequence, preferably from the amino-terminal region. The 3'-primer (i.e., reverse primer) may be a degenerate oligonucleotide that corresponds to a distal segment of the same known WOL amino acid sequence (i.e., carboxyl to the sequence that corresponds to the 5'-primer). For example, the amino acid sequence of the *Arabidopsis* WOL protein (SEQ ID NO:5) may be used to design useful 5' and 3' primers. The sequence of the optimal degenerate oligonucleotide probe corresponding to a known amino acid sequence may be determined by standard algorithms known in the art. See for example, Sambrook et al., 1989, *Molecular Cloning: A Laboratory Manual,* 2nd ed., Cold Spring Harbor Laboratory Press, Cold Spring Harbor, N.Y., Vol 2.

Further, for amplification from cDNA sources, the 3'-primer may be an oligonucleotide comprising an 3' oligo (dT) sequence. The amplification may also use as primers nucleotide sequences of WOL genes or coding sequences.

PCR amplification can be carried out, e.g., by use of a Perkin-Elmer Cetus thermal cycler and Taq polymerase (Gene Amp™). One can choose to synthesize several different degenerate primers for use in the PCR reactions. It is also possible to vary the stringency of hybridization conditions used in priming the PCR reactions, to allow for greater or lesser degrees of nucleotide sequence similarity between the degenerate primers and the corresponding sequences in the cDNA library. One of ordinary skill in the art will know that the appropriate amplification conditions and parameters depend, in part, on the length and base composition of the primers and that such conditions may be determined using standard formulae. Protocols for executing all PCR procedures discussed herein are well known to those skilled in the art, and may be found in references such as Gelfand, 1989, *PCR Technology, Principles and Applications for DNA Amplification,* H. A. Erlich, ed., Stockton Press, New York; and Ausubel et al., 1988, *Current Protocols In Molecular Biology,* Wiley & Sons, Inc, New York, Vol. 2:Ch. 15

A PCR amplified sequence may be molecularly cloned and sequenced. The amplified sequence may be utilized as a probe to isolate genomic or cDNA clones of a WOL gene, as described below. This, in turn, will permit the determination of a WOL gene's complete nucleotide sequence, including its promoter, the analysis of its expression, and the production of its encoded protein, as described infra.

A coding sequence for a WOL gene product, e.g., a WOL protein, may also be isolated by screening a plant genomic or cDNA library using a WOL nucleotide sequence (e.g., the sequence of any of the WOL nucleic acids and sequences and EST clone sequences) as hybridization probe. For example, the whole or a segment of the *Arabidopsis* WOL nucleotide sequence (FIG. 5) may be used. Alternatively, a WOL nucleic acid may be isolated from such libraries using a degenerate oligonucleotide that corresponds to a segment of a WOL amino acid sequence. For example, degenerate oligonucleotide probe corresponding to a segment of the *Arabidopsis* WOL amino acid sequence (SEQ ID NO:5) may be used.

In preparation of cDNA libraries, total RNA is isolated from plant tissues, preferably roots. Poly(A)+ RNA is isolated from the total RNA, and cDNA prepared from the poly(A)+ RNA, all using standard procedures. See, for example, Sambrook et al., 1989, *Molecular Cloning: A Laboratory Manual,* 2d ed., Vol. 2. The cDNAs may be synthesized with a restriction enzyme site at their 3'-ends by using an appropriate primer and further have linkers or adaptors attached at their 5'-ends to facilitate the insertion of the cDNAs into suitable cDNA cloning vectors. Alternatively, adaptors or linkers may be attached to the cDNAs after the completion of cDNA synthesis.

In preparation of genomic libraries, plant DNA is isolated and fragments are generated, some of which will encode parts of the whole WOL protein. The DNA may be cleaved at specific sites using various restriction enzymes. Alternatively, one may use DNase in the presence of manganese to fragment the DNA, or the DNA can be physically sheared, as for example, by sonication. The DNA fragments can then be separated according to size by standard techniques, including, but not limited to, agarose and polyacrylamide gel electrophoresis, column chromatography and sucrose gradient centrifugation.

The genomic DNA or cDNA fragments can be inserted into suitable vectors, including, but not limited to, plasmids, cosmids, bacteriophages lambda or $T_4$, and yeast artificial chromosome (YAC). See, for example, Sambrook et al., 1989, *Molecular Cloning: A Laboratory Manual,* 2d ed., Cold Spring Harbor Laboratory Press, Cold Spring Harbor, N.Y.; Glover, 1985, *DNA Cloning: A Practical Approach,* MRL Press, Ltd., Oxford, U.K., Vols. I and II.

The WOL nucleotide probe, DNA or RNA, should be at least 17 nucleotides, preferably at least 26 nucleotides, and most preferably at least 50 nucleotides in length. The nucleotide probe is hybridized under moderate stringency conditions and washed under moderate or, more preferably, high stringency conditions. Clones in libraries with insert DNA having substantial homology to the WOL probe will hybridize to the probe. Hybridization of the nucleotide probe to genomic or cDNA libraries is carried out using methods known in the art. One of ordinary skill in the art will know that the appropriate hybridization and wash conditions depend on the length and base composition of the probe and that such conditions may be determined using standard formulae. See, for example, Sambrook et al., 1989, *Molecular Cloning: A Laboratory Manual,* 2nd ed., Cold Spring Harbor Laboratory Press, Cold Spring Harbor, N.Y., Vol. 2, pp 11.45–11.57 and 15.55–15.57.

The identity of a cloned or amplified WOL nucleic acid sequence can be verified by comparing the amino acid sequences of its three open reading frames with the amino acid sequence of a WOL gene product (e.g., *Arabidopsis* WOL protein, see SEQ ID NO:5). A WOL nucleic acid or coding sequence encodes a protein or polypeptide whose amino acid sequence is substantially similar to that of a WOL protein or polypeptide (e.g., the amino acid sequence of FIG. 5). The identity of the cloned or amplified WOL nucleic acid sequence may be further verified by examining its expression pattern, which reveals highly localized expression in the embryo and root vascular tissue of the plant from which the WOL nucleic acid sequence was isolated.

Comparison of the amino acid sequences encoded by a cloned or amplified sequence may reveal that it does not contain the entire WOL gene or its promoter. In such a case the cloned or amplified WOL nucleic acid sequence may be used as a probe to screen a genomic library for clones having inserts that overlap the cloned or amplified WOL nucleic acid sequence. A complete WOL gene and its promoter may be reconstructed by splicing the overlapping WOL nucleic acid sequences.

5.2. WOL Gene Products and Expression of WOL Gene Products

WOL proteins, polypeptides and peptide fragments, mutated, truncated or deleted forms of WOL and/or WOL fusion proteins can be prepared for a variety of uses, including, but not limited to, the generation of antibodies, as reagents in assays, the identification of other cellular gene products involved in regulation of root development, etc.

WOL translational products include, but are not limited to those proteins and polypeptides encoded by the WOL nucleic acid sequences described in Section 5.1, above. The invention encompasses proteins that are functionally equivalent to the WOL gene products described in Section 5.2. Such a WOL gene product may contain one or more deletions, additions or substitutions of WOL amino acid residues within the amino acid sequence encoded by any one of the WOL nucleic acid sequences described, above, in Section 5.1, but which result in a silent change, thus producing a functionally equivalent WOL gene product. Amino acid substitutions may be made on the basis of similarity in polarity, charge, solubility, hydrophobicity, hydrophilicity, and/or the amphipathic nature of the residues involved.

The present invention also provides variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, deleting one or both of the receiver domains ($D_A$ and $D_B$). Thus, specific biological effects can be elicited by addition of a variant of limited function.

Modification of the structure of the subject polypeptides can be for such purposes as enhancing efficacy, stability, or post-translational modifications (e.g., to alter the phosphorylation pattern of the protein). Such modified peptides, when designed to retain at least one activity of the naturally-occurring form of the protein, or to produce specific antagonists thereof, are considered functional equivalents of the polypeptides. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule.

Whether a change in the amino acid sequence of a peptide results in a functional homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into nucleic acid sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983, *Nucleic Acid Res.* 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811–7815; Delgrave et al., 1993, *Protein Engineering* 6(3):327–331).

An isolated nucleic acid molecule encoding a variant protein can be created by introducing one or more nucleotide substitutions, additions or deletions into the WOL nucleotide sequence, such that one or more amino acid substitutions, additions or deletions are introduced into the encoded protein. Mutations can be introduced by standard techniques, such as site-directed mutagenesis and PCR-mediated mutagenesis. Briefly, PCR primers are designed that delete the trinucleotide codon of the amino acid to be changed and replace it with the trinucleotide codon of the amino acid to be included. This primer is used in the PCR amplification of DNA encoding the protein of interest. This fragment is then isolated and inserted into the full length cDNA encoding the protein of interest and expressed recombinantly. The resulting protein now includes the amino acid replacement.

Either conservative or non-conservative amino acid substitutions can be made at one or more amino acid residues. Both conservative and non-conservative substitutions can be made. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (See, for example, Biochemistry, 4th ed., Ed. by L. Stryer, WH Freeman and Co.: 1995).

In WOL, for example, the nucleotide at position 66 is thymine (T) (SEQ ID NO:4). In this embodiment, the amino acid at position 22 is aspartate (D) (SEQ ID NO:5). In an alternative embodiment, WOL can be engineered to contain a guanine (G) at nucleotide at position 66 (SEQ ID NO:23). In this embodiment, the amino acid at position 22 is glutamate (E) (SEQ ID NO:24), i.e., a conservative substitution.

Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In a preferred embodiment, a mutant polypeptide that is a variant of a polypeptide of the invention can be assayed for: (1) the ability to form protein-protein interactions with proteins in a signaling pathway of the polypeptide of the invention; (2) the ability to bind a ligand of the polypeptide of the invention; or (3) the ability to bind to an intracellular target protein of the polypeptide of the invention.

The invention encompasses functionally equivalent mutant WOL proteins and polypeptides. The invention also encompasses mutant WOL proteins and polypeptides that are not functionally equivalent to the gene products described in Section 5.2. Such a mutant WOL protein or polypeptide may contain one or more deletions, additions or substitutions of WOL amino acid residues within the amino acid sequence encoded by any one the WOL nucleic acid sequences described above in Section 5.1, and which result in loss of one or more functions of the WOL protein, thus producing a WOL gene product not functionally equivalent to the wild-type WOL protein.

WOL proteins and polypeptides bearing mutations can be made to WOL DNA (using techniques discussed above as well as those well known to one of skill in the art) and the resulting mutant WOL proteins tested for activity. Mutants can be isolated that display increased function, (e.g., resulting in improved root formation), or decreased function (e.g., resulting in suboptimal root function). In particular, mutated WOL proteins in which any of the domains shown in FIG. 3 are deleted or mutated are within the scope of the invention. Additionally, peptides corresponding to one or more domains of the WOL protein (e.g., shown in FIG. 3), truncated or deleted WOL protein are also within the scope of the invention. Fusion proteins in which the full length WOL protein or a WOL polypeptide or peptide fused to an unrelated protein are also within the scope of the invention and can be designed on the basis of the WOL nucleotide and WOL amino acid sequences disclosed in Sections 5.1 and 5.2 above.

While the WOL polypeptides and peptides can be chemically synthesized (e.g. see Creighton, 1983, *Proteins: Structures and Molecular Principles,* W.H. Freeman & Co., NY) large polypeptides derived from WOL and the full length WOL may advantageously be produced by recombinant DNA technology using techniques well known to those skilled in the art for expressing nucleic acid sequences.

Methods which are well known to those skilled in the art can be used to construct expression vectors containing WOL protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding WOL protein sequences may be chemically synthesized using, for example, synthesizers. See, for example, the techniques described in Gait, 1984, *Oligonucleotide Synthesis,* IRL Press, Oxford.

A variety of host-expression vector systems may be utilized to express the WOL gene products of the invention. Such host-expression systems represent vehicles by which the WOL gene products of interest may be produced and subsequently recovered and/or purified from the culture or plant (using purification methods well known to those skilled in the art), but also represent cells which may, when transformed or transfected with the appropriate nucleotide coding sequences, exhibit the WOL protein of the invention in situ. These include but are not limited to microorganisms such as bacteria (e.g., *E. coli, B. subtilis*) transformed with recombinant bacteriophage DNA, plasmid DNA or cosmid DNA expression vectors containing WOL protein coding sequences; yeast (e.g., *Saccharomyces, Pichia*) transformed with recombinant yeast expression vectors containing the WOL protein coding sequences; insect cell systems infected with recombinant virus expression vectors (e.g., baculovirus) containing the WOL protein coding sequences; plant cell systems infected with recombinant virus expression vectors (e.g., cauliflower mosaic virus, CaMV; tobacco mosaic virus, TMV); plant cell systems transformed with recombinant plasmid expression vectors (e.g., Ti plasmid) containing WOL protein coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter; the cytomegalovirus promoter/enhancer; etc.).

In bacterial systems, a number of expression vectors may be advantageously selected depending upon the use intended for the WOL protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited, to the *E. Coli* expression vector pUR278 (Ruther et al., 1983, *EMBO J.* 2:1791), in which the WOL coding sequence may be ligated individually into the vector in frame with the lac Z coding region so that a fusion protein is produced; pIN vectors (Inouye & Inouye, 1985, *Nucleic Acids Res.* 13:3101–9; Van Heeke & Schuster, 1989, *J. Biol. Chem.* 264:5503–9); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

In one such embodiment of a bacterial system, full length cDNA sequences are appended with in-frame Bam HI sites at the amino terminus and Eco RI sites at the carboxyl terminus using standard PCR methodologies (Innis et al., 1990, supra) and ligated into the pGEX-2TK vector (Pharmacia, Uppsala, Sweden). The resulting cDNA construct contains a kinase recognition site at the amino terminus for radioactive labeling and glutathione S-transferase sequences at the carboxyl terminus for affinity purification (Nilsson, et al., 1985, *EMBO J.* 4:1075; Zabeau and Stanley, 1982, *EMBO J.* 1: 1217).

The recombinant constructs of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include, but are not limited to, plasmids, cosmids, bacteriophages or viruses.

In addition, the recombinant constructs may include plant-expressible, selectable, or screenable marker genes for isolating, identifying or tracking plant cells transformed by these constructs. Selectable markers include, but are not limited to, genes that confer antibiotic resistance, (e.g., resistance to kanamycin or hygromycin) or herbicide resistance (e.g., resistance to sulfonylurea, phosphinothricin, or glyphosate). Screenable markers include, but are not limited to, reporter genes encoding β-glucuronidase (Jefferson, 1987, *Plant Mol. Biol. Rep.* 5:387–405), luciferase (Ow et al., 1986, *Science* 234:856–9), fluorescent proteins (such as GFP as described in Kain et al., 1995, *Biotech.* 19:650–5; blue GFP as described by Heim and Tsien, 1996, *Curr. Biol.* 6:178–82; or yellow and red GFP as described by Matz et al., 1999, *Nature Biotechnol.* 17:969–73), B protein that regulates anthocyanin pigment production (Goff et al., 1990, *EMBO J.* 9:2517–22).

In embodiments of the present invention which utilize the *Agrobacterium tumefacien* system for transforming plants (see infra), the recombinant constructs may additionally comprise at least the right T-DNA border sequences flanking the DNA sequences to be transformed into the plant cell. Alternatively, the recombinant constructs may comprise the right and left T-DNA border sequences flanking the DNA sequence. The proper design and construction of such T-DNA based transformation vectors are well known to those skilled in the art.

5.3. Antibodies to WOL Proteins and Polypeptides

Antibodies that specifically recognize one or more epitopes of WOL, or epitopes of conserved variants of WOL, or peptide fragments of the WOL are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

An isolated polypeptide of the invention, or a fragment thereof can be used as an immunogen to generate antibodies using standard techniques for polyclonal and monoclonal antibody preparation. Among those polypeptides suitable for use are the full length WOL protein (SEQ ID NOs:5, 29, or 30), a WOL peptide (e.g., one corresponding to a functional domain of the protein, SEQ ID NOs:6, 7, 8, 9, 10, 11, or 12), a truncated WOL polypeptide (WOL in which one or more domains has been deleted), functional equivalents of the WOL protein, or mutants of the WOL protein. Such WOL proteins, polypeptides, peptides or fusion proteins can be prepared and obtained as described in Section 5.2 supra.

The antigenic peptide of a protein of the invention comprises at least 8 (preferably 10, 15, 20, or 30) amino acid residues of the amino acid sequence of SEQ ID NOs:5, 6, 7, 8, 9, 10, 11, 12, 29, or 30, and encompasses an epitope of the protein such that an antibody raised against the peptide forms a specific immune complex with the protein. Preferred epitopes encompassed by the antigenic peptide are regions that are located on the surface of the protein, e.g., hydrophilic regions. Hydropathy plots or similar analyses can be used to identify hydrophilic regions.

Host animals which may be used for injection include, but are not limited to, rabbits, mice, and rats. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, *Nature* 256:495–7 and U.S. Pat. No.4,376,110), the human B-cell hybridoma technique (Kosbor et al., 1983, *Immunology Today* 4:72; Cole et al., 1983, *Proc. Natl. Acad. Sci. USA* 80:2026–30), and the EBV-hybridoma technique (Cole et al., 1985, *Monoclonal Antibodies And Cancer Therapy,* Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of the invention. Particularly preferred polyclonal antibody preparations are ones that contain only antibodies directed against a polypeptide or polypeptides of the invention. Particularly preferred immunogen compositions are those that contain no other contaminating proteins such as, for example, immunogen compositions made using a host cell for recombinant expression of a polypeptide of the invention. In such a manner, the only epitope or epitopes recognized by the resulting antibody compositions raised against this immunogen will be present as part of a polypeptide or polypeptides of the invention.

In addition, techniques developed for the production of "chimeric antibodies" (Morrison et al., 1984, *Proc. Natl. Acad. Sci. USA,* 81:6851–5; Neuberger et al., 1984, *Nature,* 312:604–8; Takeda et al., 1985, *Nature,* 314:452–4) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

In addition, techniques have been developed for the production of humanized antibodies. (See, e.g., U.S. Pat. No. 5,585,089.) An immunoglobulin light or heavy chain variable region consists of a "framework" region interrupted by three hypervariable regions, referred to as complementarity determining regions (CDRs). The extent of the framework region and CDRs have been precisely defined (see, Kabat ET AL., 1983, *Sequences of Proteins of Immunological Interest,* U.S. Department of Health and Human Services). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, *Science* 242:423–6; Huston et al., 1988, *Proc. Natl. Acad. Sci. USA* 85:5879–83; and Ward et al., 1989, *Nature* 334:544–6) can be adapted to produce single chain antibodies against WOL proteins or polypeptides. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, *Science,* 246:1275–81) to allow rapid and easy identification of monoclonal Fab fragments with the desired specificity.

Antibodies to a WOL protein and/or polypeptide can, in turn, be utilized to generate anti-idiotype antibodies that "mimic" WOL, using techniques well known to those skilled in the art. (See, e.g., Greenspan & Bona, 1993, *FASEB J.* 7:437–44; and Nissinoff, 1991, *J. Immunol.* 147:2429–38).

5.4. WOL Nucleic Acids or Gene Products as Markers for Quantitative Trait Loci Any of the nucleotide sequences (including EST clone sequences with GenBank Accession Numbers AA586219, SEQ ID NO:14; AI992824, SEQ ID NO:15; and T20648, SEQ ID NO:16) described in Section 5.1.1, and/or polypeptides and proteins described in Section 5.2, can be used as markers for qualitative trait loci in breeding programs for crop plants. To this end, the nucleic acid molecules, including, but not limited to, full length WOL coding sequences, and/or partial sequences (ESTs), can be used in hybridization and/or DNA amplification assays to identify the endogenous WOL genes, wol mutant alleles and/or WOL expression products in cultivars as compared to wild-type plants. They can also be used as markers for linkage analysis of qualitative trait loci. It is also possible that the WOL gene may encode a product responsible for a qualitative trait that is desirable in a crop breeding program. Alternatively, the WOL protein, peptides and/or antibodies can be used as diagnostic reagents in immunoassays to detect expression of the WOL gene in cultivars and wild-type plants.

5.5. Identification of WOL-Interacting Proteins

Any of a variety of exogenous compounds, both naturally occurring and/or synthetic (e.g., libraries of small molecules or peptides), may be screened for binding capacity to a WOL protein. Such methods may comprise the step of mixing a WOL protein or peptide with library members, allowing time for any binding to occur, and assaying for any bound complexes.

In a specific embodiment, ligands capable of binding to the WOL receptor may be isolated from libraries. WOL is an orphan receptor because no known endogenous ligand is currently known. WOL protein or peptides may be used as bait to isolate those molecules competent to bind and therefore be assigned a previously unknown ligand. The activity of WOL may be either augmented or diminished through contact with isolated proteins. Such methods are known in the art.

Many libraries are known in the art that can be used, e.g., recombinant (e.g., phage display libraries or cDNA expression libraries), in vitro translation-based libraries; and chemically synthesized libraries.

Examples of phage display libraries are described in Scott & Smith, 1990, *Science* 249:386–390; Devlin et al., 1990, *Science,* 249:404–406; Christian, et al., 1992, *J. Mol. Biol.* 227:711–718; Lenstra, 1992, *J. Immunol. Meth.* 152:149–157; Kay et al., 1993, *Gene* 128:59–65; and PCT Publication No. WO 94/18318.

In vitro translation-based libraries include but are not limited to those described in PCT Publication No. WO 91/05058 and Mattheakis et al., 1994, *Proc. Natl. Acad. Sci. USA* 91:9022–9026.

Examples of chemically synthesized libraries are described in Fodor et al., 1991, *Science* 251:767–773; Houghten et al., 1991, *Nature* 354:84–86; Lam et al., 1991, *Nature* 354:82–84; Medynski, 1994, *Bio/Technology* 12:709–710; Gallop et al., 1994, *J. Medicinal Chemistry* 37(9):1233–1251; Ohlmeyer et al., 1993, *Proc. Natl. Acad. Sci. USA* 90:10922–10926; Erb et al., 1994, *Proc. Natl. Acad. Sci. USA* 91:11422–11426; Houghten et al., 1992, *Biotechniques* 13:412; Jayawickreme et al., 1994, *Proc. Natl. Acad. Sci. USA* 91:1614–1618; Salmon et al., 1993, *Proc. Natl. Acad. Sci. USA* 90:11708–11712; Brenner & Lerner, 1992, *Proc. Natl. Acad. Sci. USA* 89:5381–5383; and PCT Publication No. WO 93/20242.

Screening the libraries can be accomplished by any of a variety of commonly known methods. See, e.g., the following references, which disclose screening of peptide libraries: Parmley and Smith, 1989, *Adv. Exp. Med. Biol.* 251:215–218; Scott and Smith, 1990, *Science* 249:386–390; Fowlkes et al., 1992; *BioTechniques* 13:422–427; Oldenburg et al., 1992, *Proc. Natl. Acad. Sci. USA* 89:5393–5397; Yu et al., 1994, *Cell* 76:933–945; Staudt et al., 1988, *Science* 241:577–580; Bock et al., 1992, *Nature* 355:564–566; Tuerk et al., 1992, *Proc. Natl. Acad. Sci. USA* 89:6988–6992; Ellington et al., 1992, *Nature* 355:850–852; Rebar and Pabo, 1993, *Science* 263:671–673; Ladner et al., U.S. Pat. No. 5,096,815; Ladner et al., U.S. Pat. No. 5,223,409; Ladner et al., U.S. Pat. No. 5,198,346; and PCT Publication No. WO 94/18318.

In a specific embodiment, screening can be carried out by contacting the library members with a WOL protein or peptide (or derivative or analog) immobilized on a solid phase and harvesting those library members that bind to the peptide (or derivative or analog). Examples of such screening methods, termed "panning" techniques are described by way of example in Parmley & Smith, 1988, *Gene* 73:305–318; Fowlkes et al., 1992, *BioTechniques* 13:422–427; PCT Publication No. WO 94/18318; and in references cited herein above.

In another embodiment, the two-hybrid system for selecting interacting proteins or peptides in yeast (Fields & Song, 1989, *Nature* 340:245–246; Chien et al., 1991, *Proc. Natl. Acad. Sci. USA* 88:9578–9582) can be used to identify molecules that specifically bind to a WOL protein or peptide.

Binding interactions between two or more components can be measured in a variety of ways. One approach is to label one of the components with an easily detectable label, place it together with the other component(s) in conditions under which they would normally interact, perform a separation step which separates bound labeled component from unbound labeled component, and then measure the amount of bound component. The effect of a test agent included in the binding reaction can be determined by comparing the amount of labeled component which binds in the presence of this agent to the amount which binds in its absence.

The separation step in this type of procedure can be accomplished in various ways. In one approach, (one of) the binding partner(s) for the labeled component can be immobilized on a solid phase prior to the binding reaction, and unbound labeled component can be removed after the binding reaction by washing the solid phase. Attachment of the binding partner to the solid phase can be accomplished in various ways known to those skilled in the art, including, but not limited to, chemical cross-linking, non-specific adhesion to a plastic surface, interaction with an antibody attached to the solid phase, interaction between a ligand attached to the binding partner (such as biotin) and a ligand-binding protein (such as avidin or streptavidin) attached to the solid phase, and so on.

Alternatively, the separation step can be accomplished after the labeled component had been allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner, a ligand-binding protein which can interact with a ligand previously attached to the binding partner, and so on.

Screening procedures should use appropriately stringent conditions. For guidance regarding such conditions see, for example, Sambrook et al., 1989, *Molecular Cloning: A Laboratory Manual*, Second Edition, Cold Spring Harbor Press, N.Y.; and Ausubel et al., 1989, *Current Protocols in Molecular Biology*, Greene Publishing Associates and Wiley Interscience, N.Y.

The above methods will isolate library members which bind the WOL protein or peptide. Stringency conditions can be varied to determine the specificity and strength of the interaction.

5.6. WOL Promoters

According to the present invention, WOL promoters and functional portions thereof described herein refer to regions of genomic DNA associated with the WOL gene which are capable of promoting expression of an operably linked coding sequence in plants, such that the resulting expression pattern is specific to vascular tissue and pericycle in embryos and vascular tissue in roots and other mature organs. The WOL promoter described herein refers to the regulatory elements of WOL genes, i.e., regulatory regions of genes which are capable of selectively hybridizing to the nucleic acids described in Section 5.1, or regulatory sequences contained, for example, in the region between the translational start site of the *Arabidopsis* WOL gene and the T23K3/3 marker 4 kb upstream of the translational start site. In one embodiment, the regulatory region is 2.5 kb upstream of the translational start site. Homologous nucleotide sequences are also part of the invention and refer to nucleotide sequences including, but not limited to, WOL promoters in diverse plant species (e.g., promoters of orthologs of *Arabidopsis* WOL) as well as genetically engineered derivatives of the promoters described herein.

The present invention also provides to variants of the promoters of the invention. Such variants have an altered nucleic acid sequence that can function similarly to the WOL promoter. Using methods well-known in the art, one may screen for equivalent functionality and variation in specificity of expression pattern among natural variants or experimentally-induced variants. In this manner it is possible to choose and design primers based on the desired specificity of expression.

Methods used for the synthesis, isolation, molecular cloning, characterization and manipulation of WOL promoter sequences are well known to those skilled in the art. See, e.g., the techniques described in Sambrook et al., 1989, *Molecular Cloning A Laboratory Manual*, 2nd. ed., Cold Spring Harbor Laboratory, Cold Spring Harbor, N.Y.

According to the present invention, WOL promoter sequences or portions thereof described herein may be obtained from appropriate plant sources from cell lines or recombinant DNA constructs containing WOL promoter sequences, and/or by chemical synthetic methods. WOL promoter sequences can be obtained from genomic clones containing sequences 5' upstream of WOL coding sequences. Such 5' upstream clones may be obtained by screening genomic libraries using WOL protein coding sequences, particularly those encoding WOL -terminal sequences, from WOL gene clones obtained as described in Sections 5.1 and 6. Standard methods that may used in such screening include, for example, the method set forth in Benton & Davis, 1977, *Science* 196:180 for bacteriophage libraries; and Grunstein & Hogness, 1975, *Proc. Nat. Acad. Sci. U.S.A.* 72:3961–3965 for plasmid libraries.

The full extent and location of WOL promoters within such 5' upstream clones may be determined by the functional assay described below. In the event a 5' upstream clone does not contain the entire WOL promoter as determined by the functional assay, the insert DNA of the clone may be used to isolate genomic clones containing sequences further 5' upstream of the WOL coding sequences. Such further upstream sequences can be spliced on to existing 5' upstream sequences and the reconstructed 5' upstream region tested for functionality as a WOL promoter (i.e., promoting specific expression in vascular tissue and pericycle of embryos and/or roots of an operably linked gene in plants). This process may be repeated until the complete WOL promoter is obtained.

The location of the WOL promoter within genomic sequences 5' upstream of the WOL gene isolated as described above may be determined using any method known in the art. For example, the 3'-end of the promoter may be identified by locating the transcription initiation site, which may be determined by methods such as RNase protection (e.g., Liang et al., 1989, *J. Biol. Chem.* 264: 14486–98), primer extension (e.g., Weissenborn & Larson, 1992, *J. Biol. Chem.* 267:6122–31), and/or reverse transcriptase/PCR. The location of the 3'-end of the promoter may be confirmed by sequencing and computer analysis, examining for the canonical AGGA or TATA boxes of promoters that are typically 50–60 bp and 25–35 bp 5'-upstream of the transcription initiation site. The 5'-end promoter may be defined by deleting sequences from the 5'-end of the promoter containing fragment, constructing a transcriptional or translational fusion of the resected fragment and a reporter gene, and examining the expression characteristics of the chimeric gene in transgenic plants. Reporter genes that may be used to such ends include, but are not limited to, GUS, CAT, luciferase, β-galactosidase and C1 and R gene controlling anthocyanin production.

According to the present invention, a WOL promoter is one that confers to an operably linked gene in a transgenic plant tissue-specific expression in the presumptive pericycle tissue and the presumptive vascular tissue of embryonic hypocotyl, and/or in the pericyle and vascular tissue of the mature organs, especially the root. A WOL promoter comprises the region between about −7,000 bp and +1 bp upstream of the transcription initiation site of the WOL gene (SEQ ID NO:33). In one embodiment, a WOL promoter fragment which comprises nucleotides 3025 to 7025 of SEQ ID NO:33 (SEQ ID NO:34) is capable of tissue specific expression in the presumptive pericycle tissue and the presumptive vascular tissue of embryonic hypocotyl, and/or in the pericyle and vascular tissue of the mature root organs, especially the root. In another embodiment, a WOL promoter fragment which comprises nucleotides 4508 to 7025 of SEQ ID NO:33 (SEQ ID NO:35) is capable of tissue specific expression in the presumptive pericycle tissue and the presumptive vascular tissue of embryonic hypocotyl, and/or in the pericyle and vascular tissue of the mature root and hypocotyl. Additional cis-regulatory elements may also be located in the intronic or 3' downstream sequences. In these embodiments, the expression patterns of gene products driven by WOL promoter fragments are not only tissue-specific, but are in part organ-specific at defined developmental stages.

A chimeric WOL promoter is within the scope of the present invention. As used herein, a "chimeric promoter" refers to a promoter that comprises functional portions of two different plant promoters. In one embodiment a native WOL promoter or portion thereof is modified by a regulatory elements from a heterologous promoter. Alternatively, a heterologous promoter is modified by the attachment of regulatory elements derived from the WOL promoter. In one embodiment the regulatory elements may be cis-regulatory elements (see Section 5.7). One example of a heterologous promoter is the SCARECROW promoter as identified in United States patent application of Benfey et al. for "Scarecrow Gene, Promoter and Uses Thereof"(WO97/41152, published Nov. 6, 1997), which is incorporated herein by reference in its entirety for its relevant teaching.

The manner of chimeric promoter constructions may be any well known in the art. For examples of approaches that can be used in such constructions, see Fluhr et al., 1986, *Science* 232:1106–12; Ellis et al., 1987, *EMBO J.* 6:11–16; Strittmatter & Chua, 1987, *Proc. Natl. Acad. Sci. USA* 84:8986–90; Poulsen & Chua, 1988, *Mol. Gen. Genet.* 214:16–23; Comai et al., 1991, *Plant Mol. Biol.* 15:373–81; Aryan et al., 1991, *Mol. Gen. Genet.* 225:65–71.

According to the present invention, where a WOL promoter or a recombinant WOL promoter is used to express a desired protein, the DNA construct is designed so that the protein coding sequence is ligated in phase with the translational initiation codon downstream of the promoter. Where the promoter fragment is missing 5' leader sequences, a DNA fragment encoding both the protein and its 5' RNA leader sequence is ligated immediately downstream of the transcription initiation site. Alternatively, an unrelated 5' RNA leader sequence may be used to bridge the promoter and the protein coding sequence. In such instances, the design should be such that the protein coding sequence is ligated in phase with the initiation codon present in the leader sequence, or ligated such that no initiation codon is interposed between the transcription initiation site and the first methionine codon of the protein.

Further, it may be desirable to include additional DNA sequences in the protein expression constructs. Examples of additional DNA sequences include, but are not limited to, those encoding: a 3' untranslated region; a transcription termination and polyadenylation signal; an intron; a signal peptide (which facilitates the secretion of the protein); or a transit peptide (which targets the protein to a particular cellular compartment such as the nucleus, chloroplast, mitochondria, or vacuole).

5.7. Cis-Regulatory Elements of WOL Promoters

According to the present invention, the cis-regulatory elements within a WOL promoter may be identified using any method known in the art. For example, the location of cis-regulatory elements within an inducible promoter may be identified using methods such as DNase or chemical footprinting (e.g., Meier et al., 1991, *Plant Cell* 3:309–15) or gel retardation (e.g., Weissenborn & Larson, 1992, *J. Biol. Chem.* 267–6122–31; Beato, 1989, *Cell* 56:335–44; Johnson et al., 1989, *Ann. Rev. Biochem.* 58:799–839). Additionally, resectioning experiments may also be employed to define the location of the cis-regulatory elements. For example, an inducible promoter-containing fragment may be resected from either the 5' or 3'-end using restriction enzyme or exonuclease digests.

To determine the location of cis-regulatory elements within the sequence containing the inducible promoter, the 5'- or 3'-resected fragments, internal fragments to the inducible promoter containing sequence, or inducible promoter fragments containing sequences identified by footprinting or gel retardation experiments may be fused to the 5'-end of a truncated plant promoter, and the activity of the chimeric promoter in transgenic plant examined. Useful truncated promoters to these ends comprise sequences starting at or about the transcription initiation site and extending to no more than 150 bp 5' upstream. These truncated promoters generally are inactive or are only minimally active. Examples of such truncated plant promoters may include, among others, a "minimal" CaMV 35S promoter whose 5' end terminates at position −46 bp with respect to the transcription initiation site (Skriver et al., 1991, *Proc. Natl. Acad. Sci. USA* 88:7266–70); the truncated "−90 35S" promoter in the X-GUS-90 vector (Benfey & Chua, 1989, *Science* 244:174–81); a truncated "−101 nos" promoter derived from the nopaline synthase promoter (Aryan et al., 1991, *Mol. Gen. Genet.* 225:65–71); and the truncated maize Adh-1 promoter in pADcat 2 (Ellis et al., 1987, *EMBO J.* 6:11–6).

According to the present invention, a cis-regulatory element of a WOL promoter is a sequence that confers tissue-specific expression in embryos and/or roots to a truncated promoter. Expression may or may not be organ exclusive.

5.8. WOL Promoter-Driven Expression Vectors

The properties of the nucleic acid sequences are varied as are the genetic structures of various potential host plant cells. In the preferred embodiments of the present invention, described herein, a number of features which an artisan may recognize as not being absolutely essential, but clearly advantageous are used. These include methods of isolation, synthesis or construction of nucleic acid constructs, the manipulation of the nucleic acid constructs to be introduced into plant cells, certain features of the nucleic acid constructs, and certain features of the vectors associated with the nucleic acid constructs.

Further, the nucleic acid constructs of the present invention may be encoded on DNA or RNA molecules. According to the present invention, it is preferred that the desired, stable genotypic change of the target plant be effected through genomic integration of exogenously introduced nucleic acid construct(s), particularly recombinant DNA constructs. Nonetheless, according to the present invention, such genotypic changes can also be effected by the introduction of episomes (DNA or RNA) that can replicate autonomously and that are somatically and germinally stable. Where the introduced nucleic acid constructs comprise RNA, plant transformation or gene expression from such constructs may proceed through a DNA intermediate produced by reverse transcription.

The present invention provides for use of recombinant DNA constructs which contain tissue-specific and developmental-specific promoter fragments and functional portions thereof. As used herein, a functional portion of a WOL promoter is capable of functioning as a tissue-specific promoter in the embryo and/or root vasculature of a plant, or in the developing vascular tissues of other organs. The functionality of such sequences can be readily established by any method known in the art. Such methods include, for example, constructing expression vectors with such sequences and determining whether they confer tissue-specific expression in the embryo and/or root vasculature to a marker gene operably linked to the above-mentioned sequences.

The WOL promoters of the invention may be used to direct the expression of any desired protein, or to direct the expression of a RNA product, including, but not limited to, an "antisense" RNA or ribozyme. Such recombinant constructs generally comprise a native WOL promoter or a recombinant WOL promoter derived therefrom, ligated to the nucleic acid sequence encoding a desired heterologous gene product.

A recombinant WOL promoter is used herein to refer to a promoter that comprises a functional portion of a native WOL promoter or a promoter that contains native promoter sequences that is modified by a regulatory element from a WOL promoter. Alternatively, a recombinant inducible promoter derived from the wol promoter may be a chimeric promoter, comprising a full-length or truncated plant promoter modified by the attachment of one or more WOL cis-regulatory elements.

The manner of chimeric promoter constructions may be any well known in the art. For examples of approaches that can be used in such constructions, see Fluhr et al., 1986, *Science* 232:1106–12; Ellis et al., 1987, *EMBO J.* 6:11–6; Strittmatter & Chua, 1987, *Proc. Natl. Acad. Sci. USA* 84:8986–90; Poulsen & Chua, 1988, *Mol. Gen. Genet.* 214:16–23; Comai et al., 1991, *Plant Mol. Biol.* 15:373–81; Aryan et al., 1991, *Mol. Gen. Genet.* 225:65–71.

According to the present invention, where a WOL promoter or a recombinant WOL promoter is used to express a desired protein, the DNA construct is designed so that the protein coding sequence is ligated in phase with the translational initiation codon downstream of the promoter. Where the promoter fragment is missing 5' RNA leader sequences, a DNA fragment encoding both the protein and its 5' RNA leader sequence is ligated immediately downstream of the transcription initiation site. Alternatively, an unrelated 5' RNA leader sequence may be used to bridge the promoter and the protein coding sequence. In such instances, the design should be such that the protein coding sequence is ligated in phase with the initiation codon present in the leader sequence, or ligated such that no initiation codon is interposed between the transcription initiation site and the first methionine codon of the protein.

Further, it may be desirable to include additional DNA sequences in the protein expression constructs. Examples of additional DNA sequences include, but are not limited to, those encoding: a 3' untranslated region; a transcription termination and polyadenylation signal; an intron; a signal peptide (which facilitates the secretion of the protein); or a transit peptide (which targets the protein to a particular cellular compartment such as the nucleus, chloroplast, mitochondria, or vacuole).

5.9. Production of Transgenic Plants and Plant Cells

According to the present invention, a desirable plant or plant cell may be obtained by transforming a plant cell with the nucleic acid constructs described herein. In some instances, it may be desirable to engineer a plant or plant cell with several different gene constructs. In one embodiment, a heterologous protein may also be expressed to produce transgenic plants with altered expression at two loci. An example of a heterologous protein includes, but is not limited to, the SCARECROW protein which has been described in U.S. patent application of Benfey et al. for "Scarecrow Gene Promoter and Uses Thereof", filed Nov. 5, 1998 (identified as docket number 5914-0075), which is incorporated herein by reference in its entirety for its relevant teaching. Thus, for example, and not by way of limitation, a WOL/SCARECROW double mutant can be produced and may have only protoxylem and a cell layer with the characteristics of endodermis and cortex. Such engineering may be accomplished by transforming a plant or plant cell with all of the desired nucleic acid constructs simultaneously. Alternatively, the engineering may be carried out sequentially. That is, transforming with one nucleic acid construct, obtaining the desired transformant after selection and screening, transforming the transformant with a second nucleic acid construct, and so on.

In an embodiment of the present invention, *Agrobacterium* is employed to introduce the nucleic acid constructs into plants. Such transformations preferably use binary *Agrobacterium* T-DNA vectors (Bevan, 1984, *Nuc. Acid Res.* 12:8711–21), and the co-cultivation procedure (Horsch et al., 1985, *Science* 227:1229–31). Generally, the *Agrobacterium* transformation system is used to engineer dicotyledonous plants (Bevan et al., 1982, *Ann. Rev. Genet.* 16:357–84; Rogers et al., 1986, *Methods Enzymol.* 118: 627–41). The *Agrobacterium* transformation system may also be used to transform, as well as transfer, DNA to monocotyledonous plants and plant cells (see Hernalsteen et al., 1984, *EMBO J.* 3:3039–41; Hooykass-Van Slogteren et al., 1984, *Nature* 311:763–4; Grimsley et al., 1987, *Nature* 325:1677–79; Boulton et al., 1989, *Plant Mol. Biol.* 12:31–40.; Gould et al., 1991, *Plant Physiol.* 95:426–34).

In other embodiments, various alternative methods for introducing recombinant nucleic acid constructs into plants and plant cells may also be utilized. These other methods are particularly useful where the target is a monocotyledonous plant or plant cell. Alternative gene transfer and transformation methods include, but are not limited to, protoplast transformation through calcium-, polyethylene glycol (PEG)- or electroporation-mediated uptake of naked DNA (see Paszkowski et al., 1984, *EMBO J.* 3:2717–22; Potrykus et al., 1985, *Mol. Gen. Genet.* 199:169–177; Fromm et al., 1985, *Proc. Natl Acad. Sci. USA* 82:5824–8; Shimamoto, 1989, *Nature* 338:274–6), and electroporation of plant tissues (D'Halluin et al., 1992, *Plant Cell* 4:1495–1505). Additional methods for plant cell transformation include microinjection, silicon carbide mediated DNA uptake (Kaeppler et al., 1990, *Plant Cell Reporter* 9:415–8), and microprojectile bombardment (Klein et al., 1988, *Proc. Natl. Acad. Sci. USA* 85:4305–9; Gordon-Kamm et al., 1990, *Plant Cell* 2:603–18).

According to the present invention, a wide variety of plants may be engineered for the desired physiological and agronomic characteristics described herein using the nucleic acid constructs of the instant invention and the various transformation methods mentioned above. In preferred embodiments, target plants for engineering include, but are not limited to, crop plants such as maize, wheat, rice, soybean, tomato, tobacco, carrots, peanut, potato, sugar beets, sunflower, yam, *Arabidopsis*, rape seed, petunia, and spruce, as well as species of the genera *Betula, Populus, Pinus,* and *Eucalyptus.*

According to the present invention, desired plants and plant cells may be obtained by engineering the nucleic acid constructs described herein into a variety of plant cell types, including, but not limited to, protoplasts, tissue culture cells, tissue and organ explants, pollen, embryos as well as whole plants. In an embodiment of the present invention, the engineered plant material is selected or screened for transformants (i.e., those that have incorporated or integrated the introduced nucleic acid construct or constructs) following the approaches and methods described below. An isolated transformant may then be regenerated into a plant. Alternatively, the engineered plant material may be regenerated into a plant, or plantlet, before subjecting the derived plant, or plantlet, to selection or screening for the marker gene traits. Procedures for regenerating plants from plant cells, tissues or organs, either before or after selecting or screening for marker gene or genes, are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amounts of the antibiotic or herbicide to which the transforming marker gene construct confers resistance. Further, transformed plants and plant cells may also be identified by screening for the activities of any visible marker genes (e.g., the β-glucuronidase, luciferase, GFP, B or C1 genes) that may be present on the recombinant nucleic acid constructs of the present invention. Such selection and screening methodologies are well known to those skilled in the art.

Physical and biochemical methods may also be used to identify a plant or plant cell transformant containing the nucleic acid constructs of the present invention. These methods include but are not limited to: 1) detection and determination of the structure of the recombinant DNA insert by Southern blot or PCR amplification; 2) detection and examination of RNA transcripts of the nucleic acid constructs by Northern blot, S-1 RNase protection, primer-extension or reverse transcriptase-PCR amplification; 3) detection of enzyme or ribozyme activity (where such gene products are encoded by the nucleic acid construct) by enzymatic assays; 4) detection of protein products of the nucleic acid construct by protein gel electrophoresis, western blot, immunoprecipitation, or enzyme-linked immunoassays; and 5) measurement of compounds produced as a consequence of the expression of the introduced nucleic acid constructs by biochemical methods. Additional techniques, such as in situ hybridization, enzyme staining, and immunostaining, may also be used to detect the presence or expression of the recombinant construct in specific plant organs and tissues. Methods of performance of the above-mentioned assays are well known to those skilled in the art.

5.9.1. Transgenic Plants that Ectopically Express WOL

In accordance to the present invention, a plant that expresses a recombinant WOL nucleic acid may be engineered by transforming a plant cell with a nucleic acid construct comprising a plant promoter operably associated with a sequence encoding a WOL protein or a fragment thereof. Operably associated is used herein to mean that transcription controlled by the associated promoter would produce a functional mRNA, whose translation would produce the WOL protein. The plant promoter may be constitutive or inducible. Useful constitutive promoters include, but are not limited to, the CaMV 35S promoter, the T-DNA mannopine synthetase promoter, and their various derivatives. Useful inducible promoters include, but are not limited to, the promoters of ribulose bisphosphate carboxylase (RUBISCO) genes, chlorophyll a/b binding protein (CAB) genes, heat shock genes, the defense responsive gene (e.g., phenylalanine ammonia lyase genes), wound induced genes (e.g., hydroxyproline rich cell wall protein genes), chemically-inducible genes (e.g., nitrate reductase genes, gluconase genes, chitinase genes, PR-1 genes etc.), dark-inducible genes (e.g., asparagine synthetase gene as described by U.S. Pat. No. 5,256,558), and developmentally regulated genes (e.g., Shoot Meristemless gene).

In yet another embodiment of the present invention, it may be advantageous to transform a plant with a nucleic acid construct operably linking a modified or artificial promoter to a sequence encoding a WOL protein or a fragment thereof. Such promoters typically have unique expression patterns and/or expression levels not found in natural promoters because they are constructed by recombining structural elements from different promoters. See, e.g., Salina et al., 1992, *Plant Cell* 4:1485–93, for examples of artificial promoters constructed from combining cis-regulatory elements with a promoter core.

In a preferred embodiment of the present invention, the associated promoter is a strong root and/or embryo-specific plant promoter such that the WOL protein is overexpressed in the transgenic plant.

In yet another preferred embodiment of the present invention, the overexpression of WOL protein in root vasculature may be engineered by increasing the copy number of the WOL gene. One approach to producing such transgenic plants is to transform with nucleic acid constructs that contain multiple copies of the complete WOL gene (i.e., with its own native wol promoter). Another approach is repeatedly transform successive generations of a plant line with one or more copies of the complete WOL gene. Yet another approach is to place a complete WOL gene in a nucleic acid construct containing an amplification-selectable marker (ASM) gene such as the glutamine synthetase or dihydrofolate reductase gene. Cells transformed with such constructs is subjected to culturing regimes that select cell lines with increased copies of complete WOL gene. See, e.g., Donn et al., 1984, *J. Mol. Appl. Genet.* 2:549–62, for a selection protocol used to isolate of a plant cell line containing amplified copies of the GS gene. Cell lines with amplified copies of the WOL gene can then be regenerated into transgenic plants.

5.9.2. Transgenic Plants that Suppress Endogenous WOL Expression

In accordance with the present invention, a desired plant may be engineered by suppressing WOL activity. In one embodiment, the suppression may be engineered by transforming a plant with a nucleic acid construct encoding an antisense RNA or ribozyme complementary to a segment or the whole of WOL RNA transcript, including the mature target mRNA. In another embodiment, WOL gene suppression may be engineered by transforming a plant cell with a nucleic acid construct encoding a ribozyme that cleaves the WOL mRNA transcript. In another embodiment, the WOL mRNA transcript can be suppressed through the use of RNA interference (RNAi). In yet another embodiment, antisense technology can be used to inhibit WOL mRNA expression. Alternatively, the plant can be engineered, e.g., via targeted homologous recombination to inactive or "knock-out" expression of the plant's endogenous WOL.

For all of the aforementioned suppression constructs, it is preferred that such nucleic acid constructs express specifically in the embryonic tissues and/or the vascular tissue of the root. Alternatively, it may be preferred to have the suppression constructs expressed constitutively. Thus, constitutive promoters, such as the nopaline, CaMV 35S promoter, may also be used to express the suppression constructs. A most preferred promoter for these suppression constructs is a WOL promoter.

In accordance with the present invention, desired plants with suppressed target gene expression may also be engineered by transforming a plant cell with a co-suppression construct. A co-suppression construct comprises a functional promoter operatively associated with a complete or partial WOL nucleic acid sequence. It is preferred that the operatively associated promoter be a strong, constitutive promoter, such as the CaMV 35S promoter. Alternatively, the co-suppression construct promoter can be one that expresses with the same tissue and developmental specificity as the wol gene.

According to the present invention, it is preferred that the co-suppression construct encodes an incomplete WOL mRNA, although a construct encoding a fully functional WOL mRNA or enzyme may also be useful in effecting co-suppression.

In accordance with the present invention, desired plants with suppressed target gene expression may also be engineered by transforming a plant cell with a construct that can effect site-directed mutagenesis of the WOL gene. For discussions of nucleic acid constructs for effecting site-directed mutagenesis of target genes in plants see, e.g., Offringa et al., 1990, *EMBO J.* 9:3077–84; and Kanevskii et al., 1990, *Dokl. Akad. Nauk. SSSR* 312:1505–7. It is preferred that such constructs effect suppression of WOL genes by replacing the endogenous WOL gene sequence through homologous recombination with either an inactive or deleted WOL protein coding sequence.

5.9.3. Transgenic Plants that Express a Transgene Controlled by the WOL Promoter In accordance with the present invention, a desired plant may be engineered to express a nucleic acid encoding a gene product of interest under the control of the WOL promoter. WOL promoters and functional portions thereof refer to regions of the nucleic acid sequence which are capable of promoting tissue-specific transcription of a gene of interest when operably linked to that gene. In the case of WOL, tissue-specific expression exists in the embryo and/or root vasculature of a plant, or in the developing vascular tissue of other organs. The WOL promoter described herein refers to the regulatory elements of WOL genes as described in Sections 5.7 and 5.8.

Genes that may be beneficially expressed in the embryo and/or root vasculature of a plant include genes involved in nitrogen fixation or cytokines or auxins, or genes which regulate growth, or growth of roots. In addition, genes encoding proteins that confer on plants herbicide, salt, or pest resistance may be engineered for tissue specific expression. The nutritional value of root crops may also be enhanced through WOL promoter driven expression of nutritional proteins (such as starch, lignin, or cellulose). Alternatively, therapeutically useful proteins may be expressed specifically in root crops.

Genes that may be beneficially expressed in the stems of plants include those involved in starch, lignin, cellulose biosynthesis, pest resistance, and cell expansion genes controlling fibre formation.

In other embodiments properties of wood in trees are altered. In one such embodiment, overexpression of a WOODEN LEG protein or polypeptide in a transgenic plant is used to increase layers of wood (vascular) tissues in trees. In another embodiment, ectopic expression of a WOODEN LEG protein or polypeptide in a transgenic plant is driven by a promoter other than the WOL promoter in order to increase vascular development in certain tissue layers, thus resulting in the formation of more wood. In still other embodiments, the WOL promoters of the invention are linked to a heterologous gene known to be involved in aspects of wood formation and genetically engineered into a plant. Such heterologous genes include, but are not limited to, genes known to have an effect on lignin production and/or composition such as the Caffeic Acid O-Methyltransferase (cOMT) gene of Moyle, et al., 1999. *Plant Physiol.* 119: 1147 and the SAM gene of Meng and Campbell,1995. *Plant Physiol.* 108: 1749. Genes related to cellulose production and degradation are also of great interest such as the cellulose synthase gene of Arioli et al., 1998. Science 279:717–720. In still other embodiments, a gene controlling pigmentation and aspects of vascular patterning effecting wood grain appearance is expressed under the control of a WOL promoter incorporated into the invention. Thus, the invention provides methods that utilize WOL promoters to improve the quality of wood and/or adjust the characteristics of wood to meet specific, e.g. commercial, specifications.

In accordance with the present invention, desired plants which express a heterologous gene of interest under the control of the WOL promoter may be engineered by transforming a plant cell with WOL promoter driven constructs using those techniques described in this Section 5.9.

5.9.4. Screening of Transformed Plants for Those Having Desired Altered Traits It will be recognized by those skilled in the art that in order to obtain transgenic plants having the desired engineered traits, screening of transformed plants (i.e., those having an nucleic acid construct of the invention) having those traits may be required. For example, where the plants have been engineered for ectopic overexpression of a WOL nucleic acid, transformed plants are examined for those expressing a WOL gene product at the desired level and in the desired tissues and developmental stages. Where the plants have been engineered for suppression of a WOL gene product, transformed plants are examined for those expressing a WOL gene product (e.g., RNA or protein) at reduced levels in various tissues. The plants exhibiting the desired physiological changes, e.g., ectopic WOL overexpression or WOL suppression, may then be subsequently screened for those plants that have the desired structural changes at the plant level (e.g., transgenic plants with overexpression or suppression of the WOL gene having the desired altered root or stem structure). Altered root structure can include, but is not limited to longer roots, shorter roots, thicker roots, thinner roots, and roots with a predominantly adventitious origin. Altered stem structure can include, but is not limited to, thicker or thinner stems. The same principle applies to obtaining transgenic plants having tissue-specific expression of a heterologous gene in embryos and/or roots by the use of a WOL promoter driven expression construct.

Alternatively, the transformed plants may be directly screened for those exhibiting the desired structural and functional changes. In one embodiment, such screening may be for the size, length or pattern of the root of the transformed plants. In other embodiments, the screening of the transformed plants may be for improved agronomic characteristics (e.g., faster growth or deeper root growth, more extensive wood production, etc.), as compared to unengineered progenitor plants, when cultivated under various growth conditions (e.g., soils or media containing different amount of nutrients, water content).

According to the present invention, plants engineered with WOL overexpression may exhibit improved vigorous growth characteristics when cultivated under conditions where large and thicker roots are advantageous. Plants engineered for WOL suppression may exhibit improved vigorous growth characteristics when cultivated under conditions where thinner roots are advantageous.

Engineered plants and plant lines possessing such improved agronomic characteristics may be identified by examining any of following parameters: 1) the rate of growth, measured in terms of rate of increase in fresh or dry weight; 2) vegetative yield of the mature plant, in terms of fresh or dry weight; 3) the seed or fruit yield; 4) the seed or fruit weight; 5) the total nitrogen content of the plant; 6) the total nitrogen content of the fruit or seed; 7) the free amino acid content of the plant; 8) the free amino acid content of the fruit or seed; 9) the total protein content of the plant; and 10) the total protein content of the fruit or seed. The procedures and methods for examining these parameters are well known to those skilled in the art.

According to the present invention, a desired plant is one that exhibits improvement over the control plant (i.e., progenitor plant) in one or more of the aforementioned parameters. In an embodiment, a desired plant is one that shows at least 5% increase over the control plant in at least one parameter. In a preferred embodiment, a desired plant is one that shows at least 20% increase over the control plant in at least one parameter. Most preferred is a plant that shows at least 50% increase in at least one parameter.

6. EXAMPLE 1

Characterization of WOL

This example shows the identification of WOL, a gene involved in the control of asymmetric cell divisions and xylem differentiation through a specific signal transduction pathway. Sequence analysis shows that the WOL protein is a novel two component signal transducer and is required for asymmetric cell divisions during vascular tissue morphogenesis. In situ studies show that WOL is expressed in the vascular cylinder and pericycle in embryogenesis through at least five days after germination. These findings indicate that the WOL gene regulates key events that establish the asymmetric division that generate vascular patterning.

6.1. Introduction

The WOL locus was previously identified by a recessive mutation that resulted in reduced cell number and exclusive xylem differentiation within the vascular tissue (Scheres et al., 1995, *Development* 121:53–62). This reduced cell number was first observed during embryogenesis, when a cell division process failed to take place in the root and lower hypocotyl region soon after the torpedo stage. Subsequently, this pattern was elaborated by the procambial initials during primary root development (Scheres et al. 1995, supra).

6.2. WOL is Essential for Vascular Asymmetric Cell Division

The WOL-dependent divisions that resulted in the patterning of xylem and phloem of the root were identified by determining the vascular cell lineage relationships in the primary root of wildtype and wol *Arabidopsis* (FIG. 1, Table 1). Examination of primary root meristem serial sections was conducted to ascertain the effects of wol mutant on this tissue. Seedlings were fixed according to Scheres et al. (1994, *Development* 120:2475–87) and embedded using Leica Historesin (Heidelberg, Germany). Sections (2–3 mm) were made on a Leica RM2165 rotary microtome, using a Leica microtome knife. Sections were stained in a 0.05% toluidine blue solution in water and photographed on an Olympus Provis microscope using a Sensicam 12 bit cooled camera (PCO, ccd imaging). Images were processed with Adobe Photoshop 4.0.1.

In serial sections of the primary root meristem (FIG. 1), xylem cell lineages formed an axis composed of 4–5 cell files very close to the underlying quiescent center (FIG. 1C, schematic). Two domains of initials (2–5 cells each; FIGS.

1B–C) that gave rise to the phloem cell lineages and to the undifferentiated procambial cell lineages through asymmetric cell divisions (FIGS. 1C–G; schematic) flanked this axis. The number and exact pattern of these procambial divisions showed some variability between individual seedlings, which is in contrasted to the invariant pattern of cell lineages in the endodermis and outer layers (Scheres et al., 1994, supra). These divisions were asymmetric in the sense that they give rise to multiple cell lineages with different fates (Horvitz & Herskowitz, 1992, Cell 68:237–55). The histologically early phloem differentiation as compared to xylem differentiation (FIGS. 1H–I) was consistent with previous descriptions in other species (Esau, K. 1977. *Anatomy of Seed Plants*. John Wiley & Sons, New York, N.Y., ed. 2).

In wol, the periclinal cell divisions described above are absent (FIGS. 1J–K, schematic) with the exception of a few divisions that slightly increased cell number in the vascular cylinder (Table 1). Furthermore, the number of vascular initials in wol was slightly lower than in wild-type, which indicated that some of the embryonic divisions required to form the initials did not occur. Taken together, WOL activity was associated with a set of formative divisions that first took place during the late stages of embryogenesis (Scheres et al. 1995, supra) and that continued to propagate the pattern in the root meristem.

TABLE 1

|  | Initial cells | Differentiated cells |
|---|---|---|
| wt | 11 ± 1.49 | 31 ± 1.71 |
| wol | 8 ± 2.23 | 9 ± 2.07 |

Cell numbers in the primary root of *Arabidopsis* (wt n=8; wol n=6). Numbers of initial cells were counted in sections made directly above the quiescent center, numbers of differentiated cells were made approximately 200 mm above the quiescent center. Mean cell numbers and ±SD are indicated.

6.3. WOL is Required for Vascular Morphogenesis

The role of WOL in phloem specification was analyzed previously in the context of a double mutant of wol and fass (a mutation resulting in supernumerary cell layers). The double mutants from the cross described in Scheres et al. (1995, supra) were isolated by analysis of the fass-looking plants of the F3 segregating in the wol background. Wol x fass double mutant seedlings were cleared with acidified methanol (20% MeOH; 4% concentrated HCl in H$_2$O) and incubated at 55°–57° C. for 15 minutes. The acidified methanol was then replaced with a basic solution (7% NaOH in 60% EtOH) and incubated for 15 minutes at room temperature. The seedlings were rehydrated in several steps by incubation in varying concentrations of EtOH (40%, then 20% and finally in 10% EtOH). The seedlings were stained for 5 minutes in 0.01% basic fuchsin solution, destained in 70% ethanol and rehydrated to 10% ethanol solution. An equal amount of 50% glycerol was added and then incubated another 30 minutes. Seedlings were mounted in 50% glycerol. CLSM images were taken on an Axiovert 135M confocal microscope with an argon ion laser (568+488 nm emission). Image processing consisted of Kalman filtering during image acquisition (Bio-Rad software). Optical sections were projected together to form a composite image of the vascular bundle.

In the wol x fass double mutant, there was an increase in the number of vascular cell layers with phloem markers observed in the vascular cylinder, indicating that WOL is not essential for phloem development. A model was proposed, in which xylem specification temporally precedes phloem development. Because the wol mutant had a reduced number of vascular precursor cells, all the available cells were specified as xylem (Scheres et al. 1995, supra). More recently, it was shown that xylem organization is also altered in wol (Cano-Delgado et al., 2000, *Development* 127:3395–3405). The xylem axis in wildtype consists of two types of cells: protoxylem, the two outermost cells with predominantly annular (ring like) cell wall thickenings which differentiates early, and metaxylem, the central cells with reticulate (more continuous) wall thickenings, which differentiates later (FIG. 2A). In contrast, the vascular cylinder of the wol primary root consists solely of protoxylem (FIG. 2B). Therefore, the status of xylem in the wol x fass background was investigated. Both protoxylem and metaxylem were found to be present (FIG. 2C). Thus, WOL was not necessary for metaxylem differentiation, but did have an indirect influence on xylem differentiation by controlling the number of cells in the vascular cylinder.

6.4. Cloning and Description of the *Arabidopsis* WOL Gene

The WOL locus of *Arabidopsis* was characterized genetically and molecularly. WOL, a putative two component histidine kinase with a receptor domain similar to that of the DhkA receptor of *Dictyostelium discoideum*, is shown to be required for a set of asymmetric cell divisions that establish the morphogenesis of vascular tissue in the root and hypocotyl region. The deduced domain structure of WOL suggests it represents a novel class among the two hybrid molecules characterized to date from plants, some other eukaryotes and bacteria. The WOL protein is a component of the signal transduction pathway regulating vascular cell proliferation and differentiation.

The molecular nature of the WOL gene product was identified through positional cloning of the WOL gene (FIG. 3A). WOL locus was cloned using chromosome walking techniques. CAPS (cleaved amplified polymorphic sequences, see Konieczny & Ausubel, 1993, *Plant J.* 4:403–10) markers T23K3/3 (SEQ ID NO:21) and Kin2/4 (SEQ ID NO:22) (and six other markers, see Table 2) between pre-existing markers RNS1 and rga were created by detecting polymorphism between Landsberg and Columbia ecotypes. Complementation vector pCOM32 was created by cloning a 13.8 kb Msc1 fragment into the SmaI of the pBIN19 derivative pRD400 (Datla et al., 1992, *Gene* 122: 383–4). The construct was transformed into *Agrobacterium tumefaciens* strain C58C1 pGV2260) (essentially as in Bevan, 1984, *Nucleic Acid Res.* 12:8711–21). wol plants were transformed with pCOM32 (Clough & Bent, 1998, *Plant J.* 16:735–43). Transgenic seedlings (T1) with long roots were selected by resistance to kanamycin. Presence of the transgene in these plants was confirmed by PCR. Segregation of the transgene in T2 generation was confirmed.

An *Arabidopsis* wol mutant was also rescued by inserting a transgene containing a fragment of pCOM32.

TABLE 2

CAPS Markers

| Marker | Location (in BAC) | Primers | Length | Restriction enzyme cutting sites (col and ler) |
|---|---|---|---|---|
| RGA (CAPS) | (F219) | GTTTAAGCAAGCGAGTATGC TTCGATTCAGTTCGGTTTAG (SEQ ID NO: 28) | 263 | RsaI: col 1 (143,120); ler 0 (263) |
| T8O11/1 (CAPS) | 4854–5743 (T8O11) | gaa ttc ttg ttt tag agt tcc tga gta gag tgt tct ttc tcc (SEQ ID NO: 37) | 890 | Hind2: col 0 (890); ler 1 (725,165) |
| Kin2/4 (CAPS) | 6274–7511 (T23K3) | ACTGAGAACCGAAGAAATCTGGG AGTCCGAAAAATGCCGAAATAC (SEQ ID NO: 22) | 1238 | Sac1: col 0 (1238); ler 1 (973,265) |
| Kin2–3 (CAPS) | 7993–9253 (T23K3) | AGA CAG ACG CCG TGA AAT CC TAT TAA TCC CAC GGG ATC G (SEQ ID NO: 38) | 1261 | Dde1: col 3: (572,421,219,49); ler 2 (572,470,219) |
| T23K3/2 (CAPS) | 13547–14655 (T23K3) | ctt gat gat tgt tga gtg ccc gtt cgg tgc gga tct tcc (SEQ ID NO: 39) | 1109 | Ksp632I: col 1 (611,498); ler 0 (1109) |
| T23K3/3 (CAPS) | 17173–18127 (T23K3) | caa aat gtg tgt gtg tcg gcc gta cca aag tcc aca cga ttc c (SEQ ID NO: 21) | 955 | Hph1: col 1 (577,377); ler 2 (577,275,102) |
| T23K3/4 (CAPS) | 66322–67455 (T23K3) | ggc tga ctt gac tct ctt ttc c ccg agt gct ttt tag agc c (SEQ ID NO: 40) | 1134 | Hinf1: col 6 (463,295,200,100,36,30,10); ler 5: (463,295,236,100,30,10) |
| T23K3/7 (SSLP) | 33713–34944 (T23K3) | tga tca cac atg gta cct ttc g gca agc tct tga tct ctc tag c (SEQ ID NO: 41) | 1232 | Dra1 + Hind3 (SSLP): col 4 (379,323,217, 273,40); ler 4 (379,323,202,273,40) |
| F504/1 (dCAPS) | 78313–78632 (F504) | gtg tga tga aac tgt ctc gcc gtg taa gct tgt taa gag ttt acc (SEQ ID NO: 42) | 319 | StyI: col 0 (319); ler 1: (25,294) |
| nga1145 (SSLP) | (T8K22) | cct tca cat cca aaa ccc ac gtg ata gac ttt gaa gaa ag (SEQ ID NO: 43) | 85–89 | ler (89); col (85) |
| RNS1 | (T17M13) | tat cca tct aac tgt gat gcc act ttg aca tca aaa cgt acc (SEQ ID NO: 27) | n.550 | Ava1: col 0 (n.550); ler 1 (n. 300,250) | ler = ecotype Landsberg erecta
col = ecotype Columbia

The wol locus was mapped to an 11 kb region between two CAPS markers in the BAC clone T23K3 (GenBank Accession Number AC007069) (FIG. 3A). The annotation (Lin et al., 1999, *Nature* 402:761–8) predicted only one gene (T23K3.2, a putative two component histidine kinase) in this region. The region between the CAPS markers was completely sequenced in wol and only one point mutation was found, converting $T_{278}$ to $I_{278}$ in the deduced amino acid sequence. The identity of the two component hybrid molecule was confirmed as WOL by complementation of the mutation with a 13.8 kb fragment of genomic DNA (pCOM32, FIG. 3A). Homozygous wol plants which contained the transgene had indeterminate root growth, normal cell number and a wild-type pattern of xylem, phloem and procambial cells (FIGS. 3C–D).

The WOL coding region was identified by sequencing the longest (T20648) of several ESTs (GenBank Accession Numbers AA586219, SEQ ID NO:14; AI992824, SEQ ID NO:15; and T20648, SEQ ID NO:16) homologous to the WOL locus. Gene specific primers were used in the RobusT RT-PCR Kit (Finnzymes Qy, Espoo, Finland) according to the manufacturer's instructions. To determine the 5'-UTR of the WOL mRNA the 5' RACE System for Rapid Amplifications of cDNA Ends version 2.0 (Life Technologies, Paisley, Scotland) was used according to the manufacturer's instructions. The major amplification products that resulted from the 5'RACE were cloned. Three different cDNA species (GenBank Accession Numbers AJ278528 (SEQ ID NO:1), AJ278529 (SEQ ID NO:2), and AJ278530 (SEQ ID NO:3)) corresponding to three different transcription start sites and alternative splicing schemes were detected (FIG. 3B). All resulted in an identical longest ORF of 1057 amino acid residues (SEQ ID NO:5), which indicated that the alternative splicing did not have an impact on the amino acid sequence of the gene product.

6.5. WOL is a Member of a Novel Family of Two Component Hybrid Molecules

The predicted WOL protein showed extensive similarity to two component hybrid molecules, and thus suggested that it functioned as a signal transducer (FIG. 3E). The WOL protein was shown to have a short N-terminal cytoplasmic domain (residues 1–105, SEQ ID NO:6) followed by an extracellular receptor (R) domain (residues 127–400, SEQ ID NO:8) flanked by two transmembrane regions (residues 106–126, SEQ ID NO:7 and residues 401–421, SEQ ID NO:9) and the C-terminal phosphorelay domain system with a histidine kinase domain (H) (residues 449–737, SEQ ID NO:10) and two receiver domains ($D_A$ and $D_B$) (residues 762–893, SEQ ID NO:11 and 922–1044, SEQ ID NO:12, respectively).

The WOL domain organization and receptor domain structure place it in a distinct subclass among previously identified plant two component receptors. The other receptors have been shown to function in ethylene or cytokinin signal transduction or in osmosensing (Chang et al., 1993, *Science* 262:539–44; Kakimoto, 1996, *Science* 274:982–5; Urao et al., 1999, *Plant Cell* 11:1743–54; Urao et al., 2000, *Trends Plant Sci.* 5: 67–74). The tandem arrangement of two putative receiver domains has been previously reported for an uncharacterized gene slr0322 of Synechochystis (Mizuno et al., 1996, *DNA Res.* 3:407–14). However, this gene does not exhibit significant homology to the WOL genes and may not be very closely related functionally. Among the two component molecules of bacteria, plants and some other eukaryotes characterized to date, the putative receptor domain, the histidine kinase domain and one of the two receiver domains ($D_B$) of WOL are most similar to DhkA receptor of *Dictyostelium discoideum* (SEQ ID NO:17). DhkA is essential for cellular organization during fruiting body development (Mizuno et al. 1996, supra) and its ligand may be a peptide (Wang et al., 1999, Mol Cell Biol. 7:4750–6). It is therefore possible that a homologous receptor-ligand interaction is specifying development both in slime molds and plants.

6.6. WOL Expression is Specific for the Vascular Cylinder

Specificity of WOL expression was determined using a gene specific probe (FIG. 3B). Genomic DNA preparation (Doyle & Doyle, 1990, *Focus* 12:13–5) was performed from 17-day-old seedlings. Southern blot analysis was performed with 15 mg of DNA and the $^{32}$P-labeled 256 bp PCR fragment (corresponding to nucleotides 10143 to 10398 of the BAC clone T23K3, SEQ ID NO:13) of WOL or a 1067 bp cDNA fragment (corresponding to nucleotides 10055 to 11204 of SEQ ID NO:1) of WOL genomic sequence as a probe (Maniatis et al., 1982, *Molecular Cloning, a Laboratory Manual* Cold Spring Harbor Laboratory Press, New York, N.Y.). Both probes were specific for the WOL gene. Southern blot analysis indicated that hybridization was specific for the WOL gene under the conditions used.

WOL expression was monitored by Northern blot analysis. Briefly, total RNA was isolated from 17-day-old *Arabidopsis thaliana* ecotype Columbia root and shoot (Martinez-Zapater & Salinas, 1998, in *Methods in Molecular Biology: Arabidopsis Protocols,* Humana Press Inc., Totowa, N.J., Vol 82). Northern blot analysis was carried out with 15 mg of total RNA. The membrane was hybridized with a $^{32}$P-labeled gene specific WOL probe (described above). A single major band of about 3.7 kb which was more abundant in root than shoot was detected in the RNA blot analysis (FIG. 3G), thus demonstrating highly localized expression in the root, though expression was not entirely exclusive to the root.

In an embodiment of the present invention, RNA in situ hybridization can be employed to analyze expression patterns of WOL genes as well as expression patterns of heterologous gene products driven by WOL promoters. Numerous alternative methods, adjustments, and variations on portions of the RNA in situ hybridization procedure are well known to those practiced in the art (Di Laurenzio et al. 1996, *Cell* 86: 423–33). The following procedure for RNA in situ hybridization has been optimized by the inventors for *Arabidopsis* roots and siliques. It is important to conduct the procedure in a RNase free work environment prior to the posthybridization washes.

Sample preparation consists of three stages: fixation, dehydration, and clearing. Roots are first cut so that 2–3 mm of hypocotyl remain contacted to the root. This helps to orient the tissue later. Siliques are cut about 1 mm of tissue away from the both ends of each silique. After cutting, the tissue is immediately immersed in a freshly prepared fixative (4% paraformaldehyde solution in 1×PBS). Sections remain in the fixative for 2–4 hours at room temperature during which time the samples are vacuum infiltrated 3–4 times for 5 minute periods.

After fixation, the fixative is replaced (optional for roots) and the samples are left to incubate overnight at 4° C. The following day all fixative is removed and the tissue samples are rinsed twice with 1×PBS, each time for 30 min. Roots are next embedded in 1% agarose (in PBS) and trimmed into a block, while silique samples are left free. The tissue samples are then dehydrated in a graded ethanol series (ethanol+water): 30% ethanol for 30 min, 50% ethanol for 30 min, 70% ethanol for 30 min (can go overnight), 85% ethanol for 30 min, 95% ethanol for 30 min, 100% ethanol for 30 min, 100% ethanol for 30 min, and 100% ethanol for 30 min. The tissue samples are then cleared by passing them through the through the following solution series:50% ethanol/50% xylene for 30 min, 100% xylene for 30 min, 100% xylene for 30 min, and 100% xylene for 30 min.

To infiltrate the samples, the xylene is removed and fresh molten Histoplast (Shandon) is added to the samples which are then allowed to incubate overnight at 60° C. The Histoplast is changed at least once a day over the next 1–4 days. The solidified blocks from the molds should be stored at 4° C. The tissue blocks are trimmed into 7–10 um thick microtome sections (Leica: Disposable microtome blade 819) and the ribbon pieces are floated on a Superfrost plus slide (Menzel-Glässer/KEBO 113.720-0) covered with DEPC-H$_2$O. The slides are warmed (50° C.) allowing the ribbon to flatten out. The water is removed and the slides are dried completely at room temperature. In order to bake the sections, slides are incubated overnight at 37–42° C. The sections are then stored at 4° C.

To synthesize probes, it is recommended to start with about 200–300 bp long single-stranded RNA probes. Template DNA can be cloned into a vector containing SP6/T7 promoters of the DIG RNA Labeling Kit (BM 1 175 025) and the RNA synthesized by using in vitro transcription system. The plasmid is linearized for making both antisense and sense (negative control) "run-off" transcripts. It is preferable to use an enzyme that leaves 5'-overhangs or blunt ends. DNA is purified by phenol/chloroform extraction, precipitated, then the pellet is resuspended in DEPC-H2O. A master mix is made for the number of reactions using the BM: DIG RNA Labeling Kit (SP6/T7) (BM 1 175 025). Exactly 9 ul of the master mix and 2 ul of appropriate RNA-polymerase are combined and allowed to incubate for 2 hours at 37° C. The DNA is then removed from the mixture (BM: DIG RNA Labeling Kit). After incubate the mixture for 15 min at 37° C., the reaction is stopped and the RNA is precipitated by adding 2 ul 0.5 M EDTA, 6 ul 4 M LiCl, and 180 ul cold 100% ethanol. The mixture is then incubated overnight at −80° C. The RNA is spun down at 13 000 rpm for 20–30 min at 4° C. and the pellet rinsed with 70% ethanol and spun for and additional 5 min. The pellet is dried and resuspend in 95 ul of DEPC- H2O and 1 ul of RNase inhibitor was added for an incubation period of 30 min at 37° C.

In order to reduce the size of long probes, they are hydrolyzed chemically in alkaline carbonate buffer at 60° C. The carbonate hydrolysis buffer (pH 10.2) is prepared by mixing 8.5 ml of 1M Na2CO3 with 1 ml of 1M NaHCO3. The hydrolysis time is calculated as follows: time (min)= (starting length in kb−final length in kb)/(rate constant) (starting length in kb)(final length in kb), where the rate constant=0.11 kb/1 min. 10 ul of the carbonate buffer are added to the probe (90 ul) and incubated at 60° C. for the calculated time.

Following incubation, 12.5 ul 5% acetic acid is added to each probe sample. To precipitate the RNA, 12.5 ul 3 M NaOAC pH 5.2, 310 ul ethanol, and 10 ug tRNA (optional) is added and the resulting mixture is allowed to incubate overnight at −80° C. The following day the RNA is spun down at 13 000 rpm for 20–30 min at 4° C. and the resulting pellet is rinsed with 70% ethanol and spun for an additional 5 min. The pellet is dried and resuspended in DEPC-H2O and 1 ul of RNase inhibitor is added to the mixture for an incubation period of 30 min at 37° C. The probe is then quantified using the protocol in "The DIG system user's guide for filter hybridization" DIG RNA Labeling Kit (BM 1 175 025).

To pretreat the slides, they are placed in a slide rack and passed through the following solution series: Xylene for 10 min, Xylene for 10 min, Methanol for 15 min, 100% ethanol for 1 min, 100% ethanol for 1 min, 95% ethanol for 1 min, 85% ethanol: 0.85% NaCl for 1 min, 70% ethanol: 0.85% NaCl for 1 min, 50% ethanol: 0.85% NaCl for 1 min, 30% ethanol: 0.85% NaCl for 1 min, 0.85% NaCl for 2 min, 1×PBS for 2 min, 0.2 M HCl for 20 min, H2O for rinse, 2×SSC for 20 min, a H20 rinse, 10 ug/ml Proteinase K (Sigma P-2308) in 100 mM Tris pH 7.5; 50 mM EDTA for 30 min at 37° C. (prewarmed), 1×PBS for 2 min, fixative (4% paraformaldehyde) for 10 min, 0.5% acetic anhydride in 0.1 M triethanolamine pH 8.0 for 10 min (done in fume hood), 1×PBS for 2 min, and 0.85% NaCl for 2 min.

In order to dehydrate the samples, the slides are passed through a second series of solutions: 30% ethanol: 0.85% NaCl for 1 min, 50% ethanol: 0.85% NaCl for 1 min, 70% ethanol: 0.85% NaCl for 1 min, 85% ethanol: 0.85% NaCl for 1 min, 95% ethanol for 1 min, 100% ethanol for 1 min, and 100% ethanol for 1 min. After this extensive washing, the rack of slides are placed into a jar with a small amount of 100% ethanol (not touching slides) which is then sealed with parafilm.

Prehybridization and hybridization were carried out in a formamide atmosphere chamber. Slides are then placed in the chamber and each was covered with 250 ul of prehybridization solution (50% formamide, 1×salts, 1×Denhardt's, 200 ug/ml tRNA, 10 U/ml RNase inhibitor). A piece of parafilm slightly smaller than the slide is placed on top of the solution and the slides, in the enclosed chamber, are allowed to incubate for 1 hour at room temperature and for at least 1 hour at 45° C.

During this time the hybridization solution is prepared and warmed to 45° C. First, the probe is readied by adding 0.05–0.5 ug/ml/kb of the probe complex to 25 ul of DEPC-$H_2O$ and incubating the mixture for 1 min at 80° C., followed by immediate cooling on ice. Second, 25 ul of formamide is added to 200 ul of hybridization solution. The parafilm is removed and the prehybridization solution is drain off completely. The slides are placed back to the same chamber and the probe is then added to the hybridization solution and the resulting solution is placed over the samples on each slide. The slides are again covered with parafilm and allowed to hybridize overnight at 45° C.

Posthybrization washes are performed by removing the parafilm and allowing the hybridization solution to drain off completely. Each slide is then rinsed in 5×SSC/50% formamide by dipping the slide couple of times in the solution. Slides are then placed in a slide rack standing in a jar containing 5×SSC/50% formamide. Slides are not allowed to dry out at any time during the washes. Slides are incubated for 4–5 hours at 45° C., rinsed shortly with NTE solution, and incubated again in 10 ug/ml RNase A (Sigma R-5503) in 0.5 M NaCl; 10 mM Tris pH 8.0; 5 mM EDTA (=NTE solution) for 30 min at 37° C. The slides are twice washed in NTE solution for 5 min at 37° C. and allowed to incubate in 0.5×SSC/50% formamide for 1 hour at 45° C., after which each slide is rinsed in 1×PBS for 5 min. Slides are then stored overnight in 1×PBS at 4° C.

In order to detect probes, Slides are first incubated with gentle agitation for 45 min in blocking solution. Following the incubation, the solution is replaced with buffer A and the incubation is continued for 45 min. The slides are placed in a same kind of chamber that is used in the hybridization step in preparation of addition of antibodies. Approximately 500 ul of antibody solution (antibody conjugate 1:1000) is spread over each slide and a piece of parafilm is put on the top of the solution. The slides are allowed to incubate for 1 hour in room temperature, after which the parafilm is removed and the slides are placed in a slide rack standing in ajar containing buffer A (1% BSA (fraction V, Sigma A-3912), 0.3% Triton X-100, 100 mM Tris pH 7.5,150 mM NaCl). The slides are washed three times with gentle agitation for 20 min. followed by a brief wash in detection buffer (2×5 min) before placing the slides back to the chamber. About 500 ul of color substrate solution is added to each slide. Each slide is then immediately covered with parafilm and kept protected from the light.

The slides are incubated for 1–2 days in room temperature taking care not to shake the slides and disrupt color development. The reaction is then stopped by removing the parafilm and dipping the slides in 1×TE-buffer (pH 8.0) for a couple of minutes. The buffer is drained off and 2–3 drops of aqueous mountant (for example 50% glycerol) are added to each slide. Finally, a coverslip is placed on each slide and if necessary sealed in place with clear nail polish.

The tissue specificity of WOL expression at the cellular level was determined by in situ localization of WOL mRNA on embryonic and root sections and images were taken using differential interference contrast (DIC) settings (FIG. 4).

In the wild-type primary root, WOL was expressed in the vascular cylinder and pericycle (FIGS. 4A–B). The expression pattern of WOL was established during the early stages of embryogenesis. At the globular stage of embryogenesis, WOL mRNA was detected in the four innermost cells, which are the precursors of the vascular tissue (procambium) (FIG. 4D). During the heart, torpedo, and nearly mature stages of embryogenesis (FIGS. 4E–G) expression was apparent in the procambium of the cotyledon shoulders, prospective hypocotyl and embryonic root (FIGS. 4E–G). WOL expression in the wol mutant primary root was detected in the vascular cells, indicating that wildtype WOL function is not necessary for its own expression (FIG. 4C).

WOL expression both spatially and temporally coincides with the divisions of the procambial cells of the embryonic and primary root which are defective in the wol mutant. The WOL gene product is a receptor molecule that controls the asymmetric cell divisions of the vascular initials through a specific signal transduction pathway involving a phosphotransfer reaction characteristic of the two component receptors. In the root tip, WOL expression can be detected both in the region of asymmetric cell divisions and in the zone of differentiation immediately above it. WOL expression during pericycle development may also be related to its role in regulating asymmetric cell divisions, since the pericycle is ontogenetically part of the vascular cylinder (Scheres et al. 1994; 1995, supra) and WOL expression can be detected prior to the separation of the pericycle cell lineages. Otherwise the pericycle appears anatomically normal in wol.

The exclusive differentiation of protoxylem in wol precludes the possibility of determining if WOL is required for division of the cambium found between xylem and phloem. The pattern of the wol-dependent procambial cell divisions around the developing xylem provides an intriguing parallel to the pattern of the cambial cell divisions between phloem and xylem, which are very prominent in wood and storage root development (Esau, 1977, *Anatomy of Seed Plants.* John Wiley & Sons, New York, N.Y., ed. 2.). It is therefore possible that at least some aspects of developmental regulation are common to the procambial and cambial cell divisions and that WOL genes contribute to the diversity of vascular patterns found in plants.

6.7. WOL Genes, Orthologs and Paralogs

Two other WOL paralogs (F17L21.11, SEQ ID NO:18 GenBank No. AC004557; and MXH1.16, SEQ ID NO:19 GenBank No. AB011485) with a similar deduced protein domain structure were found, which indicated that WOL belonged to a small protein family (FIG. 3F). The deduced sequence of the WOL protein was 57% identical to F17L21.11 (GenBank Accession Number AC004557, SEQ ID NO:18) and 54% identical to MXH1.16 (GenBank Accession Number AB011485, SEQ ID NO:19). To compare deduced amino acid sequences, SeqWeb Software (a web-based interface to the GCG Wisconsin Package: Gap program) was utilized with the default algorithm and parameter settings of the program: blosum62, gap weight 8, length weight 2. Furthermore, a WOL ortholog sequence was reported in the genome of *Hordeum vulgare* (GenBank Accession Number AJ234550, SEQ ID NO:20). Among the characterized two component receptor molecules, WOL proteins and protein products of WOL orthologs and paralogs are unique in having at least one, and preferably two, putative D domains. The closest homologue of WOL-like genes is DhkA (GenBank Accession Number U42597, SEQ ID NO:17; see Wang et al., 1996, *EMBO J.* 15:3890–8 and Wang et al., 1999, *Mol Cell Biol.* 7:4750–6) of the slime mold *Dictyostelium discoideum* (FIG. 3F). WOL and DhkA are 24% identical in the R domain, 44% identical in the H domain, and 39% identical in the $D_B$ domains. However, the $D_A$ domain (with the absolutely conserved aspartic acid residues at positions 768 and 825, and a lysine residue at position 882 characteristic to the receiver domains) is absent in DhkA (SEQ ID NO:17). The functional role of the phosphorelay domains remains to be determined. The mutation in wol results in a non-conservative change of an amino acid of the putative receptor domain that is conserved within the WOL protein family (FIG. 3F). This indicates that the fully recessive wol mutation may reduce the ability of the molecule to bind a ligand or transmit the information of ligand binding to the C-terminal part of the molecule.

WOL genes are also active in the cambial zone of a trunk of a birch tree (*Betula pendula*). Using degenerate oligonucleotides (forward primer is SEQ ID NO:31; reverse primer is SEQ ID NO:32) based on the sequence conservation within the WOL genes of *Arabidopsis*, two different WOL genes from a cDNA library representing the wood forming tissue of birch tree (*Betula pendula*) were isolated (WOL gene 1 is SEQ ID NO:25 and 29; WOL gene 2 is SEQ ID NO:26 and 30) (FIG. 6). Because of its expression during wood development in trees, WOL has a more general role in vascular development and regulates vascular development both during the primary and secondary phases of plant development.

6.8. Expression of Heterologous Gene Products Driven by the 2.7 kb WOL Promoter This example demonstrates that the 2.7 kb WOL promoter (SEQ ID NO: 36) can drive expression of a heterologous gene product in a tissue specific manner. The 2.7 kb WOL promoter was incorporated into the heterologous expression constructs WOLpro::GUS and WOLpro:GFP. The promoter sequence corresponds to 2688 base pairs, 13574–16262, of *Arabidopsis* BAC clone T23K3 (SEQ ID NO: 13) (GenBank Accession number AC007069 Chromosome II section 5; Clone available from: *Arabidopsis* Biological Resource Center, The Ohio State University, 039 Rightmire Hall, 1060 Carmack Rd., Columbus, Ohio 43210 USA). The 5' UTR end of the promoter sequence corresponds to base pair number 13575 of the T23K3 clone, immediately upstream of the first methionine of the WOL gene coding sequence found at base pairs 13572–13574 of the T23K3 clone (SEQ ID NO: 13). Both ends of the promoter were modified in order to insert XbaI and BamHI restriction sites into the 5' end and the 3' end, respectively.

The promoter was cloned into GUS gene fusion vector pBI101 T-DNA region (GenBank No. U12639). The WOL promoter::GUS construct was transformed into the Columbia ecotype background according to the methods of Clough and Bent (1998, *Plant J* 16:735–43), using transformation methods commonly known to those skilled in the art. Seedlings were stained to reveal promoter-driven expression of GUS six days after germination. The GUS expression patterns observed indicate that the WOL promoter drives expression in a tissue-specific manner (developing vasculature and progenitor cells of vascular tissue, particularly xylem). Tissue-specific expression was observed in hypocotyl (FIG. 9B), vasculature basal to the apical meristem (FIGS. 9C and 9B), and at the base of the cotyledons (FIG. 9D). Separate preparations were made of roots of five day old plants generated in the same background (Columbia) with the same transformed construct. In roots, GUS staining was limited to the pericycle/vascular initial and in developing vasculature throughout the root tip (FIG. 9G).

The WOLpromoter::GUS construct was next transformed into a homozygous recessive wol mutant background. The resultant seedlings were stained for GUS six days after germination by methods known to those skilled in the art. The observed GUS patterns again indicated that the 2.7 kb WOL promoter drives expression in a tissue-specific manner as described in the instant application. Expression was observed in developing vasculature in the stipe, basal to the silique (FIG. 9A), vasculature basal to the apical meristem (FIG. 9F), and developing vasculature at the base of the embryonic leaves (FIG. 9E).

Another construct was utilized that consisted of the 2.7 kb WOL promoter fused to the GFP reporter gene. The promoter was cloned into a "GFP-link" vector. The GFP-link vector is modified from the binary vector pBIN m-gfp5-ER (GenBank Number X77672) by removing the 35S promoter. This GFP-containing vector also has XbaI and BamHI sites upstream of the GFP gene. The green fluorescence patterns observed in the roots five days after germination indicate that the WOL promoter drives expression in a tissue-specific manner. Expression was observed in the pericycle/vascular initial and developing vasculature tissue in the roots.

The expression patterns of the GUS and GFP reporter genes that were driven by the 2.7 kb WOL promoter strongly correlate with the expression pattern of the WOL gene obtained utilizing RNA in situ hybridization techniques, the results of which are described in Section 6 of the instant application. The results described in Section 6 below show that WOL is expressed in the vascular cylinder and pericycle of roots in embryogenesis through at least five days after germination.

In summary the observed expression patterns matched those observed in experiments where in situ.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. An isolated nucleic acid molecule which encodes a WOODEN LEG protein, wherein said protein regulates the number of periclinal cell divisions of the pericycle/vascular initial thereby regulating the number of cells in the vascular cylinder, and wherein said nucleic acid molecule is selected from the group consisting of:
   a) a nucleic acid molecule comprising a nucleotide sequence selected from the group consisting of SEQ ID NO:1, SEQ ID NO:2, SEQ ID NO:3, and SEQ ID NO:4, or the complement thereof; and
   b) a nucleic acid molecule which encodes a polypeptide comprising an amino acid sequence which is at least 95% identical to the amino acid sequence of SEQ ID NO:5.

2. A vector containing the nucleic acid molecule of claim 1.

3. The vector of claim 2, that is an expression vector containing transcriptional or translational regulatory elements that control expression of the nucleic acid molecule.

4. The nucleic acid molecule of claim 1 further comprising a nucleotide sequence encoding a heterologous polypeptide.

5. An isolated genetically-engineered host cell which contains the nucleic acid molecule of claim 1.

6. A transgenic plant comprising the nucleic acid molecule of claim 1.

7. The transgenic plant of claim 6, wherein development of vascular tissue is altered.

8. The transgenic plant of claim 6 wherein said nucleic acid molecule is overexpressed.

9. A method for producing a polypeptide comprising culturing the host cell of claim 5 under conditions in which the nucleic acid molecule expresses said polypeptide.

* * * * *

SEQUENCE LISTING

<160> NUMBER OF SEQ ID NOS: 43

<210> SEQ ID NO 1
<211> LENGTH: 3620
<212> TYPE: DNA
<213> ORGANISM: Arabidopsis thaliana

<400> SEQUENCE: 1

```
agttggagca aagttgcttc ttttgagaac catgcgtttc tttctctctt ttgttcttga      60
attcgcaaaa acatgtcctt tttcgtctac aggtttctag ggtttgtttc tgtactataa     120
actatgttta tgctcagata tgaactgggc actcaacaat catcaagaag aagaagaaga     180
gccacgaaga attgaaattt ctgattccga gtcactagaa aacttgaaaa gcagcgattt     240
ttatcaactg ggtggtggtg gtgctctgaa ttcgtcagaa aagccgagaa agatcgattt     300
ttggcgttcg gggttgatgg gttttgcgaa gatgcagcag cagcaacagc ttcagcattc     360
agtggcggtg aagatgaaca ataataataa taacgatcta atgggtaata aaaaagggtc     420
aactttcata caagaacatc gagcattgtt accaaaagct ttgattctgt ggatcatcat     480
tgttgggttt ataagcagtg ggatttatca gtggatggat gatgctaata agattagaag     540
ggaagaggtt ttggtcagca tgtgtgatca aagagctaga atgttgcagg atcaatttag     600
tgttagtgtt aatcatgttc atgctttggc tattctcgtc tccacttttc attaccacaa     660
gaacccttct gcaattgatc aggagacatt tgcggagtac acgcaagaa cagcatttga      720 gagaccgttg ctaagtggag tggcttatgc tgaaaaagtt gtgaattttg agagggagat     780
gtttgagcgg cagcacaatt gggttataaa gacaatggat agaggagagc cttcaccggt     840
tagggatgag tatgctcctg ttatattctc tcaagatagt gtctcttacc ttgagtcact     900
cgatatgatg tcaggcgagg aggatcgtga gaatattttg cgagctagag aaaccggaaa     960
agctgtcttg actagccctt ttaggttgtt ggaaactcac catctcggag ttgtgttgac    1020
attccctgtc tacaagtctt ctcttcctga aaatccgact gtcgaagagc gtattgcagc    1080
cactgcaggg taccttggtg gtgcgtttga tgtggagtct ctagtcgaga atttacttgg    1140
tcagcttgct ggtaaccaag caatagttgt gcatgtgtat gatatcacca atgcatcaga    1200
tccacttgtc atgtatggta atcaagatga agaagccgac agatctctct ctcatgagag    1260
caagctcgat tttggagacc ccttcaggaa acataagatg atatgcaggt accaccaaaa    1320
ggcaccaata ccgttgaatg tgctcacaac tgtgccattg ttctttgcga ttggtttctt    1380
ggtgggttat atactgtatg gtgcagctat gcacatagta aaagtcgaag atgatttcca    1440
tgaaatgcaa gagcttaaag ttcgagcaga agctgctgat gtcgctaaat cgcagtttct    1500
tgctaccgtg tctcacgaga tcaggacacc aatgaatggc attctcggaa tgcttgctat    1560
gctcctagat acagaactaa gctcgacaca gagagattac gctcaaaccg ctcaagtatg    1620
```

-continued

```
tggtaaagct tgattgcat tgataaatga ggttcttgat cgcgccaaga ttgaagctgg      1680
aaagctggag ttggaatcag taccatttga tatccgttca atattggatg atgtcctttc      1740
tctattctct gaggagtcaa ggaacaaaag cattgagctc gcggttttcg tttcagacaa      1800
agtaccagag atagtcaaag gagattcagg gagatttaga cagataatca taaaccttgt      1860
tggaaattcg gttaaattca cagagaaagg acatatcttt gttaaagtcc atcttgcgga      1920
acaatcaaaa gatgaatctg aaccgaaaaa tgcattgaat ggtggagtgt ctgaagaaat      1980
gatcgttgtt tccaaacagt caagttacaa cacattgagc ggttacgaag ctgctgatgg      2040
tcggaatagc tgggattcat tcaagcattt ggtctctgag gagcagtcat tatcggagtt      2100
tgatatttct agcaatgtta ggcttatggt ttcaatcgaa gacacgggta ttggaatccc      2160
tttagttgcg caaggccgtg tgtttatgcc gtttatgcaa gcagatagct cgacttcaag      2220
aaactatgga ggtactggta ttggtttgag tataagcaag tgtcttgttg aacttatgcg      2280
tggtcagata aatttcataa gccggcctca tattggaagc acgttctggt tcacggctgt      2340
tttagagaaa tgcgataaat gcagtgcgat taaccatatg aagaaaccta atgtggaaca      2400
cttgccttct acttttaaag gaatgaaagc tatagttgtt gatgctaagc ctgttagagc      2460
tgctgtgact agataccata tgaaaagact cggaatcaat gttgatgtcg tgacaagtct      2520
caaaaccgct gttgttgcag ctgctgcgtt tgaaagaaac ggttctcctc tcccaacaaa      2580
accgcaactt gatatgatct tagtagaaga agattcatgg atttcaactg aagataatga      2640
ctcagagatt cgtttattga attcaagaac caacggaaac gttcatcaca agtctccgaa      2700
actagctcta ttcgcaacaa acatcacaaa ttcggagttc gacagagcta aatccgcagg      2760
atttgcagat acgtaataa tgaaaccgtt aagagcaagc atgattgggg cgtgtctgca      2820
acaagttctc gagctgagaa aaacaagaca acaacatcca gaaggatcat cacccgcaac      2880
tctcaagagc ttgcttacag ggaagaagat tcttgtggtt gatgataata tagttaacag      2940
gagagtagct gcaggagctc tcaagaaatt tggagcagaa gtggtttgtg cagagagtgg      3000
tcaagttgct ttgggtttgc ttcagattcc acacactttc gatgcttgct tcatggatat      3060
tcaaatgcca cagatggacg gatttgaagc aactcgtcag ataagaatga tggagaagga      3120
aactaaagag aagacaaatc tcgaatggca tttaccgatt ctagcgatga ctgcggatgt      3180
gatacacgcg acctacgagg aatgtctgaa aagtgggatg gatggttacg tctccaaacc      3240
ttttgaagaa gagaatctct ataaatccgt tgccaaatca ttcaaaccta tcctatctc      3300 accttcgtcg taatccaatc ttccggcgag ttttttttct ctctccgcag ccggaagagt      3360
ggaccgattc tgctgattga tatgcatttt ggttctgta catacagtag gttcacaatc      3420
tagagatttt gaaggttttt ttttctttca ccgaagtaat gtagcttgcc atgactagtg      3480
tatgttgtta aacgacaacg tctaagacga cggttcagtg ttgatcttag cgtaagtatt      3540
aatcccacgg gatcgtttgt actgtatcag atttggttag tcgtttaaac attgtaatgt      3600
tctaataata acttttccat                                                  3620
```

<210> SEQ ID NO 2
<211> LENGTH: 3503
<212> TYPE: DNA
<213> ORGANISM: Arabidopsis thaliana

<400> SEQUENCE: 2

```
cacaactcat tacagctcag atatgaactg ggcactcaac aatcatcaag aagaagaaga      60
```

-continued

```
agagccacga agaattgaaa tttctgattc cgagtcacta gaaaacttga aaagcagcga      120 ttttttatcaa ctgggtggtg gtggtgctct gaattcgtca gaaaagccga gaaagatcga    180
tttttggcgt tcggggttga tgggttttgc gaagatgcag cagcagcaac agcttcagca    240
ttcagtggcg gtgaagatga acaataataa taataacgat ctaatgggta ataaaaaagg    300
gtcaactttc atacaagaac atcgagcatt gttaccaaaa gctttgattc tgtggatcat    360
cattgttggg tttataagca gtgggattta tcagtggatg gatgatgcta ataagattag    420
aagggaagag gttttggtca gcatgtgtga tcaaagagct agaatgttgc aggatcaatt    480
tagtgttagt gttaatcatg ttcatgcttt ggctattctc gtctccactt ttcattacca    540
caagaaccct tctgcaattg atcaggagac atttgcggag tacacggcaa gaacagcatt    600
tgagagaccg ttgctaagtg gagtggctta tgctgaaaaa gttgtgaatt ttgagaggga    660
gatgtttgag cggcagcaca attgggttat aaagacaatg gatagaggag agccttcacc    720
ggttagggat gagtatgctc ctgttatatt ctctcaagat agtgtctctt accttgagtc    780
actcgatatg atgtcaggcg aggaggatcg tgagaatatt ttgcgagcta gagaaaccgg    840
aaaagctgtc ttgactagcc ttttaggtt gttggaaact caccatctcg gagttgtgtt    900
gacattccct gtctacaagt cttctcttcc tgaaaatccg actgtcgaag agcgtattgc    960
agccactgca gggtaccttg gtggtgcgtt tgatgtggag tctctagtcg agaatttact   1020
tggtcagctt gctggtaacc aagcaatagt tgtgcatgtg tatgatatca ccaatgcatc   1080
agatccactt gtcatgtatg gtaatcaaga tgaagaagcc gacagatctc tctctcatga   1140
gagcaagctc gattttggag accccttcag gaaacataag atgatatgca ggtaccacca   1200
aaaggcacca ataccgttga atgtgctcac aactgtgcca ttgttctttg cgattggttt   1260
cttggtgggt tatatactgt atggtgcagc tatgcacata gtaaaagtcg aagatgattt   1320
ccatgaaatg caagagctta agttcgagc agaagctgct gatgtcgcta atcgcagtt    1380 tcttgctacc gtgtctcacg agatcaggac accaatgaat ggcattctcg gaatgcttgc   1440
tatgctccta gatacagaac taagctcgac acagagagat tacgctcaaa ccgctcaagt   1500
atgtggtaaa gctttgattg cattgataaa tgaggttctt gatcgcgcca agattgaagc   1560
tggaaagctg gagttggaat cagtaccatt tgatatccgt tcaatattgg atgatgtcct   1620
ttctctattc tctgaggagt caaggaacaa aagcattgag ctcgcggttt tcgtttcaga   1680
caaagtacca gagatagtca aaggagattc agggagattt agacagataa tcataaaccct  1740 tgttggaaat tcggttaaat tcacagagaa aggacatatc tttgttaaag tccatcttgc   1800
ggaacaatca aaagatgaat ctgaaccgaa aaatgcattg aatggtggag tgtctgaaga   1860
aatgatcgtt gtttccaaac agtcaagtta caacacattg agcggttacg aagctgctga   1920
tggtcggaat agctgggatt cattcaagca tttggtctct gaggagcagt cattatcgga   1980
gtttgatatt tctagcaatg ttaggcttat ggtttcaatc gaagacacgg gtattggaat   2040
cccctttagt t gcgcaaggcc gtgtgtttat gccgtttatg caagcagata gctcgacttc   2100
aagaaactat ggaggtactg gtattggttt gagtataagc aagtgtcttg ttgaactat   2160 gcgtggtcag ataaatttca taagccggcc tcatattgga agcacgttct ggttcacggc   2220
tgttttagag aaatgcgata atgcagtgc gattaaccat atgaagaaac ctaatgtgga   2280
acacttgcct tctactttta aggaatgaa agctatagtt gttgatgcta agcctgttag   2340
agctgctgtg actagatacc atatgaaaag actcggaatc aatgttgatg tcgtgacaag   2400
tctcaaaacc gctgttgttg cagctgctgc gtttgaaaga aacggttctc ctctcccaac   2460
```

-continued

```
aaaaccgcaa cttgatatga tcttagtaga gaaagattca tggatttcaa ctgaagataa      2520
tgactcagag attcgtttat tgaattcaag aaccaacgga aacgttcatc acaagtctcc      2580
gaaactagct ctattcgcaa caaacatcac aaattcggag ttcgacagag ctaaatccgc      2640
aggatttgca gatacggtaa taatgaaacc gttaagagca agcatgattg gggcgtgtct      2700
gcaacaagtt ctcgagctga gaaaaacaag acaacaacat ccagaaggat catcacccgc      2760
aactctcaag agcttgctta cagggaagaa gattcttgtg gttgatgata atatagttaa      2820
caggagagta gctgcaggag ctctcaagaa atttggagca gaagtggttt gtgcagagag      2880
tggtcaagtt gctttgggtt tgcttcagat tccacacact ttcgatgctt gcttcatgga      2940
tattcaaatg ccacagatgg acggatttga agcaactcgt cagataagaa tgatggagaa      3000
ggaaactaaa gagaagacaa atctcgaatg gcatttaccg attctagcga tgactgcgga      3060
tgtgatacac gcgacctacg aggaatgtct gaaaagtggg atggatggtt acgtctccaa      3120 acctttgaa gaagagaatc tctataaatc cgttgccaaa tcattcaaac ctaatcctat       3180
ctcaccttcg tcgtaatcca atcttccggc gagtttttttt tctctctccg cagccggaag    3240
agtggaccga ttctgctgat tgatatgcat tttggtttct gtacatacag taggttcaca     3300
atctagagat tttgaaggtt ttttttttctt tcaccgaagt aatgtagctt gccatgacta    3360
gtgtatgttg ttaaacgaca acgtctaaga cgacggttca gtgttgatct tagcgtaagt     3420
attaatccca cgggatcgtt tgtactgtat cagatttggt tagtcgttta aacattgtaa     3480
tgttctaata ataactttc cat                                              3503
```

<210> SEQ ID NO 3
<211> LENGTH: 3612
<212> TYPE: DNA
<213> ORGANISM: Arabidopsis thaliana

<400> SEQUENCE: 3

```
actgcattca tctatgactg aaagcttctg atcaagccat gaaattaagt tatagaagct      60
actgtctcta agcgcacgag agaaagctac acaacccacg tcagtttcca tctacacata     120
taagctcaga tatgaactgg gcactcaaca atcatcaaga agaagaagaa gagccacgaa     180
gaattgaaat ttctgattcc gagtcactag aaaacttgaa aagcagcgat ttttatcaac     240
tgggtggtgg tggtgctctg aattcgtcag aaaagccgag aaagatcgat ttttggcgtt     300
cggggttgat gggttttgcg aagatgcagc agcagcaaca gcttcagcat tcagtggcgg     360
tgaagatgaa caataataat aataacgatc taatgggtaa taaaaaaggg tcaactttca     420
tacaagaaca tcgagcattg ttaccaaaag ctttgattct gtggatcatc attgttgggt     480
ttataagcag tgggatttat cagtggatgg atgatgctaa taagattaga agggaagagg     540
ttttggtcag catgtgtgat caaagagcta gaatgttgca ggatcaattt agtgttagtg     600
ttaatcatgt tcatgctttg gctattctcg tctccacttt tcattaccac aagaacccttt    660 ctgcaattga tcaggagaca tttgcggagt acacggcaag aacagcattt gagagaccgt     720
tgctaagtgg agtggcttat gctgaaaaag ttgtgaattt tgagagggag atgtttgagc     780
ggcagcacaa ttgggttata aagacaatgg atagaggaga gccttcaccg gttagggatg     840
agtatgctcc tgttatattc tctcaagata gtgtctctta ccttgagtca ctcgatatga     900
tgtcaggcga ggaggatcgt gagaatattt gcgagctag agaaaccgga aaagctgtct      960
tgactagccc ttttaggttg ttggaaactc accatctcgg agttgtgttg acattccctg    1020
```

```
tctacaagtc ttctcttcct gaaaatccga ctgtcgaaga gcgtattgca gccactgcag    1080
ggtaccttgg tggtgcgttt gatgtggagt ctctagtcga gaatttactt ggtcagcttg    1140
ctggtaacca agcaatagtt gtgcatgtgt atgatatcac caatgcatca gatccacttg    1200
tcatgtatgg taatcaagat gaagaagccg acagatctct ctctcatgag agcaagctcg    1260
attttggaga ccccttcagg aaacataaga tgatatgcag gtaccaccaa aaggcaccaa    1320
taccgttgaa tgtgctcaca actgtgccat tgttctttgc gattggtttc ttggtgggtt    1380
atatactgta tggtgcagct atgcacatag taaaagtcga agatgatttc catgaaatgc    1440
aagagcttaa agttcgagca gaagctgctg atgtcgctaa atcgcagttt cttgctaccg    1500
tgtctcacga gatcaggaca ccaatgaatg gcattctcgg aatgcttgct atgctcctag    1560
atacagaact aagctcgaca cagagagatt acgctcaaac cgctcaagta tgtggtaaag    1620
ctttgattgc attgataaat gaggttcttg atcgcgccaa gattgaagct ggaaagctgg    1680
agttggaatc agtaccattt gatatccgtt caatattgga tgatgtcctt tctctattct    1740
ctgaggagtc aaggaacaaa agcattgagc tcgcggtttt cgtttcagac aaagtaccag    1800
agatagtcaa aggagattca gggagattta gacagataat cataaacctt gttggaaatt    1860
cggttaaatt cacagagaaa ggacatatct ttgttaaagt ccatcttgcg gaacaatcaa    1920
aagatgaatc tgaaccgaaa aatgcattga atggtggagt gtctgaagaa atgatcgttg    1980
tttccaaaca gtcaagttac aacacattga gcggttacga agctgctgat ggtcggaata    2040
gctgggattc attcaagcat ttggtctctg aggagcagtc attatcggag tttgatattt    2100
ctagcaatgt taggcttatg gtttcaatcg aagacacggg tattggaatc ccttttagttg   2160 cgcaaggccg tgtgtttatg ccgtttatgc aagcagatag ctcgacttca agaaactatg    2220
gaggtactgg tattggtttg agtataagca agtgtcttgt tgaacttatg cgtggtcaga    2280
taaatttcat aagccggcct catattggaa gcacgttctg gttcacggct gttttagaga    2340
aatgcgataa atgcagtgcg attaaccata tgaagaaacc taatgtggaa cacttgcctt    2400
ctacttttaa aggaatgaaa gctatagttg ttgatgctaa gcctgttaga gctgctgtga    2460
ctagatacca tatgaaaaga ctcggaatca atgttgatgt cgtgacaagt ctcaaaaccg    2520
ctgttgttgc agctgctgcg tttgaaagaa acggttctcc tctcccaaca aaaccgcaac    2580
ttgatatgat cttagtagag aaagattcat ggatttcaac tgaagataat gactcagaga    2640
ttcgtttatt gaattcaaga accaacggaa acgttcatca caagtctccg aaactagctc    2700
tattcgcaac aaacatcaca aattcggagt tcgacagagc taaatccgca ggatttgcag    2760
atacggtaat aatgaaaccg ttaagagcaa gcatgattgg ggcgtgtctg caacaagttc    2820
tcgagctgag aaaaacaaga caacaacatc cagaaggatc atcacccgca actctcaaga    2880
gcttgcttac agggaagaag attcttgtgg ttgatgataa tatagttaac aggagagtag    2940
ctgcaggagc tctcaagaaa tttggagcag aagtggtttg tgcagagagt ggtcaagttg    3000
ctttgggttt gcttcagatt ccacacactt tcgatgcttg cttcatggat attcaaatgc    3060
cacagatgga cggatttgaa gcaactcgtc agataagaat gatggagaag gaaactaaag    3120
agaagacaaa tctcgaatgg catttaccga ttctagcgat gactgcggat gtgatacacg    3180
cgacctacga ggaatgtctg aaaagtggga tggatggtta cgtctccaaa ccttttgaag    3240
aagagaatct ctataaatcc gttgccaaat cattcaaacc taatcctatc tcaccttcgt    3300
cgtaatccaa tcttccggcg agttttttttt ctctctccgc agccggaaga gtggaccgat    3360
tctgctgatt gatatgcatt ttggtttctg tacatacagt aggttcacaa tctagagatt    3420
```

-continued

| | |
|---|---|
| ttgaaggttt ttttttcttt caccgaagta atgtagcttg ccatgactag tgtatgttgt | 3480 |
| taaacgacaa cgtctaagac gacggttcag tgttgatctt agcgtaagta ttaatcccac | 3540 |
| gggatcgttt gtactgtatc agatttggtt agtcgtttaa acattgtaat gttctaataa | 3600 |
| taacttttcc at | 3612 |

<210> SEQ ID NO 4
<211> LENGTH: 3170
<212> TYPE: DNA
<213> ORGANISM: Arabidopsis thaliana

<400> SEQUENCE: 4

| | |
|---|---|
| tgaactgggc actcaacaat catcaagaag aagaagaaga gccacgaaga attgaaattt | 60 |
| ctgattccga gtcactagaa aacttgaaaa gcagcgattt ttatcaactg ggtggtggtg | 120 |
| gtgctctgaa ttcgtcagaa aagccgagaa agatcgattt ttggcgttcg gggttgatgg | 180 |
| gttttgcgaa gatgcagcag cagcaacagc ttcagcattc agtggcggtg aagatgaaca | 240 |
| ataataataa taacgatcta atgggtaata aaaaagggtc aactttcata caagaacatc | 300 |
| gagcattgtt accaaaagct ttgattctgt ggatcatcat tgttgggttt ataagcagtg | 360 |
| ggatttatca gtggatggat gatgctaata agattagaag ggaagaggtt ttggtcagca | 420 |
| tgtgtgatca aagagctaga atgttgcagg atcaatttag tgttagtgtt aatcatgttc | 480 |
| atgctttggc tattctcgtc tccacttttc attaccacaa gaaccccttct gcaattgatc | 540 |
| aggagacatt tgcggagtac acggcaagaa cagcatttga gagaccgttg ctaagtggag | 600 |
| tggcttatgc tgaaaaagtt gtgaattttg agagggagat gtttgagcgg cagcacaatt | 660 |
| gggttataaa gacaatggat agaggagagc cttaccggt tagggatgag tatgctcctg | 720 |
| ttatattctc tcaagatagt gtctcttacc ttgagtcact cgatatgatg tcaggcgagg | 780 |
| aggatcgtga gaatattttg cgagctagag aaaccggaaa agctgtcttg actagccctt | 840 |
| ttaggttgtt ggaaactcac catctcggag ttgtgttgac attccctgtc tacaagtctt | 900 |
| ctcttcctga aaatccgact gtcgaagagc gtattgcagc cactgcaggg taccttggtg | 960 |
| gtgcgtttga tgtggagtct ctagtcgaga atttacttgg tcagcttgct ggtaaccaag | 1020 |
| caatagttgt gcatgtgtat gatatcacca atgcatcaga tccacttgtc atgtatggta | 1080 |
| atcaagatga agaagccgac agatctctct ctcatgagag caagctcgat tttggagacc | 1140 |
| ccttcaggaa acataagatg atatgcaggt accaccaaaa ggcaccaata ccgttgaatg | 1200 |
| tgctcacaac tgtgccattg ttctttgcga ttggtttctt ggtgggttat atactgtatg | 1260 |
| gtgcagctat gcacatagta aaagtcgaag atgatttcca tgaaatgcaa gagcttaaag | 1320 |
| ttcgagcaga agctgctgat gtcgctaaat cgcagtttct tgctaccgtg tctcacgaga | 1380 |
| tcaggacacc aatgaatggc attctcggaa tgcttgctat gctcctagat acagaactaa | 1440 |
| gctcgacaca gagagattac gctcaaaccg ctcaagtatg tggtaaagct ttgattgcat | 1500 |
| tgataaatga ggttcttgat cgcgccaaga ttgaagctgg aaagctggag ttggaatcag | 1560 |
| taccatttga tatccgttca atattggatg atgtccttc tctattctct gaggagtcaa | 1620 |
| ggaacaaaag cattgagctc gcggttttcg tttcagacaa agtaccagag atagtcaaag | 1680 |
| gagattcagg gagatttaga cagataatca taaaccttgt tggaaattcg gttaaattca | 1740 |
| cagagaaagg acatatctttt gttaaagtcc atcttgcgga acaatcaaaa gatgaatctg | 1800 |
| aaccgaaaaa tgcattgaat ggtggagtgt ctgaagaaat gatcgttgtt tccaaacagt | 1860 |

```
caagttacaa cacattgagc ggttacgaag ctgctgatgg tcggaatagc tgggattcat    1920
tcaagcattt ggtctctgag gagcagtcat tatcggagtt tgatatttct agcaatgtta    1980
ggcttatggt ttcaatcgaa gacacgggta ttggaatccc tttagttgcg caaggccgtg    2040
tgtttatgcc gtttatgcaa gcagatagct cgacttcaag aaactatgga ggtactggta    2100
ttggtttgag tataagcaag tgtcttgttg aacttatgcg tggtcagata aatttcataa    2160
gccggcctca tattggaagc acgttctggt tcacggctgt tttagagaaa tgcgataaat    2220
gcagtgcgat taaccatatg aagaaaccta atgtggaaca cttgccttct acttttaaag    2280
gaatgaaagc tatagttgtt gatgctaagc ctgttagagc tgctgtgact agataccata    2340
tgaaaagact cggaatcaat gttgatgtcg tgacaagtct caaaaccgct gttgttgcag    2400
ctgctgcgtt tgaaagaaac ggttctcctc tcccaacaaa accgcaactt gatatgatct    2460
tagtagagaa agattcatgg atttcaactg aagataatga ctcagagatt cgtttattga    2520
attcaagaac caacggaaac gttcatcaca agtctccgaa actagctcta ttcgcaacaa    2580
acatcacaaa ttcggagttc gacagagcta atccgcagg atttgcagat acggtaataa    2640
tgaaaccgtt aagagcaagc atgattgggg cgtgtctgca acaagttctc gagctgagaa    2700
aaacaagaca acaacatcca gaaggatcat cacccgcaac tctcaagagc ttgcttacag    2760
ggaagaagat tcttgtggtt gatgataata tagttaacag gagagtagct gcaggagctc    2820
tcaagaaatt tggagcagaa gtggtttgtg cagagagtgg tcaagttgct ttgggtttgc    2880
ttcagattcc acacactttc gatgcttgct tcatggatat tcaaatgcca cagatggacg    2940
gatttgaagc aactcgtcag ataagaatga tggagaagga aactaaagag aagacaaatc    3000
tcgaatggca tttaccgatt ctagcgatga ctgcggatgt gatacacgcg acctacgagg    3060
aatgtctgaa aagtgggatg gatggttacg tctccaaacc ttttgaagaa gagaatctct    3120
ataaatccgt tgccaaatca ttcaaaccta atcctatctc accttcgtcg              3170

<210> SEQ ID NO 5
<211> LENGTH: 1057
<212> TYPE: PRT
<213> ORGANISM: Arabidopsis thaliana

<400> SEQUENCE: 5

Met Asn Trp Ala Leu Asn Asn His Gln Glu Glu Glu Glu Pro Arg
 1               5                  10                  15

Arg Ile Glu Ile Ser Asp Ser Glu Ser Leu Glu Asn Leu Lys Ser Ser
             20                  25                  30

Asp Phe Tyr Gln Leu Gly Gly Gly Ala Leu Asn Ser Ser Glu Lys
             35                  40                  45

Pro Arg Lys Ile Asp Phe Trp Arg Ser Gly Leu Met Gly Phe Ala Lys
         50                  55                  60

Met Gln Gln Gln Gln Leu Gln His Ser Val Ala Val Lys Met Asn
 65                  70                  75                  80

Asn Asn Asn Asn Asp Leu Met Gly Asn Lys Lys Gly Ser Thr Phe
                 85                  90                  95

Ile Gln Glu His Arg Ala Leu Leu Pro Lys Ala Leu Ile Leu Trp Ile
            100                 105                 110

Ile Ile Val Gly Phe Ile Ser Ser Gly Ile Tyr Gln Trp Met Asp Asp
            115                 120                 125

Ala Asn Lys Ile Arg Arg Glu Glu Val Leu Val Ser Met Cys Asp Gln
        130                 135                 140
```

-continued

```
Arg Ala Arg Met Leu Gln Asp Gln Phe Ser Val Ser Val Asn His Val
145                 150                 155                 160

His Ala Leu Ala Ile Leu Val Ser Thr Phe His Tyr His Lys Asn Pro
                165                 170                 175

Ser Ala Ile Asp Gln Glu Thr Phe Ala Glu Tyr Thr Ala Arg Thr Ala
            180                 185                 190

Phe Glu Arg Pro Leu Leu Ser Gly Val Ala Tyr Ala Glu Lys Val Val
        195                 200                 205

Asn Phe Glu Arg Glu Met Phe Glu Arg Gln His Asn Trp Val Ile Lys
    210                 215                 220

Thr Met Asp Arg Gly Glu Pro Ser Pro Val Arg Asp Glu Tyr Ala Pro
225                 230                 235                 240

Val Ile Phe Ser Gln Asp Ser Val Ser Tyr Leu Glu Ser Leu Asp Met
                245                 250                 255

Met Ser Gly Glu Glu Asp Arg Glu Asn Ile Leu Arg Ala Arg Glu Thr
                260                 265                 270

Gly Lys Ala Val Leu Thr Ser Pro Phe Arg Leu Leu Glu Thr His His
        275                 280                 285

Leu Gly Val Val Leu Thr Phe Pro Val Tyr Lys Ser Ser Leu Pro Glu
    290                 295                 300

Asn Pro Thr Val Glu Glu Arg Ile Ala Ala Thr Ala Gly Tyr Leu Gly
305                 310                 315                 320

Gly Ala Phe Asp Val Glu Ser Leu Val Glu Asn Leu Leu Gly Gln Leu
                325                 330                 335

Ala Gly Asn Gln Ala Ile Val Val His Val Tyr Asp Ile Thr Asn Ala
            340                 345                 350

Ser Asp Pro Leu Val Met Tyr Gly Asn Gln Asp Glu Glu Ala Asp Arg
        355                 360                 365

Ser Leu Ser His Glu Ser Lys Leu Asp Phe Gly Asp Pro Phe Arg Lys
    370                 375                 380

His Lys Met Ile Cys Arg Tyr His Gln Lys Ala Pro Ile Pro Leu Asn
385                 390                 395                 400

Val Leu Thr Thr Val Pro Leu Phe Phe Ala Ile Gly Phe Leu Val Gly
                405                 410                 415

Tyr Ile Leu Tyr Gly Ala Ala Met His Ile Val Lys Val Glu Asp Asp
            420                 425                 430

Phe His Glu Met Gln Glu Leu Lys Val Arg Ala Glu Ala Ala Asp Val
        435                 440                 445

Ala Lys Ser Gln Phe Leu Ala Thr Val Ser His Glu Ile Arg Thr Pro
    450                 455                 460

Met Asn Gly Ile Leu Gly Met Leu Ala Met Leu Leu Asp Thr Glu Leu
465                 470                 475                 480

Ser Ser Thr Gln Arg Asp Tyr Ala Gln Thr Ala Gln Val Cys Gly Lys
                485                 490                 495

Ala Leu Ile Ala Leu Ile Asn Glu Val Leu Asp Arg Ala Lys Ile Glu
            500                 505                 510

Ala Gly Lys Leu Glu Leu Glu Ser Val Pro Phe Asp Ile Arg Ser Ile
        515                 520                 525

Leu Asp Asp Val Leu Ser Leu Phe Ser Glu Glu Ser Arg Asn Lys Ser
    530                 535                 540

Ile Glu Leu Ala Val Phe Val Ser Asp Lys Val Pro Glu Ile Val Lys
545                 550                 555                 560

Gly Asp Ser Gly Arg Phe Arg Gln Ile Ile Ile Asn Leu Val Gly Asn
```

-continued

```
                565                 570                 575
Ser Val Lys Phe Thr Glu Lys Gly His Ile Phe Val Lys Val His Leu
                580                 585                 590
Ala Glu Gln Ser Lys Asp Glu Ser Glu Pro Lys Asn Ala Leu Asn Gly
                595                 600                 605
Gly Val Ser Glu Glu Met Ile Val Ser Lys Gln Ser Ser Tyr Asn
                610                 615                 620
Thr Leu Ser Gly Tyr Glu Ala Ala Asp Gly Arg Asn Ser Trp Asp Ser
625                 630                 635                 640
Phe Lys His Leu Val Ser Glu Glu Gln Ser Leu Ser Glu Phe Asp Ile
                645                 650                 655
Ser Ser Asn Val Arg Leu Met Val Ser Ile Glu Asp Thr Gly Ile Gly
                660                 665                 670
Ile Pro Leu Val Ala Gln Gly Arg Val Phe Met Pro Phe Met Gln Ala
                675                 680                 685
Asp Ser Ser Thr Ser Arg Asn Tyr Gly Gly Thr Gly Ile Gly Leu Ser
                690                 695                 700
Ile Ser Lys Cys Leu Val Glu Leu Met Arg Gly Gln Ile Asn Phe Ile
705                 710                 715                 720
Ser Arg Pro His Ile Gly Ser Thr Phe Trp Phe Thr Ala Val Leu Glu
                725                 730                 735
Lys Cys Asp Lys Cys Ser Ala Ile Asn His Met Lys Lys Pro Asn Val
                740                 745                 750
Glu His Leu Pro Ser Thr Phe Lys Gly Met Lys Ala Ile Val Val Asp
                755                 760                 765
Ala Lys Pro Val Arg Ala Ala Val Thr Arg Tyr His Met Lys Arg Leu
                770                 775                 780
Gly Ile Asn Val Asp Val Val Thr Ser Leu Lys Thr Ala Val Val Ala
785                 790                 795                 800
Ala Ala Ala Phe Glu Arg Asn Gly Ser Pro Leu Pro Thr Lys Pro Gln
                805                 810                 815
Leu Asp Met Ile Leu Val Glu Lys Asp Ser Trp Ile Ser Thr Glu Asp
                820                 825                 830
Asn Asp Ser Glu Ile Arg Leu Leu Asn Ser Arg Thr Asn Gly Asn Val
                835                 840                 845
His His Lys Ser Pro Lys Leu Ala Leu Phe Ala Thr Asn Ile Thr Asn
850                 855                 860
Ser Glu Phe Asp Arg Ala Lys Ser Ala Gly Phe Ala Asp Thr Val Ile
865                 870                 875                 880
Met Lys Pro Leu Arg Ala Ser Met Ile Gly Ala Cys Leu Gln Gln Val
                885                 890                 895
Leu Glu Leu Arg Lys Thr Arg Gln Gln His Pro Glu Gly Ser Ser Pro
                900                 905                 910
Ala Thr Leu Lys Ser Leu Leu Thr Gly Lys Lys Ile Leu Val Val Asp
                915                 920                 925
Asp Asn Ile Val Asn Arg Arg Val Ala Ala Gly Ala Leu Lys Lys Phe
                930                 935                 940
Gly Ala Glu Val Val Cys Ala Glu Ser Gly Gln Val Ala Leu Gly Leu
945                 950                 955                 960
Leu Gln Ile Pro His Thr Phe Asp Ala Cys Phe Met Asp Ile Gln Met
                965                 970                 975
Pro Gln Met Asp Gly Phe Glu Ala Thr Arg Gln Ile Arg Met Met Glu
                980                 985                 990
```

-continued

```
Lys Glu Thr Lys Glu Lys Thr Asn Leu Glu Trp His Leu Pro Ile Leu
            995                 1000                1005

Ala Met Thr Ala Asp Val Ile His Ala Thr Tyr Glu Glu Cys Leu
        1010                1015                1020

Lys Ser Gly Met Asp Gly Tyr Val Ser Pro Phe Glu Glu Glu
        1025                1030                1035

Asn Leu Tyr Lys Ser Val Ala Lys Ser Phe Lys Pro Asn Pro Ile
        1040                1045                1050

Ser Pro Ser Ser
        1055
```

<210> SEQ ID NO 6
<211> LENGTH: 105
<212> TYPE: PRT
<213> ORGANISM: Arabidopsis thaliana

<400> SEQUENCE: 6

```
Met Asn Trp Ala Leu Asn Asn His Gln Glu Glu Glu Glu Pro Arg
1               5                   10                  15

Arg Ile Glu Ile Ser Asp Ser Glu Ser Leu Glu Asn Leu Lys Ser Ser
            20                  25                  30

Asp Phe Tyr Gln Leu Gly Gly Gly Ala Leu Asn Ser Ser Glu Lys
        35                  40                  45

Pro Arg Lys Ile Asp Phe Trp Arg Ser Gly Leu Met Gly Phe Ala Lys
    50                  55                  60

Met Gln Gln Gln Gln Leu Gln His Ser Val Ala Val Lys Met Asn
65                  70                  75                  80

Asn Asn Asn Asn Asn Asp Leu Met Gly Asn Lys Lys Gly Ser Thr Phe
                85                  90                  95

Ile Gln Glu His Arg Ala Leu Leu Pro
            100                 105
```

<210> SEQ ID NO 7
<211> LENGTH: 21
<212> TYPE: PRT
<213> ORGANISM: Arabidopsis thaliana

<400> SEQUENCE: 7

```
Lys Ala Leu Ile Leu Trp Ile Ile Ile Val Gly Phe Ile Ser Ser Gly
1               5                   10                  15

Ile Tyr Gln Trp Met
            20
```

<210> SEQ ID NO 8
<211> LENGTH: 274
<212> TYPE: PRT
<213> ORGANISM: Arabidopsis thaliana

<400> SEQUENCE: 8

```
Asp Asp Ala Asn Lys Ile Arg Arg Glu Glu Val Leu Val Ser Met Cys
1               5                   10                  15

Asp Gln Arg Ala Arg Met Leu Gln Asp Gln Phe Ser Val Ser Val Asn
            20                  25                  30

His Val His Ala Leu Ala Ile Leu Val Ser Thr Phe His Tyr His Lys
        35                  40                  45

Asn Pro Ser Ala Ile Asp Gln Glu Thr Phe Ala Glu Tyr Thr Ala Arg
    50                  55                  60
```

-continued

Thr Ala Phe Glu Arg Pro Leu Leu Ser Gly Val Ala Tyr Ala Glu Lys
65                  70                  75                  80

Val Val Asn Phe Glu Arg Glu Met Phe Glu Arg Gln His Asn Trp Val
                85                  90                  95

Ile Lys Thr Met Asp Arg Gly Glu Pro Ser Pro Val Arg Asp Glu Tyr
            100                 105                 110

Ala Pro Val Ile Phe Ser Gln Asp Ser Val Ser Tyr Leu Glu Ser Leu
        115                 120                 125

Asp Met Met Ser Gly Glu Glu Asp Arg Glu Asn Ile Leu Arg Ala Arg
130                 135                 140

Glu Thr Gly Lys Ala Val Leu Thr Ser Pro Phe Arg Leu Leu Glu Thr
145                 150                 155                 160

His His Leu Gly Val Val Leu Thr Phe Pro Val Tyr Lys Ser Ser Leu
                165                 170                 175

Pro Glu Asn Pro Thr Val Glu Arg Ile Ala Ala Thr Ala Gly Tyr
            180                 185                 190

Leu Gly Gly Ala Phe Asp Val Glu Ser Leu Val Glu Asn Leu Leu Gly
        195                 200                 205

Gln Leu Ala Gly Asn Gln Ala Ile Val Val His Val Tyr Asp Ile Thr
210                 215                 220

Asn Ala Ser Asp Pro Leu Val Met Tyr Gly Asn Gln Asp Glu Ala
225                 230                 235                 240

Asp Arg Ser Leu Ser His Glu Ser Lys Leu Asp Phe Gly Asp Pro Phe
                245                 250                 255

Arg Lys His Lys Met Ile Cys Arg Tyr His Gln Lys Ala Pro Ile Pro
            260                 265                 270

Leu Asn

<210> SEQ ID NO 9
<211> LENGTH: 21
<212> TYPE: PRT
<213> ORGANISM: Arabidopsis thaliana

<400> SEQUENCE: 9

Val Leu Thr Thr Val Pro Leu Phe Phe Ala Ile Gly Phe Leu Val Gly
1               5                   10                  15

Tyr Ile Leu Tyr Gly
            20

<210> SEQ ID NO 10
<211> LENGTH: 289
<212> TYPE: PRT
<213> ORGANISM: Arabidopsis thaliana

<400> SEQUENCE: 10

Ala Lys Ser Gln Phe Leu Ala Thr Val Ser His Glu Ile Arg Thr Pro
1               5                   10                  15

Met Asn Gly Ile Leu Gly Met Leu Ala Met Leu Leu Asp Thr Glu Leu
            20                  25                  30

Ser Ser Thr Gln Arg Asp Tyr Ala Gln Thr Ala Gln Val Cys Gly Lys
        35                  40                  45

Ala Leu Ile Ala Leu Ile Asn Glu Val Leu Asp Arg Ala Lys Ile Glu
50                  55                  60

Ala Gly Lys Leu Glu Leu Glu Ser Val Pro Phe Asp Ile Arg Ser Ile
65                  70                  75                  80

Leu Asp Asp Val Leu Ser Leu Phe Ser Glu Glu Ser Arg Asn Lys Ser

-continued

```
                    85                  90                  95
Ile Glu Leu Ala Val Phe Val Ser Asp Lys Val Pro Glu Ile Val Lys
                100                 105                 110
Gly Asp Ser Gly Arg Phe Arg Gln Ile Ile Asn Leu Val Gly Asn
            115                 120                 125
Ser Val Lys Phe Thr Glu Lys Gly His Ile Phe Val Lys Val His Leu
130                 135                 140
Ala Glu Gln Ser Lys Asp Glu Ser Glu Pro Lys Asn Ala Leu Asn Gly
145                 150                 155                 160
Gly Val Ser Glu Glu Met Ile Val Val Ser Lys Gln Ser Ser Tyr Asn
                165                 170                 175
Thr Leu Ser Gly Tyr Glu Ala Ala Asp Gly Arg Asn Ser Trp Asp Ser
                180                 185                 190
Phe Lys His Leu Val Ser Glu Glu Gln Ser Leu Ser Glu Phe Asp Ile
            195                 200                 205
Ser Ser Asn Val Arg Leu Met Val Ser Ile Glu Asp Thr Gly Ile Gly
            210                 215                 220
Ile Pro Leu Val Ala Gln Gly Arg Val Phe Met Pro Phe Met Gln Ala
225                 230                 235                 240
Asp Ser Ser Thr Ser Arg Asn Tyr Gly Gly Thr Gly Ile Gly Leu Ser
                245                 250                 255
Ile Ser Lys Cys Leu Val Glu Leu Met Arg Gly Gln Ile Asn Phe Ile
                260                 265                 270
Ser Arg Pro His Ile Gly Ser Thr Phe Trp Phe Thr Ala Val Leu Glu
            275                 280                 285
Lys

<210> SEQ ID NO 11
<211> LENGTH: 132
<212> TYPE: PRT
<213> ORGANISM: Arabidopsis thaliana

<400> SEQUENCE: 11

Met Lys Ala Ile Val Val Asp Ala Lys Pro Val Arg Ala Ala Val Thr
1               5                   10                  15
Arg Tyr His Met Lys Arg Leu Gly Ile Asn Val Asp Val Val Thr Ser
                20                  25                  30
Leu Lys Thr Ala Val Val Ala Ala Ala Phe Glu Arg Asn Gly Ser
            35                  40                  45
Pro Leu Pro Thr Lys Pro Gln Leu Asp Met Ile Leu Val Glu Lys Asp
    50                  55                  60
Ser Trp Ile Ser Thr Glu Asp Asn Asp Ser Glu Ile Arg Leu Leu Asn
65                  70                  75                  80
Ser Arg Thr Asn Gly Asn Val His His Lys Ser Pro Lys Leu Ala Leu
                85                  90                  95
Phe Ala Thr Asn Ile Thr Asn Ser Glu Phe Asp Arg Ala Lys Ser Ala
                100                 105                 110
Gly Phe Ala Asp Thr Val Ile Met Lys Pro Leu Arg Ala Ser Met Ile
            115                 120                 125
Gly Ala Cys Leu
    130

<210> SEQ ID NO 12
<211> LENGTH: 123
<212> TYPE: PRT
```

<213> ORGANISM: Arabidopsis thaliana

<400> SEQUENCE: 12

Lys Lys Ile Leu Val Asp Asp Asn Ile Val Asn Arg Arg Val Ala
1               5                   10                  15

Ala Gly Ala Leu Lys Lys Phe Gly Ala Glu Val Val Cys Ala Glu Ser
            20                  25                  30

Gly Gln Val Ala Leu Gly Leu Leu Gln Ile Pro His Thr Phe Asp Ala
            35                  40                      45

Cys Phe Met Asp Ile Gln Met Pro Gln Met Asp Gly Phe Glu Ala Thr
        50                  55                  60

Arg Gln Ile Arg Met Met Glu Lys Glu Thr Lys Glu Lys Thr Asn Leu
65                  70                  75                  80

Glu Trp His Leu Pro Ile Leu Ala Met Thr Ala Asp Val Ile His Ala
                    85                  90                  95

Thr Tyr Glu Glu Cys Leu Lys Ser Gly Met Asp Gly Tyr Val Ser Lys
                100                 105                 110

Pro Phe Glu Glu Glu Asn Leu Tyr Lys Ser Val
            115                 120

<210> SEQ ID NO 13
<211> LENGTH: 70768
<212> TYPE: DNA
<213> ORGANISM: Arabidopsis thaliana

<400> SEQUENCE: 13

| | | | | | |
|---|---|---|---|---|---|
| aattcttata | tttgacttca | acaatatac | gcaaatttaa | cgttttaaag | cgtgtttata | 60 |
| caactcacat | gtattaagtg | atttcaattt | gtattaaatg | atacttgtta | atgtagatta | 120 |
| cgttttcga | aattatatat | tgtaatttca | aaacaatgat | ttttaagaaa | agtattaaaa | 180 |
| tgaaacactt | ttaaaaaata | tttgcgcatc | ttctaaccga | aaacaaaact | atacacattt | 240 |
| ttgagtgtga | acaagacaat | gtacagttga | aaatgtgtac | aattcaaatc | actcataatt | 300 |
| ttcctatata | ctatgtcaaa | actatatgcc | tcaagactaa | cttttttttta | tcatttcaag | 360 |
| attattctgt | aaatgattgt | tttatatgtt | tgataactac | caataaataa | aagattaaga | 420 |
| aaggtagatg | actaccaata | gactaatcaa | cacaattcaa | agggaaatat | aaactttaac | 480 |
| aaaagatacc | ataaattacc | ttgcaggaga | tagagcaaaa | aagattagga | tgatcctgaa | 540 |
| tatatctttt | acaagtcaca | catgaagcac | cattcttggc | ttttgttgaa | ggtcttgcat | 600 |
| cttttgcttg | tggccttgaa | ttcaaatgta | ttgccttctc | tccatttatt | ttatatgtct | 660 |
| ttttccccca | tacataaatt | attgccaacc | aataccaaaa | ttaaaaacat | taatttggaa | 720 |
| ctctaaaaca | agaattcaaa | tgattatttt | attaattatt | gaatgattta | gatatttaaa | 780 |
| gaaaaaaaaa | acctgaatct | cggaacagtc | gaagtagttt | tggatttcga | ggagacgaat | 840 |
| aacatcttgg | taaacgtatt | tgcagatctg | aagacgacga | tggaggaaat | gagaatctgt | 900 |
| aactgtgtta | caacaatgtc | tgcatatttc | cacattacaa | tcaatgcaaa | acacattctt | 960 |
| ctcgttcttt | ctaagatact | tatgattcat | acatatccca | aagaactctg | agttcagtag | 1020 |
| tgtttcaatc | caaacttctt | cacttcttct | cttctcactc | tacaaaaatt | attgctatta | 1080 |
| ctttttttaga | tttgcataaa | cttaattatg | atttataatg | aattactatg | aagaagaaaa | 1140 |
| aaacatgaat | attatccgga | aaaaaacaat | ctgtacaaat | ttgaaacttt | attgacttta | 1200 |
| ttttttttat | atgaagaaat | ttaaaacttg | aattagagag | atcagtttac | aattaggaaa | 1260 |
| agaaaaaaaa | aataaaacta | catttttgaa | ggatatggaa | tctgcagaaa | ttttactttt | 1320 |

```
tattgaaatt tataaagaat ttataaatgg gctatatgaa gaaatcataa ctataaattt      1380
tgcagaaatt ttcttgtttc taatttatat tgaaactatg aacttgaatt gaagggattt      1440
gttttcaaca acaacaacaa caaaaactaa cactgcagaa attaataaga aaaaatgagc      1500
atgtaccaga ttcattttgg tatgagaaac tgagttcctt tgatagatca gatgagaaga      1560
ttttatattt ctccgatcaa aatcatccaa aaatatttta gtgttcttgg aggagaagaa      1620
gaagaagaag aaggccaaaa gcaaaagaa gaagagagat gtgatttgat ttgtagtgtg       1680
aataaaaata gtagaagaag gcaaacgaaa tattaaagaa atgatattag gaatgtttca      1740
attaattaca tattgtgttt tgtggagaat aataaattaa aaaaaaggaa actaaatgac      1800
aattaatatt aaaaatgagg gaaaaatcaa aagtccacag agtcaacaat aactgtgact      1860
ctttaatacc taaaatggat accaggcggg aatatgaagc atgtgtaact tttaaattac      1920
tgttttgtct ctagataaat cgataagtat gtttttaata cgaatgaaat ccactaatta      1980
ggtcattaat atgcaaattg taataattaa aaatgagtgg acataatttg actttgaggg      2040
gcaaaaagtt aagtctttat aatttagatg gtgcgataaa ggtaagcaaa gcttcctata      2100
tttactccga aatttccaag gaaacaactt atcaaattta gaattatatc attttctaca      2160
tatacataga taggaatatt tgatgtcaaa aataaccgtt ccaaagtgca cataataata      2220
tcttaggcaa attcaaatcc agcacataca tactatactt atggagagac tagattattg      2280
cttgatgttc gcatacatag acaattgaaa tttaaataga ttggtgaaat ttgttacaga      2340
tttagttgaa agtatcctaa aaaatatctt atcatttgct cataatttat aaattaaaaa      2400
aaaagtatat cacttgaaaa tcgttaagat gaatattaaa accagaaagt aatagtaaag      2460
tattttgata atgagcatag tagcatttat agattatata aaattgaaat tataagtttta     2520 ggtagatgtt tctatggcat tccatcttcg atacaacata tgacagaaag ttttccctat      2580
tcgagataat acgtatgcgg ttttcacgt ttttacgttt tagaaatatg atttagttga       2640
atacatacca tttgcaaaaa cttgcgatga ttattaaaac gtggaaataa tatgtgtttg      2700
ttcaatttat cttgcacgtt ttaatacaga ttttcgtct caacgttgtt gatctatgct       2760
gatagtagca ctggatgaaa gattagaaga aatacaacaa aaatgaacat accacttggc      2820
atggtgactc aatgatgtct taaccctaac tttatttttt gttcttgaat taatctagtg      2880
taatattgaa tacaaatcca taagataata aaataatata tatttttaaa attatgtatt      2940
aaatgtatga tcacatcaat attataagtt aataattata caaacttatc aatatatatc      3000
taaaataatt agtgacatat gagtatataa ctctagtatt gttttttgttg ttgaatctgc     3060 attatattgg agctcatatc taatcttttt taactacatc aaaagctgtg aatggtttat      3120
aagtgataat tggttcctta catgtaaacg gttaagtttg cctaacttag ttccaattat      3180
tggtgtcacc tttgatgttt agattttata tcatatgatc agtgaaccta aatagtagat      3240
gcttaatatt atgaagattg gattggacag tgtgctttat aaaatgaggg acaccaaaat      3300
catgtatttc attagaaggg aaggaccaac tggctcatag caaattgaat gaatacggag      3360
actgctttga tattccagtg ggtgtatggt ccaaagtcca aacccataaa cacatggctt      3420
tattggactt gtgggcttgg aatacaaaat gatttctcat agaaagtgta cttatagtaa      3480
tctacttgct taaaccccta acacatgtt aataacttaa accgcagtga gttcaaaata       3540
ctgtttggtt cagcttttac ggtttatgag ttggatttta ctgacgaaat attaaaattt      3600
taagaactca aagattgtta tctttgcata aaaactacac aaagtagata gataaataca      3660
```

```
ctaaccaaaa gcttgcagta gataaaaacg aagtcataag taaatatgct tcagagaaaa   3720
gcaaaaaaag ggagagcgag agagagattt atcacacaat gcttcatctt cttcttctac   3780
taaaacgttt tacgcaatct tgattttttc aacgtccatc cacagaagtg aacgagtcag   3840
caaatccaga tgggcgagtt gggatacttg tctgcgtatt gtctttgctt ccataagccg   3900
aagacgaaga tcccgagtca tccgcggtct ggcttagtcc ctcgaaagct tgccatttct   3960
taagcacctg cggaagcggc atatcgtagt ctatcccata gacgtcatca gggtcggtct   4020
cagttggttt ccattggacg gtgagtgaag aaaggacgtt aacgatgtga gccatgtcag   4080
gtctttggta aggctcacgg gcacagcaat gaccagcaag ctcccagact ttttcaatac   4140
tggctacggt atcgtcgtcg aggctgatgt ttgggtctat tgcgttttg aaggcatttt   4200 cgtctttgct ggctgctacc cgacggaacc atgtgactag atggacgctg tcttcgggtt   4260
gcgtctcgtc tagggcttta cgaccagtga ttagctccat aagtatgacc caaggctga   4320 aaatgtctac cttggtcgtc actcttcccg tcactgccaa aatcagagta tagaacaatt   4380
gccaaacgat caaaggatga aactataaca tttaggaaaa tgcaataaga tcaaagcatg   4440
aaaatttaag tgcaaaacgg ccaaagtatg aaactttgac actgggcaag tgcaaatcaa   4500
ttgaaaggca gagactttaa aatttgggta agtacaaacc tgcgtattct ggggcaaggt   4560
atccgaaagt cccagctact cgagtctcaa tggagtattt gccatcaggg gctaaacgta   4620
ctaacccaaa gtcagagact ttagcgcgca tatcatcacc aagaaggatg tttgatggct   4680
ttagatccct atggataaag ctctgatgcg caagtgtgtg cagatactcg acacctcgag   4740
ctacatccaa tgcaatcgcc agccgtctag tccagtctaa cggttttcgc ccttcctctt   4800
tccagtggaa caaatgctga cttagtgtcc cctgtggcat gtactcgtag acaagaagcc   4860
tctcgttccc gtcaaggcag taaccgagaa gcgcaacgag atgacgatga cgcattttag   4920
tcagaacagt gatctcagat ttaaactcag taagtccctt atcactcaca accgaagact   4980
ccattctctt cacagctatt tttgttccat cgtggagttc gcctttgtaa actgtcccga   5040
aaccacctct cccgagaata ttctcttcgc tgaagttatt cgtcacattc ctcaagacct   5100
gtatcgatat aaccaagttc ccagcttcaa caacgtgaat atcactcgct gcacttccgc   5160
tgtgactgta gctatcactt cctccaccac tgttaagact agaagctgca acagtgagtt   5220
taatgtcatc gttgtcaccc gaatgatgcg gatgaataac catgttgctg cttggacttt   5280
gaactctagc aggtcgcttc cttttcttcg cataaagaca cacaccaagc ccaaccaaac   5340
acaatgcacc aacaacccca ccaaccacag gaacaataat cttgacattg cttgatttct   5400
tagaagtttc actgccatca cttcctcctg aaggtttact tcctggtgaa gctccaggag   5460
catcactcgt tttgttaggt ccattcttcc ccatgttagc gttcccttca gtcaccaaag   5520
tcacagtatc ccgaaacttt ggcggtattc cataaaaatc gttgttagac acatcaagta   5580
acctaagctt agacaatgtg gtaagctcat caggtatatg cccggagagt ttattatcag   5640
caagattgat agtctccaat gaagtaagct tagctaaact cggagaaatc gtacccgaga   5700
gatcctgttt cctcatatta acaaccgtaa tgttacctcc agaacaagta atcccaaccc   5760
agttaacaca aggattgttt cctttccaac tttccgcaag cttcactgga tatccaaatg   5820
attcagctac agataccaaa gtatccacac gaggatcaca agcctcacca gctacattag   5880
tacaaaagct attcatgttg ttgactatat caacaccaac ggatttgcca acaacggag   5940 tcggtccttg aagataatta ttagtttaaat tcacagtagt aagcgaactc aaactaacca   6000
aagactgtgg aacaacacca gtgagctgat tctctctaac attaaacaca cgtagagata   6060
```

```
ccaaaccaga gagatcagga attggacctg agaactgatt tccttgaaga gaaacctcaa   6120
cgagcgaagt catgttcccc aataccgaga tcgatccatt aagcttctga ccattcaaga   6180
acagagactg aatcgaagta ccagcaaaac tcatcggtaa ctctccttct aaaccattct   6240
gagatagttt cagattcgtc aagctcggaa gtgactgaga accgaagaaa tctgggatct   6300
ttccaataat gctgcaattg gagagagtta gattctgcag agacgtagct tctttaacgg   6360
tgtctggaat tacccaagga tcaaacggat tgttctcgag atacatttct tgaagagaac   6420
tcataccaga gaagagattc ttcggtacag aggtaaaaag attgtcgtgt agattcagag   6480
tctgtaaacg agataagcca gagagatcag gaataggacc agagatacga ttgagaaaaa   6540
gctcgagaat aaccaattca gagagactct gaagattagt aggaagagtt ccacgaatcc   6600 cttttttgttt aagctgaatc ttagtaacac gattacttcc atcgcattga acagattgcc   6660
atttacaagg gttagggtta gaccaatcga cgtctgatgt aagattcaga cttgatttga   6720
gagattgcat agtcgaatca tcgagaccgg tttgagaaag tgagaaattg gccaaaccca   6780
gtaaagagat gatgaaacag agagtaccca aatgggaatt tgacattttt tgttggagaa   6840
agaaacagag tggaggaggt taaaggtgtc gcctttgaga attctgagtc tagggtttta   6900
gggaggcatt gaagaagaag aagaagaaaa ggtttacaga gaggaaaggg aaagacgaag   6960
gaatcggcgg agatcgagga agatagagag acgaagaaga ttaaaggtaa gaggatcata   7020
aaagcattgc cttttttattt attattctca ttcaaatgaa atatttattc ttctgtaata   7080
aaatggatga accataatta ataaaaatgc atactttaag ttttgcttgt gtagagtgtg   7140
tgtgtgtgtg tgaatacagc tggcaaggtg gcataattag tggtgaaaaa caatagtgaa   7200
aatcgccgaa taatccataa ttatgaataa tgagattatc tactaattgt gtttataact   7260
ttatattaaa aaaaaatcag aattaggaat aagatacaaa ttttatgaca tttagatgtt   7320
ttcagtttag gtgaatatat tattaacatt tgtaaagttt gtaaataaaa atcacatttg   7380
aaatatttta tttatatatt caattagaga attttacttt ttaggaagtt ttaacaattg   7440
atttgtgtca aaattggtaa taataaaagt aatatctcta tgattgagtg tatttcggca   7500
tttttcggac taaactgcta ataatatcga ttgtctttcc taaattttta aaatatttta   7560
ttttgtaata gatcttggat ttttgttcac attatttcca tttgcttcta taaaaaaagg   7620
atattatttc ctccttatga atatttgtgg gacgaataca atacgtggaa acttatctgt   7680
atttcttaga atagaaaaag catttaatac ggtgacggtg gttacctatt gtttagggtc   7740
aaagattagt cgaaaattga aatttcatcg taacgtgcta aagacagttt aagattacac   7800
cgttttattt aattcatttt ttgactcatt gtgtcacgac ttcgtgagta attatatact   7860
ttgaataaaa aaaattaaaa gattaatgag tactttgcat tgcatggtct taatcttctc   7920
atgactaatt ttgaccaaac aagataaatg tgatttttttt gcagtcccga caaaaaagtt   7980
tttaactgta aaagacagac gccgtgaaat ccggagcata ttagccacgc attaatcttc   8040
attcggctga ttttttaacg gtcgttatct tacgccgttt accacaattt ttaatgtttg   8100
ttaggttgga gagttattat tattacttac cagtttcact ctaacctaga actattcttc   8160
ttcttatggt attgaatgtc tgttttttatt cactagtaat aaatattata actatactat   8220
tttaaaaata gttatagtac gatatgtaga aattgggaca tgtatattgt tgttgttaat   8280
cttatagaaa aatagtaaaa gtagctaaag attggtgtat tatacgcacc aaccatatac   8340
tataaactcg cacgaaaatgt agatcgaaca cttgtgtacg tagaaagatt acgtgacaac   8400
```

| | |
|---|---|
| aacaactagt ccactttgct gttcgttacg gtcacacatc aaccacattt atttcactta | 8460 |
| cttcttttt caatcatttc ttaaattctc aataattcta aaaatcagat atttgtccaa | 8520 |
| acctctttgg tgtagtggca caaggaaact ttaactccta tacctgagtt tgatttttca | 8580 |
| tgaaaacaat aacaaatttg tttagaaagt ctctcagttg tgatttggtc caattaattt | 8640 |
| atttggtagt tagaaatgca aacggtatga ttatccttgg tattagtcgg aaggcatttc | 8700 |
| aaattagaac ctaacagtgt ggtgatccaa ttctacctaa atcgggagaa attcattctg | 8760 |
| tagtatttcg ttgcgttcct actgaaactg ataaaataag tcgatagagt atataaaaaa | 8820 |
| caaacaaaaa gtcagatatt ttctatatac tcttcttgga caagttccta attcttctca | 8880 |
| tcctttatag attacatcga gagatccgat taagggttg ttgattggct ttggttatct | 8940 |
| cactcggttt agtgagatcg acgaaccaat agtaaaacgc agtcgttttt aagctttgct | 9000 |
| ctgtttctgt tgtttgaaag ctcaagtcgt cgactgagct atagctaatg aagagttgtt | 9060 |
| tgagctcttt ctctgatctt cgttcaacta gctaaccgat ttggttgcta aacaagctca | 9120 |
| aaagatgaat caaaatggtc tcgtctcaag ttataagaag atgttatata tggaaaagtt | 9180 |
| attattagaa cattacaatg tttaaacgac taaccaaatc tgatacagta caaacgatcc | 9240 |
| cgtgggatta atacttacgc taagatcaac actgaaccgt cgtcttagac gttgtcgttt | 9300 |
| aacaacatac actagtcatg gcaagctaca ttacttcggt gaaagaaaaa aaaaccttca | 9360 |
| aaatctctag attgtgaacc tactgtatgt acagaaacca aaatgcatat caatcagcag | 9420 |
| aatcggtcca ctcttccggc tgcggagaga gaaaaaaaac tcgccggaag attggattac | 9480 |
| gacgaaggtg agataggatt aggtttgaat gatttggcaa cggatttata gagattctct | 9540 |
| tcttcaaaag gtttggagac gtaaccatcc atcccacttt tcagacattc ctcgtaggtc | 9600 |
| gcgtgtatca catccgcagt catcgctaga atcggtaaat gccattcgag atttgtcttc | 9660 |
| tctttagttt ccttctccat cattcttatc tgacgagttg cttcaaatct gagaatcaat | 9720 |
| gaagtttata aaagatttta accgaatccg aaccaaacca agtcagttat aatttggcgg | 9780 |
| gaaattttc ataccgaaca attcaaaaac cgaataatcc aaaaatagta ttagttgtga | 9840 |
| tttagttacc cgtccatctg tggcatttga atatccatga agcaagcatc gaaagtgtgt | 9900 |
| ggaatctgaa gcaaacccaa agcaacttga ccactctctg cacaaaccac ttctgctcca | 9960 |
| aatttcttga gagctcctgc agctactctc ctgttaacta tattatcatc aaccacaaga | 10020 |
| atcttcttcc ctgtaagcaa gctcttgaga gttgcgggtg atgatccttc tggatgttgt | 10080 |
| tgtcttgttt ttctcagctc gagaacttgt tgcagacacg ccccaatcat gcttgctctt | 10140 |
| aacggtttca ttattaccgt atctgcaaat cctgcggatt tagctctgtc gaactccgaa | 10200 |
| tttgtgatgt tgttgcgaa tagagctagt ttcggagact tgtgatgaac gtttccgttg | 10260 |
| gttcttgaat tcaataaacg aatctctgag tcattatctt cagttgaaat ccatgaatct | 10320 |
| ttctctacta agatcatatc aagttgcggt tttgttggga gaggagaacc gtttcttcca | 10380 |
| aacgcagcag ctgcaacaac agcggttttg agacttgtca cgacatcaac attgattccg | 10440 |
| agtcttttca tatggtatct agtcacagca gctctaacag gcttagcatc aacaactata | 10500 |
| gctttcattc ctttaaaagt agaaggcaag tgttccacat taggtttctt catatggtta | 10560 |
| atcgcactgc atttatcgca tttctctaaa acagccgtga accagaacgt gcttccaata | 10620 |
| tgaggccggc ttatgaaatt tatctgacca cgcataagtt caacaagaca cttgcttata | 10680 |
| ctcaaaccaa taccagtacc tccatagttt cttgaagtcg agctatctgc ttgcataaac | 10740 |
| ggcataaaca cacggccttg cgcaactaaa gggattccaa tacccgtgtc ttcgattgaa | 10800 |

-continued

```
accataagcc taacattgct agaaatatca aactccgata atgactgctc ctcagagacc   10860
aaatgcttga atgaatccca gctattccga ccatcagcag cttcgtaacc gctcaatgtg   10920
ttgtaacttg actgtttgga aacaacgatc atttcttcag acactccacc attcaatgca   10980
tttttcggtt cagattcatc ttttgattgt tccgcaagat ggactttaac aaagatatgt   11040
cctttctctg tgaactgtca aaagacaaac atcttgatca aacaaaaatc atatacacaa   11100
gctgccaaca aaggcagaga ttgaaatagg gactaacttt aaccgaattt ccaacaaggt   11160
ttatgattat ctgtctaaat ctccctgaat ctcctttgac tatctctggt actttgtctg   11220
aaacgaaaac cgcgagctgc caaatttgaa atcaagaaat tagcagccac aactccaaat   11280
agatgtatct ttattccttg gattgaaaac ttacctcaat gcttttgttc cttgactcct   11340
cagagaatag agaaaggaca tcatccaata ttgaacggat atcaaatggt actgattcca   11400
actccagctt tccagcttca atcttggcgc gatcaagaac ctcatttatc aatgcaatca   11460
aagctttacc acatacttga gcggtttgag cgtaatctct ctgtgtcgag cttagttctg   11520
tatctaggag catagcaagc attcctgcag aaaattttta aaacagaatc tttgaggcag   11580
tttgagaaac caaagatgaa aggcaacagt actggaattt gtttgaagat gtagtaccga   11640
gaatgccatt cattggtgtc ctgatctcgt gagacacggt agcaagaaac tgcgatttag   11700
cgacatcagc agcttctgct cgaactttaa gctcttgcat ttcatggaaa tcatcttcga   11760
cttttactat gtgcatagct gcaccataca gtatataacc caccaagaaa ccaatcgcaa   11820
agaacaatgg cacagttgtg agcacattca acggtattgg tgccttttgg tggtacctgc   11880
actcgaaatt gttcaaacaa gatatcagtt tttagatatc agagagtatt ttagctttaa   11940
gattttctgt gtggtacctg catatcatct tatgtttcct gaagggggtct ccaaaatcga   12000
gcttgctctc atgagagaga gatctgtcgg cttcttcatc ttgattacca tacatgacaa   12060
gtggatctga tgcattggtg atatcataca catgcacaac tattgcttgg ttaccagcaa   12120
gctgaccaag taaattctcg actagagact ccacatcaaa cgcaccacca aggtacctgc   12180
atttcaaatt caagcatcaa tctttacttt acacacaaac caatcttgaa atctcaaaaa   12240
acctctttcc tttacatgat cacacacata aaccaatcat gaaatctcga aaatctcttt   12300
ttacatgatc acaagcaaaa gtttgctcca gtaatcagat gggaacttta ccctgcagtg   12360
gctgcaatac gctcttcgac agtcggattt tcaggaagag aagacttgta gacagggaat   12420
gtcaacacaa ctccgagatg gtgagtttcc aacaacctaa aagggctagt caagacagct   12480
tttccggttt ctctagctcg caaaatattc tcacgatcct cctgcagaaa agatagccaa   12540
aattcagaag aggtgcaggt cggatactta accgaaaaaa caaaaccata agtgtctgat   12600
aatgtttata ttacctcgcc tgacatcata tcgagtgact caaggtaaga gacactatct   12660
tgagagaata taacaggagc atactcatcc ctaaccggtg aaggctctcc tctatccatt   12720
gtctttataa cccaattgtg ctgccgctca aacatctccc tctcaaaatt cacaactttt   12780
tcagcataag ccactccact tagcaacggt ctctcaaatg ctgttcttgc cgtgtactcc   12840
gcaaatgtct cctgcaaaat tagccacaaa ccaatgagta aagcaaaggc ctaaatttcc   12900
cttcatttac tcaataacca aacataaaag agtaaatttc aaaaacttct ggttccaaaa   12960
aaagtcaact ttgcatttat gaatcaaaaa tttcaccaaa gctttgagct tttaataaag   13020
cacacactga cctgatcaat tgcagaaggg ttccttgtggt aatgaaaagt ggagacgaga   13080
atagccaaag catgaacatg attaacacta acactaaatt gatcctgcaa cattctagct   13140
```

```
ctttgatcac acatgctgac caaaacctct tcccttctaa tcttattagc atcatccatc   13200
cactgataaa tcccactgct tataaaccca acaatgatga tccacagaat caaagctttt   13260
ggtaacaatg ctcgatgttc ttgtatgaaa gttgaccctt ttttattacc cattagatcg   13320
ttattattat tattgttcat cttcaccgcc actgaatgct gaagctgttg ctgctgctgc   13380
atcttcgcaa aacccatcaa ccccgaacgc caaaaatcga tctttctcgg cttttctgac   13440
gaattcagag caccaccacc acccagttga taaaaatcgc tgcttttcaa gttttctagt   13500
gactcggaat cagaaatttc aattcttcgt ggctcttctt cttcttcttg atgattgttg   13560
agtgcccagt tcatatctga gctacaacaa tagagaacaa aagaagaaac aatagtgaaa   13620
gaaaacaaaa gttagagcct tttttgcata catataacat aaaagcattg gtagtgtagt   13680
tatgattaag aatgttacca taaacatagt ttatagtaca gaaacaaacc ctagaaacct   13740
gtagacgaaa aaggacatgt ttttgcgaat tcaagaacaa aagagagaaa gaaacgcatg   13800
gttctcaaaa gaagcaactt tgctcagttt ccaaaggttt cttacagaga agaattaaaa   13860
actaagtaat tattgtcaga gaaattaatt aatactaaaa aacacactaa tcaatcataa   13920
gctctttaca ggcgtgattg tttattattg gaacaagaac atagctatgt tcactgtctc   13980
aaatccaaca atagaaaaaa aattaaagct ttgaccaaag aaagaaagaa cacagagaga   14040
aacataacat taggaagaac gactaataag caagcacatg gagaaattat tttagttacc   14100
tgtaatgagt tgtgagagga ttgaacattg cattattatt atacacaaaa tctcttctca   14160
tcacttcaaa tgtaggtatt ccattttctt tcttctttct tcttcttttg ttttagtgag   14220
atttttttgct tttaaaagta agaaaaaaat tgaatcgaat tttttagatt ttcttcagat   14280
acgtttctct ctctctgtgt ctctgtctat atcagttttt tgccatgaac tttcttttca   14340
tttttatatc tctctagctc tttttttcttt ttctaacttg agtccaactt tgaagaagaa   14400
aagttttgga cttttttctta atggctcatg atatgatcca tccaacaaaa gttattattt   14460
tacccaaaat ctcctcaaag ttaacattat tatacgaaat agatatattt tctctaaccg   14520
aattgtcggt atttactgtg tatttagaga aattgcaaag cgacaatgaa gaattcacaa   14580
acttctcttt atctataatt ttttataatg ctaatataaa agcgtataat ttggcgcgga   14640
agatccgcac cgaaccgcat catatcacat ttgtaaataa tatccctcag gattggttta   14700
cttgagcttt aataatttg gatgacaaaa aaaaaaatat aattattgtg acactaacta   14760
ggtttgtctt actaattaaa acatctttaa aactacattt attcaatttc attacatttc   14820
ttatacatca tttaacattt aaagtaacat ttaccatgtt taaatttctt gaataagtga   14880
agtaatatat agtcaccaac ttctcaaaat ttattatcta ttttttcctt ggtataaata   14940
agttttctga actttagaaa taaaacgttt tgttttgttt tttacttac accaaaagga   15000
aaataaaacg ttttttttgtt gaaatataag aaaacaaaaa ataggtga gtgagagact   15060
ttgtacgaga gtcgctatcg catatctttg gcgataatga catcgcgaca aagcgcagat   15120
ctggccccat agacctttta cctgaaatac ccaccattct agtctcttaa ctacgaaaat   15180
accccggtta aatgggcctg actcataagc ccatgattta tccacgtgta attcttaaga   15240
caattgcatg agttgattca ggagatttta gaattcaaaa tttatgaata acaatcaaat   15300
tatttattta ctactagtat tatacggtaa actatttttt atattattta gagtgtttct   15360
ttttttttgta atagcaaatt gttatgacct aaccacaaat ttaaaatgct catgaatttc   15420
taaaaacgtt aaaaacaaaa aatcattaaa ttattacatg tttgaggcaa tagtaaatca   15480
atcccattaa attagtacca tattaaatga taacatagtt atgagtttta taatgaaaaa   15540
```

```
tacagaaaaa aacatagagc tattattaaa gatacatgaa atatattatta ttaccttata    15600 tgtgtagatg gaaactgacg tgggttgtgt agctttctct cgtgcgctta gagacagtag    15660
cttctataac tacatgatat ttgagagaag ttttttgaata ttcaaatgga ttttaggaac   15720
acttgtatgg ttcctttgaa atatgcagaa ttagaactta aagcaagatt gataaacata    15780
gagaagatac gtgtttggga taccttaatt tcatggcttg atcagaagct ttcagtcata    15840
gatgaatgca gtgtagtttc ttttccgct attgattctt tgatcgctgc acatgtcaca     15900 gaatttagt aatgattttt gttacagatt tctatatatg tttataacag aggccagtga     15960
aactcacatt gtgctcttcc gagaaagaaa aacaaacaa tgaatctgga ataaagtgaa     16020
attaacctaa gaaaaataga agacaataaa cttggatcga ataccatttt ttctatacaa    16080
tttcatatcg atggatctgg gaatgatttt tttttttttt tggaggaagc aagagcaaga    16140
gatagattta acgtgaattg gatttttgta gaggaagata aaacggtttg gaaaatcttg    16200
agttggttac aaatttccaa agataatgat ggtgtggtgt gtgagaaaat ctaggaatat    16260 tttttttgttt ttaaatatgt agaaaaaaaa aatgagcgtt ttttttttaa aaaattttaa   16320
ataattcttt aaattataaa caaatcttat gtggcataat tttattgggc aagggacttg    16380
tactttatat tataaaggaa aaagaattta ttttatttttc tttttgttc tttattta      16440 tttttttaata tatatatata ttaaaattta actcaaatgg gtttgggtta gaccttagag   16500
aaacataaat ggttaaaacc taacgaaaat aattgaaaac aaaaatacaa tgtgtgaatc    16560
cctatacatt attagtcaat gcattgaaaa aaattgtttg aaaattgaca aaatgggtcg    16620
atggaaatat caaatatcct tttttttgtta tgtatggtta attttagggaa atgtcttata  16680 aaaaaggtga tccgtttggc attgaccatt gtttcctctt tttcttatac ttcattctct   16740
ttgatatcta tatttctact acctaggatg gacattcttt tgtatgatat ggagtcgaac    16800
caatctcatt ttacttttag tttcatcttc gcttgaacca tgttctacac aaatattctt    16860 gaacttttttc ttttaatttta aacactcttt ttcgcaactt gttgatgatc gatgttaaat  16920
gtgactagat gaagatgaag atggcgacgt tggtgtggca atattgctac tcagtttcta    16980
tcaattatag ttttccgacg tgagattcat ataaagcatc catttcatgt tcatgtagga    17040
cacactctat tttttcgaca gtttgctaa tttttatcct ttattcacaa agatgtaaaa     17100
aagtagaata tatggattta gtagtacaca aagatagggg gaaaaggggg tacacaaagg    17160
aagtggtgct aacaaaatgt gtgtgtgtcg gccatgtgag attcatgttt gactttatat    17220
cattaaatca tttagtggtt acaatttaca aattctcctt atttattaag attttataag    17280
attttgtaac atattctatt tttcggtgtt tgtatttact ctcaaattat gttttttgt     17340 cacatgctcg acaatcactc ccattcaacc aattcattta tttaaaataa caccaaaacc    17400
aatccactgt atttcataaa ttaatttggt tatattttcg ttagttctta tactgcatgt    17460
ttataacttt taacgattct tcatacaaag tgttcactat tttgagtcaa aaaagcagac    17520
tagtgtaatc gtcctttctt caaaagtttta tataaacaat cacgatttaa taattactat   17580
ctcaatcaat cgtaattcga aagtccaata gaatatttta tagagataag atcaactaca    17640
ttcattaaat aagatatcct atgttaaact ataattatca ctcataaatc aacatcgatc    17700
aatgattctt tgaccaagat aaagttattg taattaggtg aaaaaatcca aagatttcac    17760
actcaaatga cacacaaaat ctagcatatt tgttttcaag aataaagatt gtccatgttc    17820
atgaacaaac acaaacggat gcttgaaatt tcataaattt acctaagatt aagaacattg    17880
```

```
tcacaaatca ttaaaagatt ataaagttca catatatcat taaatatata ctaacaacat   17940
tgtcaaaaag atattaaaaa ttaatttttg actcacaatc attaaaaaca tgaagccatt   18000
tactaattta atactaatat atgatttgga aacaagtctt tgaatctctc tatacattgt   18060
tttgacacct taaatagcga ttactagact ttccacatat ttcatggaat cgtgtggact   18120
ttggtacgag aaatatttta aatcatattt aatttttttaa tggttttatt ttccattttt   18180
gaaaatattt tctcttttga aatgtcattt tccaatttag ttttaataat ttatgcaaaa   18240
gagagattaa atttctctga ttatactttt ttttatataa cctaactaat ttctttagtt   18300
tttctttttt accttcttac attgctttgg gccgctaaat tgtacattat gttcgtaaca   18360
gagtcataga tctaatactt agaaaatatt agaaccataa aactaccatt aagtgggctt   18420
ttacgtgaga tttcataatt ggacgagtat ttcgtatttg ggttgggtag ccatatatta   18480
aagaacttat tgagctgggc cggtttgaaa aagacgaata tagttcctct gaaatgtata   18540
tcagatattt gagatagtag aagaagtatg ggctctactg ggcttgataa tttaaggccc   18600
atattcgtgc cctgttagtt ttaatttaaa tgagaacatt cccataaaat agagaaattc   18660
aaacaacaaa acaaaataaa atagattttg ttgtttaacg ataataaata attttaagaa   18720
tcctacccat aaaaaaaaat gttttttttaa gaggatgact aataccagta ttaattaaga   18780
gataatgatt ttatagtggt tgtcactgta tttgccacaa ttctcaaagc actcttctca   18840
atattcttag tgcctttgtt aatcattttt ctcttttaac cttttacttt acataaaaaa   18900
aaaattcatc agacaaaata aaaccaaact atattttata ttttataaaa ttccgtattt   18960
tctaaagtga ttttttaatga ccaccatcaa gttgatcaat tggaatggtt attaattttc   19020 cgttttttaac atttatacgt gtcctacata tgataattgg taatcatttc ttgtttgatc   19080
atttttttta tctacaacat catcaactaa tgcgacagcc tcactaatta gtaattacac   19140
taatcttatc atctttaaaa tgttatgagg aaaatgataa tgaaattaaa taatctgtca   19200
aatataatga tattatttttc ctaacaacta cttactctat tttttttttt ttttttaacat   19260 ctgactttat taatttgtaa agggatagta caaatagagt tgtagccatc ttggtggtac   19320
atgaaaggtt tcatacaaag aagacattga gtttgcatac tttgtgagtt tgtccgctgc   19380
caagtttctc tcccgattga cataaccaat tgatgagaag ggtaacttag tcatccaaaa   19440
ccgaatgtca taaagcagtg tttcaaggag atgatgatct tcagtcttgt taattaggtt   19500
cgttagctcc agattgtcgc cttcaaacca cacataacag tatccacgta tccaaaccat   19560
ttgtagggca tgtaagaatc ccaaggcttc tgcttgtagg gctgagtatg attgttgtag   19620
tttcgcacaa cctgaatgta gtacacgtcc attgcagtca cggagtatcc aacctgtgct   19680
tgtataatcc cttccctgaa catagccact gtcaaagtta catttgagaa atccctccgg   19740
tggtgaactc cattgtttac ttcggctcaa cggtcgatca ttggactgtg ccgtgttgtg   19800
tgagatagcc gtatcattaa ccatagtttc gacccattcg gttgcttctt gttctgcttt   19860
ctgtgccacc ttccaaggga aacgatcaag ctgttgaaaa aggtattcgt tacgtgattt   19920
ccataagcgc cacattatcc aaaaaggcat caagccatta agaatgggaa ggttttggtt   19980
tttcttcccc tgcaatatta gtcgtatatt ctcttcaaga ttatccgtga agcaaagtcg   20040
attactccca gaaaagtttg cacttctcca tacaacctgc gcataagaac aagtaaaaat   20100
tatgtggtta attgtctcgt cggcattgca gcatctttga caagtcgggt ctgctggaat   20160
gttcctgttc cggagttgag tggttgtgga taaagctccg gataaacagc gccaaatgaa   20220
atgcttgatc tttggagtga tcttcaatct ccagatttct tgttttaatg gaacgtctcc   20280
```

```
ttcaagggga ttaatgattt cctcctctgt aagattgaca tgagtggcaa cccaataccc    20340
cgatctcacc gtatattgag tattgcgagt atacgcccat ttataagagt ctctagcggc    20400
atagttagag agatacaaag atttagccag ttgttgatcc tccggattaa gaactccttc    20460
gaaaatcaca ggatcccatt ctcgtttatt ttctctccat aaatctgcta ctttcatgtc    20520
ctcatccaga attgggccac gagcaggtcg cggggggaagt gttggaagcc aagggtcttc   20580
ccatatctta gtagtttggc catctccaag ccttacccgt aagccttgtt gtagtaacaa    20640
tttcccttct tgtattgagt tccagccata agatgcatgt cctcccttat tcgctcttaa    20700
ataggtagta ttgggataat acaatccttt atatagacga gcaagaagac tttgagggtt    20760
agtgagaatg cgccacgctt gcttcgcaag taaagctcga ttgaactgat ggagatcttt    20820
aaatccaaga tcgccttctt ttttagggag agtcattctt tccatgctac ccaagggatt    20880
ttctttttac cattctcctt tccccaccaa aacgccgtta tcaaactgtt tatctcattg    20940
caaattaaag taggaagtaa gaagcagttc atcgagtaga ccggtagcgc cattgctatt    21000
gccttaataa caatctcctt tccagctgga gataaataat tatatgccca tccttctgtt    21060
cgctccttca ccttcgttac aatgtattca aaaagttcca cttttctacg acctaactgt    21120
tcgggtaagc ccaaatattt acctcctccc ctaacgttat cgattcccag caatctatga    21180
agtcgttgtc gtctcatggt tggaattttt tgaccaaaaa ttattgaaga tttcgcgtag    21240
tttatcttct gacccgaagc ttcttcatat ttcttgaaaa tcaacgctag ctgctcaata    21300
ttctgattag atgctctaca gaaaaacaag gaatcatctg cgaacaagag gtgagatatg    21360
gcaaggcaat ctttggtaat cttcatccca tgaatctgtt tattaacttc agctttacgc    21420
agcatattac tcaagacttc agcgcaaaac agaaataaat aaggggatag agggtcgcct    21480
tgtcggatac ctctcgatgg gaagatctta ccataggtg atccattgat aagcacctca    21540
taagaaacgg atgttacgca agtcattatc catttgaccc atctcggtgc aaagcctaat    21600
tgtatcataa ccttttccaa aaaattccac tcaactcggt cataagcttt actaatatct    21660
gtcttaacag ccacgtaccc actttgacac tcacgtcttg atttcagaga atgaaggagt    21720
tcatgagcga ccaaaacgtt gtctgatata ttttgtcctg ggacaaacgc tgcctgagag    21780
tccgagatca catctccaag acactgcttt aagcgcttaa tcaaaatctt agagataatc    21840
ttgtagctgg cggtacagag actaatagga cgataatccg acatgtgttt aggatcgatg    21900
atcttaggga tgaggcaaat ctgagtttgg ttgatttgat tatccatgac atctgattca    21960
aaaaaatgtc gcaccatcaa acaaacatca ttcccaatca gatcccaaag atgatgatag    22020
aacgcagccg tgaagccgtc aaaacccgga gctctatctg caccaatcgc aaacactgca    22080
tctctaactt cctggtcagt tacactctga agaagctcat gattcatctg ctctgttact    22140
ttaggggcta tccctgaaat aatctcctcc cagtctgaag tctgagttgt agtaaacaag    22200
tcagcaaaat agttttctgc cactttacct atagtatcat ctctgaagtt ttctattccc    22260
tgagcatcag tgattgcctt gatcctattg cgagatttcc gaagcttagt ggaggcatag    22320
aagaacattg tatttcgatc tcctagtagc atccatctgt ttctgctttt gagatgccaa    22380
taaagttctt cgtctctata agcttggtta agatcctgtc tgagtcgaag aattgtttgg    22440
tgtggcaacg tgtggtccct ctccgccgca tctactctat attttagcgt ctcaattttc    22500
tccgcagtat tcgtctttgt tcttctcttc cactttgcta gttcttgtct gcaacaatgg    22560
agcttctcat agtatccacc atgactatct gatcggcctc gattccagcc tctttgcacg    22620
```

-continued

```
gagtcaacaa agtcttcaaa ttgaaaatga cgacgatcat atcgaaattg tccgcgttta     22680
gtgcacactt cttctgcaat gtcgattatg acagggcat gatctgatcc agcaatcggt      22740
aaaaactctg tttcaaaagc tggaaatgaa gcttgccagt cagaattgat gaagactctg     22800
tcaaggcaag attcaatggt ctcgttctgc ctctttccta cccagctgta agggtttcct     22860
ttagacttca agtccttcat attgcaacaa ttgatcatat ttgtgaaatt ttgcaggctg      22920
ccaatactgc gacgtcgacc gcctttcttt tcattcagat taaggatctc attaaaatcc     22980
ccacacatca tccaaggtcc tgaacgatgt gctgacactc tttggagttt ttcccagagg     23040
tggtggcgtt cactaggtat tgggtgccca tagatgcaag acaaatagaa attaaaattt     23100
ttatattcaa catatagatc tactagcctt acatcatgag aaataacttg aattgaaaga     23160
tgcttttttcc aatacacaac taaaccacca cttaaacctc taggtgaaat aatacacatg    23220
tcttcaaacc ccatcttaac gcccaaatcc cttgtgtagt tgtcttgttg ttttgtttca     23280
atcaggaaca acatgtccaa aaagtacact ctttgtactt cctctagacg tcgaactgtc    23340
aaaggttgtc ccaatccttg acagttccaa aatccaactc tcatgggact tgtggtggta    23400
ccggccccac cgcggctctg ccctggttct gtttgttgat gttgtcttcg gatcccactg     23460
aattctctga gtcatgacct tcagaatcct cttgagaagt tatcttcatg cggcgagagg    23520
aaccagaagc ttcacccact tcaaagttat gttttccttt tcgcagctct tgtgatagga   23580
gttccacagg tcccagaata tcacctgtcg cattagcaaa agaaggaact gggttataaa    23640
gaagatcctc atcacatgtc cattctccat ggaacatgtt acggtcattg tcggaggaga    23700
tgtcctctaa tgcattatgg gtcgggtcaa tgtcggagac ctcctctttt gcttcattga    23760
catcagcacc aacgggacct ggaacaattt cttcacccac ttcatcacca tcttgaattg    23820
gttgaccatc atcaccaatc tcctgaatgt gtactccagg atttccatga aactcttggt     23880
caccatcggc attgtcatca tcgccatcag aatcatggag agctccatt tggaggacac    23940
aacttccagc atcatgagtc attcgtccac aaacatcaca gaagccacga agacgttcat    24000
aatagaagct tagcactgtg ttcacgccaa gggagaactg gtagttgcgt tgaaatcgca    24060
ggggggtgatt cacatcccat ttgatttgga tccgaacaaa ttcgactctg gtggttgtaa    24120
aaggatcgaa gtcgaccgct tttcgctcac caagggaccc tgctatgtta tcaatgactt   24180
cgagattcag aaactgtagg ggaatttctc gcacttggat ccagaaaggt atgaaattga   24240
gcacaagagg atccatatcc ggtgtccagc gttccaccac cagcatacga tccgcaaaag    24300
accatggacc gcgtctcaga acagtgtcaa gagattcttc agatggaaag ataaattgga   24360
atcgtcgatt ttgaatgatt ctgccacgga cgaaaccaac caaacccaa gttcgtggaa     24420
ccgtagtgag gatctgacgg agattctgat ttcgcggcat gagggtcta cccaggaggc    24480
aaaagcggtt atcatccacc gcccctttgaa caatagcctg agggagagca acgggagttt    24540
cgtcgatacc gagattgatg ttctgaaggg cacgacgaac attatcagcc atgattagtc    24600
ggagaggata gaatcgaaag agataattga ttggagggt taaatgtgag ggaatggaga    24660
agaaatctgc aagtctcttc tttaaataga ttcgaatcca tcgtggagta acaacagaat    24720
cgtggggaac tcccactatc ctattatgaa caaccgcctg atcatgggag aagaggaacc   24780
gccccactcc ggcgtaaaaa actgtcagaa tcttcgagag aagatgacga agaagtaacc   24840
gtagcgaaat cgccttaaca atcgccattt ttgtttgttt ttctgagagt ctttttttttt    24900
ttatctagct ttttgttatc ctctattttt ttataaagaa tttttctaa ttataaatgt      24960
aaatatttac tatcacctag taataaaaat aaaatctcta ggaaaacaat agcactcctt     25020
```

```
tgaaacattt tttattttt ttaaaatacg cactagccat ttaaattcat tcagttttgg    25080
agaaaaatca ttcaagttac atactttata ataatctgta atcataattt caaactttat    25140
tattccgttg ttaggttgca tggacccatc gccacaggtg ttgccctatt taagaaggta    25200
cttcgattaa tcacgatgac ataaaaatca acattaatat aacgaaaaaa ctatatttga    25260
aaatataatt tttccatttc gttcacatat tcgaactttg aggatagatg ttttgactct    25320
taggtacata aaatggaccc attggtgtct ttggtccaca cgagctacat ttcaagctat    25380
atatggataa gataaacaat ttttcattta aaatgtttta ataaataagc ttcattgatt    25440
atatattggt atcaatttat cgcactgctt tcccaaattt ttttcttttc aaaataaaaa    25500
ttgtcatgag ggttatgata ttattattta tttttaata tcaggaagtt ctgcgccgaa    25560
gctcgtaacc ccctcagacc cgaaatgacc gcatttaata ttagtttcgt cctaaacgtc    25620
attcgaatcg gcgacttcta agctttgcct atactcttta ccaattgagc taatgacatt    25680
taatgagggt tatgatattg ccacacaatg gttcgaaaaa tgaggacgtg acaatattag    25740
attgagacaa attcacatcc acaaaacaat ataaacagtc tatccataac acgacttcat    25800
acttatcttc gctgtctttt tctctctacc aaatagtttt tcattaaagt tacttgcaat    25860
tgcacgtaag tttaactata ccaacaacga cattatcatg tttataaatg atccttattc    25920
atatgacata agatacaata aatcactacg cttttataag tatatgtcaa cttctatata    25980
acagtataat ttacaaacaa agccttgata acagtgatta acttaaccag atagatatac    26040
gataaataag agcattcgtg catgatctaa tacaactagt ttagttacac ccatttagaa    26100
tctaaataca taaatatttt taggatcata aagttttgtg aactttcaag ttttggagaa    26160
ataaaaagct tatgatttgt catgggatca tccaatgacc aatgtgatga accatactgc    26220
ttaatcataa ctattcatcc actagcactc agccactcac gtaaagaaac aaaaaaagga    26280
actacacaaa gagccactat taataagttt aatcaatata ttttttgtct tttttcatat    26340
ataagcggca aataaaatcc gccatggggc cagagacaga tgttcaaaat caccatgtaa    26400
tattgtaaat ttgtaatcat taaatatgta agcttcttat cgtgtatgta catcatatat    26460
atgtgctaga aaatttgtaa tctttataac taattaatta agaacttatt atctacaatg    26520
aacaaaagaa ctagatacat catatacata taacaaagat tcataacatc tttaaccaaa    26580
aaaaaaaaaa aaagtttcta tagaaacaac tttatttct tcatcggatt tgagagacg     26640 taaatttttc caagtaacta aaacgttcga ttcgcataga tgatgcaagg actaatgatg    26700
cattggaaag ctcacgcacg attagccgta cctgagttac acattacgag tttaaggaat    26760
tcgtaaattg tgtcacttac gttttataca atatgtgatt caaggaaact caaacatata    26820
ccgcatttgg agataaattg attaacactc tagtttttag acatattata tatagatgaa    26880
gtagttgtta caaaaattgc attgtatgtt tgtgatgtcg ggaatatatg atgagaaacg    26940
gacctacaaa gaaagaacaa aaattcttca aaacaaaata aataattaa caattatgaa    27000 tgaatcttgt gtatatgtac tcaatttgtt attgataaaa ttgcaccca ccacactaca    27060 taacgtttgg cctcattgcc attggttcgg cggaatctaa tgattttaaa tccatccact    27120
tgcatactat acaaaatata attttgtgga ctggaacgtt atatataaca gaccgaagaa    27180
attaaacaaa tgaatgtcca tgttcaaact ttgaagctcg agtgataaaa ccgcttgaga    27240
acaccaatca tcattttcct acactaacaa ctatttaaag atatggtata tatgatcagg    27300
aacatgttag ctaaatacaa agcaataatt attcacatga tgcagtacta tacaacattg    27360
```

```
atcaatataa tcacatggtt attagctttta tcattttcg tttgtgtcaa aaatattatt    27420
ataatactac acacctcatt aaaatttaga aatagtgaac cggctttgtt gaaactataa    27480
agttcctcaa caaatattga caaataacaa tgccttaagt aagataacaa aataaaaatc    27540
atcaacaaat atcttttga tataagtgtg cctcgtaaaa gaatgtttta taccatttta    27600
taggtgatga tatttttttt attgacagct tgaaggtaat gaattttca tatagtttca    27660
tgttattgtt gatcatatgt agtatagttt gtttttacgg caattagtat aaatttagga    27720
agaaaagata tgataatatt tgtattttc acgtaaaata tgatttggtt tggtaagcaa    27780
taagacaaaa gacgttggtt gtaaagtagt aggtgaatcc aacggagaca ggtaatatga    27840
cttcactgac aggggcaatt cagtcatatt ttatttatt gacaaattac aagtggcact    27900
aatattcgtt tattcaagaa tattgaaaca gtagaataaa ttttcactga tcaaactata    27960
ttttttaat gtaaatccgc atttacctaa acaatttgtc cttgtgtgta aagtaagta    28020
cgtgtacaca aatttgtatt ttagttttat ttcctaaaac aattaggatg atcgttttac    28080
tctagttatg atttgaatgg taggtgacag aatcacaatt gttttgtgtg tggctcataa    28140
tacaactgca tttaataaaa aatggaatgg ataatatgtt cttaattaac tacgcccaag    28200
gaacattttt attttgata aaaaaatgtt ttttttggg ctttatttg gaaatctttc    28260
ttacaatttc attcataaaa tataaagaaa aagaattaca ttatttaatt tttttatttc    28320
gtttttatca ttcaaaatat gtacttacaa ctgttttttt ttaaaaaa aaactgtctg    28380
tagtttgtat attaaagata atgattcaga actgtttgat gatatgtatg actgagtgaa    28440
cacaacatct ataaaatctg aatctttggg tccgattatg ataatcgtct ttatgttttc    28500
ttgcaaaaat ttgaaagttc actacaaacg tacttaataa cacttaataa agtatgtaat    28560
tcatttgaat ttggtattac ttctttagtt tcttcgatct gaaatataca tgatttgaca    28620
ctgattttt ttttttttt ttttgataa tatacatttt cagttgtttt aaaggaaatt    28680
caaatgtgta tttcacttgc actctcatca tcatttagct aggaggttta caaaacagaa    28740
gttcttgacc atgaaaactc tcaccaaagt gtgttgggac accgagaatc aaaaaaactt    28800
ctcaattgtt acattttgaa atagattttg ctaatgtggc cgatgatatg atcatggaac    28860
aaatggataa ttggttacta aaactatag ataatggatt atgcacttat gcagtgtatc    28920
acctctgttt ctaaaacagc aaaatataca atactgaaat atgtaaagta ttgggtaaaa    28980
ttgtcaacaa acatcttgag atatttcttc cagaaaactg ctacaaagat tctaatcacc    29040
atcgacaaga acattaaact aatgtgatta tgtgaacaac cattattcaa attatttagt    29100
tcctatatca atgaaaagaa agttcagaac gtcaatctcg tttgatacat aattctaatt    29160
ttcttctca ttgcttatt taagtaagat atcaacggct gtgattctct ctgatgacat    29220
actgatccgt gcggattaaa cccatgcaaa aaccacacgt gaatattcca cattgtcaca    29280
ttgggatctt ctaattacta ctagattcac atgtgcttat gctaattaac ctcgcacacg    29340
ttacactaaa atacgcctat caaacttgtt gggacgatga ccgttgtgac ctcaatgaaa    29400
ttattttttc ccatccacca aatatgaaat taaataata ctgatactga ttttacatgt    29460
agtactaatt attagtatct atttacgcgt gaagtattgg acttctctga cacgactgtt    29520
accaaaaatg gagttaacgg cgttaacatt gctgttaact gcgtgtctgc ttactagata    29580
tgttagtggg cccagtagag atttaacgg ttgttatgtg ctgacgtgga ctcatctttc    29640
ttaacgctgc taattaactc cggcacaggt aacagtaacc agtacgacac cgttttggg    29700
gttgcattca ttggcagcac agagccgcgt cgccaaacgt tagcgttta aaatccaccc    29760
```

```
gctccacata ttactcacca cgtgtcttta tttaaaaccc gcgtttcctt cacgcgattc   29820
tcatttaacg gagccgtgac ttttcaaaa attgtttacc gttggacaaa tgtcttattg    29880
tcctcataat gtcagcctta tttacggaaa taccattgga cggtggtcgt gaattttatt   29940
aacaaagaag ggtattttgg agaattacat cagggacggc gtattggggc ggctaaccc   30000 atccgacttt atatgcactt tatgggaaat ttcaattaat taaaatatgt aaaaactata   30060
aaaatatgaa ttaaaaattt gaaaattcaa tgatacgcct tttattttg actgtgaaag    30120 tcttaaaaaa aattgttttt aaaaaaccca aatgattcac cttttcttaa aatgtacccc   30180
gtttgtcttc gaggagagat ctctggtcca caactttttt attagacaac tcaaaaaaat   30240
tatattcttt tcttttctgt tttgtattat gagttttat ttggtatttt tgcactttat    30300
cccttctcaa agaaagctct acaaagcaaa acccaatttg aattaaactt catatttacc   30360
ataaatgatt acaccatgag gcgatttta taccattttc aagttttgtg aaaatattag    30420
tgagtttgta agttgtgatt ttatgggttt tttttgttga aaagaaattg tagtgttggt   30480
aagaatagag ttgagctgac acagcacctg tgactatttg tcgggacaca tgtgtaagaa   30540
gcaaagcctc tcatgctttc ttgcttctct ttgttttcct ctcgtcgtct tttatatatc   30600
cttcaattat cattttatg tatatatctt tttgctagaa atttaaacat atatatat     30660 attaaactaa agaatctgta tctcctttt acattgaaaa gaataaaaaa ttaattatgg    30720
tattagccta acagtaccga ttatcaaata taaatgttgt tttttttttc gtctgaaaat   30780
accaaaagcc cgcatttata tttttatttt gtcatcagat attatttaaa actcaaacga   30840
gctaaaattg cgggaaatta cgagataccg tatttacatt ttacattcta atattctata   30900
gaaaggaaaa ttttgacagg tatttagatt actgtttttg caaaattaaa atctcctaat   30960
aaaaaccaat aatacaaata tcaccaaata tgatagaaga caacacaaat acactaaaaa   31020
aggaaacata ttaggtaaca tgatttatta taattttgcc atctaaaata tggtttactt   31080
taaatatgta gacttctgga ccatataaaa ttaacataat tttggaaact atatccaatt   31140
atatcaatca aatattaaaa aactatataa attttaatta ttatatactc taaatatcta   31200
tacagctgga catataaaaa tttaacaaaa ttttggaaac taatacccaa ttatatccat   31260
caaatataaa aactaaatca atttaaagat attaaaaatt gttgagaatt cgttaaaata   31320
atttaaaaaa tcgaaatata aacgacccaa aaagacagat ggaaaccata ttcactctct   31380
cttcttcatt agcctttcgt ctccttcttc tcttctctat ctctctttag cttctctacg   31440
caagcttatt atctctttct cttaaagctt tttctatata caaacagaag cgtttgatac   31500
tgtaaaaaag atttagaaat ggagactctg agtcgtttat tggttttcat gtctctgttt   31560
tccggtttag tttctggatt tgctctgcaa aatcttccaa tcacatcttt tgaagaaagt   31620
tacactcaac tttttggtga caagaactta tttgttcatc aagatggcaa atctgtccgg   31680
ttaacgctcg atgaaagaac cggtacggtt taatcttcct ctgttttta atttccttct   31740 cattttctcg gtttagtaat gattttgttt ttgcaggttc cggttttgtt tcaaatgatt   31800
attacttgca tggattcttc agtgcttcaa ttaaattacc ttctgattat acagctggag   31860
ttgttgttgc ctttatgta agtaaaatct ctaattttag ctttagaact aaccaattat    31920
gattagtttc actatttgat ttgggtttag tataagtact aatgactttt tttatattg    31980 tgggttgttg ttatgtattc agatgtctaa tggagatatg tatgagaaga atcatgatga   32040
gatagatttt gagtttcttg gtaacattag agaaaaagaa tggagagttc agacaaacat   32100
```

```
ttacggtaat ggaagtactc attcaggaag agaagagaga tataatctct ggtttgatcc    32160
tactgaagat tttcatcaat acagtatcct ctggtctgat tctcacatca tgtaagtaaa    32220
aaaaaaagta ccaattctct cttaatcttt gtttgtttgg ttcaatttaa aggaggttag    32280
gctattgacc ccatttgatt taaaagcttt atggattcaa taatatgatc ttctatttaa    32340
ggaaacccaa gtggggtttt aatgatggga cgatctttt gttgaaaaaa tatgattcaa     32400
ttttctttgg tggatattaa ttcttattac ttccttgtgga agttttgtg atgcttggga    32460 cattatttgc ttttggttgt aatgttcctg tcaattttca gtgtgtgtg atcgcctaaa     32520 atggtttaca gctttcgttt tttggcatca acaatgaccc catagagagt atgtttgggg    32580
tccaattcac aagttgagaa tctttactta agttcatcaa aagctacaaa ttttatgcc    32640 aataatgtta tctttctaag cttacagaat ctaacttact taatccaaat aaatgttttt    32700
tttggttata attatgtagt ttgtactaaa ctactgatca aagttgtgaa attgttgttc    32760
tttttggtta tgcagattct ttgtagacaa tgttcctatt agagaggtca aacgtactgc    32820
ggaaatgggt ggtcactttc catcaaagcc gatgtctctc tacacaacaa tatgggacgg    32880
ttctaaatgg gcaactaacg gtggaaagta cggtgtaaac tacaaatatg cgccttacat    32940
tgcgcggttc tcggatctag tcctgcacgg ctgccccgtg gaccctatcg agcagtttcc    33000
gaggtgcgat gaaggcgcgg ctgaggatat gcgtgcggcg caagagatta ctccttcaca    33060
aaggagtaaa atggatgttt tcagacggag actcatgaca tattcatatt gctatgatcg    33120
ggctaggtac aatgttgctt tatcggagtg tgtggtgaat cccgctgagg ctcaaaggct    33180
tagggtttat gatccggtca gatttggcgg cattccgagg cgccaccgca atggaaagca    33240
ccggagcaag agaagccggg ttgatggaac cgagtcgata tgataacata tataggcaaa    33300
atagtatggg tgagatttgg gggttctata ataagtccat tattttggtt atttatgatt    33360
caatgcattt tcacatatag aggaggcatt tttgtcattt gttagttgta tcattata     33420 agaaaagaaa aaataattaa tttatttatt tgtgatattt tttttatata tgataaattg    33480
tttcttgttt ttgtgaatac tttacagttg tttacgaata ttatcggtgt aaataatttc    33540
agatatcttg gaatttatat ttgtattcaa ttttgtgtac tttatgtgac gagagttttg    33600
tctcgcttgt acttgtttta ttcaatgggt ccgacgaata ttgttttaat tttgtgtggt    33660
catgttcatg cacatatgta gtattattat tacatacaac aaaattttta tgtgatcaca    33720
catggtacct ttcgcattcg aacaaaattt gagcttgagt aaacaattca tttttgtcaa    33780 caaaataat gtttgtttcg ttattaacaa acgatttaac tataaggaaa atatcaaaag     33840
aaaagtatgg agcaaaaaaa ttgttttta tatacatata agtcggattt ggcaaaattt     33900
tagggaccat ctaaaagata gaattgtgaa aaactagaca aaattggctt agctcattat    33960
tcatttgtgt ttagtcgttt tgaagttgat ggttttgctt tttttgccag ctattttaca    34020
actgtataac actctacttg cttccaaagg ttttgccacg taagctaatg tttatccgca    34080
aaactacttt taaataaatt aacaaaaata tcattttcaa ttgggtcggg tcatttcggg    34140
tcgtgtttac cgggtcggat aattgattc ttcttcttct tcttcttctt cttctctcta    34200
tctcaagctc gctaagattc tcatcaaatt tcctctttag actaagatag ttctttcgta    34260
ttcttcaagg gtttttgttt ctagacctaa agtttaatcc tttttataag ctttgtgttt    34320
gatttcaaaa ccctagctgt tccggattct attgtagaaa cgattactta aggttcaatc    34380
ggaattaggg tttgaattag aaccgtaact tcgtgtgttt tttaggaatg atactacact    34440
gtcctgtctc tttgtcactt agctttcact tgaatcttcg aaccagtaga atcggaaaca    34500
```

```
taggagtaac aagagtcaac gctagtcaaa ggaatcactc taagaaactc actaagaatc   34560
tccgtaatcc acgccgtacc aagcttcctc ctgattttgg tgttaatttg tttcttagga   34620
aacccaaaat tgaaccacta gtgattgatg atgatgatga gcaagttcaa gaatcagtga   34680
atgatgatga tgatgctgtt gtatgggaac cagaagaaat cgaggctatt tcatcgctgt   34740
ttcagaaaag gataccctcaa aaacccgata accgagtcg agttaggcct ttaccacttc   34800
ctcaacctca caagttacga cctttaggtc ttccaactcc aaagaagaac attatcagat   34860
cacctgcatt gtcttctgta tcgaagcaag tgtataaaga tccaagcttt ctcattggtt   34920
tagctagaga gatcaagagc ttgccttctt ctgatgcaga tgtctctctt gttctcaata   34980
aatgggttag tttcttgcgt aaagggtcac tctctacgac tattcgagaa ttgggtcata   35040
tgggtttgcc tgagagagct ttacagacgt atcattgggc tgaaaagcat tctcatttag   35100
tccctgataa ccggattctt gcatcgacta tccaggtttt ggcgaagcac catgagctga   35160
aactgcttaa attcgacaat agtttggcta gcaagaatgt aattgaagct atgatcaagg   35220
gatgcattga aggtggatgg ttgaatctag ctcggaagct tatactgatc tcgaagagta   35280
acaatcgaat acttgactcg agtgtttacg tgaagatgat tctggaaata gctaaaaacc   35340
ctgacaagta ccatcttgtt gttgctcttc ttgaggaact gaaaaaaaga gaagatttga   35400
aattgagcca gcaggattgc acaagtatta tgaagatctg tgtgaaactg ggagaatttg   35460
agcttgttga atctctcttt gactggttta aagcatcaaa cagagaacca agcgttgtaa   35520
tgtacactac gatgatacat agccggtatt cggaacaaaa ataccgggag gcaatgagtg   35580
tggtatggga gatggaagaa tcaaattgtc ttcttgatct tccagcttat agagtagtca   35640
ttaaactatt tgtagcattg gatgatttgg gaagagcaat gaggtattac tctaaactca   35700
aggaagctgg attctcgcca acgtatgata tttatcgcga tatgattagc gtttataccg   35760
cttcagggcg attgacaaag tgtaaagaga tatgtaagga ggttgaagat gctggattga   35820
ggttggataa agatacttca tttaggttac tgcagctcga gaagcaaaca atgtctcttt   35880
tgcactgaag acaaagttcc aattttgttt ttactatcag tttcatttgt gtgaacattt   35940
cagtattgaa aacagtgaag atgtaatata cacgagatac actaagattt ctactgtttg   36000
aaagtgtttt caggcaaaga tgaaagtgga aacttaacaa tgtcagaatc agacatagca   36060
acactgtttt cttctggaac tgattctggt ccatccatgg atggttttat cactgtaatg   36120
aacaaaatgt tgtagaacaa ggtaagagct aagagaacaa aagctgaact tgtgaggaac   36180
gatccggaga tctcaggtgg ttcttcaaac atgattggat cattgttggt tctgaccaca   36240
tctgatgatg tcttgttgat gattcttggt ttctcatcag cttgagattc tatttgttga   36300
tcaagctgtt tcagagcttc tctagcttta tctctatcga tttggaatga atcttctctt   36360
tcagtggctt ggacaatacg catcaaatgt ctcttcttct ttgtctccat gattcttcca   36420
tgtgtgtacc atttaagaga ctgtaagcct aacaccacca ccattatcag tttcctctgt   36480
ttcttctgct acaccactct ggaagatgat attttttttct gtgtggacat tgttgatggc   36540
aaagttgtag ataactttac ttcttaggga gttgttttta cataaaagtc ttatatcacc   36600
agacattcaa aattgggccc attttttaatg tgataattcc aagtataagg ctttaaaggc   36660
ccaattttag tcccaaaaaa tgtattatat ttcatatcaa gtattttat aattagaata   36720 ctatgaaatt taatatttc ttaaaaggta tataagagaa atactatgaa aaacagctga   36780
ataatagaat agatgaatca catttaatac cggacaacaa ttctaagctg aataaaaatg   36840
```

-continued

```
attttttgtt tcaaacacca taaagttttt atttcgtaga ttaatgaact ttctaaaatt    36900
tagtaataat tttaaaacat gcaagataaa ctgaaaattc gcttgttatt ttcatattct    36960
atatataatt aaacacaagt ttttgtatag ccctgggtat gtggatattt gggtcggttc    37020
gggtcggatc ttttgggttc taatttagaa attttagact cgttgggtta tatgttcaat    37080
ttcggggttgg gttcggttcg ggtttacttt gggtccgcat aattcgaata ttggttaaag   37140
aacccataaa taaccaaaac tatttcgggt ttaagtacta cttacccaaa ttttgttcaa    37200
atataccgaa acatacataa aaatatccat aaaacccaaa aatctgaaat tataacaagt    37260
ttttctttaa gacaataata taaaacaaga agtaaacctt attttgagct tgttccataa    37320
ctcaaatcat taaatatgtc acaaattcaa gttattagtg aatatatgtc ctatatgtat    37380
atatatgttc gagtaataaa tattacttac gagtatcggg ttcggttcgg ataataccga    37440
tacctacaat tatttgaaaa tagaatccga tcggataatt aaccgaaact gaaatagaac    37500
aggttcgggt atttcagatc gggttcaggt attatgccca tgcctatttt tgtaaatgat    37560
atgtattcaa cggaaccacg ttttcagaac gtgaaaaaac tctatattat tcaagaccat    37620
tgtgttcaat aatcatacat caataaattt attgtaaata aaaacttaaa ttaaattgtg    37680
tgcaaatttt attcttagaa atgttattta agatgagca gatcttttgg acaatgagga     37740
tcggtgaaga acattgccgg aaacatcata gtagatgaat ttagctttgg agtgagtgat    37800
gtgaagagac atgaaacctt gtccatcgta atacagtttg agttctttg gatcccatgg     37860
ctgaacatgt cctctccatg cctttgatcc tcctccactt gtaagaaatt gggttttact    37920
tcaccatttc caaaatatat gttaagtttt ctttctttca acaaatata acaacttaat      37980
agagaaagaa acattttaaa ctcaacaaat aagtacttat aattttaccc gtgagaacca    38040
atgtgttgca agcagtgatc atgtccattt atgtacaagt ccactttatt ctccttcagt    38100
aataagtgaa aaaatcatg aaaaactatc gtagttaatt aaattggggt acatcaatgt     38160
agaaaacaat aaagataata taacatgtaa ttagcataaa agtgatatta tgaatttac     38220
ctctagaatt ggaagaagtt gatctacaag ctcttgagtc acaccgtgat tacctgcggt    38280
tttgatcccg tgatgtccca cgacaaattt ccatgtggca cgcgactttt taatctctaa    38340
atctaaatcc tgatatttca ataacataag ttataattag tagaaaattt caaaagaag     38400
attgagatat atatatgtga ttatgaaaga aaatgtatta catgtaagag gtttgagatg    38460
tatttatttc ttggtaagac atttctccaa tcataagtgt gatcttctgg ttcagtgaag    38520
tattttttcta caaaaggatt tgtgtccgcg aagaaaaaat ccaccattcc tataaccaca   38580
acaaaacata ttcactaact aaaactttga tttagttatg atagtttaat ttgtttgtt     38640
tctttcctta aaatctacct gaggataaga caaaagatct gcgacaaaac catctccaat    38700
cttttttggt gagaacttta cttagttgtg cttcaacatt tcctctgtaa tcatggttac    38760
ccaaaactgc attaacacat gaatcaatat cagattttgc cattttcttt agtggcattt    38820
atagattttg cctttttga atagtttatg gatttgcca ttttgcaagc taaaaaatta      38880
taatttaaac atgcatttta cccgttatgt ttaggtcagt cggttccatc tgatcttaag    38940
tttagtattt ggtataaaat atgtattttt aacaacaaaa aaattgaaat acgtacgaca    39000
aatctgtaag atcttagtaa aaatgacatt ttccaaaaca attgcaaact acacaataat    39060
cccataacac atttgagtgt ttaaactcag ttaggcatat agataaacaa ttaagtaact    39120
aactattaaa catgtgtata aactttgatt agaaggaagt aaattacctg aataccattg    39180
tttttggaga ctaggatgag tgtagatatg agagaaagag gcttcaaagg aaggatcatt    39240
```

```
gactcctttt aatccgtcgt cgtagaaatt atctcctact gatatcacaa aatctatgtc    39300
taatttctct cccacaactc ccatctgcca atttttcagt tttacattac ataaacaaaa    39360
ttttattaac actggtttgt tcatgtcgat attataagcg tgaaatattt ttgtaaattg    39420
atttaagata tacaacaaaa aaaggatttt gttgccaaac aaaatgatag tcaattttct    39480
gttacatctc attttaatta ggattctgct ttctaatgaa gcgtatcaat ttgtcaatta    39540
caagaatact ttacgaatat gctttctcaa ttagtactta ttgcgtagga tgcacgcaac    39600
atacgactat gtactcataa attaatagat tgatgtttac attttcatac atatttcaac    39660
tttcaacact ataaacaata cgtacattgt tcaacaaaaa aaatcaaatt caaatccttt    39720
gggttgtatt actctatatt gttgccttga acaaataatt gtcactaatt aagttgtatt    39780
tttgttattc aaacgaatta taaatgaaat aataaatctt gtatttttat cagatttaca    39840
aaacacaaac cactagtcta catatacttg ttaaatcttt ctaatacatt ataaatattg    39900
aaaaagtgat taatattact aacctgatgt gcaacgagag attgattaaa accacctttg    39960
cgtccccaat ctccgataac aagaaaactc agagagccat cagatttctt cttcaccgga    40020
tgtttcaacc tttcaagctt cgacaaagca ccattgatga agaagatgct tagaaacatc    40080
aaaatcacac taaacatac gtgcatcttc atcttcttct tactttgttt tatctggtat    40140
gagacaaaat cacaaaagaa acaaatgatg cctatataaa gagagatgaa gatgccttgc    40200
taacaattaa tatagatgga tccataagaa gaacatggtc gatacattat ttaatcaagg    40260
atgtttcttt ttggtcaact cttgaaggaa attataatca ttttactaaa ttaattaaga    40320
agactctaca acttttttgtt ttgtaatcat atagtatata ttttgttcaa tgtatgggcc    40380
aatgctgcgt gttacttaca cgtttaggtc aagggatatt tcctcctgta tatgttttta    40440
tttgtttcct actttatttc ttaattatat atctttcccc ataaatgtct aatattaata    40500
tctctcggat atttgataca aatgtataaa tttggtatcc atagttttaa aaaaatcaaa    40560
ttagttgtct tttaatgttt aaatcataaa gagaagtatt aaggatttct ctctttatgt    40620
gaaatatgca aaaataattc ttttgaatat caatatatat atagtggaat atgatggtaa    40680
tgaaaaatgt gaacacgaga accatgcgta cagtataatt atatattaaa caagatttta    40740
acccgcggta taccgcggca cgattttattt ttaaaagtaa tatatattaa aatttgcaaa    40800
ttttattttt acaaaatatt tatatttttac agtttataat tgtaattaag taacgatata    40860
ccacgaattc atgagacaat tgttaaaaaa actgaagttt tgaccccctat taaaacagca    40920 tattaataat attttaaaat tttataaata ttgattcaaa tacatccacc atataaccca    40980
attccaaaat aaaacacgtt ttgtaatttc tttacccgtc ccatgatttt ttttttaagt    41040
agtaattttt ataattttag aattattttt tatatataaa aattttgcaa attgtattat    41100
tctctaatac atttatattt tatagtttaa ttttatatat agtaacatta tacataccac    41160
ataacatttt tggttctata aattttttct aaattaggat gatttgatat gtttaatatt    41220
agtggtctta aaaataata aattaaagat ttaacccata ttgaaacggt aaattaatta    41280
tattttactt ttttattaat gttgattcaa aaactcgttc ctccaaatcc gtcttgccaa    41340
aaagtcattt attttattaa tattagtttt attaatgata tgactctgaa ttataatcta    41400 aacatttag ctaataacat aggagtgcac catatttatt taatagagga atgtaccata    41460
tgacccgaat gcattttat ccaaatccac caaaaaagtc ttgcaaaaat actatagaga    41520
taaaaaacga tagtcggttt tgatagatat aagattagca aatatattag ttagcttaaa    41580
```

```
ttagttaaag aatacaaatt aaaaaggtat attacactt  attcaaatat agtatcaaaa   41640
cttatataac acagagattt gataattttt taattgttga atactttttt ttgtgctaat   41700
tttatgtgat taagatttaa ttgatttcgt atatataata ttaaattgac ttatttgttt   41760
ataatttggt aacagataga tatttgaata ttcagtatat tttgcttcag tttaggaaat   41820
ctttgatgac ccgtctttag atccaataag tcctataatc tagagattaa tctgcagtat   41880
accgcaggta ggcttatatt ttagttaaac taaaaacttt tattgtaaag atgatttaaa   41940
aatatataat attattttat ttaattttaa atgtatagta gactgtgagt tgtatatgtt   42000
ttgttgatat tatctatatt gtttagtgtt taagattata cacttgtagt ttgattgtta   42060
atttaagagt ttcacatgta gtataccatc ttgtattaat atcgatctaa atccgtcaat   42120
tctatgattt tccagcttgt attaaaaatt gaatcacatc taatatgtta ttaactattg   42180
tagtatataa gattataaat tttcaatata atatgtatga aattgaatat atatatttca   42240
aatttatgtc ccgttactca gtagaaagtt ttcttaaata tctttttcac ccgttataat   42300
attattcatg tattgaacag tttatattcg ttttttaaaa ttcaaattat ggcatatgcg   42360
aaaaaactct aattattttt ttataatgat gatattattt ttccgtaaaa atagaatcat   42420
atcaagatga gaagtgaact ataataatta agaaaaaatt aatatgataa tttagatacc   42480
aaatatagtt tgttgatttt aattggctac ttttttggaa attaataatg tatttcgttt   42540
ttctaattaa attaaattaa ttaaaatta  gatatcaaat cttatgtgtt gattttgatt   42600
ggctattatt tttagaaatt aataatgtat tttgttttt  aattaattta attaattaaa   42660
ttagtatttg acttttaat  ctttaaagaa ataaatatat aatattaata tctctcggat   42720
atttgataca aatgtataaa tttggtatca atagtaaaaa aatcaaatta gttgtctttt   42780
aatgtttaaa tcataaagag aagtattaag gatttctctc tttatgtgaa atatgcaaaa   42840
ataattcttt tgaatatcaa tatatatata gtggaatatg atggtaatga aaaatgtgaa   42900
cacgagaacc atgcgtacag tataattata tattaaatgt aaacgaaatc aaaaccaaat   42960
catgagaaga tatgtctcca tgtattaaga taccattaag aattcgaaaa taatcacaca   43020
acattaaaaa atgtttaact cacatgaaat atcaacataa taaacaatgg actaattaat   43080
ataaataatt atgtcgtaac tcttaactac tttttttgtct gaccatcgat tagatatcgg   43140
aataaacccc attcttaaga gtgctccatc gatgcaaaac gtgaccaaga ccatcataga   43200
aaacgacgcg tagttcagct tcggatgtgt aaaccgacat gaatccttgt ccatcatagt   43260
aaaacctcat ctcttgtggg ttccaatcat tcacatctcc tttccacgcc ttggagccac   43320
ctccacttgt cataaattgt attccactat aaacaacaaa aaccgcatct ctatcttacg   43380
ttactaatcc ataattaatc gattaataaa ttatacaaac ttattataat cacctgttga   43440
tgctgcttat gtgctccaag caatgatcat gcccgtttat atagagatcc acttcattag   43500
cctaaatata tcaagaaaac caattaaatt gtttttttt  caattttt gg tattacataa   43560 ttcagtagtt tataatatag taaaaattac ctcgaggata ggtaaaagtt gtttctcaag   43620
ctctatggta tttccgtggt gacctgcact tttgatcgtg tgatggccta ccactatttt   43680
ccatttagcc attgattctt gcaatgccac atccacatcc tatatatcat taaattaggt   43740
caatgataat cacatatttt gactatattg taatcgagac aggttttagt atgatgccaa   43800
tttaattatt ctaattttca atgaatttga tgtatgact  agcttatggt agagtaagaa   43860
aaaaaaagtt accgttaaga gactgttaag gtatttattt ctcggtaata cgcctctcca   43920
atcatataca tggtcctttg gttcatcaaa atatctatct acgaacggtg ttgtatccac   43980
```

```
gaagaaaata tcgacaatct ctacaaaaga aaaagggtt aactaaagag aagtttttatt   44040
aacttgtgtt cttggtaatt tacttaccgg cgttaacaac ataagatctt aaacaaatcc   44100
aacggcagtc caaatccctg agtatggggc tgagttgcgc atagacgtta cctctataat   44160
catgatttcc taatactgca agagaaaata aatgaaaatc tactaataag tatataaatt   44220
tttgatagtc aaataacttt ttctctgtaa gtgaaagaga gatagttttta tgctcagagt   44280
ataaatacta ttaataattt acttaccatt gtaccatggt ttttgtaagc tagttgctgt   44340
gtaaatattg gtaaacgaat cttgaaattg agaatcatat ggactgatta ttccatcatc   44400
ataaaagtta tctccagtcg aaatgaggaa atcaatattt aagtccttcc ctattttttcc   44460
catctgatca atgcaaaaaa atatagacaa taattagaaa ttgctagctg cgacaaacct   44520
atccatttaa ctacaaacta aaacaaaata ataataataa aaatctctag tcagtgtctt   44580
ccttaatcca aagcatttac tcataggatt atagaagcaa ccaataatta aagtgatgac   44640
gtagaattgc aacactaatg gacagcctta agatgattat tagttccacg taagttacgt   44700
aatgaactaa agattatgta tgcaacttca tcttcacggc tccttaatta acaatgaaat   44760
atgcctcata tattatcatc aactcactca ttatatattc agatattatt acatgttaat   44820
acaacccagg cattactcag tgcagttttta ttattattgt tcgttacttg ctaatatata   44880
actacaatag ctaattaatt tgtaatttac tcaaacgatg aattcgacgt caagataaca   44940
tatatatgat ttctcttatc atttttcgtct tctcgcttga attctctcac atattttcta   45000
aaccacacca ttaaaaagaa cttgaaacta gcttaattac agacaaggaa taagtttttga   45060
ttgttcataa aaataaggtc atatctacat aaacacacac ataaatatgt acctgaagag   45120
ctacttggga ctgattataa gaacctcttc ttccccagtc gccgacaacg agaaaactga   45180
gtgaaccatc gggttctggt ggttggacga accgcggtag ctctgccgtt gaattacagg   45240
cggatagtat aataactaga cagaaaatag aaaatatgag tttgataggc ttaacatctc   45300
tcaagctatc cattgagaga ctttggagaa aaaatgtaag aggtgatgga cctgatggtg   45360
ggttttcgtg tggctttgtt tatttatagc tagtccttat gtggacaaga attaaaaata   45420
gaaaaggca agagaaaaaa taatgtaatg aactttgtca ctagaaaaat aactcttcaa   45480
aataattaat aaattttaaa gtcgaaaaaa ttgttttttct tgtttcaatc cgagactata   45540
taagactaaa atggacttta gacaattacg tgaaaattat ttgcacgtca atgaaagggg   45600
gcggtggata gaagtagtct gaatattcca tgtttaggta attaacgtgg tatatattgt   45660
tccacatata aataacattt ttagttccca tatatattaa caaggaaatt aaagagaatt   45720
ttgaaagaaa aaaaaaaaag gttgaccgga cttttttgaag gtgatttttat ttatttattt   45780
gctaattgcc ttacatatgt gaaaggccat tgtacgagtt gttaatttat acacaaaagg   45840
tttgattcat aattttttaaa aaaaaatctg tttgtcataa aactttgcta caaggaaaaa   45900
aaaaattcgt gaataataca caagtttcga ataaaagaga aaattgtttt ttgttttcct   45960
tttccaacaa agattatttg attatgtcac tggaagagtg acagagtcat tatacaaaca   46020
aatatgacaa ccatgaagga gctaggaacc tcctttatag ttttaaaact gttataattt   46080
ataaagatac aactaattat taacagtaat tggaaatagg cctctgcacc aattggaaat   46140
gtttacttcc tcgtttaaac ttaatgaaaa tagtcgttgt caacatcaaa aattatttat   46200
tgtcagttaa aaattcatat ttagaagctt ttttggttca ttggttgacc gaaggttcat   46260
taatgctttt gtacactaaa aaagtctggg gttcgagtcc cagatactgt gatttattag   46320
```

-continued

```
cagatttgca gattggtaga gacaagtgtg caggagatct tcaacaatgt gcaattatat    46380
ccattcggct atgtaacaat tctcataatt tgcataaaat aataaattta agacggtaaa    46440
aaaaattata tttttttgat agatatttat tcattttag gagtttatca gtttaattcc    46500
ggaattataa gataaaaata ttaatttatc atggatgtat atttcctcca ccatccgaag    46560
tcatgtcata caagccaaac gggaacccat accatattct tctttaagat ttgcaattat    46620
tgaaatttgt gttcatgtat tgttttctt atctagacaa gatccaagag gcgtcgacta    46680
caagaatatc caaatgcat gtgagagtcg acgaaaactt ccaaatctt ttcaattatt     46740 ttgagattcc atacatgaaa atacacatgc gaaataaat agtatccacg tatatatgat    46800
gtccgatcta tccgaaatct caaatgagat tctatgcttc ggaatgatat gatcacgagc    46860
gcgtatgata taagtatgt tgaaacaaaa gaatgtatat aaaaattggt aaagagcatc    46920
atcatatgct taagcaatga tatttgttta gaatttctct tctcttttgt ttgttataac    46980
aattacttta accaacggaa gcccaaaaca atttgtagta gttaattaga agccccaaat    47040
acttggtcag atcactaatt ggaagtagaa gcccaacagt agaacaaatg tgtagttgct    47100
tgttgaaagt tgaaacagat tttgagtaag aagaccaaat taccaaactc gttttggtta    47160
gctttcattg acttgaacca aaattgtttt cccactcgaa tgagctcata ccaataaaat    47220
tcaaatagac tgtataaaat tgatagtatg gttaataagt tcgaataacc ttttcccatt    47280
ttctcttctg atttccattg tgttgttctc agttttacca atatgatata atataaatct    47340 tataattttat gttgatttat ttgttatgaa attaaaaact cacaattttg gtaagatttt    47400
ttatttatta attttaata gacaatttat cacttatttt tatttatcca acttatgtgt     47460
tgtttgaaat tagtttattc aacaaatttg catacataaa acaatcttta gttttccatc    47520
ttattatttt ataatcatga ttatgtttga atttttccat gttatatata tcttctggat    47580
cattaaaaca gtaaaactat aatgaatatt gggttgcatt tggacatttg gtataggata    47640
ccaaactttt acaatccaaa ttaaatatgt tataccaaat caaatataca attaatgtta    47700
tatgattaaa aatataaata atcatgtata gtgcctaaaa ggaatttatg atctcagtgg    47760
tcccaaaata ttaatgaaat tgatgtagcg ttgttagctt aaccactaat agcttttac    47820 gcaaatttat ctacctctta ataagtactg tattttaca atccataatt aagaactact    47880
aaatatctct cgaatgaaag taatatgtaa tgcaatatcg gcatcttaga tatttataat    47940
tggacaaaag atgaagaaga tatttgcat aattttttct aaagtatttg cactttctgt     48000
ctaattagta aatatcctct cggctggtag gaagaattta aaattgtacg aaaataatca    48060
aatattgcac cggccagcca atgagattca attcaatata tataaaaaat taaattgatc    48120
aaagttatac taatataaat tatatagaca tatagtacgt atagctattg tctccttaaa    48180
cttgacacta ttactaattg tgtaaaatat tttggtattt gacaggtatc tatcgttcac    48240
atatatatag gtaacaatgt gaaatgacaa atcacataaa taaaaatata ccaaacaaca    48300
tgatataaat cattattgac aaaaacttgg ctagaagttt acaaatgaca ttttagata     48360 tatttattaa tttatgaaat gattgacata aattgtgaca caaaacttat gcaacaaata    48420
aattggtaaa cttgcaggat aaaattattt gcgatgaaaa aatgcaatgg ttacatatac    48480
agtatttgta tagattacac tcagtcaata taaagaaaa aaaagatga caaaaatagg    48540 aatatttgac cttaattcag aaccccaaca attcttaaga ttatcttata attttttatt     48600
attttattat tatttattat ttacttttttt attatcttat aattttttatt gattattggt    48660 tatcaatatt aatagacatg ccgcaaaaag aaaattaacc aaaccctgcc ttgcgacaat     48720
```

-continued

```
tgaaatccaa ctttcttgga atctttgtca agataccata atctttgttt tttctcaccg   48780
ggaaaatatt gaagaatcta tttatttta aggaatcaac ctattaagaa aaactattta    48840
cagtactgta tttgcttggt taaacttatc gaagcaaaaa aagtagtaga ttgattaaga   48900
taatattagg gataatgttc cacatcggaa gttaagtagg atcttaagtg gtatatataa   48960
gatatgggcc tctccaccta ttgccaatta gttttaggtt ggaagcccac actctaatat   49020
ggtatcatag cccgatccgt acatactcaa cccgatccac atcgatccgg cccaatactt   49080
ggctcgccga tccatgccca aacatatcga gatcaatggc tagaagagcc atcatctcga   49140
gggggcgtat taggaacaat attccacatc gaaagttgaa tagaatctta agtggtatat   49200
ataagatatg ggcctctcca cctattgcca attggtttta ggttggaagc ccacactcta   49260
atagatagaa gcttcgataa aagaaaaaaa caatcaagct atttataggt ttataatctt   49320
atcacaataa aacgaatgca gggaataatg gacaatttgt ccggttgtaa tctaaacatt   49380
aaacaatgaa ctatgcttct aattatatat tgttatatat tttgaaacaa ataaaaggac   49440
gacatgtcga catgtgcatt ataatactaa acaacatcta ttttctttac gacaagaata   49500
caaaatacat agaaacactg aaacgttaac atatacaact tacacacctg aatgtttcta   49560
caaggagatg atcttagatc agtggtaaaa ctatattttc tttttttata taattcttaa   49620
cggttaatcc gataaaaata tatagaagtg tttcagaata gacttttctt taatatcagc   49680
cgcctatatt tctgactagc attttaacca attaggtcaa aaaacaacta atagattttc   49740
taaacaaata tgttttgtt tttctttt ttttgaaaa atacaaaatg ttttgtttt     49800
ctttagtct tagtgaagca agggttgtct agaaccaatt tgccaatttg ttgttagtat   49860
ataatttga tttacatcat tgtaactgcc acgtgttgca tccttactta gcttgtctaa   49920
tatgtcctaa caatacaatt ctaccataat tttctcacac cccttaaaga acttttgac   49980
tatataattc aaaagtatat aaaagtatga aactaattt gaacaataaa agaaaattca   50040
tatcgttctt tttccttgtt aaagtaaaaa aataaaaatc cagataatat ttctcatcat   50100
gtaatgatca acaagaaacc aatttaagac tgctaaacat cgatgattaa tgctgaaaaa   50160
attcttatcg tgaaactgag actactaaca tcgatgatta cgctattcta atattcgttg   50220
agacaaccca atactaatta tattcttgtg ttttgtgtat gtatgcactg atacatataa   50280
catatattga tatatatagc tttcgtggag tcaccattga gaatggttgg atccagtgca   50340
agttccatac tcgaaactta atttgttttc atgcaagttg ctccataata agatacattt   50400
atttgtttaa tagggcagca atatttgctt tgtcagattt aaaatatttt caaattcaca   50460
acagttaaac aaatattgcc gtgataaata gtaattatta gattaatttt tattttttac   50520
ttatttagt ttgaattgaa atcttgatcc atactaccaa caaaaataaa ccactaacta   50580
acatactacg tgtagttatt tttaagtttt catagtttat tttgttatgt attaattact   50640
tttaattata agtgttgatt cgatattttc tgaggaaatc tatattaaaa ctcaattata   50700
taccatattt atttatttta tttaataaaa ctataaattc ttacaatttt ataaataata   50760
caaacttgtg ttttaggaag ggatgttaaa actttatggt tcttttggaa ttttttaaa    50820
aatcaatggt agttttagaa aacaaaattt aaatagtact atttgcgacc tttgatatat   50880
cacctatat atatatatat atatatatat atatatatat atatatatat atataggtca    50940
tttgataaga agcttacgaa caaattatct tctcgtaaca gttgccattt tagaaagaaa   51000
aaaatcaaat tccatctctc ctactgccaa ttggaaaatt aaaatcttat tatgcaagtt   51060
```

-continued

```
actaactcct ctggttagta catatacgag ttgcataact tactgttatt gttctttctt    51120
agttaggtta gatactattg cagagtcatg tgcttctgtg tactccataa tatataattt    51180
gagggaccta ttaaaagact aacaaaataa aactgttgaa atgacttgca agttacaaac    51240
agagcaccaa agtgatacga cgaatatttc ccatacaatg tcaccactag ccatcattat    51300
tggtgaattg attagctgct caaattataa gccgaataga gaaattaata atatcgagat    51360
taatatatcg ttaaacaaat aaaagtaagc ctttgaataa aaatatgtag aggtccacag    51420
tgattagacc gaccaaaaaa taacaatatt taatttcact gctataagaa agtttatgac    51480
ataatgataa gattcaaaga ccaaaatagt agaattctat aattagagga aaatactatt    51540
ttcttttctc attatactat acttgccagc ccattttgtc atttatcatg aaaattaaat    51600
tgttttacat atcttcattt aaatgtttat agtaacaagt tggaccctcc tcgttatcaa    51660
aggtaatcgc cttcagtgtt taataaagta atacgattga ggacacaaag tgaatggttt    51720
aaaattaatt tccgtgggat ttaaagacga atacaatgtg atcaaggtgg tttgacgtct    51780
aactatagct agtctaaact agctagctag gctaacaacc agtaataata gctgaccaat    51840
catcaacatt catttctttg gatttaataa agaagctcaa taacatcgac tgactaatta    51900
ttaaaatgat aataaaaact atttagtata ataatcgtcg tccacgtcag agtttcacct    51960
cttctctcc ggctttgcat ggctcttgt ttctccttat ctccctccct tacctattat    52020
acttcctcta caatttcatt gcttcttgat aagagctctc tcttctttct atctcttgtt    52080
ctttaatttg tctctctctt tttctctagc aatgcttgga agctatagag aagtgagtat    52140
tagtgtctct ctctttactt tcactatctc tgtttagatg tgtgtgtcgg atatataacc    52200
ggactaatat acgtataact tatagttatt ctatcttgac cattgatata tgcgaatcac    52260
tctatggtat taataaggtt atgtggccaa gacttgtggc caacaagatc ctaaggaaaa    52320
gcctcgggag caacaacttc gttgccgatt tcccacctaa tactgatcag aagcttatag    52380
aagcttccgg attagctgat gaacgatcta aatcaattct ccacaaccaa cacaaaacca    52440
ctcttctcaa ctacaagtac gtaatacatt taccctcttt gatcacattt tccttaacaa    52500
aaaccagtta tcttcgttta tattgttaat acattgaata cttgggcaga gaaagagag    52560
gatcacaata ccgttttatt gccataatta gtcacttttc ttgcgtcgca ctgcatttaa    52620
acctaattcc ggatacgcat aaaccagtag agcttaacac gtagatgaca aaattgtaat    52680
cttaaggaaa ccttcatttg attcctctgt gttccatgag ttacaatgtt tttaaataat    52740
gtaacgtttt cttttcaaa aaaaaaaaca atagtgtaac gttttgacaa tttttgtttt    52800
aaatttaatt ttaattatct gtttctaggg tttttgtaag cacatggaac gtgggtggta    52860
tcgtaccgga cgatggactt gacatggagg atctactgga aacacataaa acaccgtgcg    52920
acatatacgt gcttgggtaa ttgataaaca ctacaataaa aaattgaata tatatagtta    52980
tataacgtgt ggattttatg tctaaaattt agtttaaatg aaaatctagg tttcaagagg    53040
ttgtgcctct acgagcttcg aatgttttgg gatcagataa caacaaagtc tctacaaaat    53100
ggaactcttt gataagagat gctttgaaca agagagcaag acctcatcga gacgaagact    53160
tgtcggaatc aaagggcatt aatggtattt cacaagattt tagatgtatc ataagtaaac    53220
agatggtcgg aatcttgatc accgtttggg tccgaggtga tctctggccg tacatccgtt    53280
atcctagcgt ttcatgcgtt ggttgcggca tcatgggttg cttaggaaac aaggtaacat    53340
atatttagaa ttttctatct ttttaattat ataaaatctc actgttatag atgtggactg    53400
atttaggtat tgactgtttta tagaaaatga atacgtgcgt ttgcatttgt attcatatct    53460
```

```
gattatttta atttgtggtt gaaaatgaac tcacattatg catctttgac taagattata    53520
gcataatgag tttgattgat aaccaaaagc tgtacaagtt ttttagctgt tatctaaagt    53580
tcttagcttt atcagaatag tacaaagctg ttagaaagag ccgtatagaa aagttgttaa    53640
aaaatgctga aagtaaaact ttttataacg cttttaataa aaaatttgtg attggtaact    53700
gtcaaaactg tatacactgt ttaaaagtgt taagtggtta tcattcaaaa ccaatagtta    53760
aaaaaaatat atatatatag cataatagtt tgtacaagac tactagttac caccggcata    53820
gcctaagttt aattagcctg gaattaggta actaatattt gcattttgat taaaaaaata    53880
ggtaactaat gttttgtttg ccccgtataa tttaaactga cttcttacat tttttttttct   53940 ttcttgatca atttagggat cagtatcggt tagatttcaa ttgcacgaaa cgacattttg    54000
tttcgtttgt agccatctag cttctggtgg ccgcgaccga gatgaaagac agagaaactc    54060
cgacgtcaac gagatcttag ctagatctag ttttcctcga ggctcatctc tagatttacc    54120 caaaagatc cttgatcacg agtaagctta tgttatacta taatttttca ataatacttg     54180
gttcatatat tttgtgtacg taaattaaaa tattccaact tgttagtaat taactatatc    54240
ccaaggtcag acaaaaatga ttataatgtt aaatagttga ccgattaatt ataataagac    54300
ttgatattgt gaagtgaaaa ggctagtttg gtaagtactt attaagaaat taccaacttg    54360
tggtattaat taatttatt ttgttttgtt tttgttggat caaattctat agtcgggtga      54420 ttttttttggg agacttgaat tatagaattt cattaccgga ggagaagaca agattattgg   54480
tggaaagcaa aaaatggaac atcttactag aaaatgatca ggtaattatt tatatatgta    54540 tttttttttta cgtgttgaaa gttgtaaact cgctattatt ttcttataca tatatatgtt   54600
ttgttatatt aaaattaagc tgaggatgga gatcatgaac ggccagattt tcagagggtg   54660
gcaagaagga attgtcaaat ttgctccaac gtataaatac gttccaaatt cggatttata    54720
ttacggatgc attacataca aaaaagacga gaagaaacga gctcctgcat ggtacgtata   54780
acgtattata atttacatga tacttatatc atatatttaa ataaaagttt gatcccatgg    54840
atgcatatat ttaaataggt gtgatcgaat aatatggtac ggaaatggac tgaagcaaca    54900
tgaatataca agaggagaaa cgaagatatc tgatcatagg cctgtcaaag caattttcac    54960
cacagaaatt actgtaacac ggcgtggtaa aaagattcgt aatttctttt tctcggacag    55020
atttgaagaa agaattggtg acatagattc taaagactac tcgtggatat ctacatagtt    55080
ttattaatcg gggtgatatc ttgtcacttg ttaaatataca attcacatag atttatata    55140 aaaaaaactt atacatatgg agttttttgtt ttatacattt ttagttctta gcagattta   55200 gattaaaaaa agcttataaa agttgtgtaa taagagaatc tatagaagaa gatttgttaa    55260
atattgatta tttatgcaat cttggcgaca agtgacagtt gtatacttgt atggtaaaat    55320
attattcatg aatttcgagt tcttacaatg cttatgcaat acgtttatgc agttcaacaa    55380
ctatatggtc cgcagttata ttattcttat ttcgataaat aattttgttg atgcgattcg    55440
agataacaaa atcagcattt attttgttcg agattaattt ctaaattcta aatataaatt    55500
attaagttat atatatcatg caatagcata caagactaat acttaaacaa caaaacaaac    55560
taaggctgtt gaacaagcca tatgttggt taatttggca attggcatta tatgtggaca     55620
tgaggctagg agcatgaaca atttgggggt attttatata atattatata atcatatttt    55680
attttatctt gttttcgcaa aacaaataga tatggttttg ttaattataa tggcaagtgg    55740
ttttagtaaa tgcttgagtt gttgtcattt gtctaccaaa attttagttg ttggaaatag    55800
```

-continued

```
gataatatca aatatgaata tcgaatgaac ttttttttagt ataaatggga aaaatacaaa    55860
tgcaaaatat ctcattacta ataaacaaat gaattgttgt aagaaaaagg gaaaaataaa    55920
atagacaata atctctttac caatacaaaa ttggatcgtt acaataattt tgttttcgct    55980
aatccataat tatgtacttg caaaatacca acaaaaaatt cgcttatgaa aattatattt    56040
ttagtggaca tatctaagat aatcagaaaa ataatcaatt tcttcaaaca caaatactgt    56100
acatctaaat gggaaacata caaataaaaa atatctaatc agccaatcac caataaagaa    56160
gtgactcgtt gtcaaaaatt agggaacaaa aatatctcat taccaataaa taaatggatc    56220
tttgtaagaa agttaaaaaa aaaaaaaga caaatgaatc caatgttcca ctaaatcact    56280
aaaaaaaatt ttgtcgaaaa aaaataaaaa aattgtatat tatttacttg caaattgcga    56340
aaaagaaaag aaaacttggg attatgaata tcaaattgta tattgggcct atttaagata    56400
acgagcccag gcccatctaa atgatatgaa aatgaaatta tcggcatttc gagtttcagc    56460
gccattgaaa cgtttcaaaa ttttcacgga gagctccaaa atcagagaga gagagagatg    56520
tctacagaga tcggtcatct tcgtcggaga ttagtcgagt tcttgattca atctactact    56580
gtaagtttga tcttcttctt ctcaatcgtt atctgttgat gttttttccc tttcacttca    56640 aaatttctc tcctgatttc ttcaaaaatt ttgtttctca tcgtgaaagc tactcgaact    56700
tcctccgatc gttaaatatt cagctctatc gctattcttc gatcgatttc gtcctaattt    56760
agtcaggtat taccattttc ctcttccaat gattcctgat ttgagtaatt tttagtgaat    56820
tcgattgatt ttagggtata attgacgaaa tcggtaatca atgtcggtgt atatatttgg    56880
atcagtgctt gttttcggag gattgataga tttacgatgt gttagtattt gactcgagat    56940
caactaacat taggcttata ttcatgttgg atgatttcat aattttcagt ttattagctt    57000
tggatcaagt cttgtataat ggattctaga gttatggtga aaactatagt catgtttgtg    57060
aatctttggg tttataggtt tttacagaaa aagaaagcag aacattggct attgcaacct    57120
ttgaatgaaa gcaatctgca gttatttgtg ttaatctcca tttggatctc atgtaaagtg    57180
ggtctacttc tttgcttctg ctattgtttt ttgtgtgttt gttctcttat atgtgtacct    57240
agaactgaat tgtttgcttc tgcagatgca ttgtacacga ggtttatcgg ttcatagttt    57300
gaaatccttt ggggataaag tgattactga gcaactcttc atggttcgcg atttcttgga    57360
tgcagtaaga tagtcttgaa aaccttaaat ctgtgactga attttgtttg atgctttcaa    57420
tgagttttga ggtttctttt gcaggaactg gttttttctga aggtaaccat tgtacacttg    57480
tgggaatgtt gtttacgcta tagaaggcta gaagctcatt cgaactaaat gtctctcttc    57540
ctcattgaac atgaggagca ggttctgaaa tttgagattg gcactctaaa tatagcttat    57600
acacggcttg aagatcttct tattcagttc aagtaagttg tttcatcctt atcaagtatc    57660
taaagtctta acgctcctga atgatatttgt gctagtccat gttgttatta tctaactcct    57720
taaccatatt ttcttctatc agagaagttg caaaagttgg ggaacagttg aactttgaag    57780
catgtatgga catgatggat cttctttacg agaaagagga cacatccctt ctttatcaat    57840
cttcaaaatc tctggctgct tccatttttgg taaacttatt tgctctccat taccctctgt    57900 tttttttttcc ttaattgctc tccattacca tctgtttgaa tagacattaa aaatgaaact    57960
aaaatggtgt tattctcttg gccacaggtc tcttcttaca taataacagt gcctaaacag    58020
cagtacgaat tccctattct cccctggggt aagcattcat cttctgctc tttctatcaa    58080 aaccatttta taaatacaat taccaatgat agatttatat taatcaagtc ataggatact    58140
gaataagtta gaaacaggtt atagcatata ggatcaataa ggcccaatgt tcaccttttt    58200
```

```
gacaatgcat tcaacatca caaaaaagag tgtcttgttc acacttcaag gtcttcttca   58260
aattgcccct tagacctgga cattgtatgt tcctcaccta atacttaatt attatgataa   58320
tgagcccatc aaggttgact tatcagttct gaccaccggc catatacgta tatacggttt   58380
acggatcaat cagatctttt gtggtccata acattttgct aaacctaaca tatctccggt   58440
ccggaccact caaatattgt accggaccgt ataagatata ggagacagta atagtagaag   58500
tcactagtca aacgtcagca tttcctttat cttattgaaa aaacatacct cattttcatg   58560
gagttatagc tgttacacac tcacacacat acacaaaaag atagaaagaa gaaaagtcta   58620
tttctattta tttcttcggg tccctctcca aaatttattc ttcttcattt atggagtcta   58680
cactacattg ttctgagatt tgttctctat atactccttt tcagtttttt ttcacatttc   58740
atggtaacaa ataggatctc tttcgaacta taccaaattc tagaagacat gatttctgtc   58800
taaatctttc acctactctt ttatatacac atgtacatgt tgatccacgt ggtagagtct   58860
ttagtataaa gttaaaaaaa tgttaggcct atcttattta tagggaccat tgtcgaaact   58920
agaaagaagt agagtgaggt ttctaaggtt aggagagggt aggcactaga catagtttta   58980
ttctgcttct gtgttacatg actctgttac tagagaatag aaacaacaaa aatttaagac   59040
ttggaggcaa tgatgaccct aatttttatg agtaggggat gtatagttta attattcatc   59100
aatattattt ggccctactt cgaccaccta ccatttttcat tttcagtttg attttcaaaa   59160
aatggatatg atgttgtgaa ataacaacaa cttcaaataa gtattttga aattcaatag   59220 atagcaaaag cttccattga gattttttagt tcttgggata atgacaaata tgagctattt   59280
tcataacaaa ctttaaaatt tttctaattc cattttatat ttatgttatc ttgctttcac   59340
ttaaagctcg attctttgtt tgtttgttta agaggctcat acataaaata taaccagaaa   59400
tgtacaccaa agatgtttgt tgagttagga gtagtttcca aggagtcctt ttgagttttg   59460
agtaacagtc ccatcttaaa ttgtctcttt atcttttta atatgatgat tatgaatttt   59520
gtatttttgg cagttaaaat ggtgacaaat aaggaagaaa gggaggtggt ggagcttgtt   59580
gaatacatac ttgctcatgt cctttactcg aactctcctt aaaccctaca ggtacacgca   59640
tcttaaatcc cttcctatct actccttttt taaaaaacac aaattaaaat ttaaaataga   59700
aattgtatat atattttaaa gatatatatg aacatgtagg gtctatatac acacacacat   59760
gcttattata tacacatcaa atacgcattt tcctactttt aaaatttaat tttctcgcct   59820
tcaaactgtt ttatatagat cgttaaatat aaattccact atatcattat cacctataat   59880
tagagttaaa ttctgcacaa ttagtgatag aactaacaga ggttattcaa ttgaaaaaac   59940
tgtagtagaa tgataagttt ttttgaagta tgaaacatcc taataaaaat gacaattccg   60000
cacaattaca tcattgctat aatattgcaa atctttaga gtcattccac tcttgatatc   60060
actaaaaagt tttgagagtt gggacacgtg tattctataa cgttttatga aattttaaat   60120
cgtataaatg tgtatgtata tatgtaaatc ggatagattg atcgatatgc ataatacatg   60180
tggatctaat gatatgtgta tgcttcacaa ggcaatgacg gttgcgatgc gacataccat   60240
gcatgtgagt tactagatcc acttcgaacc atctaaaata atttttatttt cacctacata   60300 aatgtgcgaa tttattatat cttctcctaa atgatattgg tactttaact ccgaatattt   60360
gtccttactg tacccacatt aggctttgtc ttctccaaat aattagtttc actatttaac   60420
cgaaaaatct caccccaacat aagagacaaa taactaaagt tgacaaaaga aaagacaaaa   60480
aaatgtgaaa ataagagag aaataactaa gtttgcttgg catttataga ttttttgttg   60540
```

```
caagctttct ctggcggaat cctaacttca ctgtaatatt tactattaca caaaacaaat    60600
gtgagctgtg ctataacaaa aatttcaata aaccccttcca aattgtatag ttttttttaat   60660 tattattctc aaacaatcaa taattcagga ctgttgagtt gtgaattggg tgtgccatgt    60720
cgatgataaa atccaaccac tagataagta tatgattaga tgatatgatt agatgatatg    60780
attagacact taatcccagt agcatcctaa gggggttaag cacattatta aagtgatttt    60840
atacctcttt tcagtattta aatctcattt agttttgttt tgataaataa ttctctttgc    60900
tttctacttt atcaatctta atatataaaa cgaataatgt gattattagt taagtacatt    60960
cctcttctaa tagtataaaa gtgattatgt ttcttcataa tcgtatcacg actgtatcca    61020
gcacgacgtt gacttttaat attcagtctc ccacacatgc ggtattaaat tgggagatac    61080
agaaacaaat ccaaaaaaaa caaagttttt cgtaaagatt gttagtttat gtgtctaatt    61140
ctgttttatt aagttaccca agcctaatta ttgagagaag tatatataaa ctactcccat    61200
aattatttag atcatatact taatgataga atcatggaat ttaaattgct acgaataagt    61260
cttatggtta ttgacttact gtataattgc atggaccgta ttaaaaattt cattacccta    61320
cccaaagttg aaacctattc tacttgttgt tttctgccca accaccttaa atgttatttt    61380
tctggttctt tatgttagga gtttatgtgt catcttttgt cttttaattc caaaaaatta    61440
tagagatata tataattcag ttaaacaaaa aaaaattaat tagacactta cactgtagaa    61500
atatatggta aaagaatttg aataaaaact tatgtatggt aaaatgatac gtatactaat    61560
tttataaaat tattaagctt gatcgttact cgtttataat aaaactattt tggtaaaaca    61620
aaatctaata tataatattg tatatgtata tatatacata taatgatttg cagcttgatt    61680
agttggtacg gggagcgagc aataattatg tttggatggg aatgggatac taaaacaaaa    61740
gttgttaatt aaattaattt aaaaaaataga catctacttt tctcgatgaa actggtggag    61800
aagagcggta atgagagaga ccatactttt gattagacca aattggcatc tttcttgtta    61860
ttaagagggg tacatagtat catcatcatc cttaattaat tagagtccac gcaataacaa    61920
tagaagactc tgtcctcccc atttgtggta aatcctcttc tcatgattat tgtttggttg    61980
agtatatgtt ttattctatt actactcacc agaagaacat tttcatatgt gattcgaata    62040
caatgttaca tttctaatat gagagataac atatgcacct acttttttata catgcagttg    62100 tatattgtgt gatgtatagt tatatatttt cgtctaattt ctgttgagtt catatgtcat    62160
acctaatttg ctataggatt ttattgactg aacaaaaaaa aatgtataca tggtctttat    62220
cttagaataa tggatatatc tatttctttt atttgatttg cttcgcaaat gtacgaatat    62280
tcgatctttc taaatcgaat tgaatcaaat aacagatcga aacaaatcta acgaatattt    62340
tgtccaaccc taatattttt tttaaaaaaa atgttagttg tttaattata ttactaaaat    62400
catgaaaata taataaatgt tgtaaatgat agaaaaaaaa attgaaagaa cgttttctg    62460 aagagtttat ataccttgta tacaaacatc ttttaataaa aaaacaaat aattcatatt    62520 aatggtgaca tagactgcac ccaaaaccgc agcgcaacag tgctgtaaca gtattaaaat    62580
ctttacatat acatatgtat ctatgtatttt ttgttactat tcgaaccgta tcgcactttt    62640
tcgtaaaacg cagttactag tcagaaatta aaatatata attttaaatg aaagcaaaaa    62700
attatcgtaa agtttacact tcaccgtcaa aacacagcta cttatgtcag tgactcttct    62760
tctatcacca ctacacgaca ccaaagaaaa acactaacac actctctctg ataactctcg    62820
cgtgactctc ctccttcaac tctaactggt tcgtacccct cacgctccat taccggcaac    62880
gcgcttatcg tctggcacac tcacccgcac cgtacccgtc gtcggtcttt tcgccaattt    62940
```

-continued

```
atcgtatttt tccgtgaaag agaataatat aatactctaa taaagtgtta taataaatta   63000
caacgttact atttacaacg attttttaaaa gaagctgatt attatttctt ctgtaactct  63060
cttctctgtt gctctacctg ttcttttctc tctgttcatt ctcttttctt tagcttaatt  63120
cagcaaaaaa tttatctttg tttctctctt ttgtttcttt cctctgcaaa gtaaagttat  63180
gagagcttaa taatgtttgt ctcatcttca agcttcagat ctgattcctt gtttctacaa  63240
gtaattgtct ctttctttt cgattaacca ccatttctgt gaagaaaacc tttttgcttg    63300
cttcaagatt cgagtgagga aaattttagc tgaaaatgct ggaaattgga agtcccaatg  63360
ctctgttttt ccgtacgaat actacttgta ataatcttct ccgtgagctt caggtttgtt  63420
tttcttcctc tcttttgat ttgttggttt cttgacgatg acggttgatg ataaaaaaaa   63480
aagtctttgt ttttttttaa ctctcaaggg ttaaaggatt ggactcataa tgagtttggt  63540
agagacaatt taactgaatt tttagtcttt tgttttcatt atcttttctt ctcttaggtc  63600
aaaaggattc ctgtgaattt tgactaaaac atgtcagttt ctggaaattt ctttactttt  63660 ttttggtct tcatgtgttg atgttctttg gttttaattt catgcataag ctcttgtact    63720
agaaaatctc tgttttttgtg ttgtattgtg attgatttca tgagtttaat ggggttttttt  63780 ttgggtgtat gaaacagaaa atatgggttg aaattggtga gactgagact gagaaagata  63840
gaatgcttat ggaattagag agagaatgtc ttcaaatcta tcaaagaaaa gttgatgagg  63900
ctgcaaattc taaggcaaag cttcatcagt ctgttgcatc aatagaagct gaagttgctt  63960
ctttaatggc tgcccttggt gtgttaaaca tcaactcacc ggtacatagc tatcttcatg  64020
atagatcgat ttagattgtg tgttttagct taacaactat tgctaaaaaa tttgtgtgtt  64080
ttcttgcatt ttgatgttca gattaaactg gataaaggtt caaaatcatt gaagaaaag   64140 cttgcagctg tgacacctct agttgaggaa ttgagaattc aaaagagga gagaatgaag    64200 cagttttccg atataaaggc gcaaattgag aagattagtg gggaaatctc aggatacagt  64260
gaccatctca acaaggccat gaacatttca ttgactcttg aagaacaaga cttgactttg  64320 aggaaccttta acgagtatca aacacatctc cgcacacttc aaaaggaaaa ggtaagagca  64380
atgaacaaca aatatccatc atttctgttt tcttataaac atgattatgt tccttttatg  64440
cagtctgatc gtctcaacaa agtgttgggt tatgtcaacg aagtccacgc actatgcggt  64500
gttcttggag ttgactttag tcaaacagtt agtgcagttc atccaagctt gcatagaaca  64560
gaccaagagc aatctacaaa cattagtgat agcacattag agggtcttga gcacatgatt  64620
caaaagctta aaactgaaag aaaatcccga tttcaaaagg tagacttgta tttatatact  64680
tgtttgaaca atactattct tctatgtcat attcatttat tgacttgtca tttttgtgtt  64740
ctcaataata cttctaaatc tgcagctaaa ggatgtagtg gcttcactct tcgagctatg  64800
gaatctaatg gacacaccac aggaagacag aactaaattt gggaaagtta cttatgttgt  64860
aagatcatct gaagctaata tcactgagcc gggaatcctt tcgaccgaaa caattgaaca  64920
ggttcagtag aagcacttat ataattctac atctacatct ttaacctcgt tcttgatttg  64980
agtctttgtt ttggttttac aataggtatc tacggaagtg gacagtctca gtaaactgaa  65040
agcaagcaga atgaaggagc ttgtaatgaa acgaagatcc gagttagagg atctttgcag  65100
actaactcac attcaacctg acacaagcac ttccgctgag aaatcaacgg cattaataga  65160
ttctggtata tgtgattgag gtttggtttt tttgaatagt tggtttattc ttgccacttc  65220
aacttgtttt taagcctagc ttccttatgt ttcttcagga ttagtggacc cttcagagct  65280
```

```
tcttgcaaat attgaaatgc aaataaacaa aattaaagac gaagcacaga gtcgaaaaga   65340
tatcatggac agaattgacc gttggctctc tgcatgtgaa aagaaaatt ggctggaaga    65400 gtataatctg gtatgagaac cttaaaacaa aaaactcata aaagaaaaat gtattctaaa   65460
aattctttat ttggttttag gatgagaacc ggtatagtgc tggaagaggg ggacatgtaa   65520
acctcaagcg tgcagagcga gctcgggtta caatcaataa gatccccggt actttgctcc   65580
tttcgcatta tactagtttt tgaagattaa atcaaatgaa taattgtaag cttatacctt   65640
tgtgtgttat ttacttcagg aatggttgac actcttatca agaaaacact tgtgtgggaa   65700
gaagacatgc agaagtcatt tctatacgac ggtgtaagct aaaactattt aaagtaagtg   65760
cagagtcatg aactgccaaa gtcctttctt tgattcttgt gactacttt tgtaggttcg     65820 attggttaac atactagaag actataaact gacaaggaaa caacaggaag aggaaaagaa   65880
aagatacagg gtttgtccca aaacactctc ttaaaaccac tcaagatttt ttcgttttcc   65940
cgttttaaaa caagctctat atcctttgtg caggatcaaa agaagaggca ggatctccta   66000
ctaacccaaa gggaatccat ttacggatca aaaccgagtc caagaagaag cagcagcttc   66060
agaaagccca atggtttcaa cattagcaat gggaatggtt cagtgcctcc cacgcctcgt   66120
agaggctcgg tagggacaac aactcctgac gttcttctaa ccccaagatc ttactctggt   66180
catcatcgcc aaaacgggta tttcaaagaa gttagaagac tctctactac tcccttaaac   66240
tatgtggcca tgcaaaagga agatactgtt tctactacct acacatcgat ttatagctct   66300
gagccagact cgcctctcca aggctgactt gactctcttt tccaccggta agagaaataa   66360
tcaaaacttt aaagcatcaa ttgttcttgt ggtgatctga aactttgtgt agacagagat   66420
tgatgttaga agttggatct atgatgcagg atttgtggag taatgttaat ggtaaaaaaa   66480
gaaggaagtg aagaagaagg aaggagactt gtgaatacag aaggtgactg acttttagga   66540
gatatggtga gataagagta aaaaaaataa atgtgaaatt tgttattctt tagaggttac   66600
aagttttcta ttttgaagtg aagaatacta ttgttttgtg taatgccagt gtgaaagtgt   66660
gtgaatggtc attgttgtgc gtacgtattt gtgtataata tacgtatttg ctatattttt   66720
gtgctttaaa ttagtcttgc ttttgaaatt taaccatttt gcgtgtactt aaactagaga   66780
attaagatgg atagattcat tatgtgttgc tgttcagttt ttgtcacaaa gaaaaaacag   66840
agccaagttc atcaacaact atggaaatga agttttttt ctcgtacttt agagattcat     66900
gcgtaaacaa ttcattgtat tatgcatatt ttttcatta aaattttact caataacatt    66960
gtgatcactt aacattgcat tctctgttaa ccttaacttg agaagcacat tcattttttg   67020
ttttgcgaac atctttggtt tggttatacg tatttgcttt gagctatgaa gatgtgcgta   67080
tgtgcttcta gtagagagct ttagatatca cataaagcac atctttactt cgcaactcaa   67140
atcaaatgaa tacgtaaacc tgggcataat acccgaaccc aaagaaccga atcaaatccg   67200
acccaaaaat ctcgatccga atccgaactc gtaccgaagt tcaaaatatc catgcagatc   67260
ctaaacttca taaccccaaaa acctgaaccc aaacccgaac caaacgcgaa caagtacccg   67320
aacatgcccg aaatataagt gtatagttaa atatattagt aatatttata tttgtaataa   67380
cctaagtgtc taaatatttt gaatgtaaag ttttttcgaa tcttttaact acttttggct   67440
ctaaaaagca ctcgggtttg tagattttt gggtattatc caatagttta catagactcg      67500
aatacaaaaa ttcgatattt ggatactttg ggtatactcg attccaaacc cgaaatacct   67560
aatcgaaccc gacccaaagc tgaagtttta aaatatctga acagattcta gattctaaat   67620
ccaaaaaaac ttaacccaaa aaatcaaacc caagcccgat ctgaatatcc gaacgcctag   67680
```

-continued

```
acctataaat acgtattcct cttcacatgt ttaccaaaga cagtagcgag cgtaaaaata    67740
tggtgcaagt cagcaagatc ataaaattga tgggaaaaaa aaatatatat aacaaattat    67800
ttgaacttag aaagtatagc ccagttaagc ccatatattg actttcataa acacggccc     67860 attctaacgt aggattatac tgaaaatgcc catgcactca taagaaacta gaaaagtaga    67920
aattataaca ttttttaagc tgttaaccga atctgaccgg accggttatc accgaataac    67980
aatataaata acaagtatac cgaaactttg gtactacata gaactactac attaccccaa    68040
cataaacatc tcaaagagat ttgatatttt gttacgactc gaactcctga acttgttgaa    68100
gaactcggta gaacgtgacg ttggatcttc gagaggtggt ttcgtcatca tcatgagatc    68160
tcgtgaagaa attgttgttc ccttccacgt caaacgagtt gtgtctcttt cgtacgttac    68220
gtacatgatg acgtggcggt ggataaaccg gagtttcgta gctgctggct ctgtgtttaa    68280
cccaccccgg tttcgatttc tcctttggtt tcttcacaat ttaaaagctg tgatttaatt    68340
ggttatatga gaaattttttg atttggtgta attattttca cttacgtgga tgagagaaga    68400
tgatattggt acgggacatt taaccggacg atcttcttcc tccggttcaa taggatgctc    68460
aaccggacaa aattcaacgt cgaattgatt ggtttcttca tcgtattcca tcatcactgt    68520
ctcctccaca ctctctcgtt tgtcctaaag aaaacaaaac agataatagg gtttcctttt    68580
gtaatgttca aaattacgg tccaaatttg taaaacaaat gaattcaaag ggtttgttta     68640
tatcaaaatt aataagtaga gtaaagattt ggttaggaga ggaaataaaa actcactgcg    68700
gaatcgaagt ccatgagagt ttggtgaaga tgaaatgaaa tgagagagag gaggaatgtg    68760
aatgtgaatg tgaatgtgag aagagtttgt gtgtataaaa gggtaaaaat aaaagagaaa    68820
gcgaagaggt aaaaaataaa taaacaaaag ttggttttgg catgaaaagg agggattttt    68880
aaccccacag tgaaaaaaga tgtgaggcag aaaaagattc cttaaccttc cactattttt    68940
tctttctttt ttcaggacca ttttcatatc gttcaaatgg cgtatgggtg atcaaacttt    69000
ttgtagattg tcttttttt ttttatatt agcaatcggt gccaaacttc aaaacatgca     69060
ttgtgttaat ggagtgtata aaagttaca aaacatatca cattcaaacc cttatataac     69120
caacagcatg ttggtcctgt ggtaaatttt aggattttct aggtggaggt gatgggtttg    69180
agacacgttg agagatatct tttttccaa aggagatgaa tttaaccttt tcggtcccgt     69240
ctcttgaaaa tgtatggatt ttgggcctga actttcagat attttttaaaa aatatagata   69300 tataaccgct atatataaac aaattatcaa atatatatat gacaatcaca atattaatgt    69360
aaaagagtaa aacaaacaat ttatttgtct cctttgtaaa tcagtcaaac attataaaaa    69420
aatgtaattt ttactgtatt tgtggaattg tatcactatt atgttcaggg tctaaaaaga    69480
tgacaagaac aactaccata tattatatac acttttcttg cttttaacaa aaggagatgc    69540
tatctttctt tgaaaatccg aacaatcttt cgctttgttt catgtcttac ttttttttc     69600 ctttcttctt tcccttttag ggctttgaag aagattggtg atgtagagaa aagctattga    69660
tttgctcgta ttccgttaaa attacaaatt gcaaaaaagg aaaaccaaaa cacactaaag    69720
ccggccgtta agggggaaagc atgaggtaca ccactttgct ttacttcaac aagccgtttt    69780
tgtatgcgaa tggaaaaagc aagcttacta taaatacacc aatatagtct atataaaata    69840
ccataattat acggtaaaat attagcggta tttctataag tagccacaaa attttcatac    69900
aaaacaaaca ttgttaagca aattttgcta ataaacaca agagatttta tatttttgcg     69960
gctcgaactc gttaacttgt tgaagaactc ggtcgaaagt ttaacaaaag aaaattttgc    70020
```

-continued

```
tgaattactt atatactgat tctgatttta tcaaaggtcc aacaatttgt tatgtaaaaa      70080
tgtatatatg aatctcgtag tgatttgaaa agagtgttat agggtaataa ctcctcgggg      70140
attgagttta agtaattagc aatgttttga agtttagctt tttttttttt ttgaacggtt      70200
gtttgctcac atatgctatg atttctttat gtaggtaggt aagtttctta agatgacaag      70260
ataaatcgta caaaaaacat tgccaactt  tttctcttgt cacttgtatt ttcactagtg      70320
ttttcttttg gatagacaag aaagaacatg acaacaaatg cgaatcgatt gcctaaacta      70380
atattatatt gttcgaaatt aaattcgagg gaagatatca tcgaggattg caacaatatt      70440
aatatagtac tccaacacct tagtttcatc tccatctcta gctgcataat ccatctacca      70500
tttccaaagt atagttaata aattaatagt aatgagtata tagtaatgag agcaaaatga      70560
agataaatgt accttggtga ttgagttaaa gagagaggaa taaagagacc taaaagagg      70620 tctatcctta ggaggctttg cttggatgat taagtaaaag tcttgcttca tgtttgatgc      70680
acttctcctt agctctttcc ctccttcttt ccacaacttc ttttctatca taatctcctt      70740
gattcttttt atattctctg catttttt                                         70768
```

<210> SEQ ID NO 14
<211> LENGTH: 316
<212> TYPE: DNA
<213> ORGANISM: Arabidopsis thaliana
<220> FEATURE:
<221> NAME/KEY: misc_feature
<222> LOCATION: 22, 24, 25, 42, 53, 55, 85, 128, 142, 144, 199, 204
<223> OTHER INFORMATION: n = Unknown Nucleic Acid

<400> SEQUENCE: 14

```
aatctttccg gcggagtttc tntnntcccc gcagccggaa gnatggactg ctncngctga       60
tttgattggg atacaatatg cattntggtt actgtacata tagtaggttc acaatctaga      120
gattttgnag gttttttttta antnctcact taagtaatgt agcttgccat gactagtgta      180
tgttgttaaa cgacgacgnc taagatggnt cagtgttgat cttagcgtaa gtattaatcc      240
catgggaatc ggttgtactg tatcagattt ggttagtcgt ttaaacattg taatgttcta      300
ataatcactt tttcat                                                      316
```

<210> SEQ ID NO 15
<211> LENGTH: 468
<212> TYPE: DNA
<213> ORGANISM: Arabidopsis thaliana

<400> SEQUENCE: 15

```
gagattcgtt tattgaattc aagaaccaac ggaaacgttc atcacaagtc tccgaaacta       60
gctctattcg caacaaacat cacaaattcg gagttcgaca gagctaaatc cgcagatttg      120
cagatacggt aataatgaaa ccgttaagag caagcatgat tggggcgtgt ctgcaacaag      180
ttctcgagct gagaaaaaca agacaacaac atccagaagg atcatcaccc gcaactctca      240
agagcttgct tacagggaag aagattcttg tggttgatga taatatagtt aacaggagag      300
tagctgcagg agctctcaag aaatttggag cagaagtggt ttgtgcagag aatggtcaag      360
ttgctttggg tttgcttcag attccacaca ctttcgatgc ttgcttcatt ggtattcaaa      420
tgccacagat ggacgggttt gaagcaactc gtcagataag aatgatgg                   468
```

<210> SEQ ID NO 16
<211> LENGTH: 286
<212> TYPE: DNA
<213> ORGANISM: Arabidopsis thaliana

```
<220> FEATURE:
<221> NAME/KEY: misc_feature
<222> LOCATION: 9, 26, 67
<223> OTHER INFORMATION: n = unknown nucleic acid

<400> SEQUENCE: 16
attaccaanc aaccaaaaga atcctncttc ccctgtaagc aagctcttga gagttgcggg      60
tgatgancct tctggatgtt gttgtcttgt ttttctcagc tcgagaactt gttgcagaca     120
cgccccaatc atgcttgctc ttaacggttt cattattacc gtatctgcaa atcctgcgga     180
tttagctctg tcgaactccg aatttgtgat gtttgttgcg aatagagcta gtttcggaga     240
cttgtgatga acgtttccgt tggttcttga attcaataaa cgaatc                    286

<210> SEQ ID NO 17
<211> LENGTH: 2150
<212> TYPE: PRT
<213> ORGANISM: Arabidopsis thaliana

<400> SEQUENCE: 17
```

| | | | | | | | | | | | | | | | |
|---|---|---|---|---|---|---|---|---|---|---|---|---|---|---|---|
| Met | Glu | Leu | Lys | Thr | Phe | Lys | Asp | Leu | Asn | Asp | Ile | Ile | Gly | Asp | |
| 1 | | | | 5 | | | | | 10 | | | | | 15 | |
| Thr | Ser | Pro | Val | Ile | Asn | Thr | Gly | Asp | Gln | Pro | Asn | Pro | Leu | Arg | Thr |
| | | | 20 | | | | | 25 | | | | | 30 | | |
| Gln | Gln | Gln | Gln | Leu | Gln | Gln | Gln | Gln | Gln | Gln | Gln | Gln | Gln | | |
| | | 35 | | | | | 40 | | | | | 45 | | | |
| Gln | Gln | Gln | Gln | Gln | Gln | Gln | Gln | Gln | Gln | Gln | Gln | Gln | Gln | | |
| 50 | | | | | 55 | | | | | 60 | | | | | |
| Gln | Gln | His | His | Ile | Pro | Gln | Gln | Leu | Tyr | Gln | Lys | Gln | Gln | Gln | Gln |
| 65 | | | | | 70 | | | | | 75 | | | | | 80 |
| Gln | His | Ser | His | Ser | Tyr | Gly | Asn | His | Ser | Phe | Ile | His | Asn | Val | Ser |
| | | | | 85 | | | | | 90 | | | | | 95 | |
| Pro | Thr | Ser | Pro | Ser | Tyr | Asp | Ile | Asn | Asn | Asn | Asn | Asn | Asn | Asn | Asn |
| | | | 100 | | | | | 105 | | | | | 110 | | |
| Asn | Asn | Asn | Asn | Asn | Asn | Asn | Asn | Asn | Asn | Asn | Asn | Asn | Asn | Ser | |
| | | 115 | | | | | 120 | | | | | 125 | | | |
| Asn | Asn | Asn | Asn | Asn | Asn | Asn | Asn | Asn | Lys | Asn | Asn | Tyr | Asn | Asn | |
| 130 | | | | | 135 | | | | | 140 | | | | | |
| Asn | Tyr | Tyr | Tyr | Ser | Pro | Ile | Glu | Asn | Ser | Asn | Ile | Ser | Lys | Ser | Leu |
| 145 | | | | | 150 | | | | | 155 | | | | | 160 |
| Glu | Glu | Ser | Val | Leu | Asn | Gln | Phe | Pro | His | Asn | Phe | Asn | Leu | Asn | Ser |
| | | | | 165 | | | | | 170 | | | | | 175 | |
| Ser | Asn | Asn | Asn | Tyr | Leu | Asn | Asn | Ser | Ser | Ser | Leu | His | Asn | Ile | Asn |
| | | | 180 | | | | | 185 | | | | | 190 | | |
| Gln | Ser | Val | Asn | Ser | Leu | Ser | Asn | Asn | Asn | Asn | Asn | Gln | Thr | Asn | Gln |
| | | 195 | | | | | 200 | | | | | 205 | | | |
| Gln | Pro | Ile | Asn | Asn | Asn | Asn | Asn | Asn | Asn | Asn | Asn | Asn | Asn | | |
| 210 | | | | | 215 | | | | | 220 | | | | | |
| Asn | Ser | Asn | Asn | Ser | Asn | Asn | Ser | Asn | Asn | Asn | Asn | Gly | Asn | Asn | |
| 225 | | | | | 230 | | | | | 235 | | | | | 240 |
| Asn | Asn | Asn | Ile | Thr | Asp | Ser | Pro | Thr | Lys | Ser | Lys | Arg | His | Ser | Thr |
| | | | | 245 | | | | | 250 | | | | | 255 | |
| Tyr | Glu | Thr | Asn | Ile | Gly | Ser | His | Gln | Arg | Arg | Lys | Ser | Ile | Gln | Ser |
| | | | 260 | | | | | 265 | | | | | 270 | | |
| Leu | Ile | Ala | Asn | Ser | Ala | Ile | His | Ser | Phe | Ser | Lys | Leu | Lys | Asn | Lys |
| | | 275 | | | | | 280 | | | | | 285 | | | |

-continued

Pro Leu Ser Ser Ser Thr Pro Ser Thr Val Asn Thr Cys Gly Ala Val
    290                 295                 300

Asn Asn Asn Ser Asn Asn Asn Asn Asn Asn Asn Asn Ser Thr Gly
305                 310                 315                 320

Ser Leu Gly Ala Ile Pro Met Asp Arg Ser Phe Asp Gly Asn Ile Asn
                325                 330                 335

Thr Ile Thr Glu Glu Ser Thr Gly Gly Asn Asn Ser Pro Arg Ser Asn
            340                 345                 350

Cys Gly Ser Asn Cys Gly Ser Asn Gly Gly Ile Pro Leu Ser Pro Arg
            355                 360                 365

Asn Leu Ser Ser Leu Asn Ser Gly Val Asn Val Ser Pro Arg Asn Ile
    370                 375                 380

His Leu Asn Asn Leu Asn Asn Asn Ser Ser Asn Leu Pro Pro Leu Ser
385                 390                 395                 400

Pro Arg His Ile Asn Phe His Ile Asn Val Ser Asn Leu Asn Asn Asn
                405                 410                 415

Asn Asn Asn Asn Ile Asn Pro Asn Asn Asn Pro Asn Asn Ser Asn Asn
            420                 425                 430

Ser Asn Asn Asn Val Ser Pro Arg Asn Asn His Asn Ile Ser Pro
            435                 440                 445

Arg Gly Ser Asn Ile Ser Pro Arg Ser Asn Asn Gly Gly Ser Thr Thr
    450                 455                 460

Ile Ser Pro Arg Asn Ile Ser Asn Asn Asn Ile Ile Asn Asn Ile
465                 470                 475                 480

Asn Asn Asn Asn Ile Leu Thr Pro Pro Arg Asn Ser Pro Arg Leu Glu
                485                 490                 495

Asn Val Asn Pro Thr Asn Ser Pro Arg Leu Leu Ala Thr Ser Leu Asn
            500                 505                 510

Ser Thr Leu Pro Ile Val Ser Ser Leu Thr Ser Ser Asn Asn Asn Asn
            515                 520                 525

Gln Ser Asn Asn Asn Thr Asn Pro Ser Ile Asn Asn Asn Asn Gly Arg
    530                 535                 540

Asn Gly His Cys Ile Gln Thr Ile Ser Glu Glu Ile Leu Gly Asn Lys
545                 550                 555                 560

Pro Val Val Tyr Asn Asn Gly Asn Asn Asn Asn Asn Asn Thr Asn
                565                 570                 575

Asn Ser Thr Thr Ser Asn Asn Asn Ile Thr Thr Asn Asn Asn Asn
            580                 585                 590

Asn Asn Asn Asn Ile Asn Asn Asn Val Leu Ser Thr Pro Arg Lys Arg
    595                 600                 605

Thr Lys Gly Asn His Ser Lys Thr Asn Ser Leu Gln Asp Phe Glu Thr
610                 615                 620

Ser Ser Met Asn Gly Gly Asp Asp Ser Ile Ser Gly Ala Gly Ser Gly
625                 630                 635                 640

Gly Ser Leu Arg Arg Arg Asn Lys Asp Asp Asn Asp Glu Asn Asp Gly
                645                 650                 655

Asn Ser Asn Asn Thr Asn Ser Asn Asn Ser Asn Asn Asn Asn Asn
            660                 665                 670

Asn Asn Asn Ser Ser Asn Asn Asn Asn Asn Ser Asn Asn Asn Asn
            675                 680                 685

Asn Asn Asn Asn Asn Asn Asn Asn Asn Asn Asn Asn Asn Asn Asn
    690                 695                 700

Asn Asn Asn Asn Asn Asn Asn Asn Asn Asn Asn Asn Asn Asn Asn

```
                705                 710                 715                 720
Asn Asn Asn Asn Asn Asn Asn Tyr His Asn Gly Ala Thr Met Met Met
                    725                 730                 735
Ser His Asn His Gln Ser Ile Gly Met Ser Ser Ser Pro Lys Lys Asn
            740                 745                 750
Asn Phe Lys Pro Phe Ser Arg Asn Cys Ser Leu Met Gly Met Gly Arg
        755                 760                 765
Arg Ala Trp Ala Ile Ile Leu Gly Leu Phe Ile Val Gly Ser Ser Ile
    770                 775                 780
Ser Ile Leu Ala Thr Leu Val Leu Arg Tyr Ser Glu Glu Asn Ser Ile
785                 790                 795                 800
Ala Asp Asp Phe Ala Arg Val Ala Arg Asp Arg Phe Thr Met Leu Arg
            805                 810                 815
Ile Glu Phe Asn Asn Arg Leu Tyr Ile Thr Gln Thr Leu Ser Leu Leu
        820                 825                 830
Leu Ser Val Phe Pro Ser Thr Ser Glu Asp Gln Phe Val Pro Phe Ser
    835                 840                 845
Lys Leu Trp Ser Asp Asn Ala Glu Gly Leu Glu Gly Ile Met Trp Ala
    850                 855                 860
Pro Arg Val Ser Asn Leu Asp Arg Tyr Thr Trp Glu Ile Glu His Ser
865                 870                 875                 880
Val Lys Ile Arg Glu Ile Val Thr Asn Pro Asn Asn Ser Ser Asp Met
            885                 890                 895
Arg Asp Val Pro Ala Ala Ala Ser Asp Tyr Tyr Pro Ile Leu Phe
        900                 905                 910
Ser Glu Pro Gln Ser Ser Asn Asp His Phe Lys Gly Tyr Asn Ile Tyr
    915                 920                 925
Ser Asp Met Trp Arg Arg Pro Ser Leu Asn Lys Thr Arg Asp Thr Gly
    930                 935                 940
Glu Lys Val Ser Val Ala Ser Pro Tyr Ile Asn Lys Leu Ala Asn Val
945                 950                 955                 960
Pro Lys Asn Ser Arg Ser Asn Val Leu Leu Tyr Ile Tyr Gln Ala Val
            965                 970                 975
Tyr Thr Tyr Gly Lys Val Leu Ser Thr Val Glu Asp Arg Arg His Glu
        980                 985                 990
Val Ile Gly Phe Ala Ser Cys Arg  Phe Phe Ile Ser Arg  Met Val Ser
    995                 1000                 1005
Ala Ser  Leu Gln Arg Leu Thr  Glu Glu Asp Ser Leu  Asp Leu Tyr
    1010                 1015                 1020
Val Phe Asp Leu Asp Ser Thr  Pro Ile Gly Glu Leu  Ile Tyr Tyr
    1025                 1030                 1035
Arg Ala  Ser Asn Ala Gly Asn  Asp Asp Gly Ser Ser  Pro Thr Asn
    1040                 1045                 1050
Ile Met  Asn Gly Lys Met Leu  Glu Asp Arg Ser Asp  Met Ile Tyr
        1055                 1060                 1065
Tyr Asn  Thr Met Asn Val Gly  Gly Arg Asn Trp Met  Ile Ala Leu
    1070                 1075                 1080
Arg Pro  Ser Arg Lys Phe Thr  Asn Lys His Tyr Thr  Phe Tyr Pro
    1085                 1090                 1095
Tyr Ala  Ile Gly Gly Val Cys  Met Leu Leu Ser Ala  Leu Val Ser
    1100                 1105                 1110
Phe Trp  Phe Ala Val Asn Thr  Lys His Asn Ile Lys  Leu Ser Ala
    1115                 1120                 1125
```

-continued

```
Thr Asn Glu Asp Leu His Lys Glu Ile Tyr Asn Arg Lys Leu Ala
    1130                1135                1140

Glu Lys Ala Leu Ala Glu Ser Gln Glu Arg Leu Glu Leu Ala Met
1145                1150                1155

Glu Gly Ser Glu Asp Ala Val Trp Asp Trp Lys Val Asn Thr Gly
1160                1165                1170

Glu Leu His Ile Ser Ser Arg Trp Phe Gln Ile Leu Lys Ala His
1175                1180                1185

Asp Thr Ser Tyr Gln Ser Arg Thr Leu Tyr Glu Glu Leu Lys Ser
1190                1195                1200

Ser Ser Thr Asn Asn Leu Asn Phe Lys Gly Asp Ser Lys Asn Gly
1205                1210                1215

Gly Ser Asn Asn Gly Thr Phe Asn Leu Phe Lys Asn Gly Lys Val
1220                1225                1230

Asp Ser Ser Ser Pro Gln Ser Ile Thr Asn Val Asn Thr Thr Asn
1235                1240                1245

Gly Gly Gly Gly Gly Glu Leu Arg Lys Ser Asn Ser Gly Tyr Leu
1250                1255                1260

Tyr Asn Asp Glu Leu Phe Ser Pro Ile Ile Leu Glu Glu Met Val
1265                1270                1275

Ser Ser Pro Asn Thr His Gln Leu Ala Ile Trp Asn Met Lys Phe
1280                1285                1290

Leu Ala Glu Leu Ile His Pro Asp Asp Lys Gln Lys Phe Ile Ser
1295                1300                1305

Glu Ile Lys Lys Thr Ile Thr Arg Glu Thr Ala Ile Met Glu Ile
1310                1315                1320

Glu Cys Arg Met Arg Lys Lys Tyr Gly Gly Tyr Leu Tyr Ile Ile
1325                1330                1335

Met Arg Gly Lys Val Val Ser Asn Glu Thr Ser Phe Lys Asp Asn
1340                1345                1350

Ser Leu Arg Met Ala Gly Thr Leu Arg Asp Met Thr Ser Arg Lys
1355                1360                1365

Asp Met Gln Arg Leu Ile Leu Glu Lys Glu Ala Ala Glu Glu Ala
1370                1375                1380

Asn Lys Ala Lys Ser Ala Phe Val Ala Thr Val Ser His Glu Val
1385                1390                1395

Arg Thr Pro Leu Ser Gly Val Ile Gly Val Ser Asp Leu Leu Leu
1400                1405                1410

Glu Thr Asn Leu Ser Glu Glu Gln Arg Asp Tyr Val Gln Thr Ile
1415                1420                1425

Gln Lys Ser Ser Gln Ala Leu Leu Thr Ile Ile Asn Asp Ile Leu
1430                1435                1440

Asp Tyr Ser Lys Leu Glu Ser Arg Gln Leu Lys Met Glu Thr Leu
1445                1450                1455

Pro Phe Ser Ile Ile Glu Thr Cys Gln Ala Val Ile His Met Leu
1460                1465                1470

Ser Val Ala Ala Asn Asp Asp Val Asp Ile Leu Leu Arg Val Pro
1475                1480                1485

Pro Asn Val Pro Arg Ile Ile Phe Gly Asp Ala Met Arg Met Arg
1490                1495                1500

Gln Val Leu Leu Asn Arg Leu Ser Asn Ala Ile Lys Phe Thr Ser
1505                1510                1515
```

-continued

```
Arg Gly His Val Leu Thr Asp Ile Ser Val Asp Asp Ser Ile Pro
        1520                1525                1530

Pro Thr Asn Thr Glu Glu Glu Ile Ile His Leu Cys Ile Thr Ile
    1535                1540                1545

Glu Asp Thr Gly Ile Gly Ile Pro Gln Ser Leu Phe Asp Ser Ile
    1550                1555                1560

Phe Glu Pro Phe Ser Gln Ala Asp Asn Ser Thr Thr Arg Lys Tyr
    1565                1570                1575

Gly Gly Thr Gly Leu Gly Leu Ser Ile Thr Lys Arg Leu Ile Glu
    1580                1585                1590

Glu Val Met Gly Gly Thr Ile Gln Val Ser Ser Ile Val Gly Gln
    1595                1600                1605

Gly Ser Lys Phe Lys Cys Ile Ile Pro Phe Leu Leu Pro Asn Thr
    1610                1615                1620

Ser Pro Ser Asp Leu Asn Leu Ile Ser Pro Ser Ser Leu Pro Lys
    1625                1630                1635

Pro Phe Ile Asn Arg Ser Pro Lys Ser Thr Tyr Ser Phe Thr Asp
    1640                1645                1650

Lys Lys Asn Ser Val Pro Ser Thr Pro Ile Pro Ser Gly Asp Ile
    1655                1660                1665

Leu Ile Asn Lys Val Cys Leu Leu Ile Cys Arg Asp Thr Val Thr
    1670                1675                1680

Glu Leu Val Phe Lys Glu Gln Leu Glu Trp Leu Gly Met Ile Val
    1685                1690                1695

Lys Gln Val Pro Arg Asn Val Ile Asp Ser Ile Lys Asn Thr Ile
    1700                1705                1710

Leu Asn Asn Asn Asn Asn Asn Asn Asn Asn Asn Asn Asn Asn Asn
    1715                1720                1725

Asn Asn Ser Asn Asn Ser Ser Ser Ile Ile Ser Pro Ser Ser Leu
    1730                1735                1740

Asp Tyr Ser Asp Glu Asn Glu His Leu Asp Leu Val Leu Ile Asp
    1745                1750                1755

Leu Glu Ile Leu Thr Glu His Leu Lys Ile Pro Ser Asn Val Pro
    1760                1765                1770

Ile Ile Phe Ile Thr Pro Thr Lys Phe Asn Ile Ser Lys His Asn
    1775                1780                1785

Gly Ile Leu Asn Lys Trp Ile Thr Lys Ser Pro Asn Gln Arg Val
    1790                1795                1800

Glu Leu Ile Arg Arg Pro Ala Ile Thr Asp Lys Leu Ile Pro Ile
    1805                1810                1815

Ile Ser Lys Cys Ile Lys Ser Gln Val Gln Phe Thr Ser Gly Ser
    1820                1825                1830

Ser Gln Leu Gln Ser Gln Gln Ala Asn Leu Gln Gln Gln Leu Leu
    1835                1840                1845

His Gln Gln Leu Cys Asn Asn Gly Gln Thr Leu Asn Asn Asn Tyr
    1850                1855                1860

Asn Ser Gly Gly Ile Gly Gly Gly Gly Gly Gly Ser Asn
    1865                1870                1875

Thr Met Asn Gly Ser Ser Gly Asn Leu Ser Asn Asn Asn Asn Phe
    1880                1885                1890

Gly Gln Thr Pro Leu Ser Ser Gly Leu Val Leu Leu Val His Thr
    1895                1900                1905

Gly Arg Thr Pro Pro Leu Phe Asn Asn Asn Gly Asn Ser Ile Ile
```

```
                1910               1915               1920
Pro Pro Leu Glu Leu Ala Val Asp His His Gly Asn Gln Gln Gln
    1925               1930               1935

Gln Leu Tyr Gln Gln Gln Gln Gln Gln Asn Asn Ser Ser Gly
    1940               1945               1950

Asn Phe Gln Gln Phe Tyr Gln Gln Gln Asn Asn Asn Ser Asn Asn
    1955               1960               1965

Ser Phe Thr Pro Thr Leu Pro Asn Glu Asn Ser Asn Asn Ser Ile
    1970               1975               1980

Met Asn Asn Ser Leu Asn Asn Asn Asn Thr Thr Pro Ser Asn Val
    1985               1990               1995

Thr Pro Thr Leu Phe Thr Ser Ser Pro Leu Asp Leu Gln Gly Arg
    2000               2005               2010

Asp Thr Pro Val Leu Gln Pro Pro Ala Tyr Arg Lys Lys Ala Leu
    2015               2020               2025

Ile Val Glu Asp Asn Glu Leu Asn Arg Lys Val Leu Ala Gln Leu
    2030               2035               2040

Phe Lys Lys Ile Asp Trp Thr Ile Ser Phe Ala Glu Asn Gly Arg
    2045               2050               2055

Glu Ala Leu Lys Glu Ile Thr Gly Glu Arg Cys Phe Asp Ile Val
    2060               2065               2070

Phe Met Asp Cys Gln Met Pro Val Leu Asp Gly Phe Gln Thr Thr
    2075               2080               2085

Lys Ile Ile Arg Ser Lys Glu Arg Glu Asn Asn Trp Lys Arg Met
    2090               2095               2100

Asn Ile Val Ala Leu Ser Ala Gly Ser Ser Ser Phe Val Gln
    2105               2110               2115

Asp Cys Leu Asp Ser Gly Met Asp Ser Phe Met Gly Lys Pro Ile
    2120               2125               2130

Thr Leu Ala Thr Leu Lys Asp Ala Leu Ala Lys Trp Gly Gly Tyr
    2135               2140               2145

Asn Asn
    2150

<210> SEQ ID NO 18
<211> LENGTH: 1092
<212> TYPE: PRT
<213> ORGANISM: Arabidopsis thaliana

<400> SEQUENCE: 18

Met Ser Leu Phe His Val Leu Gly Phe Gly Val Lys Ile Gly His Leu
1               5                   10                  15

Phe Trp Met Leu Cys Cys Trp Phe Val Ser Trp Phe Val Asp Asn Gly
                20                  25                  30

Ile Glu Asp Lys Ser Gly Leu Leu Val Gly Ser Val Gly Asp Leu Glu
            35                  40                  45

Lys Thr Lys Met Thr Thr Leu Lys Lys Lys Asn Lys Met Trp Phe Trp
        50                  55                  60

Asn Lys Ile Ser Ser Ser Gly Leu Lys Ile Pro Ser Phe Ser Tyr Gln
65                  70                  75                  80

Phe Leu Gly Ser Val Lys Phe Asn Lys Ala Trp Trp Arg Lys Leu Val
                85                  90                  95

Val Val Trp Val Val Phe Trp Val Leu Val Ser Ile Trp Thr Phe Trp
                100                 105                 110
```

```
Tyr Phe Ser Ser Gln Ala Met Glu Lys Arg Lys Glu Thr Leu Ala Ser
        115                 120                 125

Met Cys Asp Glu Arg Ala Arg Met Leu Gln Asp Gln Phe Asn Val Ser
        130                 135                 140

Met Asn His Val Gln Ala Met Ser Ile Leu Ile Ser Thr Phe His His
145                 150                 155                 160

Gly Lys Ile Pro Ser Ala Ile Asp Gln Arg Thr Phe Ser Glu Tyr Thr
                165                 170                 175

Asp Arg Thr Ser Phe Glu Arg Pro Leu Thr Ser Gly Val Ala Tyr Ala
            180                 185                 190

Met Arg Val Leu His Ser Glu Arg Glu Phe Glu Arg Gln Gln Gly
        195                 200                 205

Trp Thr Ile Arg Lys Met Tyr Ser Leu Glu Gln Asn Pro Val His Lys
        210                 215                 220

Asp Asp Tyr Asp Leu Glu Ala Leu Glu Pro Ser Pro Val Gln Glu Glu
225                 230                 235                 240

Tyr Ala Pro Val Ile Phe Ala Gln Asp Thr Val Ser His Val Val Ser
                245                 250                 255

Leu Asp Met Leu Ser Gly Lys Glu Asp Arg Glu Asn Val Leu Arg Ala
            260                 265                 270

Arg Ser Ser Gly Lys Gly Val Leu Thr Ala Pro Phe Pro Leu Ile Lys
        275                 280                 285

Thr Asn Arg Leu Gly Val Ile Leu Thr Phe Ala Val Tyr Lys Arg Asp
        290                 295                 300

Leu Pro Ser Asn Ala Thr Pro Lys Glu Arg Ile Glu Ala Thr Asn Gly
305                 310                 315                 320

Tyr Leu Gly Gly Val Phe Asp Ile Glu Ser Leu Val Glu Asn Leu Leu
                325                 330                 335

Gln Gln Leu Ala Ser Lys Gln Thr Ile Leu Val Asn Val Tyr Asp Ile
            340                 345                 350

Thr Asn His Ser Gln Pro Ile Ser Met Tyr Gly Thr Asn Val Ser Ala
        355                 360                 365

Asp Gly Leu Glu Arg Val Ser Pro Leu Ile Phe Gly Asp Pro Leu Arg
        370                 375                 380

Lys His Glu Met Arg Cys Arg Tyr Leu Gln Leu Ala His Thr Tyr Val
385                 390                 395                 400

Cys Asn Phe Phe Leu Phe Ala Arg Ile Gln Val Leu Thr Phe Cys Cys
                405                 410                 415

Glu Leu Leu Pro Leu Cys Arg Phe Lys Gln Lys Pro Pro Trp Pro Val
            420                 425                 430

Leu Ser Met Val Thr Ser Phe Gly Ile Leu Val Ile Ala Leu Leu Val
        435                 440                 445

Ala His Ile Ile His Ala Thr Val Ser Arg Ile His Lys Val Glu Glu
450                 455                 460

Asp Cys Asp Lys Met Lys Gln Leu Lys Lys Ala Glu Ala Asp
465                 470                 475                 480

Val Ala Lys Ser Gln Phe Leu Ala Thr Val Ser His Glu Ile Arg Thr
                485                 490                 495

Pro Met Asn Gly Val Leu Gly Met Leu His Met Leu Met Asp Thr Glu
            500                 505                 510

Leu Asp Val Thr Gln Gln Asp Tyr Val Arg Thr Ala Gln Ala Ser Gly
        515                 520                 525

Lys Ala Leu Val Ser Leu Ile Asn Glu Val Leu Asp Gln Ala Lys Ile
```

```
            530                 535                 540
Glu Ser Gly Lys Leu Glu Leu Glu Glu Val Arg Phe Asp Leu Arg Gly
545                 550                 555                 560

Ile Leu Asp Asp Val Leu Ser Leu Phe Ser Ser Lys Ser Gln Gln Lys
                565                 570                 575

Gly Val Glu Leu Ala Val Tyr Ile Ser Asp Arg Val Pro Asp Met Leu
                580                 585                 590

Ile Gly Asp Pro Gly Arg Phe Arg Gln Ile Leu Thr Asn Leu Met Gly
            595                 600                 605

Asn Ser Ile Lys Phe Thr Glu Lys Gly His Ile Phe Val Thr Val His
610                 615                 620

Leu Val Asp Glu Leu Phe Glu Ser Ile Asp Gly Glu Thr Ala Ser Ser
625                 630                 635                 640

Pro Glu Ser Thr Leu Ser Gly Leu Pro Val Ala Asp Arg Gln Arg Ser
                645                 650                 655

Trp Glu Asn Phe Lys Ala Phe Ser Ser Asn Gly His Arg Ser Phe Glu
                660                 665                 670

Pro Ser Pro Asp Ile Asn Leu Ile Val Ser Val Glu Asp Thr Gly
                675                 680                 685

Val Gly Ile Pro Val Glu Ala Gln Ser Arg Ile Phe Thr Pro Phe Met
            690                 695                 700

Gln Val Gly Pro Ser Ile Ser Arg Thr His Gly Gly Thr Gly Ile Gly
705                 710                 715                 720

Leu Ser Ile Ser Lys Cys Leu Val Gly Leu Met Lys Gly Glu Ile Gly
                725                 730                 735

Phe Ser Ser Thr Pro Lys Val Gly Ser Thr Phe Thr Phe Thr Ala Val
                740                 745                 750

Phe Ser Asn Gly Met Gln Pro Ala Glu Arg Lys Asn Asp Asn Asn Gln
                755                 760                 765

Pro Ile Phe Ser Glu Phe Arg Gly Met Lys Ala Val Val Asp His
            770                 775                 780

Arg Pro Ala Arg Ala Lys Val Ser Trp Tyr His Phe Gln Arg Leu Gly
785                 790                 795                 800

Ile Arg Val Glu Val Val Pro Arg Val Glu Gln Ala Leu His Tyr Leu
                805                 810                 815

Lys Ile Gly Thr Thr Thr Val Asn Met Ile Leu Ile Glu Gln Glu Ile
                820                 825                 830

Trp Asn Arg Glu Ala Asp Asp Phe Ile Lys Lys Leu Gln Lys Asp Pro
                835                 840                 845

Leu Phe Leu Ser Pro Lys Leu Ile Leu Leu Ala Asn Ser Val Glu Ser
            850                 855                 860

Ser Ile Ser Glu Ala Leu Cys Thr Gly Ile Asp Pro Pro Ile Val Ile
865                 870                 875                 880

Val Lys Pro Leu Arg Ala Ser Met Leu Ala Ala Thr Leu Gln Arg Gly
                885                 890                 895

Leu Gly Ile Gly Ile Arg Glu Pro Pro Gln His Lys Gly Pro Pro Ala
                900                 905                 910

Leu Ile Leu Arg Asn Leu Leu Gly Arg Lys Ile Leu Ile Val Asp
            915                 920                 925

Asp Asn Asn Val Asn Leu Arg Val Ala Ala Gly Ala Leu Lys Lys Tyr
            930                 935                 940

Gly Ala Asp Val Val Cys Ala Glu Ser Gly Ile Lys Ala Ile Ser Leu
945                 950                 955                 960
```

Leu Lys Pro Pro His Glu Phe Asp Ala Cys Phe Met Asp Ile Gln Met
                965                 970                 975

Pro Glu Met Asp Gly Phe Glu Ala Thr Arg Arg Ile Arg Asp Met Glu
            980                 985                 990

Glu Glu Met Asn Lys Arg Ile Lys Asn Gly Glu Ala Leu Ile Val Glu
        995                 1000                1005

Asn Gly Asn Lys Thr Ser Trp His Leu Pro Val Leu Ala Met Thr
    1010                1015                1020

Ala Asp Val Ile Gln Ala Thr His Glu Glu Cys Leu Lys Cys Gly
    1025                1030                1035

Met Asp Gly Tyr Arg Ile Ile Arg Gly Asp Gly Ala Gly Arg Arg
    1040                1045                1050

Thr Ala Lys Glu Thr Gln Lys Leu Val Ser Pro Met His Leu Glu
    1055                1060                1065

Val Val Glu Lys Gln Ile Asp Asp Cys Lys Lys Ser Val Tyr Arg
    1070                1075                1080

Lys Ala Gly Val Thr Arg Pro Arg Thr
    1085            1090

<210> SEQ ID NO 19
<211> LENGTH: 1173
<212> TYPE: PRT
<213> ORGANISM: Arabidopsis thaliana

<400> SEQUENCE: 19

Met Ser Ile Thr Cys Glu Leu Leu Asn Leu Thr Ser Lys Lys Ala Lys
1               5                   10                  15

Lys Ser Ser Ser Ser Asp Lys Lys Trp Leu Lys Pro Leu Phe Phe
            20                  25                  30

Leu Ile Leu Cys Gly Ser Leu Val Ile Val Leu Val Met Phe Leu Arg
            35                  40                  45

Leu Gly Arg Ser Gln Lys Glu Glu Thr Asp Ser Cys Asn Gly Glu Glu
        50                  55                  60

Lys Val Leu Tyr Arg His Gln Asn Val Thr Arg Ser Glu Ile His Asp
65                  70                  75                  80

Leu Val Ser Leu Phe Ser Asp Ser Asp Gln Val Thr Ser Phe Glu Cys
                85                  90                  95

His Lys Glu Ser Ser Pro Gly Met Trp Thr Asn Tyr Gly Ile Thr Cys
            100                 105                 110

Ser Leu Ser Val Arg Ser Asp Lys Gln Glu Thr Arg Gly Leu Pro Trp
        115                 120                 125

Asn Leu Gly Leu Gly His Ser Ile Ser Ser Thr Ser Cys Met Cys Gly
    130                 135                 140

Asn Leu Glu Pro Ile Leu Gln Gln Pro Glu Asn Leu Glu Glu Asn
145                 150                 155                 160

His Glu Glu Gly Leu Glu Gln Gly Leu Ser Ser Tyr Leu Arg Asn Ala
                165                 170                 175

Trp Trp Cys Leu Ile Leu Gly Val Leu Val Cys His Lys Ile Tyr Val
            180                 185                 190

Ser His Ser Lys Ala Arg Gly Glu Arg Lys Glu Lys Val His Leu Gln
        195                 200                 205

Glu Ala Leu Ala Pro Lys Lys Gln Gln Gln Arg Ala Gln Thr Ser Ser
    210                 215                 220

Arg Gly Ala Gly Arg Trp Arg Lys Asn Ile Leu Leu Leu Gly Ile Leu

```
             225                 230                 235                 240
Gly Gly Val Ser Phe Ser Val Trp Trp Phe Trp Asp Thr Asn Glu Glu
                245                 250                 255
Ile Ile Met Lys Arg Arg Glu Thr Leu Ala Asn Met Cys Asp Glu Arg
            260                 265                 270
Ala Arg Val Leu Gln Asp Gln Phe Asn Val Ser Leu Asn His Val His
        275                 280                 285
Ala Leu Ser Ile Leu Val Ser Thr Phe His His Gly Lys Ile Pro Ser
    290                 295                 300
Ala Ile Asp Gln Arg Thr Phe Glu Glu Tyr Thr Glu Arg Thr Asn Phe
305                 310                 315                 320
Glu Arg Pro Leu Thr Ser Gly Val Ala Tyr Ala Leu Lys Val Pro His
                325                 330                 335
Ser Glu Arg Glu Lys Phe Glu Lys Glu His Gly Trp Ala Ile Lys Lys
            340                 345                 350
Met Glu Thr Glu Asp Gln Thr Val Val Gln Asp Cys Val Pro Glu Asn
        355                 360                 365
Phe Asp Pro Ala Pro Ile Gln Asp Glu Tyr Ala Pro Val Ile Phe Ala
    370                 375                 380
Gln Glu Thr Val Ser His Ile Val Ser Val Asp Met Met Ser Gly Glu
385                 390                 395                 400
Glu Asp Arg Glu Asn Ile Leu Arg Ala Arg Ala Ser Gly Lys Gly Val
                405                 410                 415
Leu Thr Ser Pro Phe Lys Leu Leu Lys Ser Asn His Leu Gly Val Val
            420                 425                 430
Leu Thr Phe Ala Val Tyr Asp Thr Ser Leu Pro Pro Asp Ala Thr Glu
        435                 440                 445
Glu Gln Arg Val Glu Ala Thr Ile Gly Tyr Leu Gly Ala Ser Tyr Asp
    450                 455                 460
Met Pro Ser Leu Val Glu Lys Leu Leu His Gln Leu Ala Ser Lys Gln
465                 470                 475                 480
Thr Ile Ala Val Asp Val Tyr Asp Thr Thr Asn Thr Ser Gly Leu Ile
                485                 490                 495
Lys Met Tyr Gly Ser Glu Ile Gly Asp Ile Ser Glu Gln His Ile Ser
            500                 505                 510
Ser Leu Asp Phe Gly Asp Pro Ser Arg Asn His Glu Met His Cys Arg
        515                 520                 525
Phe Lys His Lys Leu Pro Ile Pro Trp Thr Ala Ile Thr Pro Ser Ile
    530                 535                 540
Leu Val Leu Val Ile Thr Phe Leu Val Gly Tyr Ile Leu Tyr Glu Ala
545                 550                 555                 560
Ile Asn Arg Ile Ala Thr Val Glu Glu Asp Cys Gln Lys Met Arg Glu
                565                 570                 575
Leu Lys Ala Arg Ala Glu Ala Ala Asp Ile Ala Lys Ser Gln Phe Leu
            580                 585                 590
Ala Thr Val Ser His Glu Ile Arg Thr Pro Met Asn Gly Val Leu Gly
        595                 600                 605
Met Leu Lys Met Leu Met Asp Thr Asp Leu Asp Ala Lys Gln Met Asp
    610                 615                 620
Tyr Ala Gln Thr Ala His Gly Ser Gly Lys Asp Leu Thr Ser Leu Ile
625                 630                 635                 640
Asn Glu Val Leu Asp Gln Ala Lys Ile Glu Ser Gly Arg Leu Glu Leu
                645                 650                 655
```

-continued

Glu Asn Val Pro Phe Asp Met Arg Phe Ile Leu Asp Asn Val Ser Ser
         660                 665                 670

Leu Leu Ser Gly Lys Ala Asn Glu Lys Gly Ile Glu Leu Ala Val Tyr
         675                 680                 685

Val Ser Ser Gln Val Pro Asp Val Val Gly Asp Pro Ser Arg Phe
         690                 695                 700

Arg Gln Ile Ile Thr Asn Leu Val Gly Asn Ser Ile Lys Glu Arg Gly
705                 710                 715                 720

His Ile Phe Ile Ser Val His Leu Ala Asp Glu Val Lys Glu Pro Leu
                 725                 730                 735

Thr Ile Glu Asp Ala Val Leu Lys Gln Arg Leu Ala Leu Gly Cys Ser
         740                 745                 750

Glu Ser Gly Glu Thr Val Ser Gly Phe Pro Ala Val Asn Ala Trp Gly
         755                 760                 765

Ser Trp Lys Asn Phe Lys Thr Cys Tyr Ser Thr Glu Ser Gln Asn Ser
770                 775                 780

Asp Gln Ile Lys Leu Leu Val Thr Val Glu Asp Thr Gly Val Gly Ile
785                 790                 795                 800

Pro Val Asp Ala Gln Gly Arg Ile Phe Thr Pro Phe Met Gln Ala Asp
         805                 810                 815

Ser Ser Thr Ser Arg Thr Tyr Gly Gly Thr Gly Ile Gly Leu Ser Ile
         820                 825                 830

Ser Lys Arg Leu Val Glu Leu Met Gln Gly Glu Met Gly Phe Val Ser
         835                 840                 845

Glu Pro Gly Ile Gly Ser Thr Phe Ser Phe Thr Gly Val Phe Gly Lys
         850                 855                 860

Ala Glu Thr Asn Thr Ser Ile Thr Lys Leu Glu Arg Phe Asp Leu Ala
865                 870                 875                 880

Ile Gln Glu Phe Thr Gly Leu Arg Ala Leu Val Ile Asp Asn Arg Asn
                 885                 890                 895

Ile Arg Ala Glu Val Thr Arg Tyr Glu Leu Arg Arg Leu Gly Ile Ser
                 900                 905                 910

Ala Asp Ile Val Ser Ser Leu Arg Met Ala Cys Thr Cys Cys Ile Ser
         915                 920                 925

Lys Leu Glu Asn Leu Ala Met Ile Leu Ile Asp Lys Asp Ala Trp Asn
         930                 935                 940

Lys Glu Glu Phe Ser Val Leu Asp Glu Leu Phe Thr Arg Ser Lys Val
945                 950                 955                 960

Thr Phe Thr Arg Val Pro Lys Ile Phe Leu Leu Ala Thr Ser Ala Thr
                 965                 970                 975

Leu Thr Glu Arg Ser Glu Met Lys Ser Thr Gly Leu Ile Asp Glu Val
         980                 985                 990

Val Ile Lys Pro Leu Arg Met Ser Val Leu Ile Cys Cys Leu Gln Glu
         995                 1000                1005

Thr Leu Val Asn Gly Lys Lys Arg Gln Pro Asn Arg Gln Arg Arg
     1010                1015                1020

Asn Leu Gly His Leu Leu Arg Glu Lys Gln Ile Leu Val Val Asp
     1025                1030                1035

Asp Asn Leu Val Asn Arg Arg Val Ala Glu Gly Ala Leu Lys Lys
     1040                1045                1050

Tyr Gly Ala Ile Val Thr Cys Val Glu Ser Gly Lys Ala Ala Leu
     1055                1060                1065

```
Ala Met Leu Lys Pro Pro His Asn Phe Asp Ala Cys Phe Met Asp
    1070                1075                1080

Leu Gln Met Pro Glu Met Asp Gly Phe Glu Ala Thr Arg Arg Val
    1085                1090                1095

Arg Glu Leu Glu Arg Glu Ile Asn Lys Lys Ile Ala Ser Gly Glu
    1100                1105                1110

Val Ser Ala Glu Met Phe Cys Lys Phe Ser Ser Trp His Val Pro
    1115                1120                1125

Ile Leu Ala Met Thr Ala Asp Val Ile Gln Ala Thr His Glu Glu
    1130                1135                1140

Cys Met Lys Cys Gly Met Asp Gly Tyr Val Ser Lys Pro Phe Glu
    1145                1150                1155

Glu Glu Val Leu Tyr Thr Ala Val Ala Arg Phe Phe Glu Pro Cys
    1160                1165                1170

<210> SEQ ID NO 20
<211> LENGTH: 85
<212> TYPE: PRT
<213> ORGANISM: Arabidopsis thaliana

<400> SEQUENCE: 20

His Arg Arg Arg Pro Ser Glu Pro Gln Ser Lys Gln His Glu Ile Lys
1               5                   10                  15

Pro Arg Asn Arg Gly Thr Asp Leu Ala Gly His His Val Glu Ala Leu
            20                  25                  30

Asp Val Gly His Gly Leu Leu Gly Val Asp Asp Arg Arg Val Leu Val
        35                  40                  45

Leu Arg Arg Gly Gly Leu Val Leu His Gly Leu Asp Asp Pro Ala Leu
    50                  55                  60

Leu Pro Leu Glu Gly Leu Pro Val Gly Val His His Pro Leu Arg Val
65                  70                  75                  80

Arg His Pro Ala Gln
                85

<210> SEQ ID NO 21
<211> LENGTH: 43
<212> TYPE: DNA
<213> ORGANISM: Arabidopsis thaliana

<400> SEQUENCE: 21
caaaatgtgt gtgtgtcggc cgtaccaaag tccacacgat tcc                 43

<210> SEQ ID NO 22
<211> LENGTH: 44
<212> TYPE: DNA
<213> ORGANISM: Arabidopsis thaliana

<400> SEQUENCE: 22
actgagaacc gaagaaatct gggagtcgaa aaatgccgaa atac                44

<210> SEQ ID NO 23
<211> LENGTH: 3170
<212> TYPE: DNA
<213> ORGANISM: Arabidopsis thaliana

<400> SEQUENCE: 23
tgaactgggc actcaacaat catcaagaag aagaagaaga gccacgaaga attgaaattt    60
ctgaggccga gtcactagaa aacttgaaaa gcagcgattt ttatcaactg ggtggtggtg   120
```

-continued

```
gtgctctgaa ttcgtcagaa aagccgagaa agatcgattt ttggcgttcg gggttgatgg      180
gttttgcgaa gatgcagcag cagcaacagc ttcagcattc agtggcggtg aagatgaaca      240
ataataataa taacgatcta atgggtaata aaaaagggtc aactttcata caagaacatc      300
gagcattgtt accaaaagct ttgattctgt ggatcatcat tgttgggttt ataagcagtg      360
ggatttatca gtggatggat gatgctaata agattagaag ggaagaggtt ttggtcagca      420
tgtgtgatca aagagctaga atgttgcagg atcaatttag tgttagtgtt aatcatgttc      480
atgctttggc tattctcgtc tccacttttc attaccacaa gaacccttct gcaattgatc      540
aggagacatt tgcggagtac acggcaagaa cagcatttga gagaccgttg ctaagtggag      600
tggcttatgc tgaaaaagtt gtgaattttg agagggagat gtttgagcgg cagcacaatt      660
gggttataaa gacaatggat agaggagagc cttcaccggt tagggatgag tatgctcctg      720
ttatattctc tcaagatagt gtctcttacc ttgagtcact cgatatgatg tcaggcgagg      780
aggatcgtga gaatattttg cgagctagag aaaccggaaa agctgtcttg actagccctt      840
ttaggttgtt ggaaactcac catctcggag ttgtgttgac attccctgtc tacaagtctt      900
ctcttcctga aaatccgact gtcgaagagc gtattgcagc cactgcaggg taccttggtg      960
gtgcgtttga tgtggagtct ctagtcgaga atttacttgg tcagcttgct ggtaaccaag     1020
caatagttgt gcatgtgtat gatatcacca atgcatcaga tccacttgtc atgtatggta     1080
atcaagatga agaagccgac agatctctct ctcatgagag caagctcgat tttggagacc     1140
ccttcaggaa acataagatg atatgcaggt accaccaaaa ggcaccaata ccgttgaatg     1200
tgctcacaac tgtgccattg ttctttgcga ttggtttctt ggtgggttat atactgtatg     1260
gtgcagctat gcacatagta aaagtcgaag atgatttcca tgaaatgcaa gagcttaaag     1320
ttcgagcaga agctgctgat gtcgctaaat cgcagtttct tgctaccgtg tctcacgaga     1380
tcaggacacc aatgaatggc attctcggaa tgcttgctat gctcctagat acagaactaa     1440
gctcgacaca gagagattac gctcaaaccg ctcaagtatg tggtaaagct ttgattgcat     1500
tgataaatga ggttcttgat cgcgccaaga ttgaagctgg aaagctggag ttggaatcag     1560
taccatttga tatccgttca atattggatg atgtcctttc tctattctct gaggagtcaa     1620
ggaacaaaag cattgagctc gcggttttcg tttcagacaa agtaccagag atagtcaaag     1680
gagattcagg gagatttaga cagataatca taaaccttgt tggaaattcg gttaaattca     1740
cagagaaagg acatatcttt gttaaagtcc atcttgcgga acaatcaaaa gatgaatctg     1800
aaccgaaaaa tgcattgaat ggtggagtgt ctgaagaaat gatcgttgtt tccaaacagt     1860
caagttacaa cacattgagc ggttacgaag ctgctgatgg tcggaatagc tgggattcat     1920
tcaagcattt ggtctctgag gagcagtcat tatcggagtt tgatatttct agcaatgtta     1980
ggcttatggt ttcaatcgaa gacacgggta ttggaatccc tttagttgcg caaggccgtg     2040
tgtttatgcc gttatgcaa gcagatagct cgacttcaag aaactatgga ggtactggta     2100
ttggtttgag tataagcaag tgtcttgttg aacttatgcg tggtcagata aatttcataa     2160
gccggcctca tattgaagc acgttctggt tcacggctgt tttagagaaa tgcgataaat     2220
gcagtgcgat taaccatatg aagaaaccta atgtggaaca cttgccttct acttttaaag     2280
gaatgaaagc tatagttgtt gatgctaagc ctgttagagc tgctgtgact agataccata     2340
tgaaaagact cggaatcaat gttgatgtcg tgacaagtct caaaaccgct gttgttgcag     2400
ctgctgcgtt tgaagaaaac ggttctcctc tcccaacaaa accgcaactt gatatgatct     2460
tagtagagaa agattcatgg atttcaactg aagataatga ctcagagatt cgtttattga     2520
```

-continued

```
attcaagaac caacggaaac gttcatcaca agtctccgaa actagctcta ttcgcaacaa    2580
acatcacaaa ttcggagttc gacagagcta atccgcagg atttgcagat acgtaataa     2640 tgaaaccgtt aagagcaagc atgattgggg cgtgtctgca acaagttctc gagctgagaa    2700
aaacaagaca acaacatcca gaaggatcat cacccgcaac tctcaagagc ttgcttacag    2760
ggaagaagat tcttgtggtt gatgataata tagttaacag gagagtagct gcaggagctc    2820
tcaagaaatt tggagcagaa gtggtttgtg cagagagtgg tcaagttgct ttgggtttgc    2880
ttcagattcc acacactttc gatgcttgct tcatggatat tcaaatgcca cagatggacg    2940
gatttgaagc aactcgtcag ataagaatga tggagaagga aactaaagag aagacaaatc    3000
tcgaatggca tttaccgatt ctagcgatga ctgcggatgt gatacacgcg acctacgagg    3060
aatgtctgaa aagtgggatg gatggttacg tctccaaacc ttttgaagaa gagaatctct    3120
ataaatccgt tgccaaatca ttcaaaccta atcctatctc accttcgtcg              3170
```

<210> SEQ ID NO 24
<211> LENGTH: 1057
<212> TYPE: PRT
<213> ORGANISM: Arabidopsis thaliana

<400> SEQUENCE: 24

```
Met Asn Trp Ala Leu Asn Asn His Gln Glu Glu Glu Glu Pro Arg
1               5                   10                  15

Arg Ile Glu Ile Ser Glu Ser Glu Ser Leu Glu Asn Leu Lys Ser Ser
            20                  25                  30

Asp Phe Tyr Gln Leu Gly Gly Gly Gly Ala Leu Asn Ser Ser Glu Lys
        35                  40                  45

Pro Arg Lys Ile Asp Phe Trp Arg Ser Gly Leu Met Gly Phe Ala Lys
    50                  55                  60

Met Gln Gln Gln Gln Leu Gln His Ser Val Ala Val Lys Met Asn
65                  70                  75                  80

Asn Asn Asn Asn Asp Leu Met Gly Asn Lys Lys Gly Ser Thr Phe
                85                  90                  95

Ile Gln Glu His Arg Ala Leu Leu Pro Lys Ala Leu Ile Leu Trp Ile
            100                 105                 110

Ile Ile Val Gly Phe Ile Ser Ser Gly Ile Tyr Gln Trp Met Asp Asp
        115                 120                 125

Ala Asn Lys Ile Arg Arg Glu Glu Val Leu Val Ser Met Cys Asp Gln
    130                 135                 140

Arg Ala Arg Met Leu Gln Asp Gln Phe Ser Val Ser Val Asn His Val
145                 150                 155                 160

His Ala Leu Ala Ile Leu Val Ser Thr Phe His Tyr His Lys Asn Pro
                165                 170                 175

Ser Ala Ile Asp Gln Glu Thr Phe Ala Glu Tyr Thr Ala Arg Thr Ala
            180                 185                 190

Phe Glu Arg Pro Leu Leu Ser Gly Val Ala Tyr Ala Glu Lys Val Val
        195                 200                 205

Asn Phe Glu Arg Glu Met Phe Glu Arg Gln His Asn Trp Val Ile Lys
    210                 215                 220

Thr Met Asp Arg Gly Glu Pro Ser Pro Val Arg Asp Glu Tyr Ala Pro
225                 230                 235                 240

Val Ile Phe Ser Gln Asp Ser Val Ser Tyr Leu Glu Ser Leu Asp Met
                245                 250                 255
```

```
Met Ser Gly Glu Glu Asp Arg Glu Asn Ile Leu Arg Ala Arg Glu Thr
            260                 265                 270
Gly Lys Ala Val Leu Thr Ser Pro Phe Arg Leu Leu Glu Thr His His
        275                 280                 285
Leu Gly Val Val Leu Thr Phe Pro Val Tyr Lys Ser Ser Leu Pro Glu
    290                 295                 300
Asn Pro Thr Val Glu Glu Arg Ile Ala Thr Ala Gly Tyr Leu Gly
305                 310                 315                 320
Gly Ala Phe Asp Val Glu Ser Leu Val Glu Asn Leu Leu Gly Gln Leu
                325                 330                 335
Ala Gly Asn Gln Ala Ile Val Val His Val Tyr Asp Ile Thr Asn Ala
            340                 345                 350
Ser Asp Pro Leu Val Met Tyr Gly Asn Gln Asp Glu Glu Ala Asp Arg
        355                 360                 365
Ser Leu Ser His Glu Ser Lys Leu Asp Phe Gly Asp Pro Phe Arg Lys
    370                 375                 380
His Lys Met Ile Cys Arg Tyr His Gln Lys Ala Pro Ile Pro Leu Asn
385                 390                 395                 400
Val Leu Thr Thr Val Pro Leu Phe Phe Ala Ile Gly Phe Leu Val Gly
                405                 410                 415
Tyr Ile Leu Tyr Gly Ala Ala Met His Ile Val Lys Val Glu Asp Asp
            420                 425                 430
Phe His Glu Met Gln Glu Leu Lys Val Arg Ala Glu Ala Ala Asp Val
        435                 440                 445
Ala Lys Ser Gln Phe Leu Ala Thr Val Ser His Glu Ile Arg Thr Pro
    450                 455                 460
Met Asn Gly Ile Leu Gly Met Leu Ala Met Leu Leu Asp Thr Glu Leu
465                 470                 475                 480
Ser Ser Thr Gln Arg Asp Tyr Ala Gln Thr Ala Gln Val Cys Gly Lys
                485                 490                 495
Ala Leu Ile Ala Leu Ile Asn Glu Val Leu Asp Arg Ala Lys Ile Glu
            500                 505                 510
Ala Gly Lys Leu Glu Leu Glu Ser Val Pro Phe Asp Ile Arg Ser Ile
        515                 520                 525
Leu Asp Asp Val Leu Ser Leu Phe Ser Glu Glu Ser Arg Asn Lys Ser
    530                 535                 540
Ile Glu Leu Ala Val Phe Val Ser Asp Lys Val Pro Glu Ile Val Lys
545                 550                 555                 560
Gly Asp Ser Gly Arg Phe Arg Gln Ile Ile Asn Leu Val Gly Asn
                565                 570                 575
Ser Val Lys Phe Thr Glu Lys His Ile Phe Val Lys Val His Leu
            580                 585                 590
Ala Glu Gln Ser Lys Asp Glu Ser Pro Lys Asn Ala Leu Asn Gly
        595                 600                 605
Gly Val Ser Glu Glu Met Ile Val Ser Lys Gln Ser Ser Tyr Asn
    610                 615                 620
Thr Leu Ser Gly Tyr Glu Ala Ala Asp Gly Arg Asn Ser Trp Asp Ser
625                 630                 635                 640
Phe Lys His Leu Val Ser Glu Glu Gln Ser Leu Ser Glu Phe Asp Ile
                645                 650                 655
Ser Ser Asn Val Arg Leu Met Val Ser Ile Glu Asp Thr Gly Ile Gly
            660                 665                 670
Ile Pro Leu Val Ala Gln Gly Arg Val Phe Met Pro Phe Met Gln Ala
```

```
                675                 680                 685
Asp Ser Ser Thr Ser Arg Asn Tyr Gly Gly Thr Gly Ile Gly Leu Ser
            690                 695                 700

Ile Ser Lys Cys Leu Val Glu Leu Met Arg Gly Gln Ile Asn Phe Ile
705                 710                 715                 720

Ser Arg Pro His Ile Gly Ser Thr Phe Trp Phe Thr Ala Val Leu Glu
                725                 730                 735

Lys Cys Asp Lys Cys Ser Ala Ile Asn His Met Lys Lys Pro Asn Val
            740                 745                 750

Glu His Leu Pro Ser Thr Phe Lys Gly Met Lys Ala Ile Val Val Asp
        755                 760                 765

Ala Lys Pro Val Arg Ala Ala Val Thr Arg Tyr His Met Lys Arg Leu
770                 775                 780

Gly Ile Asn Val Asp Val Val Thr Ser Leu Lys Thr Ala Val Val Ala
785                 790                 795                 800

Ala Ala Ala Phe Glu Arg Asn Gly Ser Pro Leu Pro Thr Lys Pro Gln
                805                 810                 815

Leu Asp Met Ile Leu Val Glu Lys Asp Ser Trp Ile Ser Thr Glu Asp
            820                 825                 830

Asn Asp Ser Glu Ile Arg Leu Leu Asn Ser Arg Thr Asn Gly Asn Val
        835                 840                 845

His His Lys Ser Pro Lys Leu Ala Leu Phe Ala Thr Asn Ile Thr Asn
850                 855                 860

Ser Glu Phe Asp Arg Ala Lys Ser Ala Gly Phe Ala Asp Thr Val Ile
865                 870                 875                 880

Met Lys Pro Leu Arg Ala Ser Met Ile Gly Ala Cys Leu Gln Gln Val
                885                 890                 895

Leu Glu Leu Arg Lys Thr Arg Gln Gln His Pro Glu Gly Ser Ser Pro
            900                 905                 910

Ala Thr Leu Lys Ser Leu Leu Thr Gly Lys Lys Ile Leu Val Val Asp
        915                 920                 925

Asp Asn Ile Val Asn Arg Arg Val Ala Ala Gly Ala Leu Lys Lys Phe
930                 935                 940

Gly Ala Glu Val Val Cys Ala Glu Ser Gly Gln Val Ala Leu Gly Leu
945                 950                 955                 960

Leu Gln Ile Pro His Thr Phe Asp Ala Cys Phe Met Asp Ile Gln Met
                965                 970                 975

Pro Gln Met Asp Gly Phe Glu Ala Thr Arg Gln Ile Arg Met Met Glu
            980                 985                 990

Lys Glu Thr Lys Glu Lys Thr Asn Leu Glu Trp His Leu Pro Ile Leu
        995                 1000                1005

Ala Met Thr Ala Asp Val Ile His Ala Thr Tyr Glu Glu Cys Leu
1010                1015                1020

Lys Ser Gly Met Asp Gly Tyr Val Ser Lys Pro Phe Glu Glu Glu
    1025                1030                1035

Asn Leu Tyr Lys Ser Val Ala Lys Ser Phe Lys Pro Asn Pro Ile
    1040                1045                1050

Ser Pro Ser Ser
    1055
```

<210> SEQ ID NO 25
<211> LENGTH: 305
<212> TYPE: DNA
<213> ORGANISM: Arabidopsis thaliana -continued

<400> SEQUENCE: 25

```
agatgctggt ggtggatgac aatgcagtta atagaagagt agcagaaggt gctctaaaga    60
agtatggagc aattgtgacc tgtgtagaga gtggcaaggc tgctttagcg atgcttaagc   120
caccccacaa ctttgatgct tgctttatgg atctccagat gccagaaatg gatgggtttg   180
aagcaacaag gcgaatccgc agtttagaaa gtgaggctaa tgaggaagtt gcatcaagag   240
aaatgtttgg gaatgtggct tattggcaca ccaatatt agctatgacc gccgagtcat    300
ccagt                                                              305
```

<210> SEQ ID NO 26
<211> LENGTH: 314
<212> TYPE: DNA
<213> ORGANISM: Arabidopsis thaliana

<400> SEQUENCE: 26

```
agatgcttgt ggtggatgac aatagggtta accgcagagt tgctgaaggt gcactaaaga    60
agtttggagc tgatgtagag tgtgctgaga gtggcaaagc tgcactggcg ctgcttcaac   120
taccacataa tttcgatgcc tgcttcatgg acattcagat gccagaaatg gatgggtttg   180
aggcaacccg tcaaatacgc gtaatggaga gcaaggaaaa tgagcaaata aatggtggag   240
ccacagatga aggagctatt agaaagagag agtggcatgt gccaatatta gccatgaccg   300
ccgacgtcat cgta                                                    314
```

<210> SEQ ID NO 27
<211> LENGTH: 42
<212> TYPE: DNA
<213> ORGANISM: Arabidopsis thaliana

<400> SEQUENCE: 27

```
tatccatcta actgtgatgc cactttgaca tcaaaacgta cc                      42
```

<210> SEQ ID NO 28
<211> LENGTH: 40
<212> TYPE: DNA
<213> ORGANISM: Arabidopsis thaliana

<400> SEQUENCE: 28

```
gtttaagcaa gcgagtatgc ttcgattcag ttcggtttag                         40
```

<210> SEQ ID NO 29
<211> LENGTH: 100
<212> TYPE: PRT
<213> ORGANISM: Arabidopsis thaliana

<400> SEQUENCE: 29

```
Met Leu Val Val Asp Asp Asn Ala Val Asn Arg Arg Val Ala Glu Gly
  1               5                  10                  15
Ala Leu Lys Lys Tyr Gly Ala Ile Val Thr Cys Val Glu Ser Gly Lys
             20                  25                  30
Ala Ala Leu Ala Met Leu Lys Pro Pro His Asn Phe Asp Ala Cys Phe
         35                  40                  45
Met Asp Leu Gln Met Pro Glu Met Asp Gly Phe Glu Ala Thr Arg Arg
     50                  55                  60
Ile Arg Ser Leu Glu Ser Glu Ala Asn Glu Glu Val Ala Ser Arg Glu
 65                  70                  75                  80
Met Phe Gly Asn Val Ala Tyr Trp His Thr Pro Ile Leu Ala Met Thr
```

Ala Glu Ser Ser
        100

<210> SEQ ID NO 30
<211> LENGTH: 104
<212> TYPE: PRT
<213> ORGANISM: Arabidopsis thaliana

<400> SEQUENCE: 30

Met Leu Val Val Asp Asp Asn Arg Val Asn Arg Arg Val Ala Glu Gly
1               5                   10                  15

Ala Leu Lys Lys Phe Gly Ala Asp Val Glu Cys Ala Glu Ser Gly Lys
            20                  25                  30

Ala Ala Leu Ala Leu Leu Gln Leu Pro His Asn Phe Asp Ala Cys Phe
        35                  40                  45

Met Asp Ile Gln Met Pro Glu Met Asp Gly Phe Glu Ala Thr Arg Gln
    50                  55                  60

Ile Arg Val Met Glu Ser Lys Glu Asn Glu Gln Ile Asn Gly Gly Ala
65                  70                  75                  80

Thr Asp Glu Gly Ala Ile Arg Lys Arg Glu Trp His Val Pro Ile Leu
                85                  90                  95

Ala Met Thr Ala Asp Val Ile Val
            100

<210> SEQ ID NO 31
<211> LENGTH: 22
<212> TYPE: DNA
<213> ORGANISM: Arabidopsis thaliana
<220> FEATURE:
<221> NAME/KEY: misc_feature
<222> LOCATION: 5, 11
<223> OTHER INFORMATION: n = inosine
<220> FEATURE:
<221> NAME/KEY: misc_feature
<222> LOCATION: 8, 14
<223> OTHER INFORMATION: n = a, c, g, or t

<400> SEQUENCE: 31
agatnytnrt ngtngaygay aa                                              22

<210> SEQ ID NO 32
<211> LENGTH: 23
<212> TYPE: DNA
<213> ORGANISM: Arabidopsis thaliana
<220> FEATURE:
<221> NAME/KEY: misc_feature
<222> LOCATION: 6, 12
<223> OTHER INFORMATION: n = inosine
<220> FEATURE:
<221> NAME/KEY: misc_feature
<222> LOCATION: 15, 21
<223> OTHER INFORMATION: n =a, g, c, or t

<400> SEQUENCE: 32
tgdatnacrt cngcngtcat ngc                                             23

<210> SEQ ID NO 33
<211> LENGTH: 7028
<212> TYPE: DNA
<213> ORGANISM: Arabidopsis thaliana

<400> SEQUENCE: 33
ccaaactact aagatatggg aagacccttg gcttccaaca cttcccccgc gacctgctcg    60

-continued

| | |
|---|---|
| tggcccaatt ctggatgagg acatgaaagt agcagattta tggagagaaa ataaacgaga | 120 |
| atgggatcct gtgattttcg aaggagttct taatccggag gatcaacaac tggctaaatc | 180 |
| tttgtatctc tctaactatg ccgctagaga ctcttataaa tgggcgtata ctcgcaatac | 240 |
| tcaatatacg gtgagatcgg ggtattgggt tgccactcat gtcaatctta cagaggagga | 300 |
| aatcattaat cccttgaag gagacgttcc attaaaacaa gaaatctgga gattgaagat | 360 |
| cactccaaag atcaagcatt tcatttggcg ctgtttatcc ggagctttat ccacaaccac | 420 |
| tcaactccgg aacaggaaca ttccagcaga cccgacttgt caaagatgct gcaatgccga | 480 |
| cgagacaatt aaccacataa tttttacttg ttcttatgcg caggttgtat ggagaagtgc | 540 |
| aaacttttct gggagtaatc gactttgctt cacggataat cttgaagaga atatacgact | 600 |
| aatattgcag gggaagaaaa accaaaacct tcccattctt aatggcttga tgcctttttg | 660 |
| gataatgtgg cgcttatgga aatcacgtaa cgaataccct tttcaacagc ttgatcgttt | 720 |
| cccttggaag gtggcacaga aagcagaaca agaagcaacc gaatgggtcg aaactatggt | 780 |
| taatgatacg gctatctcac acaacacggc acagtccaat gatcgaccgt tgagccgaag | 840 |
| taaacaatgg agttcaccac cggagggatt tctcaaatgt aactttgaca gtggctatgt | 900 |
| tcagggaagg gattatacaa gcacaggttg gatactccgt gactgcaatg gacgtgtact | 960 |
| acattcaggt tgtgcgaaac tacaacaatc atactcagcc ctacaagcag aagccttggg | 1020 |
| attcttacat gccctacaaa tggtttggat acgtggatac tgttatgtgt ggtttgaagg | 1080 |
| cgacaatctg gagctaacga acctaattaa caagactgaa gatcatcatc tccttgaaac | 1140 |
| actgctttat gacattcggt tttggatgac taagttaccc ttctcatcaa ttggttatgt | 1200 |
| caatcgggag agaaacttgg cagcggacaa actcacaaag tatgcaaact caatgtcttc | 1260 |
| tttgtatgaa acctttcatg taccaccaag atggctacaa ctctatttgt actatcccctt | 1320 |
| tacaaattaa taaagtcaga tgttaaaaaa aaaaaaaaa tagagtaagt agttgttagg | 1380 |
| aaaataatat cattatattt gacagattat ttaatttcat tatcattttc ctcataacat | 1440 |
| tttaaagatg ataagattag tgtaattact aattagtgag gctgtcgcat tagttgatga | 1500 |
| tgttgtagat aaaaaaaatg atcaaacaag aaatgattac caattatcat atgtaggaca | 1560 |
| cgtataaatg ttaaaaacgg aaaattaata accattccaa ttgatcaact tgatggtggt | 1620 |
| cattaaaaat cactttagaa aatacggaat tttataaaat ataaaatata gtttggtttt | 1680 |
| attttgtctg atgaatttt ttttatgta aagtaaaagg ttaaagaga aaatgatta | 1740 |
| acaaaggcac taagaatatt gagaagagtg ctttgagaat tgtggcaaat acagtgacaa | 1800 |
| ccactataaa atcattatct cttaattaat actggtatta gtcatcctct taaaaaaaca | 1860 |
| tttttttttta tgggtaggat tcttaaaatt atttattatc gttaaacaac aaaatctatt | 1920 |
| ttattttgtt ttgttgtttg aatttctcta tttttatggga atgttctcat ttaaattaaa | 1980 |
| actaacaggg cacgaatatg ggccttaaat tatcaagccc agtagagccc atacttcttc | 2040 |
| tactatctca aatatctgat atacatttca gaggaactat attcgtcttt ttcaaaccgg | 2100 |
| cccagctcaa taagttcttt aatatatggc tacccaaccc aaatacgaaa tactcgtcca | 2160 |
| attatgaaat ctcacgtaaa agcccactta atggtagttt tatggttcta atatttctta | 2220 |
| agtattagat ctatgactct gttacgaaca taatgtacaa tttagcggcc caaagcaatg | 2280 |
| taagaaggta aaaagaaaa actaagaaa ttagttaggt tatataaaaa aaagtataat | 2340 |
| cagagaaatt taatctctct tttgcataaa ttattaaaac taaattggaa aatgacattt | 2400 |

-continued

```
caaaagagaa aatattttca aaaatggaaa ataaaaccat taaaaaatta aatatgattt    2460
aaaatatttc tcgtaccaaa gtccacacga ttccatgaaa tatgtggaaa gtctagtaat    2520
cgctatttaa ggtgtcaaaa caatgtatag agagattcaa agacttgttt ccaaatcata    2580
tattagtatt aaattagtaa atggcttcat gtttttaatg attgtgagtc aaaaattaat    2640
ttttaatatc tttttgacaa tgttgttagt atatatttaa tgatatatgt gaactttata    2700 atctttttaat gatttgtgac aatgttctta atcttaggta aatttatgaa atttcaagca    2760
tccgtttgtg tttgttcatg aacatggaca atctttattc ttgaaaacaa atatgctaga    2820
ttttgtgtgt catttgagtg tgaaatcttt ggattttttc acctaattac aataacttta    2880
tcttggtcaa agaatcattg atcgatgttg atttatgagt gataattata gtttaacata    2940
ggatatctta tttaatgaat gtagttgatc ttatctctat aaaatattct attggacttt    3000
cgaattacga ttgattgaga tagtaattat taaatcgtga ttgtttatat aaacttttga    3060
agaaaggacg attacactag tctgcttttt tgactcaaaa tagtgaacac tttgtatgaa    3120
gaatcgttaa aagttataaa catgcagtat aagaactaac gaaaatataa ccaaattaat    3180
ttatgaaata cagtggattg gttttggtgt tattttaaat aaatgaattg gttgaatggg    3240
agtgattgtc gagcatgtga caaaaaaaca taatttgaga gtaaatacaa acaccgaaaa    3300
atagaatatg ttacaaaatc ttataaaatc ttaataaata aggagaattt gtaaattgta    3360
accactaaat gatttaatga tataaagtca aacatgaatc tcacatggcc gacacacaca    3420 catttgtta gcaccacttc ctttgtgtac cccctttcc ccctatcttt gtgtactact    3480
aaatccatat attctacttt tttacatctt tgtgaataaa ggataaaaat tagcaaactt    3540
gtcgaaaaaa tagagtgtgt cctacatgaa catgaaatgg atgctttata tgaatctcac    3600
gtcggaaaac tataattgat agaaactgag tagcaatatt gccacaccaa cgtcgccatc    3660
ttcatcttca tctagtcaca tttaacatcg atcatcaaca agttgcgaaa aagagtgttt    3720
aaattaaaag aaaaagttca agaatatttg tgtagaacat ggttcaagcg aagatgaaac    3780
taaaagtaaa atgagattgg ttcgactcca tatcatacaa aagaatgtcc atcctaggta    3840
gtagaaatat agatatcaaa gagaatgaag tataagaaaa agaggaaaca atggtcaatg    3900
ccaaacggat caccttttt ataagacatt tccctaaatt aaccatacat aacaaaaaaa    3960
ggatatttga tatttccatc gacccatttt gtcaattttc aaacaatttt tttcaatgca    4020
ttgactaata atgtataggg attcacacat tgtattttg ttttcaatta ttttcgttag    4080
gttttaacca tttatgtttc tctaaggtct aacccaaacc catttgagtt aaattttaat    4140
atatatatat attaaaaaat aaaataaaag aacaaaaaag aaaataaaat aaattctttt    4200
tcctttataa tataaagtac aagtccctttg cccaataaaa ttatgccaca taagatttgt    4260
ttataattta aagaattatt taaaattttt taaaaaaaaa acgctcattt tttttttcta    4320
catatttaaa aacaaaaaaa tattcctaga ttttctcaca caccacacca tcattatctt    4380
tggaaatttg taaccaactc aagatttttcc aaaccgtttt atcttcctct acaaaaatcc    4440
aattcacgtt aaatctatct cttgctcttg cttcctccaa aaaaaaaaaa aaatcattcc    4500
cagatccatc gatatgaaat tgtatagaaa aaatggtatt cgatccaagt ttattgtctt    4560 ctattttct taggttaatt tcactttatt ccagattcat tgtttgtttt ttctttctcg    4620
gaagagcaca atgtgagttt cactggcctc tgttataaac atatatagaa atctgtaaca    4680
aaaatcatta ctaaaattct gtgacatgtg cagcgatcaa agaatcaata gcggaaaaag    4740
aaactacact gcattcatct atgactgaaa gcttctgatc aagccatgaa attaaggtat    4800
```

```
cccaaacacg tatcttctct atgtttatca atcttgcttt aagttctaat tctgcatatt    4860
tcaaaggaac catacaagtg ttcctaaaat ccatttgaat attcaaaaac ttctctcaaa    4920
tatcatgtag ttatagaagc tactgtctct aagcgcacga gagaaagcta cacaacccac    4980
gtcagtttcc atctacacat ataaggtaat aataatattt tcatgtatct ttaataatag    5040
ctctatgttt ttttctgtat ttttcattat aaaactcata actatgttat catttaatat    5100
ggtactaatt taatgggatt gatttactat tgcctcaaac atgtaataat ttaatgattt    5160
tttgttttta acgttttag aaattcatga gcattttaaa tttgtggtta ggtcataaca     5220
atttgctatt acaaaaaaaa gaaacactct aaataatata aaaaatagtt taccgtataa    5280
tactagtagt aaataaataa tttgattgtt attcataaat tttgaattct aaaatctcct    5340
gaatcaactc atgcaattgt cttaagaatt acacgtggat aaatcatggg cttatgagtc    5400
aggcccattt aaccggggta ttttcgtagt taagagacta gaatggtggg tatttcaggt    5460
aaaaggtcta tggggccaga tctgcgcttt gtcgcgatgt cattatcgcc aaagatatgc    5520
gatagcgact ctcgtacaaa gtctctcact cacctatatt ttttgttttc ttatatttca    5580
acaaaaaaac gttttatttt cctttggtg taagtaaaaa aacaaaacaa aacgttttat     5640
ttctaaagtt cagaaaactt atttatacca aggaaaaaat agataataaa ttttgagaag    5700
ttggtgacta tatattactt cacttattca agaaatttaa acatggtaaa tgttacttta    5760
aatgttaaat gatgtataag aaatgtaatg aaattgaata aatgtagttt taaagatgtt    5820
ttaattagta agacaaacct agttagtgtc acaataatta tatttttttt tttgtcatcc    5880
aaaattatta aagctcaagt aaaccaatcc tgagggatat tatttacaaa tgtgatatga    5940
tgcggttcgg tgcggatctt ccgcgccaaa ttatacgctt ttatattagc attataaaaa    6000
attatagata aagagaagtt tgtgaattct tcattgtcgc tttgcaattt ctctaaatac    6060
acagtaaata ccgacaattc ggttagagaa aatatatcta tttcgtataa taatgttaac    6120
tttgaggaga ttttgggtaa aataataact tttgttggat ggatcatatc atgagccatt    6180
aagaaaaagt ccaaaacttt tcttcttcaa agttggactc aagttagaaa agaaaaaaag    6240
agctagagag atataaaaat gaaagaaag ttcatggcaa aaaactgata tagacagaga     6300
cacagagaga gagaaacgta tctgaagaaa atctaaaaaa ttcgattcaa tttttttctt    6360
acttttaaaa gcaaaaaatc tcactaaaac aaaagaagaa gaaagaagaa agaaatgga    6420
ataccacat ttgaagtgat gagaagagat tttgtgtata ataataatgc aatgttcaat     6480
cctctcacaa ctcattacag gtaactaaaa taatttctcc atgtgcttgc ttattagtcg    6540
ttcttcctaa tgttatgttt ctctctgtgt tctttctttc tttggtcaaa gctttaattt    6600
tttttctatt gttggatttg agacagtgaa catagctatg ttcttgttcc aataataaac    6660
aatcacgcct gtaaagagct tatgattgat tagtgtgttt tttagtatta attaatttct    6720
ctgacaataa ttacttagtt tttaattctt ctctgtaaga aacctttgga aactgagcaa    6780
agttgcttct tttgagaacc atgcgtttct ttctctcttt tgttcttgaa ttcgcaaaaa    6840
catgtccttt ttcgtctaca ggtttctagg gtttgtttct gtactataaa ctatgtttat    6900
ggtaacattc ttaatcataa ctacactacc aatgcttta tgttatatgt atgcaaaaaa     6960
ggctctaact tttgttttct ttcactattg tttcttcttt tgttctctat tgttgtagct    7020
cagatatg                                                             7028
```

<210> SEQ ID NO 34

-continued

```
<211> LENGTH: 4001
<212> TYPE: DNA
<213> ORGANISM: Arabidopsis thaliana

<400> SEQUENCE: 34
aattattaaa tcgtgattgt ttatataaac ttttgaagaa aggacgatta cactagtctg      60
cttttttgac tcaaaatagt gaacactttg tatgaagaat cgttaaaagt tataaacatg     120
cagtataaga actaacgaaa atataaccaa attaatttat gaaatacagt ggattggttt     180
tggtgttatt ttaaataaat gaattggttg aatgggagtg attgtcgagc atgtgacaaa     240
aaaacataat ttgagagtaa atacaaacac cgaaaaatag aatatgttac aaaatcttat     300
aaaatcttaa taaataagga gaatttgtaa attgtaacca ctaaatgatt taatgatata     360
aagtcaaaca tgaatctcac atggccgaca cacacacatt tgttagcac cacttccttt      420 gtgtaccccc ttttccccct atctttgtgt actactaaat ccatatattc tacttttta     480 catctttgtg aataaaggat aaaaattagc aaacttgtcg aaaaaataga gtgtgtccta     540
catgaacatg aaatggatgc tttatatgaa tctcacgtcg gaaaactata attgatagaa     600
actgagtagc aatattgcca caccaacgtc gccatcttca tcttcatcta gtcacattta     660
acatcgatca tcaacaagtt gcgaaaaaga gtgtttaaat taaaagaaaa agttcaagaa     720
tatttgtgta gaacatggtt caagcgaaga tgaaactaaa agtaaaatga gattggttcg     780
actccatatc atacaaaaga atgtccatcc taggtagtag aaatatagat atcaaagaga     840
atgaagtata agaaaaagag gaaacaatgg tcaatgccaa acggatcacc ttttttataa     900
gacatttccc taaattaacc atacataaca aaaaaggat atttgatatt ccatcgacc      960 cattttgtca attttcaaac aattttttc aatgcattga ctaataatgt atagggattc    1020
acacattgta tttttgtttt caattatttt cgttaggttt taaccattta tgtttctcta    1080
aggtctaacc caaacccatt tgagttaaat tttaatatat atatatatta aaaaataaaa    1140
taaaagaaca aaaagaaaa taaaataaat tcttttttcct ttataatata agtacaagt     1200 cccttgccca ataaaattat gccacataag atttgtttat aatttaaaga attatttaaa    1260 atttttaaa aaaaaacgc tcattttttt tttctacata tttaaaaaca aaaaaatatt     1320
cctagatttt ctcacacacc acaccatcat tatctttgga aatttgtaac caactcaaga    1380
ttttccaaac cgttttatct tcctctacaa aaatccaatt cacgttaaat ctatctcttg    1440
ctcttgcttc ctccaaaaaa aaaaaaaat cattcccaga tccatcgata tgaaattgta    1500
tagaaaaaat ggtattcgat ccaagtttat tgtcttctat ttttcttagg ttaatttcac    1560
tttattccag attcattgtt tgttttttct ttctcggaag agcacaatgt gagtttcact    1620
ggcctctgtt ataaacatat atagaaatct gtaacaaaaa tcattactaa aattctgtga    1680
catgtgcagc gatcaaagaa tcaatagcgg aaaaagaaac tacactgcat tcatctatga    1740
ctgaaagctt ctgatcaagc catgaaatta aggtatccca aacacgtatc ttctctatgt    1800
ttatcaatct gctttaagt tctaattctg catatttcaa aggaaccata caagtgttcc    1860
taaaatccat ttgaatattc aaaaacttct ctcaaatatc atgtagttat agaagctact    1920
gtctctaagc gcacgagaga aagctacaca acccacgtca gtttccatct acacatataa    1980
ggtaataata atattttcat gtatcttaa taatagctct atgttttttt ctgtattttt     2040
cattataaaa ctcataacta tgttatcatt taatatggta ctaatttaat gggattgatt    2100
tactattgcc tcaaacatgt aataatttaa tgattttttg ttttaacgt ttttagaaat     2160 tcatgagcat tttaaatttg tggttaggtc ataacaattt gctattacaa aaaaaagaaa    2220
```

```
cactctaaat aatataaaaa atagtttacc gtataatact agtagtaaat aaataatttg    2280
attgttattc ataaattttg aattctaaaa tctcctgaat caactcatgc aattgtctta    2340
agaattacac gtggataaat catgggctta tgagtcaggc ccatttaacc ggggtatttt    2400
cgtagttaag agactagaat ggtgggtatt tcaggtaaaa ggtctatggg gccagatctg    2460
cgctttgtcg cgatgtcatt atcgccaaag atatgcgata gcgactctcg tacaaagtct    2520
ctcactcacc tatattttt gttttcttat atttcaacaa aaaacgtttt tattttcctt     2580
ttggtgtaag taaaaaaaca aaacaaaacg ttttatttct aaagttcaga aaacttattt    2640
ataccaagga aaaaatagat aataaattt gagaagttgg tgactatata ttacttcact    2700
tattcaagaa atttaaacat ggtaaatgtt actttaaatg ttaaatgatg tataagaaat    2760
gtaatgaaat tgaataaatg tagttttaaa gatgttttaa ttagtaagac aaacctagtt    2820
agtgtcacaa taattatatt ttttttttttg tcatccaaaa ttattaaagc tcaagtaaac    2880
caatcctgag ggatattatt tacaaatgtg atatgatgcg gttcggtgcg gatcttccgc    2940
gccaaattat acgcttttat attagcatta taaaaaatta tagataaaga gaagtttgtg    3000
aattcttcat tgtcgctttg caatttctct aaatacacag taaataccga caattcggtt    3060
agagaaaata tatctatttc gtataataat gttaactttg aggagatttt gggtaaaata    3120
ataacttttg ttggatggat catatcatga gccattaaga aaaagtccaa aacttttctt    3180
cttcaaagtt ggactcaagt tagaaaaaga aaaagagct agagagatat aaaaatgaaa    3240
agaaagttca tggcaaaaaa ctgatataga cagagacaca gagagagaga aacgtatctg    3300
aagaaaatct aaaaaattcg attcaatttt tttcttactt ttaaaagcaa aaaatctcac    3360
taaaacaaaa gaagaagaaa gaagaaagaa aatggaatac ctcatttga agtgatgaga    3420 agagattttg tgtataataa taatgcaatg ttcaatcctc tcacaactca ttacaggtaa    3480
ctaaaataat ttctccatgt gcttgcttat tagtcgttct tcctaatgtt atgtttctct    3540
ctgtgttctt tctttctttg gtcaaagctt taatttttt tctattgttg gatttgagac    3600
agtgaacata gctatgttct tgttccaata ataacaatc acgcctgtaa agagcttatg    3660
attgattagt gtgttttta gtattaatta atttctctga caataattac ttagttttta    3720
attcttctct gtaagaaacc tttggaaact gagcaaagtt gcttcttttg agaaccatgc    3780
gtttctttct ctcttttgtt cttgaattcg caaaaacatg tccttttcg tctacaggtt    3840 tctagggttt gttctgtac tataaactat gtttatggta acattcttaa tcataactac    3900
actaccaatg cttttatgtt atatgtatgc aaaaaaggct ctaactttg ttttctttca    3960 ctattgtttc ttcttttgtt ctctattgtt gtagctcaga t                       4001
```

<210> SEQ ID NO 35
<211> LENGTH: 2517
<212> TYPE: DNA
<213> ORGANISM: Arabidopsis thaliana

<400> SEQUENCE: 35

```
tcgatatgaa attgtataga aaaatggta ttcgatccaa gtttattgtc ttctattttt    60
cttaggttaa tttcactta ttccagattc attgtttgtt ttttctttct cggaagagca    120
caatgtgagt ttcactggcc tctgttataa acatatatag aaatctgtaa caaaaatcat    180
tactaaaatt ctgtgacatg tgcagcgatc aaagaatcaa tagcggaaaa agaaactaca    240
ctgcattcat ctatgactga aagcttctga tcaagccatg aaattaaggt atcccaaaca    300
```

-continued

```
cgtatcttct ctatgtttat caatcttgct ttaagttcta attctgcata tttcaaagga      360
accatacaag tgttcctaaa atccatttga atattcaaaa acttctctca aatatcatgt      420
agttatagaa gctactgtct ctaagcgcac gagagaaagc tacacaaccc acgtcagttt      480
ccatctacac atataaggta ataataatat tttcatgtat ctttaataat agctctatgt      540 tttttctgt attttcatt ataaaactca taactatgtt atcatttaat atggtactaa        600
tttaatggga ttgatttact attgcctcaa acatgtaata atttaatgat tttttgtttt      660
taacgttttt agaaattcat gagcatttta aatttgtggt taggtcataa caatttgcta      720
ttacaaaaaa aagaaacact ctaaataata taaaaaatag tttaccgtat aatactagta      780
gtaaataaat aatttgattg ttattcataa attttgaatt ctaaaatctc ctgaatcaac      840
tcatgcaatt gtcttaagaa ttacacgtgg ataaatcatg ggcttatgag tcaggcccat      900
ttaaccgggg tattttcgta gttaagagac tagaatggtg ggtatttcag gtaaaaggtc      960
tatgggccca gatctgcgct tgtcgcgat gtcattatcg ccaaagatat gcgatagcga       1020
ctctcgtaca aagtctctca ctcacctata ttttttgttt tcttatattt caacaaaaaa     1080
acgttttatt ttccttttgg tgtaagtaaa aaaacaaaac aaaacgttt atttctaaag      1140 ttcagaaaac ttatttatac caaggaaaaa atagataata aattttgaga agttggtgac     1200
tatatattac ttcacttatt caagaaattt aaacatggta aatgttactt taaatgttaa     1260
atgatgtata agaaatgtaa tgaaattgaa taaatgtagt tttaaagatg ttttaattag     1320
taagacaaac ctagtagtg tcacaataat tatattttt ttttgtcat ccaaaattat        1380 taaagctcaa gtaaaccaat cctgagggat attatttaca aatgtgatat gatgcggttc     1440
ggtgcggatc ttccgcgcca aattatacgc ttttatatta gcattataaa aaattataga    1500
taaagagaag tttgtgaatt cttcattgtc gctttgcaat ttctctaaat acacagtaaa     1560
taccgacaat tcggttagag aaaatatatc tatttcgtat aataatgtta actttgagga    1620 gatttttgggt aaaataataa cttttgttgg atggatcata tcatgagcca ttaagaaaaa    1680
gtccaaaact tttcttcttc aaagttggac tcaagttaga aaaagaaaaa agagctagag     1740
agatataaaa atgaaaagaa agttcatggc aaaaaactga tatagacaga gacacagaga     1800
gagagaaacg tatctgaaga aaatctaaaa aattcgattc aatttttttc ttactttta    1860 aagcaaaaaa tctcactaaa acaaaagaag aagaagaag aaagaaatg gaataccctac   1920 atttgaagtg atgagaagag attttgtgta taataataat gcaatgttca atcctctcac     1980
aactcattac aggtaactaa aataaatttct ccatgtgctt gcttattagt cgttcttcct     2040
aatgttatgt ttctctctgt gttctttctt tctttggtca aagctttaat tttttttcta     2100 tgttggatt tgagacagtg aacatagcta tgttcttgtt ccaataataa acaatcacgc     2160
ctgtaaagag cttatgattg attagtgtgt tttttagtat taattaattt ctctgacaat    2220
aattacttag ttttttaattc ttctctgtaa gaaacctttg gaaactgagc aaagttgctt     2280
cttttgagaa ccatgcgttt cttttctctct tttgttcttg aattcgcaaa acatgtcct     2340 ttttcgtcta caggtttcta gggtttgttt ctgtactata aactatgttt atggtaacat      2400
tcttaatcat aactacacta ccaatgcttt tatgttatat gtatgcaaaa aaggctctaa     2460
cttttgtttt ctttcactat tgtttcttct tttgttctct attgttgtag ctcagat        2517
```

<210> SEQ ID NO 36
<211> LENGTH: 2688
<212> TYPE: DNA
<213> ORGANISM: Arabidopsis thaliana

<400> SEQUENCE: 36

```
tctagatttt ctcacacacc acaccatcat tatctttgga aatttgtaac caactcaaga      60
ttttccaaac cgttttatct tcctctacaa aaatccaatt cacgttaaat ctatctcttg     120
ctcttgcttc ctccaaaaaa aaaaaaaat cattcccaga tccatcgata tgaaattgta     180
tagaaaaaat ggtattcgat ccaagtttat tgtcttctat ttttcttagg ttaatttcac     240
tttattccag attcattgtt tgttttttct ttctcggaag agcacaatgt gagtttcact     300
ggcctctgtt ataaacatat atagaaatct gtaacaaaaa tcattactaa aattctgtga     360
catgtgcagc gatcaaagaa tcaatagcgg aaaagaaac tacactgcat tcatctatga     420
ctgaaagctt ctgatcaagc catgaaatta aggtatccca acacgtatc ttctctatgt     480
ttatcaatct tgctttaagt tctaattctg catatttcaa aggaaccata caagtgttcc     540
taaaatccat ttgaatattc aaaacttct ctcaaatatc atgtagttat agaagctact     600
gtctctaagc gcacgagaga aagctacaca acccacgtca gtttccatct acacatataa     660
ggtaataata atattttcat gtatctttaa taatagctct atgttttttt ctgtattttt     720
cattataaaa ctcataacta tgttatcatt taatatggta ctaatttaat gggattgatt     780
tactattgcc tcaaacatgt aataatttaa tgatttttg tttttaacgt ttttagaaat     840
tcatgagcat tttaaatttg tggttaggtc ataacaattt gctattacaa aaaaagaaa     900
cactctaaat aatataaaaa atagtttacc gtataatact agtagtaaat aaataatttg     960
attgttattc ataaattttg aattctaaaa tctcctgaat caactcatgc aattgtctta    1020
agaattacac gtggataaat catgggctta tgagtcaggc ccatttaacc ggggtatttt    1080
cgtagttaag agactagaat ggtgggtatt tcaggtaaaa ggtctatggg gccagatctg    1140
cgctttgtcg cgatgtcatt atcgccaaag atatgcgata gcgactctcg tacaaagtct    1200
ctcactcacc tatatttttt gttttcttat atttcaacaa aaaaacgttt tattttcctt    1260
ttggtgtaag taaaaaaaca aaacaaaacg ttttatttct aaagttcaga aaacttattt    1320
ataccaagga aaaatagat aataaatttt gagaagttgg tgactatata ttacttcact    1380
tattcaagaa atttaaacat ggtaaatgtt actttaaatg ttaaatgatg tataagaaat    1440
gtaatgaaat tgaataaatg tagttttaaa gatgttttaa ttagtaagac aaacctagtt    1500
agtgtcacaa taattatatt ttttttttg tcatccaaaa ttattaaagc tcaagtaaac    1560
caatcctgag ggatattatt tacaaatgtg atatgatgcg gttcggtgcg gatcttccgc    1620
gccaaattat acgcttttat attagcatta taaaaatta tagataaaga aagtttgtg    1680
aattcttcat tgtcgctttg caatttctct aaatacacag taaataccga caattcggtt    1740
agagaaaata tatctatttc gtataataat gttaactttg aggagatttt gggtaaaata    1800
ataacttttg ttggatggat catatcatga gccattaaga aaagtccaa acttttctt      1860
cttcaaagtt ggactcaagt tagaaaaga aaaagagct agagagatat aaaaatgaaa    1920
agaaagttca tggcaaaaaa ctgatataga cagagacaca gagagagaga aacgtatctg    1980
aagaaaatct aaaaaattcg attcaatttt tttcttactt ttaaaagcaa aaaatctcac    2040
taaaacaaaa gaagaagaaa gaagaaagaa aatggaatac ctacatttga agtgatgaga    2100
agagattttg tgtataataa taatgcaatg ttcaatcctc tcacaactca ttacaggtaa    2160
ctaaaataat ttctccatgt gcttgcttat tagtcgttct tcctaatgtt atgtttctct    2220
ctgtgttctt tctttctttg gtcaaagctt taattttttt tctattgttg gatttgagac    2280
```

```
agtgaacata gctatgttct tgttccaata ataaacaatc acgcctgtaa agagcttatg    2340
attgattagt gtgttttta gtattaatta atttctctga caataattac ttagttttta    2400
attcttctct gtaagaaacc tttggaaact gagcaaagtt gcttcttttg agaaccatgc    2460
gtttctttct ctcttttgtt cttgaattcg caaaaacatg tccttttcg tctacaggtt    2520 tctagggttt gtttctgtac tataaactat gttatggta acattcttaa tcataactac    2580
actaccaatg cttttatgtt atatgtatgc aaaaaaggct ctaacttttg ttttctttca    2640
ctattgtttc ttcttttgtt ctctattgtt gtagctcaga taggatcc              2688
```

<210> SEQ ID NO 37
<211> LENGTH: 42
<212> TYPE: DNA
<213> ORGANISM: Artificial Sequence
<220> FEATURE:
<223> OTHER INFORMATION: PRIMER
<220> FEATURE:
<221> NAME/KEY: misc_feature
<223> OTHER INFORMATION: PRIMER

<400> SEQUENCE: 37

```
gaattcttgt tttagagttc ctgagtagag tgttctttct cc                     42
```

<210> SEQ ID NO 38
<211> LENGTH: 39
<212> TYPE: DNA
<213> ORGANISM: Artificial Sequence
<220> FEATURE:
<223> OTHER INFORMATION: PRIMER

<400> SEQUENCE: 38

```
agacagacgc cgtgaaatcc tattaatccc acgggatcg                         39
```

<210> SEQ ID NO 39
<211> LENGTH: 39
<212> TYPE: DNA
<213> ORGANISM: Artificial Sequence
<220> FEATURE:
<223> OTHER INFORMATION: PRIMER

<400> SEQUENCE: 39

```
cttgatgatt gttgagtgcc cgttcggtgc ggatcttcc                         39
```

<210> SEQ ID NO 40
<211> LENGTH: 41
<212> TYPE: DNA
<213> ORGANISM: Artificial Sequence
<220> FEATURE:
<223> OTHER INFORMATION: PRIMER

<400> SEQUENCE: 40

```
ggctgacttg actctctttt ccccgagtgc tttttagagc c                      41
```

<210> SEQ ID NO 41
<211> LENGTH: 44
<212> TYPE: DNA
<213> ORGANISM: Artificial Sequence
<220> FEATURE:
<223> OTHER INFORMATION: PRIMER

<400> SEQUENCE: 41

```
tgatcacaca tggtaccttt cggcaagctc ttgatctctc tagc                   44
```

<210> SEQ ID NO 42

```
-continued
<211> LENGTH: 45
<212> TYPE: DNA
<213> ORGANISM: Artificial Sequence
<220> FEATURE:
<223> OTHER INFORMATION: PRIMER

<400> SEQUENCE: 42
gtgtgatgaa actgtctcgc cgtgtaagct tgttaagagt ttacc            45

<210> SEQ ID NO 43
<211> LENGTH: 40
<212> TYPE: DNA
<213> ORGANISM: Artificial Sequence
<220> FEATURE:
<223> OTHER INFORMATION: PRIMER

<400> SEQUENCE: 43
ccttcacatc caaaacccac gtgatagact ttgaagaaag                  40
```